United States Patent
Edwards et al.

(10) Patent No.: US 11,951,172 B2
(45) Date of Patent: Apr. 9, 2024

(54) THERAPEUTIC MOLECULES THAT BIND TO LAG3 AND PD1

(71) Applicant: CRESCENDO BIOLOGICS LIMITED, Cambridge (GB)

(72) Inventors: Carolyn Edwards, Cambridge (GB); Angelica Sette, Cambridge (GB); Isabelle Osuch, Cambridge (GB); Yumin Teng, Cambridge (GB); James Legg, Cambridge (GB); David Escors Murugarren, Pamplona (ES)

(73) Assignee: CRESCENDO BIOLOGICS LIMITED, Cambridge (GB)

( * ) Notice: Subject to any disclaimer, the term of this patent is extended or adjusted under 35 U.S.C. 154(b) by 180 days.

(21) Appl. No.: 16/969,905

(22) PCT Filed: Feb. 18, 2019

(86) PCT No.: PCT/GB2019/050425
§ 371 (c)(1),
(2) Date: Aug. 13, 2020

(87) PCT Pub. No.: WO2019/158942
PCT Pub. Date: Aug. 22, 2019

(65) Prior Publication Data
US 2021/0015937 A1    Jan. 21, 2021

(30) Foreign Application Priority Data
Feb. 16, 2018    (GB) ...................... 1802573

(51) Int. Cl.
*A61K 39/395* (2006.01)
*A61K 47/68* (2017.01)
(Continued)

(52) U.S. Cl.
CPC ...... *A61K 47/6801* (2017.08); *A61K 39/3955* (2013.01); *C07K 16/2818* (2013.01);
(Continued)

(58) Field of Classification Search
None
See application file for complete search history.

(56) References Cited

U.S. PATENT DOCUMENTS

| | | |
|---|---|---|
| 7,851,598 B2 | 12/2010 | Davis |
| 9,872,852 B2 | 1/2018 | Chupak et al. |

(Continued)

FOREIGN PATENT DOCUMENTS

| | | |
|---|---|---|
| CN | 103087171 A | 5/2013 |
| CN | 105384825 A | 3/2016 |

(Continued)

OTHER PUBLICATIONS

Reeck et al., "Homology" in proteins and nucleic acids: a terminology muddle and a way out of it, Cell, 50: 667, 1987.*

(Continued)

*Primary Examiner* — Claire Kaufman
(74) *Attorney, Agent, or Firm* — Sterne, Kessler, Goldstein & Fox P.L.L.C.

(57) ABSTRACT

The invention relates to LAG-3 binding agents, in particular variable heavy chain ($V_H$) sdAbs and bispecific agents that target both LAG-3 and PD-1, and the use of such binding agents in the treatment, prevention and detection of disease.

Figure 1:
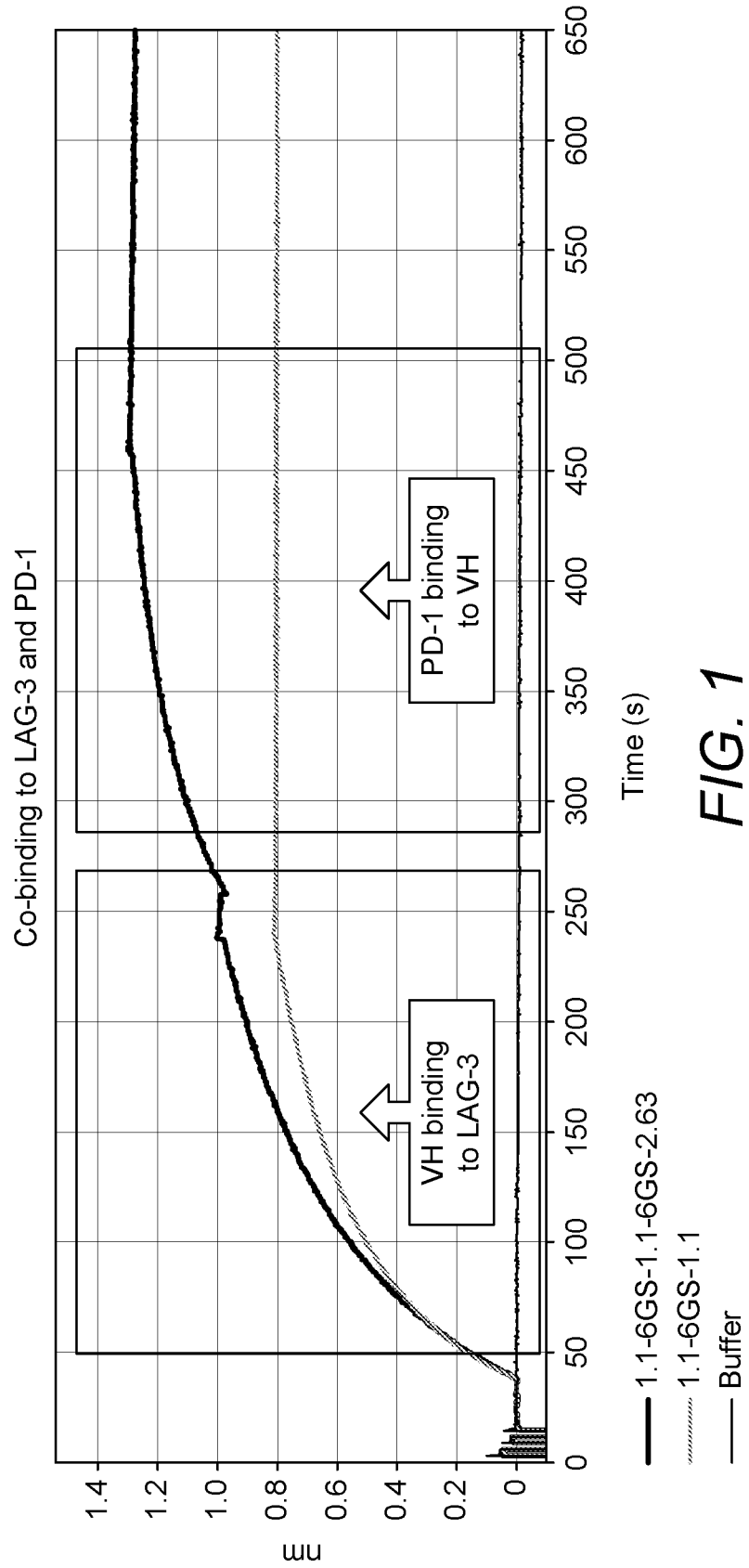

24 Claims, 7 Drawing Sheets
Specification includes a Sequence Listing.

(51) Int. Cl.
  *C07K 16/18* (2006.01)
  *C07K 16/28* (2006.01)
  *C12N 15/10* (2006.01)
  *C07K 16/46* (2006.01)
(52) U.S. Cl.
  CPC ............. *C12N 15/10* (2013.01); *C07K 16/28* (2013.01); *C07K 16/2803* (2013.01); *C07K 16/46* (2013.01); *C07K 2317/31* (2013.01); *C07K 2317/565* (2013.01); *C07K 2317/569* (2013.01); *C07K 2317/626* (2013.01); *C07K 2317/94* (2013.01); *C07K 2319/00* (2013.01)

(56) References Cited

U.S. PATENT DOCUMENTS

| | | | |
|---|---|---|---|
| 10,202,458 | B2 | 2/2019 | Goetsch et al. |
| 10,323,090 | B2* | 6/2019 | Bowman ................. A61P 31/00 |
| 10,975,161 | B2 | 4/2021 | Balloi et al. |
| 11,117,964 | B2 | 9/2021 | Hsu et al. |
| 11,236,174 | B2 | 2/2022 | McGuinness et al. |
| 11,312,771 | B2 | 4/2022 | Edwards et al. |
| 11,591,398 | B2 | 2/2023 | Hayes et al. |
| 11,814,429 | B2 | 11/2023 | Edwards et al. |
| 2010/0122358 | A1 | 5/2010 | Bruggemann et al. |
| 2013/0202623 | A1 | 8/2013 | Chomont et al. |
| 2014/0356908 | A1 | 12/2014 | Grosveld et al. |
| 2015/0210769 | A1 | 7/2015 | Freeman et al. |
| 2015/0210796 | A1 | 7/2015 | Kim et al. |
| 2017/0240644 | A1 | 8/2017 | Zhou et al. |
| 2018/0362666 | A1 | 12/2018 | Teng et al. |
| 2019/0023807 | A1 | 1/2019 | Balloi et al. |
| 2019/0144561 | A1 | 5/2019 | McGuinness et al. |
| 2019/0322749 | A1 | 10/2019 | Edwards et al. |
| 2020/0131274 | A1 | 4/2020 | Royle et al. |
| 2020/0216540 | A1* | 7/2020 | Geuijen ............. C07K 16/2818 |
| 2020/0227870 | A1* | 7/2020 | Lollo ................... H02J 7/0045 |
| 2020/0239570 | A1 | 7/2020 | Edwards et al. |
| 2020/0239573 | A1 | 7/2020 | Hayes et al. |
| 2020/0362047 | A1 | 11/2020 | Brucklacher-Waldert et al. |
| 2020/0362051 | A1 | 11/2020 | Brucklacher-Waldert et al. |
| 2020/0392244 | A1 | 12/2020 | Balloi et al. |
| 2021/0340233 | A1 | 11/2021 | Edwards et al. |
| 2022/0112305 | A1 | 4/2022 | McGuinness et al. |
| 2022/0220215 | A1 | 7/2022 | Enever et al. |
| 2022/0227850 | A1 | 7/2022 | Dunlevy et al. |
| 2022/0306744 | A1 | 9/2022 | Edwards et al. |
| 2023/0357405 | A1 | 11/2023 | Hayes et al. |

FOREIGN PATENT DOCUMENTS

| | | | |
|---|---|---|---|
| EP | 2363404 | A2 | 9/2011 |
| EP | 2363404 | B1 | 9/2016 |
| EP | 3470426 | A1 | 4/2019 |
| JP | 2017532059 | A | 11/2017 |
| JP | 2021502104 | A | 1/2021 |
| WO | WO-2003000737 | A2 | 1/2003 |
| WO | WO-2004076618 | A2 | 9/2004 |
| WO | WO-2006089230 | A2 | 8/2006 |
| WO | WO-2007117264 | A2 | 10/2007 |
| WO | WO-2009114335 | A2 | 9/2009 |
| WO | WO-2009117335 | A2 | 9/2009 |
| WO | WO-2010036959 | A2 | 4/2010 |
| WO | WO-2011110621 | A1 | 9/2011 |
| WO | WO-2012072731 | A2 | 6/2012 |
| WO | WO-2013126712 | A1 | 8/2013 |
| WO | WO-2013167883 | A1 | 11/2013 |
| WO | WO-2014141192 | A1 | 9/2014 |
| WO | WO-2014198223 | A1 | 12/2014 |
| WO | WO-2015034820 | A1 | 3/2015 |
| WO | WO-2015112900 | A1 | 7/2015 |
| WO | WO-2015116539 | A1 | 8/2015 |
| WO | WO-2015142675 | A2 | 9/2015 |
| WO | WO-2015143079 | A1 | 9/2015 |
| WO | WO-2015156268 | A1 | 10/2015 |
| WO | WO-2015200119 | A1 | 12/2015 |
| WO | WO-2016020856 | A2 | 2/2016 |
| WO | WO-2016025880 | A1 | 2/2016 |
| WO | WO-2016062990 | A1 | 4/2016 |
| WO | WO-2016073760 | A1 | 5/2016 |
| WO | WO-2016106159 | A1 | 6/2016 |
| WO | WO-2016184882 | A1 | 11/2016 |
| WO | WO-2016197497 | A1 | 12/2016 |
| WO | WO-2017019846 | A1 | 2/2017 |
| WO | WO-2017020801 | A1 | 2/2017 |
| WO | WO-2017060144 | A1 | 4/2017 |
| WO | WO-2017087589 | A2 | 5/2017 |
| WO | WO-2017122017 | A1 | 7/2017 |
| WO | WO-2017122018 | A1 | 7/2017 |
| WO | WO-2017122019 | A1 | 7/2017 |
| WO | WO-2017123650 | A2 | 7/2017 |
| WO | WO-2017191476 | A1 | 11/2017 |
| WO | WO-2017201488 | A1 | 11/2017 |
| WO | WO-2017205738 | A1 | 11/2017 |
| WO | WO-2018104444 | A1 | 6/2018 |
| WO | WO-2018127709 | A1 | 7/2018 |
| WO | WO-2018127710 | A1 | 7/2018 |
| WO | WO-2018127711 | A1 | 7/2018 |
| WO | WO-2018224439 | A1 | 12/2018 |
| WO | WO-2019012260 | A1 | 1/2019 |
| WO | WO-2019092451 | A1 | 5/2019 |
| WO | WO-2019092452 | A1 | 5/2019 |
| WO | WO-2019158942 | A1 | 8/2019 |
| WO | WO-2020099871 | A1 | 5/2020 |
| WO | WO-2020229842 | A1 | 11/2020 |
| WO | WO-2020229844 | A1 | 11/2020 |

OTHER PUBLICATIONS

Yan et al. Construction of a synthetic phage-displayed Nanobody library with CDR3 regions randomized by trinucleotide cassettes for diagnostic applications, J. Translational Med. 12:343, http://www.translational-medicine.com/content/12/1/343, 12 pages, 2014.*

Steven et al., In Vitro Maturation of a Humanized Shark VNAR Domain to Improve Its Biophysical Properties to Facilitate Clinical Development, Front. Immunol. 8:1361, doi: 10.3389/fimmu.2017.0136, 15 pages, Oct. 2017.*

Chen et al., Enhancement and destruction of antibody function by somatic mutation: unequal occurrence is controlled by V gene combinatorial associations, EMBO J. 14 (12): 2784-2794, 1995.*

Burnell et al., Seven mysteries of LAG-3: a multi-faceted immune respectr of increasing complexity, Immunother. Adv. 2:1-14, doi.org/10.1093/immadv/ltab025, 2022.*

Agata, Y., "Expression of the PD-1 antigen on the surface of stimulated mouse T and B lymphocytes," Int. Immunology, 8(5):765-772 (May 1996).

Castelli, C., et al., "Lymphocyte activation gene-3 (LAG-3, CD223) in plasmacytoid dendritic cells (pDCs): a molecular target for the restoration of active antitumor immunity," Oncoimmunology, 3(11):e967146, 4 pages, (Dec. 2014).

D'Huyvetter, M., et al., "Radiolabeled nanobodies as theranostic tools in targeted radionuclide therapy of cancer," Expert Opin. Drug Deliv., 11(12):1939-54 (Dec. 2014).

Francisco, L., et al., "The PD-1 pathway in tolerance and autoimmunity," Immunol. Rev., 236:219-242 (Jul. 2010).

GenBank, "Alpha-synuclein," Accession No. P37840, accessed at https://www.ncbi.nlm.nih.gov/protein/P37840, accessed on Sep. 24, 2020, 13 pages.

GenBank, "C-type lectin domain family 4 member G isoform 1 [*Homo sapiens*]," Accession No. NP_940894.1, accessed at https://www.ncbi.nlm.nih.gov/protein/NP_940894, accessed on Sep. 24, 2020, 3 pages.

GenBank, "E3 ubiquitin-protein ligase CBL-B isoform b [*Homo sapiens*]," Accession No. NP_001308717.1, accessed at https://www.ncbi.nlm.nih.gov/protein/NP_001308717, accessed on Sep. 24, 2020, 4 pages.

GenBank, "galectin-3 [*Homo sapiens*]," Accession No. BAA22164.1, accessed at https://www.ncbi.nlm.nih.gov/protein/BAA22164, accessed on Sep. 24, 2020, 2 pages.

(56) References Cited

OTHER PUBLICATIONS

GenBank, "*Homo sapiens* lymphocyte activating 3 (LAG3), mRNA," Accession No. NM_002286.6, accessed at https://www.ncbi.nlm.nih.gov/nuccore/NM_002286, accessed on Sep. 24, 2020, 5 pages.
GenBank, "Human hPD-1 (hPD-1) mRNA, complete cds," Accession No. U64863.1, accessed at https://www.ncbi.nlm.nih.gov/nuccore/U64863, accessed on Sep. 24, 2020, 3 pages.
GenBank, "Macaca fascicularis chromosome 11, Macaca_fascicularis_5.0, whole genome shotgun sequence," Accession No. NC_022282.1, accessed at https://www.ncbi.nlm.nih.gov/nuccore/NC_022282, accessed on Sep. 24, 2020, 2 pages.
GenBank, "Macaca mulatta lymphocyte activating 3 (LAG3), mRNA," Accession No. XM_001108923.4, accessed at https://www.ncbi.nlm.nih.gov/nuccore/XM_001108923, accessed on Sep. 24, 2020, 2 pages.
Geng, Y., et al., "Single domain antibodies against immune checkpoint targets PD-1 and PD-L1," presented at the 2nd International Conference on Antibodies and Therapeutics (Jul. 11-12, 2016) in Philadelphia, USA, Immunome Res. 12(2_Suppl):47, 1 page, (Jul. 2016).
Grosso, J., et al., "LAG-3 regulates CD8+ T cell accumulation and effector function in murine self- and tumor-tolerance systems," J. Clin. Invest., 117(11):3383-92 (Nov. 2007).
Holt, L., et al., "Domain antibodies: proteins for therapy," Trends Biotechnol., 21(11):484-90 (Nov. 2003).
Huang, C., et al., "Role of LAG-3 in regulatory T cells," Immunity, 21(4):503-13 (Oct. 2004).
Huang, R., et al., "Compensatory upregulation of PD-1, LAG-3, and CTLA-4 limits the efficacy of single-agent checkpoint blockade in metastatic ovarian cancer," Oncoimmunol. 6(1):e1249561, 14 pages, (Oct. 2016).
Huard, B., et al., "Characterization of the major histocompatibility complex class II binding site on LAG-3 protein," Proc. Natl. Acad. Sci., 94(11):5744-5749 (May 1997).
Huard, B., et al., "Lymphocyte-activation gene 3/major histocompatibility complex class II interaction modulates the antigenic response of CD4+ T lymphocytes," Eur. J. Immunol., 24(12):3216-21 (Dec. 1994).
Huard, B., et al., "T cell major histocompatibility complex class II molecules down-regulate CD4+ T cell clone responses following LAG-3 binding," Eur. J. Immunol., 26(5):1180-6 (May 1996).
International Preliminary Report on Patentability of the International Searching Authority directed to related International Patent Application No. PCT/GB2019/050425, dated Aug. 18, 2020, 7 pages.
International Search Report and Written Opinion of the International Searching Authority directed to related International Patent Application No. PCT/GB2019/050425, dated Apr. 17, 2019; 10 pages.
Ishida, Y., et al., "Induced expression of PD-1, a novel member of the immunoglobulin gene superfamily, upon programmed cell death," EMBO J., 11(11): 3887-3895 (Nov. 1992).
Karwacz, K., et al., "PD-L1 co-stimulation contributes to ligand-induced T cell receptor down-modulation on CD8+ T cells," EMBO Mol. Med., 3(10): 581-592 (Oct. 2011).
Kisielow, M., et al., "Expression of lymphocyte activation gene 3 (LAG-3) on B cells is induced by T cells," Eur. J. Immunol., 35(7):2081-8 (Jul. 2005).
Kouo, T., et al., "Galectin-3 Shapes Antitumor Immune Responses by Suppressing CD8+ T Cells via LAG-3 and Inhibiting Expansion of Plasmacytoid Dendritic Cells," Cancer Immunol. Res., 3(4):412-423 (Apr. 2015).
Kraman, M., et al., "A LAG-3/PD-L1 bispecific antibody inhibits tumor growth in two syngeneic colon carcinoma models," Society for Immunotherapy of Cancer Conference (Nov. 2016).
Matsuzaki, J., et al., "Tumor-infiltrating NY-ESO-1-specific CD8+ T cells are negatively regulated by LAG-3 and PD-1 in human ovarian cancer," Proc. Natl. Acad. Sci., 107(17):7875-7880 (Apr. 2010).

McGuinness, B., "Humabody fragments: Small and perfectly formed," Biopharmadealmakers, accessed at www.crescendobiologics.com, pp. B12-B13, 2 pages (2013).
Nishimura, H., et al., "Autoimmune dilated cardiomyopathy in PD-1 receptor-deficient mice," Science, 291(5502):319-322 (Jan. 2001).
Nishimura, H., et al., "Development of lupus-like autoimmune diseases by disruption of the PD-1 gene encoding an ITIM motif-carrying immunoreceptor," Immunity, 11(2):141-151 (Aug. 1999).
Ren, L., et al., "Silencing of the immunoglobulin heavy chain locus by removal of all eight constant-region genes in a 200-kb region," Genomics, 84(4):686-695 (Oct. 2004).
Riley, J., "PD-1 signaling in primary T cells," Immunol Rev., 229(1):114-125 (May 2009).
Roe, M., "Superior Human Single Domain VH Antibody Fragments from a Transgenic Mouse," Biopharmadealmakers, accessed at www.crescendobiologics.com, p. B23, 1 page (2013).
Rudikoff, S., et al., "Single Amino Acid Substitution Altering Antigen-Binding Specificity," Proc. Natl. Acad. Sci., 79(6):1979-1983 (Mar. 1982).
Triebel, F., et al., "LAG-3, a novel lymphocyte activation gene closely related to CD4," J. Exp. Med., 171(5):1393-1405 (May 1990).
Tseng, S., et al., "B7-DC, a new dendritic cell molecule with potent costimulatory properties for T cells," J. Exp. Med., 193(7):839-45 (Apr. 2001).
UK Search Report for Application No. GB1700207.2, Nov. 24, 2017; 4 pages.
UniParc, "UPI0000119BF0," accessed at https://www.uniprot.org/uniparc/UPI0000119BF0, accessed on Sep. 24, 2020, 1 page.
UniProt, "E3 ubiquitin-protein ligase CBL," Accession No. P22681, accessed at https://www.uniprot.org/uniprot/P22681, accessed on Sep. 24, 2020, 10 pages.
UniProt, "E3 ubiquitin-protein ligase CBL-B," Accession No. Q13191, accessed at https://www.uniprot.org/uniprot/Q13191, accessed on Sep. 24, 2020, 10 pages.
UniProt, "Programmed cell death protein 1," Accession No. Q15116, accessed at https://www.uniprot.org/uniprot/Q15116, accessed on Sep. 24, 2020, 7 pages.
Wesolowski, J., et al., "Single domain antibodies: promising experimental and therapeutic tools in infection and immunity," Medical Microbiology and Immunology, 198(3)157-174 (Aug. 2009).
Wong, Y., et al., "Structural Requirements for a Specificity Switch and for Maintenance of Affinity Using Mutational Analysis of a Phase-Displayed Anti-Arsonate Antibody of Fab Heavy Chain First Complementarily-Determining Region," J. Immunol., 160(12):5990-7 (Jun. 1998).
Workman, C., et al., "Cutting edge: molecular analysis of the negative regulatory function of lymphocyte activation gene-3," J. Immunol., 169(10):5392-5395 (Nov. 2002).
Xu, F., et al., "LSECtin expressed on melanoma cells promotes tumor progression by inhibiting antitumor T-cell responses," Cancer Res., 74(13):3418-3428 (Jul. 2014).
Yokosuka, T., et al., "Programmed cell death 1 forms negative costimulatory microclusters that directly inhibit T cell receptor signaling by recruiting phosphatase SHP2," J. Exp. Med., 209(6):1201-1217 (Jun. 2012).
Zhang, X., et al., "Structural and functional analysis of the costimulatory receptor programmed death-1," Immunity, 20(3):337-347 (Mar. 2004).
Zou, X., et al., "Block in development at the pre-B-II to immature B cell stage in mice without Ig kappa and Ig lambda light chain," J. Immunol., 170(3):1354-61 (Feb. 2003).
International Preliminary Report on Patentability of the International Searching Authority directed to related International Patent Application No. PCT/GB2018/050035, dated Jul. 9, 2019, 11 pages.
International Preliminary Report on Patentability of the International Searching Authority directed to related International Patent Application No. PCT/GB2018/050036, dated Jul. 9, 2019, 11 pages.
International Preliminary Report on Patentability of the International Searching Authority directed to related International Patent Application No. PCT/GB2018/050037, dated Jul. 9, 2019, 12 pages.

(56) References Cited

OTHER PUBLICATIONS

International Search Report and Written Opinion of the International Searching Authority directed to related International Patent Application No. PCT/GB2018/050035, dated Apr. 25, 2018, 16 pages.
International Search Report and Written Opinion of the International Searching Authority directed to related International Patent Application No. PCT/GB2018/050036, dated May 3, 2018, 16 pages.
International Search Report and Written Opinion of the International Searching Authority directed to related International Patent Application No. PCT/GB2018/050037, dated Apr. 25, 2018, 18 pages.
NCT02061761, "Safety Study of Anti-LAG-3 in Relapsed or Refractory Hematologic Malignancies," ClinicalTrials.gov, posted Feb. 13, 2014, accessed at https://www.clinicaltrials.gov/ct2/show/NCT02061761 on Dec. 14, 2020, 4 pages.
NCT02460224, "Safety and Efficacy of LAG525 Single Agent and in Combination With PDR001 in Patients With Advanced Malignancies," ClinicalTrials.gov, posted Jun. 2, 2015, accessed at https://www.clinicaltrials.gov/ct2/show/NCT02460224 on Dec. 14, 2020, 5 pages.
Caldas, C., et al., "Humanization of the anti-CD18 antibody 6.7: an unexpected effect of a framework residue in binding to antigen," *Molecular Immunology* 39(15):941-952, Elsevier, Netherlands (May 2003).
Du, J., et al., "Molecular basis of recognition of human osteopontin by 23C3, a potential therapeutic antibody for treatment of rheumatoid arthritis," *Journal of Molecular Biology* 382(4):835-842, Elsevier, Netherlands (published online Jul. 2008, published in print Oct. 2008).
Kunik, V., et al., "Structural consensus among antibodies defines the antigen binding site," *PLoS Comput Biol* 8(2):e1002388, 12 pages, Public Library of Science, United States (published online Feb. 2012).
Bennett, F., et al., "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," Journal of Immunology 170(2):711-718, The American Association of Immunologists, Inc., United States (2003).
Bruschi, C.V., and Gjuracic, K., "Yeast Artifical Chromosomes" in the Encyclopedia of Life Sciences, pp. 1-6, Macmillan Publishers Ltd., United Kingdom (2002).
Callahan, M.K., and Wolchok, J.D., "At the bedside: CTLA-4- and PD-1-blocking antibodies in cancer immunotherapy," J Leukoc Biol 94(1):41-53, Society for Leukocyte Biology, United States (2013).
Dietz, L.J., et al., "Volumetric capillary cytometry: a new method for absolute cell enumeration," Cytometry 23(3):177-186, John Wiley & Sons, United States (1996).
He, J., et al., "Development of PD-1/PD-L1 Pathway in Tumor Immune Microenvironment and Treatment for Non-Small Cell Lung Cancer," Scientific Reports 5:13110, 9 pages, Nature Publishing Group, United Kingdom (2015).
Keir, M.E., et al., "Programmed death-1 (PD-1):PD-ligand 1 interactions inhibit TCR-mediated positive selection of thymocytes," J Immunol 175(11):7372-7379, The American Association of Immunologists, Inc., United States (2005).
Lowther, D.E., et al., "PD-1 marks dysfunctional regulatory T cells in malignant gliomas," JCI Insight 1(5):e85935, 15 pages, The American Society for Clinical Investigation, United States (2016).
Main, S., et al., "A potent human anti-eotaxinl antibody, CAT-213: isolation by phage display and in vitro and in vivo efficacy," J Pharmacol Exp Ther 319(3):1395-404, American Society for Pharmacology and Experimental Therapeutics, United States (2006).
Marks, J.D., and Bradbury, A., "Chapter 8: Selection of Human Antibodies from Phage Display Libraries" in Methods in Molecular Biology, Antibody Engineering: Methods and Protocols, Lo, B., ed., pp. 161-176, Springer Nature, Switzerland (2004).
Marks, J.D., "Chapter 19: Antibody Affinity Maturation by Chain Shuffling" in Methods in Molecular Biology, Antibody Engineering: Methods and Protocols, Lo, B., ed., pp. 327-343, Springer Nature, Switzerland (2004).
Miraglia, S., et al., "Homogeneous Cell- and Bead-Based Assays for High Throughput Screening Using Fluorometric Microvolume Assay Technology," J Biomol Screening 4(4):193-204, SAGE Journals, United States (1999).
Posthumus, W.P., et al., "Analysis and simulation of a neutralizing epitope of transmissible gastroenteritis virus," J Virology 64(7):3304-3309, American Society for Microbiology, United States (1990).
Wang, C., et al., "In vitro characterization of the anti-PD-1 antibody nivolumab, BMS-936558, and in vivo toxicology in non-human primates," Cancer Immunol Res 2(9):846-856, American Association for Cancer Research, United States (2014).
Wang, W., et al., "PD1 blockade reverses the suppression of melanoma antigen-specific CTL by CD4+ $CD25^{Hi}$ regulatory T cells," Int Immunol 21(9):1065-1077, Oxford University Press, United Kingdom (2009).
Goel, Manisha, et al., "Plasticity within the antigen-combining site may manifest as molecular mimicry in the humoral immune response." The Journal of Immunology 173(12): 7358-7367, American Association of Immunology, United States (2004).
Lloyd, C., et al., "Modelling the human immune response: performance of a $10^{11}$ human antibody repertoire against a broad panel of therapeutically relevant antigens." Protein Engineering, Design & Selection 22(3): 159-168, Oxford University Press, England (2009).
Edwards, Bryan M., et al. "The remarkable flexibility of the human antibody repertoire; isolation of over one thousand different antibodies to a single protein, BLyS." Journal of Molecular Biology 334(1): 103-118, Elsevier, Netherlands (2003).
Padlan, Eduardo A., "X-ray crystallography of antibodies." Advances in Protein Chemistry 49: 57-133, Academic Press, United States (1996).
Berglund, Lisa, et al. "The epitope space of the human proteome." Protein Science 17(4): 606-613, John Wiley, United States (2008).
Tzartos, Socrates J. "Epitope mapping by antibody competition." Epitope Mapping Protocols: in Methods in Molecular Biology, 68: 55-66, Humana Press, United States (1996).
Chen, Longxin, et al. "Epitope-directed antibody selection by site-specific photocrosslinking," Science Advances 6(14): eaaz7825, 9 pages, American Association for the Advancement of Science, United States (2020).
Paul, "Fv Structure and Diversity in Three Dimensions," Fundamental Immunology, 3rd Edition, pp. 292-295, Oxford Academic, England (1993).
Muyldermans, Serge, "Nanobodies: natural single-domain antibodies." Annual Review of Biochemistry 82: 17.1-17.23, 23 pages, Annual Reviews, United States (2013).
Zabetakis, Dan, et al. "Contributions of the complementarity determining regions to the thermal stability of a single-domain antibody." PloS One 8(10): e77678, 7 pages, Public Library of Science, United States (2013).
Vincke, Cecile, et al. "General strategy to humanize a camelid single-domain antibody and identification of a universal humanized nanobody scaffold." Journal of Biological Chemistry 284(5): 3273-3284, American Society for Biochemistry and Molecular Biology, United States (2009).
Saerens, Dirk, et al. "Identification of a universal VHH framework to graft non-canonical antigen-binding loops of camel single-domain antibodies." Journal of Molecular Biology 352(3): 597-607, Elsevier, Netherlands (2005).
Colman, P. M. "Effects of amino acid sequence changes on antibody-antigen interactions." Research in Immunology 145(1): 33-36, Elsevier, United States (1994).
Office Action dated Jun. 30, 2021, in U.S. Appl. No. 16/475,597, Hayes et al., 371(c) Date: Jul. 2, 2019, 23 pages.
Office Action dated Jun. 11, 2021, in U.S. Appl. No. 16/475,599, Edwards, C. et al., 371(c) Date: Jul. 2, 2019, 10 pages.
An, Z., ed., "Section 3.4.3—Glycan Profiles of Recombinant IgG Produced in Rodent Cell Lines," in *Therapeutic Monoclonal Antibodies: From Bench to Clinic*, pp. 73-76, John Wiley & Sons, United States (2009).

(56) References Cited

OTHER PUBLICATIONS

Bahara, N.H.H., et al., "Construction of a Semisynthetic Human VH Single-Domain Antibody Library and Selection of Domain Antibodies against a-Crystalline of Mycobacterium tuberculosis," Journal of Biomolecular Screening 21(1):35-43, Sage Publications, United States (2015).
Bander, N.H., et al., "Targeted Systemic Therapy of Prostate Cancer with a Monoclonal Antibody to Prostate-Specific Membrane Antigen," Seminars in Oncology 30(5):667-676, W.B. Saunders, United States (Oct. 2003).
Barve, A., et al., "Prostate Cancer Relevant Antigens and Enzymes for Targeted Drug Delivery," Journal of Control Release 187:118-132, Elsevier Science Publishers, Netherlands (Aug. 2014).
Bayachou, M., et al., "Catalytic Two-Electron Reductions of $N_2O$ and $N_3^-$ by Myglobin in Surfactant Films," Inorganic Chemistry 39(2):289-293, American Chemical Society, United States (Jan. 2000).
Bruggemann, M., et al., "A Repertoire of Monoclonal Antibodies With Human Heavy Chains From Transgenic Mice," Proc Natl Acad Sci USA 86(17):6709-6713, National Academy of Sciences, United States (Sep. 1989).
Bulliard, Y., et al., "OX40 Engagement Depletes Intratumoral Tregs via Activating FcγRs, Leading to Antitumor Efficacy," Immunology and Cell Biology 92(6):475-480, Nature Publishing Group, United Kingdom (2014).
Chalupny, N.J., et al., "T-cell Activation Molecule 4-1BB Binds to Extracellular Matrix Proteins," Proc Natl Acad Sci USA 89(21):10360-10364, National Academy of Sciences, United States (Nov. 1992).
Chatalic, K.L.S., et al., "A Novel $^{111}$In-Labeled Anti-Prostate-Specific Membrane Antigen Nanobody for Targeted SPECT/CT Imaging of Prostate Cancer," The Journal of Nuclear Medicine 56(7):1094-1099, Society of Nuclear Medicine and Molecular Imaging, United States (Jul. 2015).
Chen, L., et al., "Epitope-Directed Antibody Selection by Site-Specific Photocrosslinking," Science Advances 6(14):eaaz7825, pp. 1-9, American Association for the Advancement of Science, United States (Apr. 2020).
Chothia, C. and Lesk, A. M., "Canonical Structures for the Hypervariable Regions of Immunoglobulins," Journal of Molecular Biology 196(4):901-917, Elsevier, United Kingdom (Aug. 1987).
Cizeau, J., et al., "Abstract 5770: Engineering and Characterization of Anti-PSMA Humabody-deBouganin Fusion Proteins," Cancer Research 78(13 Suppl):5770, AACR Annual Meeting 2018 (Apr. 4-18, 2018), 2 pages, American Association for Cancer Research, United States (2018).
ClinicalTrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.
Communication from the Examining Division for EP Application No. EP 17 700 734.1, European Patent Office, Munich, Germany, dated Jul. 24, 2020, 10 pages.
Communication from the Examining Division for EP Application No. EP 17 701 006.3, European Patent Office, Munich, Germany, dated Jun. 5, 2019, 6 pages.
Communication from the Examining Division for EP Application No. EP 17 724 869.7, European Patent Office, Munich, Germany, dated Dec. 4, 2019, 6 pages.
Communication from the Examining Division for EP Application No. EP 19 707 094.9, European Patent Office, Munich, Germany, dated Nov. 22, 2021, 4 pages.
Conrath, E., et al., "Camel Single-Domain Antibodies as Modular Building Units in Bispecific and Bivalent Antibody Constructs," Journal of Biological Chemistry 276(10):7346-7350, American Society for Biochemistry and Molecular Biology, United States (Mar. 2001).
Crescendo Biologics, "Humabody fragments: small and perfectly formed," CrescendoBiologics.com, pp. B12-B13, accessed at https://www.crescendobiologics.com/wpcontent/uploads/2016/03/20150309-Crescendo0315.pdf, accessed on Oct. 13, 2020, 2 pages.

Drabek, D., et al., "Expression Cloning and Production of Human Heavy-Chain-Only Antibodies from Murine Transgenic Plasma Cells," Frontiers in Immunology 7(619):1-10, Frontiers Media SA, United States (Dec. 2016).
Dubrot, J., et al., "Treatment With Anti-CD 137 mAbs Causes Intense Accumulations of Liver T Cells Without Selective Antitumor Immunotherapeutic Effects in This Organ," Cancer Immunology, Immunotherapy 59(8):1223-1233, Springer Verlag, Germany (2010).
Elsadek, B. and Kratz, F., "Impact of Albumin on Drug Delivery-New Applications on the Horizon," Journal of Controlled Release 157(1):4-28, Elsevier Science Publishers, Netherlands (Jan. 2012).
Evazalipour, M., et al., "Camel Heavy Chain Antibodies against Prostate-Specific Membrane Antigen," Hybridoma (Larchmt) 31(6):424-429, Mary Ann Liebert Inc., United States (Dec. 2012).
Evazalipour, M., et al., "Generation and Characterization of Nanobodies Targeting PSMA for Molecular Imaging of Prostate Cancer," Contrast Media & Molecular Imaging 9(3):211-220, Hindawi in collaboration with John Wiley & Sons, Inc, United Kingdom (May-Jun. 2014).
Fan, G., et al., "Bispecific Antibodies and their Applications," Journal of Hematology & Oncology 8, Article No. 130, 14 pages, BioMed Central: Part of Springer Nature, United Kingdom (Dec. 2015).
Fan, X., et al., "Ultrasonic Nanobubbles Carrying Anti-Psma Nanobody: Construction and Application in Prostate Cancer-Targeted Imaging," PLoS One 10(6) :e0127419, Public Library of Science, United States (Jun. 2015).
Fisher, T.S., et al., "Targeting of 4-1BB by monoclonal antibody PF-05082566 enhances T-cell function and promotes anti-tumor activity," Cancer Immunology Immunotherapy, 61: 1721-1733, Springer Nature Limited, Germany (2012).
Gauttier, V., et al., "Agonistic anti-CD137 Antibody Treatment Leads to Antitumor Response in Mice with Liver Cancer," International Journal of Cancer 135(2):2857-2867, Wiley-Liss Inc., United States (Dec. 2014).
Genbank, "*Homo sapiens* TNF receptor superfamily member 9 (TNFRSF9), mRNA," NCBI Reference Sequence: NM _001561.6, https ://www.ncbi.nlm. nih. gov /nuccore/NM001561, last accessed on May 19, 2020, 5 pages, Accessed May 19, 2020.
Genbank, "tumor necrosis factor receptor superfamily member 9 precursor [*Homo sapiens*]," Accession No. NP_001552.2, accessed on https://www.ncbi.nlm.nih.gov/protein/NP001552, Oct. 7, 2016, 4 pages, Accessed Jan. 12, 2016.
Gordon, S. R., et al., "PD-1 expression by tumor-associated macrophages inhibits phagocytosis and tumour immunity," with methods and extended data, Nature 545(7655): 495-499 (13 pages total), Nature Publishing Group, United Kingdom (May 2017).
Guo, Y., et al., "Chimeric Antigen Receptor-Modified T Cells for Solid Tumors: Challenges and Prospects," Journal of Immunology Research 2016:3850839, 11 pages, Hindawi Publishing Corporation, Egypt (2016).
Henry, K. A., et al., "Identification of Cross-reactive Single-domain Antibodies Against Serum Albumin Using Next-generation DNA Sequencing," Protein Engineering, Design & Selection 28(10):379-383, Oxford University Press, United Kingdom (Aug. 2015).
Holliger, P, and Hudson, P.J., "Engineered Antibody Fragments and the Rise of Single Domains," Nature Biotechnology 23(9):1126-1136, Nature America Publishing, United States (2005).
Holt, L. J., et al., "Anti-Serum Albumin Domain Antibodies for Extending the Half-lives of Short Lived Drugs," Protein Engineering, Design and Selection 21(5):283-288, Oxford University Press, United Kingdom (May 2008).
Homayouni, V., et al., "Preparation and characterization of novel nanobody against T-cell immunoglobulin and mucin-3 (TIM-3)," Iranian Journal of Basic Medical Sciences 19(11):1201-1208, Mashhad University of Medical Sciences, Iran (2016).
Houot, R., et al., "Therapeutic Effect of CD137 Immunomodulation in Lymphoma and Its Enhancement by $T_{reg}$ Depletion," Blood 114(16):3431-3438, American Society of Hematology, United States (2009).

(56) References Cited

OTHER PUBLICATIONS

International Preliminary Report on Patentability for International Application No. PCT/GB2019/053220, The International Bureau of WIPO, Switzerland, dated May 18, 2021, 11 pages.
International Preliminary Report on Patentability for International Application No. PCT/GB2020/051199, The International Bureau of WIPO, Switzerland, dated Nov. 16, 2021, 8 pages.
International Preliminary Report on Patentability for International Application No. PCT/GB2020/051201, The International Bureau of WIPO, Switzerland, dated Nov. 16, 2021, 17 pages.
International Preliminary Report on Patentability for International Application No. PCT/GB2017/050074, The International Bureau of WIPO, Switzerland, dated Jul. 17, 2018, 11 pages.
International Preliminary Report on Patentability for International Application No. PCT/GB2017/051272, The International Bureau of WIPO, Switzerland, dated Nov. 6, 2018, 11 pages.
International Preliminary Report on Patentability for International Application No. PCT/GB2018/051941, The International Bureau of WIPO, Switzerland, dated Jan. 14, 2020, 6 pages.
International Preliminary Report on Patentability for International Application No. PCT/GB2018/053279, The International Bureau of WIPO, Switzerland, dated May 19, 2020, 11 pages.
International Preliminary Report on Patentability for International Application No. PCT/GB2018/053280, The International Bureau of WIPO, Switzerland, dated May 19, 2020, 12 pages.
International Preliminary Report on Patentability for International Application No. PCT/GB2017/050075, The International Bureau of WIPO, Switzerland, dated Jul. 17, 2018, 7 pages.
International Search Report and Written Opinion for International Application No. PCT/GB2017/050074, European Patent Office, Netherlands, dated May 30, 2017, 17 pages.
International Search Report and Written Opinion for International Application No. PCT/GB2017/050075, European Patent Office, Netherlands, dated Mar. 23, 2017, 12 pages.
International Search Report and Written Opinion for International Application No. PCT/GB2017/051272, European Patent Office, Netherlands, dated Sep. 11, 2017, 17 pages.
International Search Report and Written Opinion for International Application No. PCT/GB2018/051941, European Patent Office, Netherlands, dated Sep. 14, 2018, 11 pages.
International Search Report and Written Opinion for International Application No. PCT/GB2018/053279, European Patent Office, Netherlands, dated Feb. 1, 2019, 15 pages.
International Search Report and Written Opinion for International Application No. PCT/GB2018/053280, European Patent Office, Netherlands, dated Feb. 11, 2019, 17 pages.
International Search Report and Written Opinion for International Application No. PCT/GB2019/050425, European Patent Office, Netherlands, dated Apr. 17, 2019, 10 pages.
International Search Report and Written Opinion for International Application No. PCT/GB2019/053220, European Patent Office, Netherlands, dated Apr. 3, 2020, 17 pages.
International Search Report and Written Opinion for International Application No. PCT/GB2020/051199, European Patent Office, Netherlands, dated Aug. 20, 2020, 13 pages.
International Search Report and Written Opinion for International Application No. PCT/GB2020/051201, European Patent Office, Netherlands, dated Oct. 13, 2020, 23 pages.
Jamnani, F.R., et al., "T Cells Expressing VHH-Directed Oligoclonal Chimeric Her2 Antigen Receptors: Towards Tumor-Directed Oligoclonal T Cell Therapy," Biochimica et Biophysica Acta 1840(1):378-386, Elsevier Pub. Co, Netherlands (Jan. 2014).
Japanese Office Action dated Dec. 13, 2021, in Japanese Patent Application No. 2019-536937, filed Jan. 18, 2018, 21 pages.
Japanese Office Action dated Dec. 6, 2021, in Japanese Patent Application No. 2019-536936, filed Jan. 8, 2018, 17 pages.
Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (1971).
Kabat, E.A., et al., "Sequences of proteins of immunological interest," 5th Edition, NIH publication No. 91-3242, pp. 1-1137, U.S. Department of Public Health and Human Services, National Institutes of Health, United States (1991).
Kwon, B.S., and Weissman, S.M., "cDNA Sequences of Two Inducible T-Cell Genes," Proc Natl Acad Sci USA 86(6):1963-1967, National Academy of Science, United States (Mar. 1989).
Lefranc, M.P., et al., "IMGT Unique Numbering for Immunoglobulin and T Cell Receptor Constant Domains and Ig Superfamily C-like Domains," Developmental and Comparative Immunology 29(3):185-203, Elsevier Science, United States (2005).
Legg, J.W., et al., "CB307: A novel T-cell costimulatory Humabody® VH therapeutic for PSMA-positive tumors," retrieved from: https://www.crescendobiologics.com/wp-content/uploads/2019/08/20190412-CB307-A-novel-T-cell-costimulatory-Humabody%C2%AE-VH-therapeutic-for-PSMA-positive-tumors.pdf, 1 page (2019).
Madireddi, S., et al., "Galectin-9 Controls the Therapeutic Activity of 4-1BB-Targeting Antibodies," The Journal of Experimental Medicine 211(7): 1433-1448, The Rockefeller University Press, United States (Jun. 2014).
McGuinness, B., et al., "Abstract 5766: Multifunctional biologics for targeted T-cell therapy based on in vivo matured fully human VH domains," Cancer Research 78(13_Suppl):5766, AACR Annual Meeting 2018 (Apr. 4-18, 2018), 2 pages, American Association for Cancer Research, United States (2018).
Muyldermans, S., et al., "Nanobodies: Natural Single-domain Antibodies," Annual Review of Biochemistry, 82:17.1-17.23, Annual Reviews, United States (2013).
Muyldermans, S., et al., "Recognition of Antigens by Single-Domain Antibody Fragments: the Superfluous Luxury of Paired Domains," Trends in Biochemical Sciences 26(4):230-235, Elsevier Trends Journals, United Kingdom (Apr. 2001).
Muyldermans, S., "Single Domain Camel Antibodies: Current Status," Reviews in Molecular Biotechnology 74(4):277-302, Elsevier Science Publishers, Netherlands (2001).
Office Action for Japanese Patent Application No. 2018-537519, dated Feb. 5, 2021, Japan Patent Office, Japan, 9 pages.
Office Action for Japanese Patent Application No. 2018-537533, dated Feb. 16, 2021, Japan Patent Office, Japan, 6 pages.
Office Action dated Apr. 22, 2022, in U.S. Appl. No. 16/475,597, Hayes et al., 371(c) Date: Jul. 2, 2019, 26 pages.
Office Action dated Aug. 11, 2020, in U.S. Appl. No. 16/069,495, Balloi, E., et al., filed Jul. 11, 2018, 18 pages.
Office Action dated Mar. 1, 2022, in U.S. Appl. No. 16/475,590, inventor Edwards; B., et al., int'l filing date Jan. 8, 2018, 17 pages.
Office Action dated Nov. 15, 2021, in U.S. Appl. No. 16/475,597, Hayes et al., 371(c) Date: Jul. 2, 2019, 15 pages.
Office action dated Sep. 20, 2021, in U.S. Appl. No. 16/475,590, inventor Edwards; B., et al., int'l filing date Jan. 8, 2018, 15 pages.
Patel, T. P., et al., "Different Culture Methods Lead to Differences in Glycosylation of a Murine IgG Monoclonal Antibody," Biochemical Journal 285(Pt 3):839-845, Portland Press on behalf of the Biochemical Society, United Kingdom (1992).
Perez-Ruiz, E., et al., "Anti-CD137 and PD-1/PD-L1 Antibodies En Route toward Clinical Synergy," Clinical Cancer Research 23(18):5326-5328, American Cancer Research, United States (Sep. 2017).
Roovers, R.C., et al., "A Biparatopic Anti-EGFR Nanobody Efficiently Inhibits Solid Tumour Growth," International Journal of Cancer 129(8):2013-2024, Wiley-Liss Inc., United States (Oct. 2011).
Sanchez-Paulete, A.R., et al., "Deciphering CD137 (4-1BB) Signaling in T-cell Costimulation for Translation Into Successful Cancer Immunotherapy," European Journal of Immunology 46(3):513-522, Wiley-VCH Verlag GmbH & Co. KGaA, Germany (Mar. 2016).
Segal, N.H., et al., "Results from an Integrated Safety Analysis of Urelumab, an Agonist Anti-CD137 Monoclonal Antibody," Clinical Cancer Research 23(8): 1929-1936, American Association for Cancer Research, United States (Oct. 2016).
Strohl, W.R., "Fusion Proteins for Half-Life Extension of Biologics as a Strategy to Make Biobetters," BioDrugs 29(4):215-239, Springer International, New Zealand (Jul. 2015).

(56) References Cited

OTHER PUBLICATIONS

Trinklein, N., et al., "Abstract LB-090: Sequence-based discovery of fully human anti-CD3 and anti-PDL1 single domain antibodies using novel transgenic rats," Cancer Research 76(14):1-4, American Association of cancer Research, United States (Jul. 2016).
UniProtKB, "Glutamate carboxypeptidase 2," UniProtKB-Q04609 (FOLH1_HUMAN), https://www.uniprot.org/uniprot/Q04609, last accessed on May 19, 2020, 24 pages.
UniProtKB, "Tumor necrosis factor receptor superfamily member 9," UniProtKB-Q07011 (TNR9 HUMAN), https://www.uniprot.org/uniprot/Q07011, last accessed on May 19, 2020, 12 pages.
Vinay, D. S., and Kwon, B. S., "Therapeutic Potential of Anti-CD137 (4-1BB) Monoclonal Antibodies," Expert Opinion on Therapeutic Targets 20(3):361-373, Informa Healthcare, United Kingdom (2016).
Vinay, D.S., and Kwon, B.S., "4-1BB (CD137), an Inducible Costimulatory Receptor, as a Specific Target for Cancer Therapy," BMB Reports 47(3):122-129, The Korean Society for Biochemistry and Molecular Biology, South Korea (Mar. 2014).
Vinay, D.S and Kwon, B.S., "Immunotherapy of cancer with 4-1BB," Molecular Cancer Therapeutics 11(5): 1062-1070, American Association for Cancer Research, United States (May 2012).
Vinay, D.S., and Kwon, B.S., "Role of 4-1BB in Immune Responses, " Seminars in Immunology 10(6):481-489, Article No. si980157, Academic Press, United Kingdom (Dec. 1998).
Vincke, C., and Muyldermans, S., "Introduction to Heavy Chain Antibodies and Derived Nanobodies," Methods in Molecular Biology 911:15-26, Springer Science + Business Media, Germany (2012).
Viuff, D., et al., "Generation of a Double Transgenic Humanized Neonatal Fc Receptor (FcRn)/Albumin Mouse to Study the Pharmcokinetics of Albumin-Linked Drugs," Journal of Controlled Release 223:22-30, Elsevier Science Publishers, Netherlands (Feb. 2016).
Ward, E. S., et al., "Binding Activities of a Repertoire of Single Immunoglobulin Variable Domains Secreted from *Escherichia coli*," Nature 341(6242):544-546, Nature Publishing Group, United Kingdom (Oct. 1989).
Zapata, J.M., et al., "CD137 (4-1BB) Signalosome: Complexity Is a Matter of TRAFs," Frontiers in Immunology 9:2618, 12 pages, Frontiers Research Foundation, Switzerland (Nov. 2018).
Zare, H., et al., "Production of Nanobodies against Prostate-Specific Membrane Antigen (PSMA) Recognizing LnCaP Cells," and supplemental figures, Int J Biol Markers 29(2):e169-e179 (12 total pages), SAGE Publications, United States (Jun. 2014).
Zak, K.M., et al., "Structural basis for small molecule targeting of the programmed death ligand 1 (PD-L1)," Oncotarget 7:30323-30335, Impact Journals, United States (Apr. 2016).
Translation of Japanese Office Action dated Jul. 4, 2022, in Japanese Patent Application No. 2019-536936, filed Jan. 18, 2018, 5 pages.
Co-pending U.S. Appl. No. 17/706,839, filed Mar. 29, 2022, inventor Edwards; C., et al., US 2022/0306744.
Kunik, V., et al., "The indistinguishability of epitopes from protein surface is explained by the distinct binding preferences of each of the six antigen-binding loops," Protein Engineering, Design & Selection 26(10):599-609, Oxford University Press, United Kingdom (2013).
Office Action dated Sep. 23, 2022, in U.S. Appl. No. 16/475,590, inventor Edwards et al., int'l filing date Jan. 8, 2018, 11 pages.
Brown, M., et al., "Tolerance of Single, but not Multiple, Amino Acid Replacements in Antibody $V_H$ CDR2: A Means of Minimizing B Cell Wastage from Somatic Hypermutation?," Journal of Immunology 156(9):3285-3291, American Association of Immunologists, United States (May 1996).
Chinese Office Action dated May 27, 2023, in Chinese Patent Application No. 2019800881645, filed Nov. 13, 2019, 15 pages.
GenBank, "Immunoglobulin G heavy chain variable region, partial [*Homo sapiens*]," Accession No. AEX29928.1, accessed at https://www.ncbi.nlm.nih.gov/protein/AEX29928.1, accessed on Jan. 10, 2014, 2 pages.
GenBank, "Immunoglobulin G heavy chain variable region, partial [*Homo sapiens*]," Accession No. ACS95976.1, accessed at https://www.ncbi.nlm.nih.gov/protein/ACS95976.1, accessed on Jul. 24, 2016, 2 pages.
Fujiwara, M., et al., "Cbl-b Deficiency Mediates Resistance to Programmed Death-Ligand 1/Programmed Death-1 Regulation," Frontiers in Immunology 8:42, pp. 1-12, Frontiers Research Foundation, Switzerland (Jan. 2017).
Japanese Office Action dated Jul. 18, 2023, in Japanese Patent Application No. 2020-543560, filed Feb. 18, 2019, 7 pages.
Wang, S., et al., "E3 Ubiquitin Ligases Cbl-b and c-Cbl Downregulate PD-L1 in EGFR Wild-type Non-small Cell Lung Cancer," FEBS letters 592(4):621-630, John Wiley & Sons Ltd , England (Feb. 2018).
Office action dated Oct. 5, 2023, in U.S. Appl. No. 16/763,059, inventors Brucklacher-Waldert, V., et al., 371(c) date: May 11, 2020, 6 pages.
Office action dated Sep. 14, 2023, in U.S. Appl. No. 16/763,063, inventors Brucklacher-Waldert, V., et al., 371(c) date: May 11, 2020, 12 pages.
Abdiche, Y.N., et al, "Assessing Kinetic and Epitopic Diversity Across Orthogonal Monoclonal Antibody Generation Platforms," mAbs, 8(2):264-277, Taylor & Francis Group, United States (Feb. 2016).
Boyd, S.D., et al, "Deep Sequencing and Human Antibody Repertoire Analysis," Current Opinion in Immunology 40:103-109, Elsevier, Netherlands (Apr. 2016).
Casset, F., et al., "A Peptide Mimetic of an Anti-CD4 Monoclonal Antibody by Rational Design," Biochemical and Biophysical Research Communications 307(1):198-205, Academic Press, United States (Jul. 2003).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, United Kingdom (Nov. 1999).
Conroy, P.J., et al, "Antibodies: From Novel Repertoires to Defining and Refining the Structure of Biologically Important Targets," Methods 116:12-22, Elsevier, Netherlands (Jan. 2017).
Damschroder, M.M., et al, "Analysis of Human and Primate CD2 Molecules by Protein sequence and Epitope mapping with Anti-Human CD2 Antibodies," Molecular Immunology 41: 985-1000, Elsevier, Netherlands (Jun. 2004).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
Ferrara, F., et al, "Recombinant Renewable Polyclonal Antibodies," mAbs 7(1):32-41, Taylor & Francis Group, United States (Dec. 2014).
Japanese Office Action dated Jan. 27, 2023, in Japanese Patent Application No. 2020-543560, filed Feb. 18, 2019, 13 pages.
Kanyavuz, A., et al, "Breaking the Law: Unconventional Strategies for Antibody Diversification," Nature Reviews: Immunology 19:355-368, Nature Reviews, United Kingdom (Jun. 2019).
Khan, L., et al., "Cross-neutralizing Anti-HIV-1 Human Single Chain Variable Fragments (scFvs) Against CD4 Binding Site and N332 Glycan Identified From a Recombinant Phage Library," Scientific Reports 7:45163, 12 pages, Nature Publishing Group, United Kingdom (Mar. 2017).
Konitzer, J.D., et al, "Generation of a Highly Diverse Panel of Antagonistic Chicken Monoclonal Antibodies Against the GIP Receptor," mAbs 9(3):536-549, Taylor & Francis Group, United States (Feb. 2017).
Lamminmäki, U. and Kankare, J.A., "Crystal Structure of a Recombinant Anti-estradiol Fab Fragment in Complex With 17beta-estradiol," The Journal of Biological Chemistry 276(39):36687-36694, Elsevier Inc., United States (Sep. 2001).
Lee, J., et al, "Molecular-level Analysis of the Serum Antibody Repertoire in Young Adults Before and After Seasonal Influenza

(56) References Cited

OTHER PUBLICATIONS

Vaccination," Nature Medicine 22(12):1456-1464, with Supplemental Methods and Data, Nature Publishing Group, United Kingdom (Nov. 2016).

MacCallum, R. M., et al., "Antibody-antigen Interactions: Contact Analysis and Binding Site Topography," Journal of Molecular Biology 262(5):732-745, Academic Press, United Kingdom (Oct. 1996).

Parola, C., et al, "Integrating High-throughput Screening and Sequencing for Monoclonal Antibody Discovery and Engineering," Immunology 153:31-41, John Wiley & Sons Ltd., United States (Sep. 2017).

Sheehan, J., et al, "Phage and Yeast Display," Microbiology Spectrum 3(1):1-17, American Society for Microbiology Press, United States (Feb. 2015).

Vajdos, F. F., et al., "Comprehensive Functional Maps of the Antigen-binding Site of an Anti-Erbb2 Antibody Obtained with Shotgun Scanning Mutagenesis," Journal of Molecular Biology 320(2):415-428, Academic Press, United Kingdom (Jul. 2002).

Van Regenmortel, M.H.V., "Development of a Preventive HIV Vaccine Requires Solving Inverse Problems Which Is Unattainable by Rational Vaccine Design," Hypothesis and Theory 8: Article 2009, 11 pages, Frontiers in Immunology, United Kingdom (Jan. 2018).

Wu, H., et al., "Humanization of a Murine Monoclonal Antibody by Simultaneous Optimization of Framework and CDR Residues," Journal of Molecular Biology 294(1):151-162, Elsevier, United Kingdom (Nov. 1999).

Zhou, T., et al, "Structural Repertoire of HIV-1-Neutralizing Antibodies Targeting the CD4 Supersite in 14 Donors," with Supplemental Information, Figures, Methods, and References, Cell 161:1280-1292, Elsevier, Netherlands (Jun. 2015).

Office action dated Jan. 24, 2023, in U.S. Appl. No. 16/763,059, inventors Brucklacher-Waldert, V., et al., 371(c) date: May 11, 2020, 25 pages.

Office action dated Jun. 12, 2023, in U.S. Appl. No. 16/763,059, inventors Brucklacher-Waldert, V., et al., 371(c) date: May 11, 2020, 7 pages.

Office Action dated Feb. 23, 2023, in U.S. Appl. No. 16/475,590, inventor Edwards; B., et al., int'l filing date Jan. 8, 2018, 9 pages.

Office Action dated Apr. 10, 2023, in U.S. Appl. No. 16/099,099, inventors McGuinness, B., et al., int'l filing date: Nov. 8, 2017, 10 pages.

Office Action dated Apr. 25, 2023, in U.S. Appl. No. 16/763,063, inventors Brucklacher-Waldert, V., et al., 371(c) date: May 11, 2020, 11 pages.

Japanese Office Action dated Jun. 7, 2023, in Japanese Patent Application No. 2020-526245, filed Nov. 11, 2018, 6 pages.

\* cited by examiner

THERAPEUTIC MOLECULES THAT BIND TO LAG3 AND PD1

CROSS-REFERENCE TO RELATED APPLICATIONS

This application is a national phase entry of International Application No. PCT/GB2019/050425, filed Feb. 18, 2019, which claims the priority benefit of GB Application No. 1802573.4, filed Feb. 16, 2018, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 4577_0040001_Seqlisting_ST25.K Size: 249,272 bytes; and Date of Creation: Aug. 13, 2020) is herein incorporated by reference in its entirety.

INTRODUCTION

Antibody-based therapeutics have emerged as important components of therapies for an increasing number of human malignancies in such fields as oncology, inflammatory and infectious diseases. Indeed, antibodies are one of the best-selling classes of drugs today; five of the top ten best selling drugs are antibodies.

Lymphocyte activation gene 3 (LAG-3, LAG3, CD223) is a transmembrane protein of the immunoglobulin superfamily. It has 4 extracellular domains and shares homology with CD4 (Triebel 1990 J. Exp.Med. 171:1393-1405).

LAG-3 is expressed on CD4+ T cells, CD8+ T cells, T regulatory cells, B cells, NK cells and plasmacytoid dendritic cells (Huard 1994 Eur. J. Immunol. 24:3216-21; Grosso 2007 J. Clin. Invest. 117:3383-92; Huang 2004 Immunity. 21:503-13; Kieslow 2005 Eur. J. Immunol. 35:2081-88; Triebel 1990 J. Exp.Med. 171:1393-140; Castelli 2014 Oncoimmunology. 3:11).

A role of LAG-3 on T cells is to regulate T cell activation (Huard 1994 Eur. J. Immunol. 24:3216-21). LAG-3 engages with MHC class II and this leads to downregulation of CD4+ T cells (Huard 1996 Eur. J. Immunol. 26:1180-6). Upon T cell activation, LAG-3 surface expression increases. The engagement of LAG-3 dimer with ligand induces signalling through an intracellular KIEELE domain (Workman 2002 J.Immunol 169:5392-5) leading to downregulation of the T cell activity. Therefore, LAG-3 serves to modulate responses to antigens, preventing over-stimulation and maintaining immune homeostasis.

LAG-3 is composed of the intracellular signalling domain, a transmembrane domain and 4 extracellular domains numbered 1-4 (Huard 1997 Proc. Natl. Acad. Sci. 94:5744-9). Domain 1-2 associates with MHC class II ligand and it has been shown that the tip of domain 1 (extra loop) forms the binding site (Huard 1997 Proc. Natl. Acad. Sci. 94:5744-9). LAG-3 can also associate with alternative ligands, Galectin-3 and LSECtin, which induce its inhibitory signalling (Kouo 2015 Cancer Immunol Res. 3(4):412-23; Xu 2014 Cancer Res 74(13):3418-28). Association with Galectin-3 on cells or within the extracellular matrix could downregulate T cells that would not normally engage with MHC class II, such as CD8+ T cells. Therefore blockade of this ligand could serve as a mechanism for enhancing broad T cell function.

Antibodies that bind to LAG-3 have therapeutic potential. In mice, anti-LAG-3 antibodies reverse functionally unresponsive T cells, delaying tumour progression (Grosso 2007 J. Clin. Invest. 117: 3383-92). LAG-3 is expressed on human tumour infiltrating lymphocytes and this localisation makes blockade a favourable route for stimulation of these cells (Matsuzaki 2010 PNAS 107(17):7875-80).

The Programmed Death 1 (PD-1) protein is encoded by the PDCD1 gene and expressed as a 55 kDa type I transmembrane protein (Agata 1996 Int Immunol 8(5):765-72). PD-1 is an immunoglobulin superfamily member (Ishida 1992 EMBO 11(11):3887-95) and it is an inhibitory member of the extended CD28/CTLA-4 family of T cell regulators. Other members of this family include CD28, CTLA-4, ICOS and BTLA. PD-1 exists as a monomer, lacking the unpaired cysteine residue characteristic of other CD28 family members (Zhang 2004 Immunity 20:337-47). Its cytoplasmic domain contains an immunoreceptor tyrosine-based inhibitory motif (ITIM) and an immunoreceptor tyrosine-based switch motif (ITSM) that are phosphorylated during signal transduction (Riley 2009 Immunol Rev 229(1):114-25).

PD-1 is expressed on B cells, T cells, and monocytes (Agata 1996). The role of PD-1 in maintaining immunologic self-tolerance was demonstrated in PDCD1-/- mice, which develop autoimmune diseases (Nishimura 1999 Immunity 11:141-51, Nishimura 2001 Science 291(5502):319-22). The PD-1 pathway therefore regulates antigen responses, balancing autoimmunity and tolerance.

LAG-3 and PD-1 both regulate T cell activation. Engagement with their ligands leads to inhibition of T cell activation, providing modulation of antigen-specific responses. There are two ligands for PD-1 that mediate its regulatory function. PD-L1 (B7-H1) is expressed on dendritic cells, macrophages, resting B cells, bone marrow-derived mast cells and T cells as well as non-hematopoietic cell lineages (reviewed in Francisco 2010 Immunol Rev 236:219-42). PD-L2 (B7-DC) is largely expressed on dendritic cells and macrophages (Tseng 2001 J Exp Med 193(7):839-45). PD-1 engagement with ligand cross-links PD-1 and clusters it into the T cell receptor (TCR) complex within the immunological synapse (Yokosuka 2012 J Exp Med 209(9):1201-17). Within the T cell cytoplasm, PD-1 signalling domains, ITIM and ITSM, are phosphorylated. This induces Src-homology-2 domain-containing tyrosine phosphatase (SHP1/2) that attenuates various components of the T cell receptor (TCR) signalling. The engagement of LAG-3 dimer with ligand induces signalling through an intracellular KIEELE domain (Workman 2002 J.Immunol 169:5392-5). Signalling leads to dampened T cell activation, which leads to a reduction in cytokine response, proliferation and cytolytic activity. Blockade of these pathways means T cell function can be rescued and allows restoration of antigen or tumour-specific cellular responses.

Antibodies that block the PD-1:PD-L1 interaction are used in the clinic for oncology and also treatment of diseases other than cancer but the limitation is low response rates. There is a need to expand the proportion of patients that benefit from such blockade treatment, address resistance to treatment, improve the safety profile and overcome redundancy pathways. Combination therapy is being used to improve responses to PD-1 blockade. Anti-LAG-3 antibodies are currently being evaluated in clinical trials as single agents and in combination with PD-1 pathway blocking antibodies. One reason that combination treatment could be beneficial is that single-agent checkpoint blockade leads to compensatory upregulation of other checkpoints (Huang 2017, Oncoimmunol 6(1) e1249561).

LAG-3-specific antibodies are known in the art and are in clinical trials for cancer treatment (e.g. NCT02061761, NCT02460224). However, there is a need for potent blockade and improved response rates. There is also a need for providing agents that bind to LAG-3 and block LAG-3 signalling and can be combined with other agents, such as immunotherapy agents, to achieve a beneficial therapeutic effect. In particular, bispecific antibodies that bind to both PD-1 and LAG-3 and engage these receptors on exhausted tumour-specific cells could enhance the function of such cells and lead to tumour regression. Bispecific antibodies that bind to both PD-1 and LAG-3 may also offer advantages over combination therapies as use of the latter results in universal blockade of each target on cells expressing either target. A bispecific antibody on the other hand targets cells that express both targets which can result in better targeting of T cells with the most exhausted phenotype (expressing both PD-1 and LAG-3).

The invention is aimed at addressing the needs for alternative and improved therapies and provides LAG-3 binding agents that can act as immune checkpoint inhibitors and may be used in immunotherapy for treating diseases such as cancer, for example in a bispecific format for dual blockade of PD-1 and LAG-3.

SUMMARY

The invention relates to proteins that bind to LAG-3, in particular those comprising or consisting of anti-LAG-3 single domain antibodies (sdAb), such as variable heavy chain ($V_H$) sdAbs and their use in the treatment, prevention and detection of disease.

In one aspect, the invention relates to isolated binding molecules that comprise at least one single domain antibody (sdAb), such as at least one $V_H$ single domain antibody, that binds to human LAG-3. In one aspect, the invention relates to isolated binding molecules that are bivalent for LAG-3 binding and comprise or consist of two sdAbs, in particular two $V_H$ single domain antibodies, that bind to human LAG-3.

The binding molecules listed above have a number of desirable properties as explained herein.

The binding molecules of the present invention bind to human LAG-3 and modulate the interaction of LAG-3 with its ligands. The binding molecules preferably bind to LAG-3 with high affinity and block the functional interaction of LAG-3 with its ligands as described below. In some embodiments, the binding molecules of the invention may stimulate or enhance T-cell activation. In some embodiments, the binding molecules may be useful for stimulating or enhancing the immune response and/or for treating a subject suffering from cancer or other diseases.

Anti-LAG-3 $V_H$ sdAbs of the invention exhibit a number of beneficial properties. In particular, the sdAbs of the invention can be used as functional building blocks in multivalent binding molecules, for example in multispecific molecules, i.e. molecules that bind to LAG-3 and have one or more other antigen binding site. Also, two anti-LAG-3 $V_H$ sdAbs can be combined in a fusion protein to obtain an enhanced effect as described herein.

The invention thus also relates to multivalent and/or multispecific binding agents comprising at least one anti-LAG-3 $V_H$ single domain antibody, preferably two anti-LAG-3 $V_H$ single domain antibodies.

In one aspect, the invention relates to a multispecific binding molecule that binds to, e.g. simultaneously binds to, LAG-3 and PD-1 present on the same cell, and comprises at least one anti-LAG-3 $V_H$ single domain antibody, preferably two anti-LAG-3 $V_H$ single domain antibodies. In another aspect, the invention relates to a multispecific binding molecule that simultaneously binds to LAG-3 and PD-1 and comprises two anti-LAG-3 $V_H$ single domain antibodies. In one embodiment, the multispecific binding molecule that simultaneously binds to LAG-3 and PD-1 comprises or consists of two anti-LAG-3 $V_H$ single domain antibodies and a $V_H$ single domain that binds to PD-1 and optionally a half life extending moiety.

As demonstrated herein, using the bispecific agents of the invention provides certain benefits as this selectively targets the molecule to tumor specific cells thus selectively exerting an effect on signalling and proliferation. For example, the bispecific agents that bind to both PD-1 and LAG-3 have beneficial properties compared to combination therapies where PD-1 and LAG-3 monoclonal antibodies are administered separately. This is because the bispecific antibody targets cells that express both targets, i.e. PD-1 and LAG-3 on its surface. Thus, using a bispecific molecule can result in better targeting of T-cells with the most exhausted phenotype (expressing both PD-1 and LAG-3). Combination therapy on the other hand results in universal blockade of each target on cells expressing either target. It is also known that PD-1 blockade results in an increase in LAG-3 expression. Therefore, therapy with bispecific agents may be particularly useful in treating patients that do not respond to PD-1 blockade or have ceased to respond to PD-1 blockade. The bispecific agents described herein ARE selective for the most dysfunctional Tumor Infiltrating Lymphocytes (TIL). They can find use in reversing intrinsic or acquired PD-1 resistance. The reduced PD-1 blockade spares peripheral T cells and avoids over-activation of immunologically functional PD-1 positive cells and thus improves the safety profile. Thus, the bispecific agent provides improved targeting and activity on specifically double positive cells, that is cells that display both LAG-3 and PD-1 on their surface. Moreover, as shown herein, the molecules also have improved properties over larger bispecific antibody formats. Without wishing to be bound by theory, this effect may be due to the specific configuration of the molecules described herein which provides a smaller size, superior flexibility and delivers more complete and potent clustering (recruiting LAG-3 and PD-1 on the cell surface). Thus, the format of the molecules which is based on the $V_H$, the smallest antigen binding entity, confers additional benefits.

Preferred binding agents of the invention comprise at least one $V_H$ single domain antibody targeting LAG-3 and at least one $V_H$ single domain antibody targeting PD-1. Compared to large bispecific monoclonal antibodies, this format has benefits due to the lack of an Fc domain as Fc mediated clearance may restrict therapeutic efficacy.

Thus, the invention relates to an isolated human heavy chain variable domain ($V_H$) single domain antibody that binds to human LAG-3 comprising a CDR3 sequence selected from SEQ ID NO: 3 or 7 or a sequence with at least 70%, 80% or 90% homology/identify thereto.

In one embodiment, the $V_H$ single domain antibody according to claim 1 comprising a CDR1 as shown in SEQ ID NO: 1 or a sequence with at least 70%, 80% or 90% homology/identify thereto, a CDR2 as shown in SEQ ID NO: 2 or a sequence with at least 70%, 80% or 90% homology/identify thereto and a CDR3 as shown in SEQ ID NO: 3 or a sequence with at least 70%, 80% or 90% homology/identify thereto.

In one embodiment, the $V_H$ single domain antibody comprises a CDR1 as shown in SEQ ID NO: 5 or a sequence with at least 70%, 80% or 90% homology/identify thereto, a CDR2 as shown in SEQ ID NO: 6 or a sequence with at least 70%, 80% or 90% homology thereto and a CDR3 as shown in SEQ ID NO: 7 or a sequence with at least 70%, 80% or 90% homology/identify thereto.

In one embodiment, the $V_H$ single domain antibody comprises a sequence selected from SEQ ID NO: 4 or 8 or a sequence with at least 70%, 80% or 90% homology/identify thereto.

In another aspect, the invention relates to the use of an anti-LAG-3 single domain antibody or binding agent comprising an anti-LAG-3 single domain antibody, for example as described herein, for modifying or blocking the interaction of LAG-3 with galectin 3, LSECtin and/or alpha synuclein. Methods for modifying or blocking the interaction of LAG-3 with galectin 3, LSECtin and/or synuclein by administering a sdAb or binding agent of the invention are also within the scope of the invention.

In another aspect, the invention relates to the treatment of a neurological condition comprising administration of an anti-LAG-3 single domain antibody or binding agent comprising an anti-LAG-3 single domain antibody, for example as described herein.

FIGURES

The disclosure is further described in the following non-limiting figures.

FIG. 1. Bispecific binding agents comprising $V_H$ sdAbs can bind targets simultaneously. LAG3-Fc was immobilised via amine coupling to Octet® biosensors. Bispecific binding agent (i.e. binding to LAG-3 and PD-1) 1.1-6GS-1.1-6GS-2.63 was added at 100 nM, followed by PD-1-Fc. Profile demonstrates the binding of bispecific (dark grey) to LAG-3 and subsequent additive binding of PD-1. LAG-3 specific (bivalent 1.1-6GS-1.1) shows binding to LAG-3, but as expected, addition of PD-1 does not show further binding (mid-grey curve).

Figure 2:
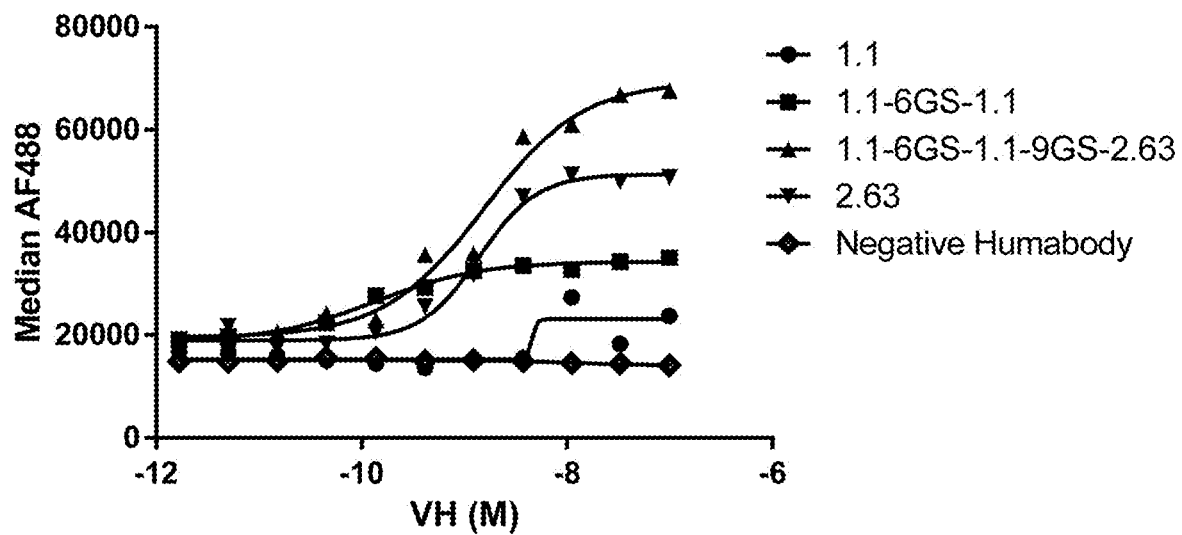

FIG. 2. CD4+ T cells were stimulated with anti-CD3 and anti-CD28. Cells were stained with HIS tagged $V_H$ plus anti-HIS tag labelled with biotin and streptavidin AlexaFluor488. Cells were analysed using Intellicyte® cytometer. The bispecific (i.e. binding to LAG-3 and PD-1) binding agent 1.1-6GS-1.1-9GS-2.63 binds with higher median fluorescence than its individual components. The negative control is a $V_H$ that does not bind to the targets.

FIG. 3. 3a) Enhancement of IL-2 in combination. Human PBMC were stimulated with 10 ng/ml Staphylococcal Enterotoxin B (SEB) for 2 days. Cells were restimulated with 1 ng/ml SEB and 25 nM $V_H$ or full monoclonal antibodies (Pembrolizumab and Relatlimab analogues). Where a combination of antibodies was used, equal concentration was used, e.g. 25 nM PD-1 antibody (mAb) with 25 nM LAG-3 $V_H$/antibody. After 3 days, culture supernatant was harvested for IL-2 measurement using HTRF kit (Cisbio). 3b) Enhancement of IL-2 by bispecific molecule. Human PBMC were stimulated with 10 ng/ml Staphylococcal Enterotoxin B (SEB) for 2 days. Cells were restimulated with 10 ng/ml SEB and a titration of $V_H$ or full monoclonal antibodies (Nivolumab and Relatlimab analogues). Where a combination of antibodies was used, equal concentration was used, e.g. 50 nM PD-1 antibody (mAb) with 50 nM LAG3 antibody (mAb). After 2 days, culture supernatant was harvested for IL-2 measurement using HTRF kit (Cisbio). The negative control is $V_H$ that does not bind to the targets. 3c) Bispecific molecule induces more IL-2 than its component $V_H$. PBMC were stimulated with 10 ng/ml SEB and restimulated with 0.1 ng/ml SEB for 3 days in the presence of 50 nM or 50+50 nM $V_H$. 3d) Enhancement of IL-2 is more potent with bivalent LAG-3 single domain antibody construct than monovalent LAG-3 in the context of the bispecific molecule. Human PBMC were stimulated with 50 ng/ml Staphylococcal Enterotoxin B (SEB) overnight. Cells were restimulated for 2 days with 40 ng/ml SEB and a titration of $V_H$ bispecifics (i.e. binding to LAG-3 and PD-1). 3e) Enhancement of IL-2 is more potent in asymmetric format than several 1:1 formats. Human PBMC were stimulated with 20 ng/ml Staphylococcal Enterotoxin B (SEB) overnight. Cells were restimulated for 3 days with 5 ng/ml SEB and 10 nM $V_H$. 3f) Bispecific molecule induces proinflammatory cytokines. Human PBMC were stimulated with 10 ng/ml SEB overnight. Cells were restimulated for 3-6 days with 1 ng/ml SEB and 50 nM $V_H$. Supernatant was tested using HTRF kits.

Figure 4:
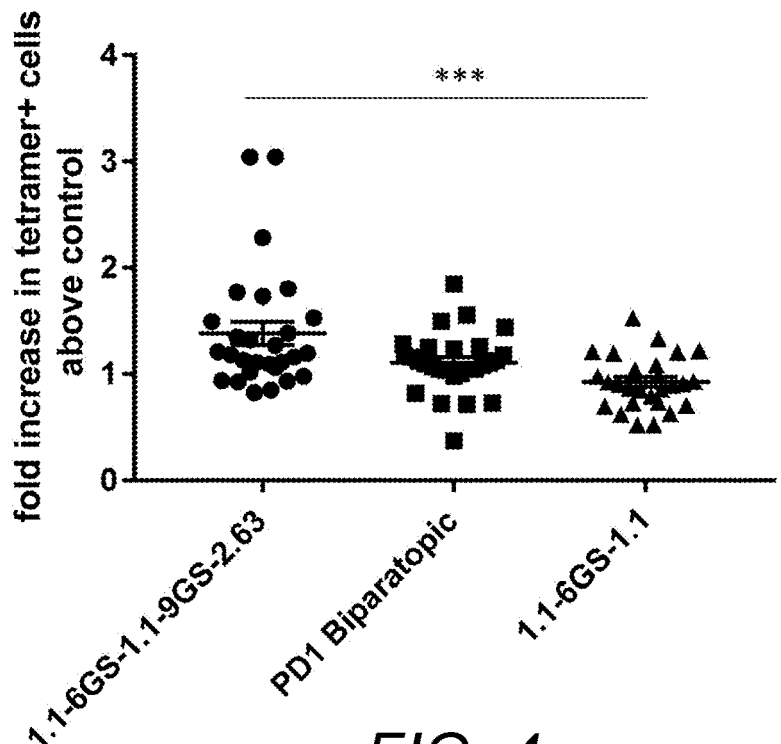

FIG. 4. Proliferation of CMV-specific CD8+ T cells is enhanced by bispecific 1.1-6GS-1.1-9GS-2.63. PBMC from 8 donors were pulsed with 100 µM CMV peptides for 1 hour. $V_H$ were added to the cells at 100 nM and cultured for 5 days. Percentage of CD8+ T cells that were positive for 7 different HLA tetramers were analysed, dependent on HLA typing. Fold increases above irrelevant $V_H$ were calculated. Each point describes 1 donor and 1 tetramer. Statistical significance calculated using 1 way ANOVA and Dunns multiple comparison test. p=0.0002.

Figure 5:
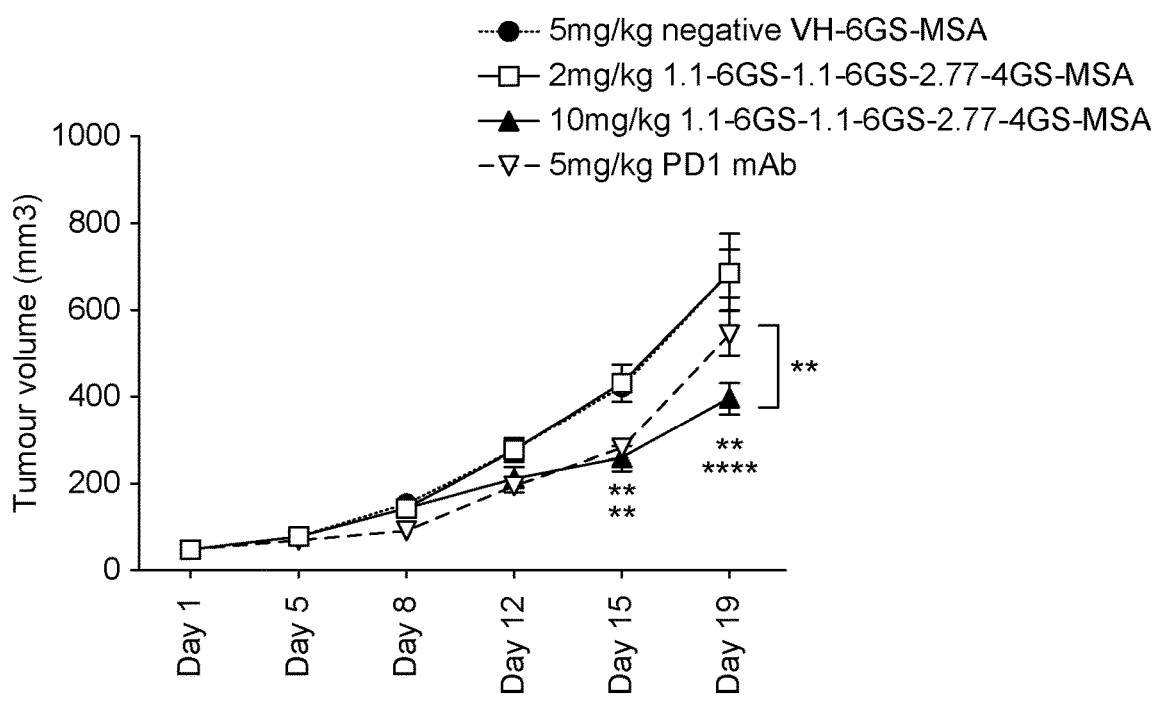

FIG. 5. Bispecific (i.e. binding to LAG-3 and PD-1) binding agent 1.1-6GS-1.1-6GS-2.77 with anti-mouse serum albumin (MSA) $V_H$ at 10 mg/kg reduces tumour growth rate of RKO colon carcinoma cells when compared with control $V_H$. Mean tumour volume at time points (n=6 animals/group). Statistical significance was determined using 2-way Anova with Tukey's post-test (p<0.01, **p<0.0001). The negative control is $V_H$ that does not bind to the targets.

Figure 6:
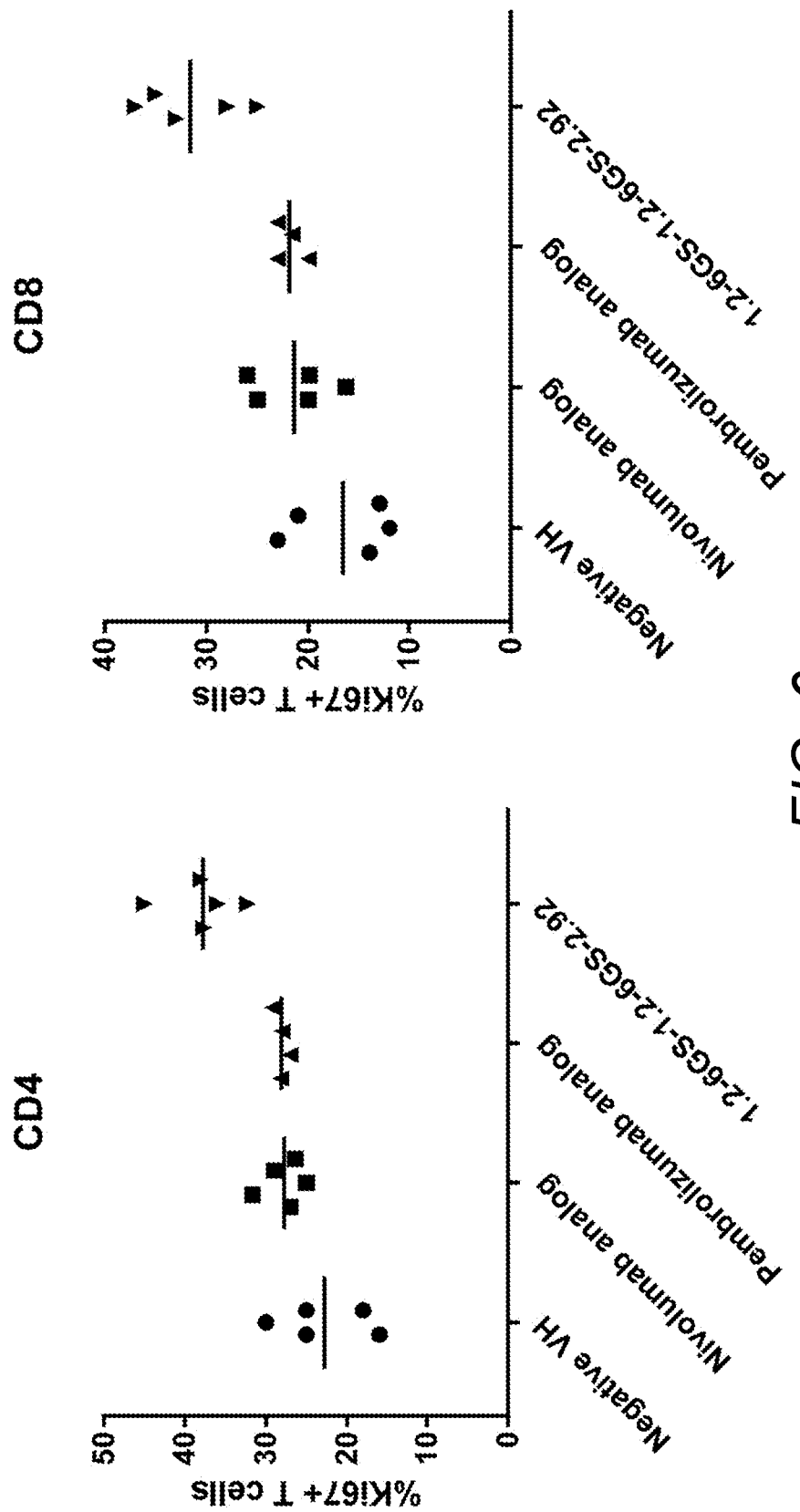

FIG. 6. Proliferation of patient T cells is enhanced by bispecific, where PD-1 antibodies show little increase. Patient CD4+ or CD8+ T cells were incubated with a tumour cell line and the percentage of Ki67-positive cells were measured by flow cytometry.

DETAILED DESCRIPTION

The present disclosure will now be further described. In the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012); Therapeutic Monoclonal Antibodies: From Bench to Clinic, Zhiqiang An (Editor), Wiley, (2009); and Antibody Engineering, 2nd Ed., Vols. 1 and 2, Ontermann and Duebel, eds., Springer-Verlag, Heidelberg (2010).

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The inventors have produced binding agents capable of specifically binding to the human LAG-3 antigen and which have a number of beneficial properties. These binding agents comprise or consist of at least one $V_H$ single domain antibody that binds to human LAG-3. We generated human heavy chain only antibodies in transgenic mice that express a transgene with human V, D and J regions and which are not capable of making functional endogenous heavy and kappa light chain and lambda light chains. Heavy chain only antibodies are generated in the mice in the absence of light chain and undergo the normal processes of somatic hypermutation and affinity maturation.

The invention thus provides isolated binding molecules comprising at least one single domain antibody, such as a $V_H$ single domain antibody, that binds human LAG-3 and blocks the interaction of LAG-3 with its ligands, pharmaceutical compositions comprising such binding molecules, as well as isolated nucleic acids, isolated recombinant expression vectors and isolated host cells for making such binding proteins. For example, the single domain antibody is a single domain antibody wherein the domain is a human variable heavy chain ($V_H$) domain.

In one embodiment, the binding molecule comprises two or more $V_H$ single domain antibodies wherein at least one $V_H$ single domain antibody binds to human LAG-3. In one embodiment, the binding molecule comprises $V_H$ single domain antibodies that each bind to human LAG-3 and does not comprise further entities that bind to LAG-3. In one embodiment, the binding molecule comprises two $V_H$ single domain antibodies that each bind to human LAG-3 and further comprises a half life extending moiety. In one embodiment, the binding molecule comprises one, two or more $V_H$ single domain antibodies that each bind to human LAG-3 and a $V_H$ single domain antibody that binds to another target, for example PD-1.

Also provided are methods of using the binding molecules and single domain antibodies of the invention to detect human LAG-3, methods of treating disease and methods for producing the binding molecules.

In one aspect, the invention relates to a $V_H$ single domain antibody or binding molecule comprising one or more $V_H$ single domain antibody, for example comprising two $V_H$ single domain antibodies, wherein the one and/or more $V_H$ single domain antibody exhibits one or more or all of the following properties, including a combination thereof:
  a) binds human LAG-3;
  b) binds monkey LAG-3;
  c) does not bind to mouse LAG-3;
  d) binds within the N-terminal domains of LAG-3;
  e) blocks binding of LAG-3 to major histocompatibility (MHC) class II thereby restoring T cell signalling in a reporter cell line
  f) blocks binding of LAG-3 to human galectin-3 (Genbank accession BAA22164);
  g) blocks binding of LAG-3 to human LSECtin (Genbank accession NP_940894);
  h) blocks binding of LAG-3 to human alpha-synuclein (Genbank accession P37840) and/or
  j) stimulates interleukin-2 (IL-2) production in T cells stimulated with superantigen and PD-1 blockade, see example 10.

Suitable assays to measure the properties as set out above are described in the examples and alternatives will be known to the skilled person.

For example, according to the invention, a cell expressing MHC class II is inhibited from interaction with a reporter T cell expressing LAG-3, leading to increases in NFAT-driven luciferase activity. We have shown that monovalent LAG-3 $V_H$ single domain antibodies inhibit the interaction at high concentrations only (e.g. >about 333 nM). Bivalent LAG-3 $V_H$ single domain antibodies and bispecific $V_H$ single domain antibodies (targeting both LAG-3 and PD-1) inhibit and exhibit a dose-dependent increase in luciferase activity with EC50 values in the nanomolar range, for example about 1.2 to about 8.3 nM.

For example, binding to human galectin-3 can be measured using an ELISA assay and sdAb of the invention have IC50 values in the nanomolar range.

For example, binding to LSECtin can be measured using an ELISA assay and sdAb of the invention have IC50 values in the nanomolar range.

For example, binding to alpha-synuclein can be measured using an ELISA and sdAb of the invention have 1050 values in the nanomolar range. For example, $V_H$1.1 inhibits the interaction between LAG-3 and alpha-synuclein with an IC50 of about 44.9 nM.

Stimulation of interleukin-2 (IL-2) production in superantigen-stimulated PBMC can be assessed by measuring secreted IL-2 in HTRF as shown in the examples. A bispecific $V_H$ single domain antibody shows a 2-3 fold increase in IL-2 above PD-1 blockade alone.

In one aspect, the invention relates to a single domain antibody, for example a $V_H$ single domain antibody, that binds to human LAG-3 and blocks binding of LAG-3 to human galectin-3, LSECtin and/or alpha-synuclein. In some embodiments, the $V_H$ single domain antibody has a sequence as described herein.

The properties of the binding molecules and single domain antibodies as described above can be exploited in therapeutic and diagnostic methods and uses as described herein. Such methods and uses are within the scope of the invention. Compared to large monoclonal antibodies the single domain format has benefits due to the lack of an Fc domain as Fc mediated clearance may restrict therapeutic efficacy. Also, due to the small size, the target, i.e. LAG-3 can be more easily accessed. This is of particular benefit for this target because of its expression in the immune synapse.

In particular, as explained below, single domain antibodies that bind to human LAG-3 described herein can be used in multivalent and/or multispecific formats. Thus, we provide building blocks for the construction of multifunctional molecules.

Molecules as described herein bind specifically to wild type human LAG-3 (accession number NM_002286). The amino acid sequence for wild type human LAG-3 is shown below (SEQ ID NO: 9).

MWEAQFLGLLFLQPLWVAPVKPLQPGAEVPVVWAQEGAPAQLPCSPTIPL

QDLSLLRRAGVTWQHQPDSGPPAAAPGHPLAPGPHPAAPSSWGPRPRRYT

VLSVGPGGLRSGRLPLQPRVQLDERGRQRGDFSLWLRPARRADAGEYRAA

-continued

VHLRDRALSCRLRLRLGQASMTASPPGSLRASDWVILNCSFSRPDRPASV

HWFRNRGQGRVPVRESPHHHLAESFLFLPQVSPMDSGPWGCILTYRDGFN

VSIMYNLTVLGLEPPTPLTVYAGAGSRVGLPCRLPAGVGTRSFLTAKWTP

PGGGPDLLVTGDNGDFTLRLEDVSQAQAGTYTCHIHLQEQQLNATVTLAI

ITVTPKSFGSPGSLGKLLCEVTPVSGQERFVWSSLDTPSQRSFSGPWLEA

QEAQLLSQPWQCQLYQGERLLGAAVYFTELSSPGAQRSGRAPGALPAGHL

LLFLILGVLSLLLLVTGAFGFHLWRRQWRPRRFSALEQGIHPPQAQSKIE

ELEQEPEPEPEPEPEPEPEPEPEPEQL

The terms "LAG-3, LAG3, lymphocyte activation gene 3" and "CD223" are used interchangeably herein, and include variants, isoforms, species homologs of human LAG-3.

Unless otherwise specified, the term LAG-3 as used herein refers to human LAG-3. Thus, a single domain antibody that is described as binding to LAG-3 binds to human LAG-3.

The terms "LAG-3 binding molecule/protein/polypeptide/agent", "LAG-3 antigen binding molecule protein/polypeptide/agent", "anti-LAG-3 single domain antibody", "anti-LAG-3 single immunoglobulin variable domain", "anti-LAG-3 heavy chain only antibody", "anti-LAG-3 $V_H$ single domain antibody" "anti-LAG-3 $V_H$" or "anti-LAG-3 antibody" all refer to a molecule capable of specifically binding to the human LAG-3 antigen as described above. The binding reaction may be shown by standard methods, for example with reference to a negative control test using an antibody of unrelated specificity. The terms "binding agent" and "binding molecule" are used interchangeably herein. The terms binding molecule and binding agent all refer to a biological entity, for example a protein, such as a fusion protein, capable of specifically binding to the human LAG-3 antigen as described above.

A single domain antibody or binding molecule comprising a single domain antibody as described herein, "which binds" or is "capable of binding" an antigen of interest, e.g. human LAG-3, is one that binds the antigen with sufficient affinity such that the antibody is useful as a therapeutic agent in targeting a cell or tissue expressing the antigen.

A single domain antibody or binding molecule comprising a single domain antibody described herein does not cross react with mouse LAG-3.

In one embodiment, the single domain antibodies described herein bind to human LAG-3 and also bind to cyno LAG-3.

Single domain antibodies and binding agents described herein that bind to LAG-3 are also described as "blocking single domain antibody or antibody" or a "neutralizing single domain antibody or antibody", herein to refer to a single domain antibody or binding agent whose binding to LAG-3 results in inhibition of at least one biological activity of LAG-3. For example, said biological activity of LAG-3 is selected from one or more of:

a) interaction with MHC class II;
b) interaction with Galectin-3;
c) interaction with LSECtin;
d) ligand-mediated signalling within any LAG-3-expressing cell;
e) impact on T cell receptor signalling pathway;
f) oligomerisation of LAG-3 or interaction with other cell surface receptors at the immunological synapse;
g) binding of soluble LAG-3 cleaved from cell surface and/or
h) regulation of T regulatory cells.

The term "specific binding" or "specifically binds to" or is "specific for" a particular polypeptide or an epitope on a particular polypeptide target as used herein can be exhibited, for example, by a molecule having a KD for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

In one embodiment, the monovalent single domain antibodies described herein have a KD of $10^{-9}$ up to at least $10^{-5}$. In another embodiment, the bivalent single domain antibodies described herein have a KD of $10^{-9}$ down to $10^{-12}$ M or greater.

The term "antibody" broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art.

In a full-length antibody, each heavy chain is comprised of a heavy chain variable region or domain (abbreviated herein as HCVR) and a heavy chain constant region. The heavy chain constant region is comprised of three domains, $C_H1$, $C_H2$ and $C_H3$. Each light chain is comprised of a light chain variable region or domain (abbreviated herein as LCVR) and a light chain constant region. The light chain constant region is comprised of one domain, CL.

The heavy chain and light chain variable regions can be further subdivided into regions of hypervariability, termed complementarity determining regions (CDR), interspersed with regions that are more conserved, termed framework regions (FR). Each heavy chain and light chain variable region is composed of three CDRs and four FRs, arranged from amino-terminus to carboxy-terminus in the following order: FR1, CDR1, FR2, CDR2, FR3, CDR3, FR4.

Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "CDR" refers to the complementarity-determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs can be defined differently according to different systems known in the art.

The Kabat Complementarity Determining Regions (CDRs) are based on sequence variability and are the most commonly used (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242). Chothia refers instead to the location of the structural loops (Chothia and Lesk J. Mol. Biol. 196:901-917 (1987)). The Kabat numbering system is generally used when referring to a residue in the variable domain (approximately residues 1-107 of the light chain and residues 1-113 of the heavy chain).

The system described by Kabat is used herein unless otherwise specified. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion.

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences).

The constant domains of the antibody molecule are derived from those of a human antibody. In certain embodiments, a limited number of framework region amino acid residues from the parent (rodent) antibody may be substituted into the human antibody framework region sequences.

The term "antigen binding site" refers to the part of the antibody or antibody fragment that comprises the area that specifically binds to an antigen. An antigen binding site may be provided by one or more antibody variable domains. Preferably, an antigen binding site is comprised within the associated $V_H$ and $V_L$ of an antibody or antibody fragment.

An antibody fragment is a portion of an antibody, for example as $F(ab')_2$, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs.

scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv).

The smallest antigen binding fragment is the single variable fragment, namely the $V_H$ or $V_L$ domain. Binding to a light chain/heavy chain partner respectively is not required for target binding. Such fragments are termed single domain antibodies. A single domain antibody (~12 to 15 kDa) therefore has either the $V_H$ or $V_L$ domain and does not comprise other parts of an antibody. $V_H$ and $V_L$ domains respectively are capable of binding to an antigen. The antigen-binding entity of an antibody, reduced in size to one single domain (corresponding to the $V_H$ or $V_L$ domain), is generally referred to as a "single-domain antibody" or "immunoglobulin single variable domain". Single domain antibodies derived from camelid heavy chain only antibodies that are naturally devoid of light chains as well as single domain antibodies that have a human heavy chain domain have been described (Muyldermans J Biotechnol. 2001 June; 74(4):277-302, Holliger Nat Biotechnol. 2005 September; 23(9): 1126-36).

Antigen binding single $V_H$ domains have also been identified from, for example, a library of murine $V_H$ genes amplified from genomic DNA from the spleens of immunized mice and expressed in *E. coli* (Ward et al., 1989, Nature 341: 544-546). Ward et al. named the isolated single $V_H$ domains "dAbs," for "domain antibodies." The term "dAb" generally refers to a single immunoglobulin variable domain ($V_H$, $V_{HH}$ or $V_L$) polypeptide that specifically binds antigen. For use in therapy, human single domain antibodies are preferred over camelid derived $V_{HH}$, primarily because they are not as likely to provoke an immune response when administered to a patient.

The terms "single domain antibody (sdAb), variable single domain or immunoglobulin single variable domain (ISV)" are all well known in the art and describe the single variable fragment of an antibody that binds to a target antigen. These terms are used interchangeably herein. A "single heavy chain domain antibody, single variable heavy chain domain, immunoglobulin single heavy chain variable domain (ISV), human $V_H$ single domain, $V_H$ single domain antibody" describes the isolated single heavy chain variable fragment of an antibody which retains binding specificity to the antigen in the absence of light chain or other antibody fragments. Thus, a single domain antibody does not comprise other parts of a full antibody molecule. A single variable heavy chain domain antibody is capable of binding to an antigen in the absence of light chain. Human heavy chain single variable domain antibodies ($V_H$ domain antibodies) are preferred.

In one aspect, we provide an isolated single variable heavy chain domain antibody that binds to human LAG-3.

As explained below, certain embodiments relate to isolated single variable heavy chain domain antibodies/immunoglobulin single variable heavy chain domains which bind a LAG-3 antigen. Thus, the single variable heavy chain domain antibody is capable of binding to LAG-3 in the absence of light chain. Human single variable heavy chain domain antibodies ("$V_H$ single domain antibody") are particularly preferred. Such binding molecules are also termed Humabody® herein. Humabody® is a registered trademark of Crescendo Biologics Ltd.

In some embodiments, we provide isolated binding agents/molecules comprise or consist of at least one single domain antibody wherein said domain is a human variable heavy chain domain; they are devoid of $V_L$ domains or other antibody fragments and bind to the target antigen.

The term "isolated" single domain antibody refers to a single domain antibody that is substantially free of other single domain antibodies, antibodies or antibody fragments having different antigenic specificities. Moreover, an isolated single domain antibody may be substantially free of other cellular material and/or chemicals. sdAbs of the invention and binding molecules comprising such sdAbs are preferably derived from/isolated from heavy chain only antibodies isolated transgenic mice expressing a transgene with human V, D and J regions and which produce heavy chain only antibodies. This is described in more detail in the examples.

Each single $V_H$ domain antibody comprises three CDRs and four FRs, arranged from amino-terminus to carboxy-terminus in the following order: FR1-CDR1-FR2-CDR2-FR3-CDR3-FR4.

Thus, in one embodiment, the domain is a human variable heavy chain ($V_H$) domain with the following formula FR1-CDR1-FR2-CDR2-FR3-CDR3-FR4.

Modifications to the C or N-terminal $V_H$ framework sequence may be made to the single domain antibodies of the invention to improve their properties. For example, the $V_H$ domain may comprise C or N-terminal extensions or deletions. C-terminal extensions can be added to the C-terminal end of a $V_H$ domain which terminates with the residues VTVSS.

In one embodiment, the single domain antibodies described herein comprise C-terminal extensions of from 1 to 50 residues, for example 1 to 10, 1 to 20, 1 to 30, 1 to 40, for example 1, 2, 3, 4, 5, 6, 7, 8, 9, 10, 11, 12, 13, 14, 15, 16, 17, 18, 19 or 20 additional amino acids. In one embodiment, the single domain antibodies described herein comprise additional amino acids of the human $C_H1$ domain thus that the C terminal end extends into the $C_H1$ domain. In one embodiment, said extension comprises at least one alanine residue, for example a single alanine residue, a pair of alanine residues or a triplet of alanine residues.

In another embodiment, additional C or N-terminal residues are selected from linkers that are used to conjugate the single domain antibodies described herein to another moiety, such as a peptide linker, or tags that aid the detection of the molecule. Such tags are well known in the art and include for, example linker His tags, e.g., hexa-His or myc tags.

As used herein, the terms "homology" or "identity" generally refer to the percentage of amino acid residues in a sequence that are identical with the residues of the reference polypeptide with which it is compared, after aligning the sequences and in some embodiments after introducing gaps, if necessary, to achieve the maximum percentage homology, and not considering any conservative substitutions as part of the sequence identity. Thus, the percentage homology between two amino acid sequences is equivalent to the percentage identity between the two sequences. Neither N- or C-terminal extensions, tags or insertions shall be construed as reducing identity or homology. Methods and computer programs for the alignment, such as Blast, are well known. The percentage homology or identity between two amino acid sequences can be determined using well known mathematical algorithms. Where homology is used herein, it can be interchanged with identity.

According to some embodiments of the various aspects described herein, the variable domain of the single domain antibodies as described herein is a $V_H$ domain, a $V_{HH}$ domain, a humanised $V_{HH}$ domain, a camelized $V_H$ domain, a sequence modified $V_H$ or $V_{HH}$ domain. In a preferred embodiment, the variable domain of the single domain antibodies as described herein is a human variable domain ($V_H$). The term "$V_H$", e.g. $V_H$ domain antibody, as used herein designates a single human variable heavy chain domain antibody.

As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples. In one embodiment, a human $V_H$ domain can also include a $V_H$ domain that is derived from or based on a human $V_H$ domain amino acid or nucleic acid sequence encoding such $V_H$ domain. Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified for example to correct a sequence liability. For example, a substantially human $V_H$ domain may include up to 20, for example 1, 2, 3, 4, 5, 6, 7, 8, 9, or 10 amino acid modifications compared to a fully human sequence.

However, the term "human $V_H$ domain" or "substantially human $V_H$ domain", as used herein, is not intended to include antibodies in which CDR sequences derived from the germline of another mammalian species, such as a mouse, have been grafted onto human framework sequences. Preferably, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

Exemplary Sequence Features

In one embodiment, the single $V_H$ domain antibody that binds to human LAG-3 comprises a CDR3 sequence as shown Table 1 below or a sequence with at least 60%, 70%, 80%, 90%, 95% or more sequence homology or identity thereto. Thus, in one aspect, we describe an isolated single $V_H$ domain antibody capable of binding to human LAG-3 comprising a CDR3 sequence selected from SEQ ID NO: 3 or 7 or a sequence with at least 60%, 70%, 80%, 90%, 95% or more sequence homology or identity to one of these sequences. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment, said sequence homology is at least 90%, 91%, 92%, 93%, 94%, 95%, 96%, 97%, 98% or 99%.

In one embodiment, the single $V_H$ domain antibody that binds to human LAG-3 further comprises a CDR1 that comprises or consists of the amino acid sequence SEQ ID NO: 1 or 5 or a sequence with at least at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology or identity thereto. In one embodiment, the single $V_H$ domain antibody that binds to human LAG-3 further comprises a CDR2 that comprises or consists of the amino acid sequence SEQ ID NO: 2 or 6 or a sequence with at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology or identity thereto.

In one embodiment, the $V_H$ single domain antibody comprises a CDR1 having SEQ ID NO: 1 or a sequence with at least 60%, 70%, 80%, 90%, 95% or more sequence homology thereto, a CDR2 having SEQ ID NO: 2 or a sequence with at least 60%, 70%, 80%, 90%, 95% or more sequence homology or identity thereto and a CDR3 having SEQ ID NO: 3 or a sequence with at least 60%, 70%, 80%, 90%, 95% or more sequence homology thereto. In one embodiment, the $V_H$ single domain antibody comprises a CDR1 having SEQ ID NO: 5 or a sequence with at least 60%, 70%, 80%, 90%, 95% or more sequence homology thereto, a CDR2 having SEQ ID NO: 6 or a sequence with at least 60%, 70%, 80%, 90%, 95% or more sequence homology or identity thereto and a CDR3 having SEQ ID NO: 7 or a sequence with at least 60%, 70%, 80%, 90%, 95% or more sequence homology thereto.

In one embodiment, the $V_H$ single domain antibody comprises or consists of SEQ ID NO: 4 or SEQ ID NO: 8 or a sequence with at least 60%, 70%, 80%, 90%, 95% or more sequence homology thereto, for example 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98% or 99% homology or identity.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into a single domain by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include

TABLE 1

Full length sequences and CDR sequences of $V_H$ single domain antibodies that bind to LAG-3

| Name | CDR1 | CDR2 | CDR3 | FULL LENGTH |
|---|---|---|---|---|
| 1.1 | SEQ ID NO. 1<br>DYGMS | SEQ ID NO. 2<br>GIHWNGGNSGYA<br>DSVKG | SEQ ID NO. 3<br>IPREDCSSASCY<br>TDAIDF | SEQ ID NO. 4<br>EVQLVESGGGVVRPGGSLRLSCS<br>ASGFTFDDYGMSWVRQAPGKGLE<br>WVSGIHWNGGNSGYADSVKGRFT<br>ISRDNAKNSLYLQMNSLRAEDTA<br>LYYCARIPREDCSSASCYTDAID<br>FWGPGTMVTVSS |
| 1.2 | SEQ ID NO. 5<br>DYGMS | SEQ ID NO. 6<br>GIHWNGGSTGYA<br>DSVKG | SEQ ID NO. 7<br>IPREDCSSASCY<br>TDAIDF | SEQ ID NO. 8<br>EVQLVESGGGVVRPGGSLRLSCA<br>ASGFTFDDYGMSWVRQAPGKGLE<br>WVSGIHWNGGSTGYADSVKGRFT<br>ISRDNAKNSLYLQMNSLRAEDTA<br>LYYCARIPREDCSSASCYTDAID<br>FWGQGTMVTVSS |

In some embodiments, we provide a $V_H$ single domain antibody that is a variant of any of the above single $V_H$ domain antibodies binding to human LAG-3.

A variant $V_H$ single domain antibody as used herein has one or more amino acid substitutions, deletions, insertions or other modifications, and which retains the functional properties as set out herein. For example, with reference to a variant $V_H$ single domain antibody that binds to LAG-3, a functional property may be the binding to LAG-3 or one of the other properties listed above.

A variant $V_H$ single domain antibody can be sequence engineered. Modifications may include one or more substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions, substitutions or deletions may optionally be in the range of 1 to 20 amino acids. i.e. 1, 2, 3, 4, 5, 6, 7, 8, 9, 10, 11, 12, 13, 14, 15, 16, 17, 18, 19 or 20 or 1 to 10. In one embodiment, the variant has 1, 2, 3, 4 or 5 substitutions. The variation allowed may be determined by systematically making insertions, deletions or substitutions of amino acids in the sequence and testing the resulting variants for activity exhibited by the full-length or mature native sequence.

amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody described herein can be replaced with other amino acid residues from the same side chain family and the altered antibody can be tested for retained function (i.e., the functions set forth in (c) through (I) above) using the functional assays described herein.

Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity. Abbreviations for the amino acid residues that comprise polypeptides and peptides described herein, and conservative substitutions for these amino acid residues are shown in Table 2 below.

TABLE 2

Amino Acid Residues and Examples of Conservative Amino Acid Substitutions

| Original residue<br>Three letter code, single letter code | Conservative substitution |
|---|---|
| Alanine, Ala, A | Gly, Ser |
| Arginine, Arg, R | Lys, His |
| Asparagine, Asn, N | Gln, His |
| Aspartic acid Asp, D | Glu, Asn |
| Cysteine, Cys, C | Ser, Ala |
| Glutamine, Gln, Q | Asn |
| Glutamic acid, Glu, E | Asp, Gln |
| Glycine, Gly, G | Ala |
| Histidein, His, H | Asn, Gln |
| Isoleucine, Ile, I | Leu, Val |
| Leucine, Leu, L | Ile, Val |
| Lysine, lys, K | Ar, His |
| Methionine, Met, M | Leu, Ile, Tyr |
| Phenylalanine, Phe, F | Tyr, Met, Leu |
| Proline, Pro, P | Ala |
| Serine, Ser, S | Thr |
| Threonine, Thr, T | Ser |
| Tryptophan, Trp, W | Tyr, Phe |
| Tyrosine, Tyr, Y | Try, Phe |
| Valine, Val, V | Ile, Leu |

In some embodiments, we provide a $V_H$ single domain antibody that is a variant of a single domain antibody that binds to LAG-3 selected from those shown in Table 1 and which comprises one or more sequence modification and has improvements in one or more of a property such as binding affinity, specificity, thermostability, expression level, effector function, glycosylation, reduced immunogenicity, or solubility as compared to the unmodified single domain antibody.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. We therefore also provide sequence optimised variants of the single domain antibodies described herein.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived. To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody.

In still another embodiment, the glycosylation of the molecule is modified. Glycosylation can be altered to, for example, increase the affinity of the molecule for the antigen. Such carbohydrate modifications can be accomplished by, for example, altering one or more sites of glycosylation within the molecule sequence. For example, one or more amino acid substitutions can be made that result in elimination of one or more variable region framework glycosylation sites to thereby eliminate glycosylation at that site. Such aglycosylation may increase the affinity of the molecule for antigen.

In one embodiment, the $V_H$ single domain antibody has a CDR1 as shown in SEQ ID NO: 1 or SEQ ID NO: 1 with 1 to 5 amino acid substitutions, a CDR2 as shown in SEQ ID NO: 2 or SEQ ID NO: 2 with 1 to 5 amino acid substitutions and a CDR3 as shown in SEQ ID NO: 3 or SEQ ID NO: 3 with 1 to 5 amino acid substitutions. In one embodiment, the $V_H$ single domain antibody has a CDR1 as shown in SEQ ID NO: 5 or SEQ ID NO: 1 with 1 to 5 amino acid substitutions, a CDR2 as shown in SEQ ID NO: 5 or SEQ ID NO: 2 with 1 to 5 amino acid substitutions and a CDR3 as shown in SEQ ID NO: 7 or SEQ ID NO: 3 with 1 to 5 amino acid substitutions.

In one embodiment, the variant $V_H$ single domain antibody is selected from any one of SEQ ID NO: 4 or 8, but comprises one or more amino acid substitutions, for example 1 to 20, for example 1, 2, 3, 4, 5, 6, 7, 8, 9 or 10 amino acid substitutions. In one embodiment, the variant has 1, 2, 3, 4 or 5 substitutions.

In one embodiment, the $V_H$ single domain antibody comprises SEQ ID NO: 4 ($V_H$ 1.1) but with amino acid substitutions at one or more of the following positions: S23, P119, N57, S58, N54, D30, Y32, S58, G55, G56, N57, G59, Y95, S106, S108 and/or A107. In one embodiment, two or more substitutions at these 16 positions are combined, for example the variant may comprise 2, 3, 4, 5, 6, 7, 8, 9, 10, 11, 12, 13, 14, 15 or 16 substitutions wherein the position is selected from those recited above. In one embodiment, the variant comprises a substitution at S23 and one or more substitution from those described above.

In one embodiment, the one or more of the following amino acid substitutions are selected from: S23A, P119Q, N57S, S58T, N54I, D30N, Y32F, S58T, G55S, G56D, N57I, N57S, S58T G59A, Y95H, S106V, S108A and/or A107T. In one embodiment, the variant comprises the substitution at S23A and one or more substitution from those described above.

In one embodiment, the substitution is S23A (variant 1). In one embodiment, the substitutions are S23A, P119Q, N57S and S58T (variant 2, $V_H$1.2). In one embodiment, the substitutions are S23A, N57S and S58T (variant 3). In one embodiment, the substitutions are S23A and N54I (variant 4). In one embodiment, the substitutions are S23A, D30N, Y32F and S58T (variant 5). In one embodiment, the substitutions are S23A, Y32F, G55S, G56D, N57I, S58T and G59A (variant 6). In one embodiment, the substitutions are S23A, Y32F, S58T, S106V and S108A (variant 7). In one embodiment, the substitutions are S23A, D30N and A107T (variant 8). In one embodiment, the substitutions are S23A, Y95H, G56D, N57S and S58T (variant 9).

Variants listed above were all tested for binding to LAG-3 and demonstrated a KD in the nanomolar range.

TABLE 3

Exemplary variants of $V_H$ 1.1 (SEQ ID NO. 4)

| Name | Substitutions with reference to SEQ ID NO. 4 |
|---|---|
| variant 1 | S23A |
| VH 1.2 | S23A, P119Q, N57S, S58T |

TABLE 3-continued

Exemplary variants of $V_H$ 1.1 (SEQ ID NO. 4)

| Name | Substitutions with reference to SEQ ID NO. 4 |
|---|---|
| variant 3 | S23A, N57S, S58T |
| variant 4 | S23A, N54I |
| variant 5 | S23A, D30N, Y32F, S58T |
| variant 6 | S23A, Y32F, G55S, G56D, N57I, S58T, G59A |
| variant 7 | S23A, Y32F, S58T, S106V, S108A |
| variant 8 | S23A, D30N, A107T |
| variant 9 | S23A, Y95H, G56D, N57S, S58T |

Numbering above is according to the position of the residue in the protein as shown herein.

$V_H$ single domain antibodies described herein have shown excellent stability. They have been shown to be resistant to heat stress at high concentration. Furthermore, $V_H$ single domain antibodies described herein also show specificity for human LAG-3, binding to human T cells, blockade of LAG-3 ligand binding and stimulation of T cell activity (see examples).

The $V_H$ single domain antibodies that bind to LAG-3 described herein preferably have KD values as further described herein and as shown in the examples. For example, the KD can be least about $10^{-8}$ M as measured by biolayer interferometry (biomolecular interaction analysis, Octet®).

The term "KD" refers to the "equilibrium dissociation constant" and refers to the value obtained in a titration measurement at equilibrium, or by dividing the dissociation rate constant (Koff) by the association rate constant (Kon). "KA" refers to the affinity constant. The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as HTRF, flow cytometry and Fluorescence Microvolume Assay Technology can be used. In some embodiment, the binding molecules may be able to bind LAG-3 with a KD value of at most about 6.15 µM or even lower, such as about 50 nM, about 10 nM or about 5 nM or even lower, for example, when the fusion polypeptide is measured using biolayer interferometry (Octet®) essentially as described in Example 8.

The binding molecules may be able to bind LAG-3 with an EC50 value of at most 100 nM or even lower, such as about 10 nM, about 5 nM or about 2 nM or even lower, for example when the fusion polypeptide is measured in an HTRF binding assay as described in Example 8.

In one embodiment, the $V_H$ single domain antibody above that binds to LAG-3 is obtained from a transgenic mouse which expresses human $V_H$ genes as further described herein or is a sequence optimised variant of a $V_H$ single domain antibody that binds to LAG-3 obtained from a transgenic mouse.

The present disclosure further provides an isolated nucleic acid encoding a single domain antibody that binds to LAG-3 as described herein. Nucleic acid may include DNA and/or RNA. In one aspect, we provide a nucleic acid that codes for a CDR, for example CDR3, a set of two or three CDRs or a $V_H$ single domain antibody as shown in Table 1 and as further defined above.

Nucleic Acid Sequences

In one aspect, we provide an isolated nucleic acid sequence comprising or consisting of a sequence selected from SEQ ID NO: 10 or 11 as shown in Table 4. The nucleic acid sequences in Table 4 encode $V_H$ single domain antibodies as shown in Table 1.

In one embodiment, the nucleic acid sequence has at least 60%, 70%, 80%, 90%, 95% or more sequence homology or identity to one of the sequences selected from Table 2. In one embodiment, said sequence homology is at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment, the nucleic acid sequence, the nucleic acid sequences has 1 to 20 substitutions compared to SEQ ID NO: 10 or 11.

TABLE 4

Nucleic acid sequences encoding $V_H$ single domain antibodies as shown in Table 1.

| Name | Nucleic acid sequence |
|---|---|
| 1.1 | SEQ ID NO. 10<br>GAGGTGCAGCTGGTGGAGTCTGGGGGAGGTGTGGTACGGCCTGG<br>GGGGTCCCTGAGACTCTCCTGTTCAGCCTCTGGATTCACCTTTG<br>ATGATTATGGCATGAGCTGGGTCCGCCAAGCTCCAGGGAAGGGG<br>CTGGAGTGGGTCTCTGGTATTCATTGGAATGGTGGTAACTCAGG<br>TTATGCAGACTCTGTGAAGGGCCGATTCACCATCTCCAGAGACA<br>ACGCCAAAAACTCCCTGTATCTGCAAATGAACAGTCTGAGAGCC<br>GAGGACACGGCCTTGTATTACTGTGCGAGAATCCCCCGAGAAGA<br>TTGTAGTAGTGCCAGCTGCTATACGGATGCTATTGATTTCTGGG<br>GCCCAGGGACAATGGTCACTGTCTCCTCA |
| 1.2 | SEQ ID NO. 11<br>GAGGTGCAGCTGGTGGAGTCTGGGGGAGGTGTGGTACGGCCTGG<br>GGGGTCCCTGAGACTCTCCTGTGCAGCCTCTGGATTCACCTTTG<br>ATGATTATGGCATGAGCTGGGTCCGCCAAGCTCCAGGGAAGGGG<br>CTGGAGTGGGTCTCTGGTATTCATTGGAATGGTGGTAGCACAGG<br>TTATGCAGACTCTGTGAAGGGCCGATTCACCATCTCCAGAGACA<br>ACGCCAAAAACTCCCTGTATCTGCAAATGAACAGTCTGAGAGCC<br>GAGGACACGGCCTTGTATTACTGTGCGAGAATCCCCCGAGAAGA<br>TTGTAGTAGTGCCAGCTGCTATACGGATGCTATTGATTTCTGGG<br>GCCAAGGGACAATGGTCACTGTCTCCTCA |

A nucleic acid according to the present invention may comprise DNA or RNA and may be wholly or partially synthetic or recombinantly produced. Reference to a nucleotide sequence as set out herein encompasses a DNA molecule with the specified sequence, and encompasses an RNA molecule with the specified sequence in which U is substituted for T, unless context requires otherwise. Variants of the nucleic acids shown above, for example with up to 20 codon changes are also within the scope of the invention, in particular those that encode the $V_H$ variants provided herein (see table 3).

Furthermore, we provide an isolated nucleic acid construct comprising at least one nucleic acid as defined above. The construct may be in the form of a plasmid, vector, transcription or expression cassette.

The invention also relates to an isolated recombinant host cell comprising one or more nucleic acid constructs as described above. The host cell may be a bacterial, viral, plant, fungal, mammalian or other suitable host cell. In one embodiment, the cell is an *E. coli* cell. In another embodiment, the cell is a yeast cell. In another embodiment, the cell is a Chinese Hamster Ovary (CHO) cell, HeLa cell or other cell that would be apparent to the skilled person. In one embodiment, a host cell is a mammalian host cell, but is not a human host cell.

In one embodiment, a method of making an anti-LAG-3 single domain antibody as described herein is provided, wherein the method comprises culturing a host cell under conditions suitable for expression of the polynucleotide encoding the single domain antibody, and isolating the single domain antibody.

Agents that Compete with the Molecules for Binding to Human LAG-3

In another aspect, we provide binding molecules, e.g. antibodies, antibody fragments or antibody mimetics that bind to the same epitope on human LAG-3 as any of the LAG-3 single domain antibodies of the invention (i.e., antibodies that have the ability to cross-compete for binding to human LAG-3 with any of the single domain antibodies. The single domain antibodies can thus be used as a reference antibody). In some embodiments, the reference antibody for cross-competition studies is single domain antibody $V_H$ 1.1 as shown herein (see table 1).

Such cross-competing antibodies can be identified based on their ability to cross-compete with single domain antibody 1.1 or 1.2 for binding to human LAG-3 in standard binding assays. For example, BIAcore® analysis, ELISA assays or flow cytometry may be used to demonstrate cross-competition with the single domain antibodies of the current invention.

In one embodiment, we provide a binding agent capable of binding human LAG-3 wherein a single domain antibody described above displaces the binding agent in a competitive assay. In some embodiments, the binding agent is an antibody, a functional fragment thereof, for example a single domain antibody, or an antibody mimetic protein. In another aspect, we provide a binding agent capable of binding human LAG-3 wherein the binding agent displaces a single domain antibody described above in a competitive assay. In another aspect, we provide a binding agent capable of binding human LAG-3 wherein the binding agent binds to essentially the same epitope, including an overlapping epitope, as the single domain antibody described herein.

In another aspect, we provide $V_H$ single domain antibodies as described above for use in a multivalent molecule, for example a bivalent molecule, or multispecific molecule comprising one or two $V_H$ single domain antibodies as described above.

Heavy Chain Only Antibodies

In another aspect, we provide an isolated heavy chain only antibody comprising a $V_H$ domain as described herein and listed in Table 1 or an isolated heavy chain only antibody with at least 60%, 70%, 80%, 90% or 95% homology or identity thereto.

Multivalent Binding Agents

Single domain antibodies that bind to LAG-3 described herein can be administered in combination with another therapeutic agent as further explained below.

Moreover, single domain antibodies that bind to LAG-3 described herein can form part of a multivalent binding agent/molecule. Such agent comprises a single domain antibody that binds to LAG-3 and one or more subunit/moiety that binds to a target antigen or antigen(s). In a multivalent binding agent as described herein, at least two binding entities are covalently or non-covalently linked. For example, in the embodiments described below, the multi-specific binding agent is preferably a fusion protein and the disclosure thus provides a fusion protein comprising a single domain antibody that binds to LAG-3 described herein. Preferably, the fusion polypeptide is a translational fusion between the two or more subunits. Techniques for generating the translational fusion are well known and include genetically engineering the coding sequence for one subunit in a reading frame with the coding sequence of a further subunit. The two subunits are for example linked by a nucleic acid sequence encoding a peptide linker. Exemplary peptide linkers are described in more detail below. In a preferred embodiment, the binding agent comprises or consists of 2 or 3 or more single domain antibodies, e.g. a fusion protein wherein a single domain antibody is linked to another single domain antibody. As will be clear to a skilled person, such a protein does not include other parts of a full antibody molecule—the binding to the targets is mediated by the single domain antibody.

Thus, in another aspect, the invention provides a $V_H$ single domain antibody that binds to LAG-3 (e.g. see the single domain antibodies as shown in Table 1 or a variant thereof) for use in a building a multivalent and/or multifunctional fusion protein. Thus, another aspect relates to the use of a $V_H$ single domain antibody that binds to LAG-3 as described herein (e.g. has a sequence as shown in Table 1 or a variant thereof) in a multifunctional fusion protein. Another aspect also relates to a method for making a multivalent binding agent comprising expressing a nucleic acid construct comprising a nucleic acid encoding a $V_H$ single domain antibody that binds to LAG-3 (for example as shown in Table 4) linked to a second nucleic acid that encodes a protein that binds to a second therapeutic target in a host cell and isolating the multifunctional protein from said host cell. Thus, a further aspect also relates to a multivalent binding agent that comprises a single domain antibody that binds to LAG-3 described herein, e.g. as shown in Table 1.

Molecules made up of the LAG-3 binding building blocks described herein can be designed for optimal target engagement, for example through linker design. This can lead to improved function or lower dosing. In addition to the functional advantages described herein, the benefits of a multifunctional molecule above over a combination of molecules include, but are not limited to, a simpler route through manufacture, preclinical testing and clinical administration.

A multivalent binding agent is a binding agent that includes at least two moieties with binding specificity to the same or different epitope on the same or different target. A "multi-specific" binding agent is a binding agent that recognizes more than one epitope on one or more antigens. A bispecific binding agent is a binding agent which recognizes two distinct epitopes on the same or different antigens.

Thus, one aspect relates to a multivalent binding agent comprising a single domain antibody that binds to LAG-3, for example one having an amino acid as described herein, and one or more further moiety, for example a second sdAb. For example, the binding agent may be a bispecific binding agent as further described below. In one embodiment, the second moiety binds to an antigen of therapeutic interest. In one embodiment, the second moiety is a binding molecule that binds to an antigen, for example a binding molecule selected from an antibody or antibody fragment (e.g., a Fab, F(ab')$_2$, Fv, a single chain Fv fragment (scFv) or single domain antibody, for example a $V_H$ domain) or an antibody mimetic protein. In another embodiment, the single domain antibody described herein can be linked to an antibody Fc region or fragment thereof, comprising one or both of $C_H2$ and $C_H3$ domains, and optionally a hinge region. In one preferred embodiment, the second moiety is a single $V_H$ domain antibody.

The binding agent may be multivalent, for example bivalent, or multiparatopic, for example biparatopic. Thus, in one embodiment, the binding molecule comprises or consists of a first $V_H$ single domain antibody $V_H(A)$ that binds to LAG-3 and a second $V_H$ single domain antibody $V_H(B)$ that binds to LAG-3 or another target antigen and thus has the following formula: $V_H(A)$-L-$V_H(B)$ wherein L is a linker, for example a peptide linker.

Each $V_H$ comprises CDR and FR regions. Thus, in one embodiment, the binding molecule that comprises a first $V_H$ single domain antibody $V_H(A)$ and a second $V_H$ single domain antibody $V_H(B)$ has the following formula: FR 1(A)-CDR 1(A)-FR2(A)-CDR2(A)-FR3(A)-CDR3(A)-FR4 (A)-L-FR1(B)-CDR1(B)-FR2(B)-CDR2(B)-FR3(B)-CDR3 (B)-FR4(B). The order of the immunoglobulin single variable domains A and B is not particularly limited, so that, within a polypeptide described herein, immunoglobulin single variable domain A may be located N-terminally and immunoglobulin single variable domain B may be located C-terminally, or vice versa. The $V_H$ domain antibodies are typically connected via a linker connecting the C terminus of the first $V_H$ with the N terminus of the second $V_H$.

In one embodiment, the binding molecule is biparatopic. In one embodiment, the binding molecule is bivalent. In one embodiment, the binding molecule is multispecific, for example bispecific, trispecific or tetraspecific.

Bivalent Binding Molecules

The inventors have surprisingly found that combining two $V_H$ single domain antibodies that both bind to LAG-3 in a single molecule is beneficial and enhances the effects compared to a monovalent $V_H$ single domain antibody that binds to LAG-3. As demonstrated in the examples, bivalent molecules that combine two $V_H$ single domain antibodies bind to LAG-3 with an increased KD and have improved EC50 and IC50 values compared to the monovalent LAG-3 binding $V_H$ single domain antibody. For example, monovalent LAG-3 $V_H$ binds weakly to cells whereas formatting as a bivalent molecule enhances this (see FIG. 2, example 8).

In one aspect, the invention therefore provides a molecule, fusion protein, construct or binding molecule comprising or consisting of two $V_H$ single domain antibodies that bind to human LAG-3, for example two molecules of the same sequence or of a different sequence. Each $V_H$ single domain antibody may bind to the same epitope on LAG3 or a different epitope on LAG3 (biparatopic). Such a molecule that is bivalent for LAG3 binding has the format $V_H$-L-$V_H$, L being a peptide linker, optionally $V_H$-L-$V_H$-L-X wherein X is another binding moiety, such as another $V_H$ single domain antibody. Such a molecule thus comprises solely single domain antibodies, there are no other parts of an antibody present. Optionally, the molecule may comprise a further C-terminal moiety, such as a half life extending moiety and/or an additional amino acid sequence, such as a tag or amino acid sequence of up to 25 amino acids. L is a protein linker as further explained herein. In another aspect, there is provided a bivalent construct, protein or binding molecule comprising or consisting of two $V_H$ single domain antibodies that bind to human LAG-3 selected from those shown in table 1 or a variant thereof. In one embodiment, the two $V_H$ single domain antibodies that bind to human LAG-3 have the same sequence. In another embodiment, the binding molecule may comprise two $V_H$ single domain antibodies that bind to human LAG-3 and have different sequences, e.g. each selected from the sequences shown in Table 1 or variants thereof and as described herein. The molecule or construct is a fusion protein.

Thus, in the various embodiments, the binding molecule has a first $V_H$ single domain antibody $V_H(A)$ and a second $V_H$ single domain antibody $V_H(A)$ or $V_H(A')$ and thus has the following formula: $V_H(A)$-L-$V_H(A)$ or $V_H(A)$-L-$V_H(A')$ wherein L is a linker, for example a peptide linker. Both $V_H(A)$ and $V_H(A')$ bind to human LAG-3.

In one embodiment, the binding molecule comprises $V_H$ 1.1 linked to $V_H$ 1.1. In one embodiment, the binding molecule comprises $V_H$ 1.2 linked to $V_H$ 1.2, i.e. the molecules can be described as $V_H$ 1.2-L-$V_H$ 1.2. In one embodiment, the binding molecule comprises $V_H$ 1.1 linked to $V_H$ 1.2.

Bivalent binding molecules described herein can be constructed using methods known in the art and as described in the examples.

In one embodiment, such bivalent fusion protein comprises one of the following: SEQ ID No 4-(G4S)n-SEQ ID No 4, SEQ ID No 8-(G4S)n- SEQ ID No 8, SEQ ID No 4-(G4S)n- SEQ ID No 8, SEQ ID No 8-(G4S)n- SEQ ID No 4.

Another aspect relates to a nucleic acid molecule encoding such fusion protein.

In one embodiment, the bivalent binding agent comprising two $V_H$ single domain antibodies that bind to LAG-3 as described above has one or more or all of the following properties: high purity and stability, binding to human LAG-3, binding to T cells and stimulation of T cells.

A bivalent binding agent can bind potently to LAG-3-Fc protein as shown in example 8.

A bivalent binding agent may be able to bind LAG-3 protein or on T cells with an EC50 value of at most 50 nM or even lower, such as about 10 nM, about 1 nM or about 0.1 nM or even lower, for example when the LAG-3 binding is measured in assays as described in Example 8.

A bivalent binding agent is capable of enhancing T cell function. When human cells are stimulated with superantigen (staphylococcal enterotoxin B) and anti-PD-1 antibodies, a bivalent binding agent increases secretion of inflammatory cytokines such as IL-2, indicative of activation (example 10a). Reporter cells that measure T cell signalling via the NFAT signalling pathway can also be stimulated upon blockade of LAG-3 with bivalent molecules, producing an IC50 value of at least 3 nM (example 9b).

For example, the bivalent binding agent retains >95% purity after heating at 40° C., as measured by size exclusion chromatography.

Multispecific Binding Agents

In certain aspects, there is provided a multispecific binding agent that binds to LAG-3 and blocks the functional interaction of LAG-3 with one or more of its ligands and comprises one or more $V_H$ sdAb as described herein and which also binds to another target. A multispecific binding agent binds to at least two different targets, i.e. is at least bispecific.

Bispecific antibody formats are generally known in the art. Typically, as reviewed in Fan et al. (Journal of Hematology & Oncology (2015) 8:130), bispecific antibodies are divided into two categories: immunoglobulin G (IgG)-like molecules and non-IgG-like molecules. IgG-like bsAbs retain Fc-mediated effector functions such as antibody-dependent cell-mediated cytotoxicity (ADCC), complement-dependent cytotoxicity (CDC), and antibody-dependent cellular phagocytosis (ADCP). As explained below, in preferred embodiments, bispecific molecules of the invention do not have an Fc domain.

A multispecific binding agent as provided herein comprises at least one $V_H$ single domain antibody that has a binding specificity to LAG-3 as described herein and is for example selected from table 1 and at least one second binding molecule with a second binding specificity to a second antigen that is not LAG-3. The binding entities are joined by a linker, such as a peptide linker. Said second binding molecule can be selected from an antibody, an antibody fragment or antibody mimetic. In one embodiment, said antibody fragment is selected from a F(ab')$_2$, Fab, Fv, sFv or domain antibody. In one preferred embodiment, the antibody fragment is a V$_H$ single domain antibody. Thus, preferred embodiments relate to a binding molecule wherein a one V$_H$ single domain antibody that has a binding specificity to LAG-3 is linked to a second V$_H$ single domain antibody.

Thus, in one aspect, we provide a binding molecule with the following formula: V$_H$(A)-L-V$_H$(B) wherein V$_H$(A) is a V$_H$ single domain antibody that binds to LAG-3, V$_H$(B) is a V$_H$ single domain antibody that binds to a second target and wherein L is a linker, for example a peptide linker.

In one embodiment, the binding agent is bispecific and comprises a single domain antibody that has a binding specificity to LAG-3 as described herein and is for example selected from a V$_H$ single domain antibody as shown in table 1 and a second binding molecule with a second binding specificity.

In another aspect, we provide a bispecific binding agent as described above which comprises two or more V$_H$ single domain antibodies that bind to LAG-3 as described herein linked, specifically under the section bivalent molecules above, to a further moiety that binds to a second target. The third moiety can be selected from a V$_H$ single domain antibody. This has the following formula: V$_H$(A')-L1-V$_H$(A')-L2-V$_H$(B) wherein L1 and L2 are linkers, for example a peptide linker. L1 and L2 may be the same or different linkers.

In one embodiment, the second binding molecule binds to an immunomodulatory agent, a checkpoint modulator, an agent involved in T-cell activation, a tumor microenvironment modifier (TME) or a tumour-specific target.

For example, the immunomodulator can be an inhibitor of an immune checkpoint molecule selected from an inhibitor of one or more of PD-L1, PD-L2, CTLA-4, TIM-3, PD-1, CEACAM, VISTA, BTLA, TIGIT, LAIR1, CD160, 2B4 or TGFR beta. In another embodiment, the immunomodulator can be an activator of a costimulatory molecule selected from an agonist of one or more of IL-2, IL-12, OX40, OX40L, CD2, CD3, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, B7-H4 or CD83 ligand, CD3, CD8, CD28, CD4 or ICAM-1.

For example, we provide a multispecific binding agent comprising two V$_H$ single domain antibodies that bind to LAG-3 linked to a V$_H$ single domain antibody that blocks PD-1 signalling. Such format increases potency compared to the monovalent entities.

Dual blockade of PD-1 and LAG-3 is a promising combinatorial strategy for cancer treatment, in particular given that both PD-1 and LAG-3 regulate T cell activation. Thus, in one aspect, we provide a binding molecule with the following formula: V$_H$(A)-L-V$_H$(B) or preferably V$_H$(A)-L-V$_H$(A)-L V$_H$(B) wherein V$_H$(A) is a V$_H$ single domain antibody that binds to LAG-3, V$_H$(B) is a V$_H$ single domain antibody that binds to PD-1 and wherein L is a linker, for example a peptide linker.

By simultaneously targeting immune checkpoints PD-1 and LAG-3, the binding agent of the disclosure may generate a potent anti-tumor and/or anti-infection response, increase anti-tumor lymphocyte cell activity, and enhance anti-tumor immunity, thereby producing at least additive or synergistic anti-tumor results.

Indeed, we have shown that combining a V$_H$ single domain antibody that binds to LAG-3 with a V$_H$ single domain antibody that binds to PD-1 in a bi- or multispecific fusion protein provides enhanced functions compared to the monovalent entities. Moreover and as explained elsewhere, in contrast to the universal blockade resulting from combination therapies, the bispecific molecules of the invention bind to cells that express both LAG-3 and PD-1. The bispecific molecules of the invention selectively bind and activate such dual positive cells and blockade of PD-1 positive cells, that is cells that only display PD-1 on their surface is reduced. Thus, we provide a bi- or multispecific molecule comprising a V$_H$ single domain antibody that binds to LAG-3 and a V$_H$ single domain antibody that binds to PD-1. Accordingly, in preferred embodiment, the invention provides a binding agent that comprises at least one V$_H$ single domain antibody that binds to LAG-3 and at least one V$_H$ single domain antibody that binds to PD-1, is capable of engaging LAG-3 and PD-1 on the same cell and does not comprise other antibody fragments, such as an Fc region.

These molecules bind specifically to wild type human PD-1 (UniProt Accession No. Q15116, GenBank Accession No. U64863). The amino acid sequence for wild type human PD-1 is shown below (SEQ ID NO: 12).

MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL

Unless otherwise specified, the term PD-1 as used herein refers to human PD-1. The terms "Programmed Death 1," "Programmed Cell Death 1," "Protein PD-1," "PD-1," PD-1," "PDCD1," "hPD-1" and "hPD-1" are used interchangeably, and include variants, isoforms, species homologs of human PD-1.

The terms "PD-1 binding molecule/protein/polypeptide/agent", "PD-1 antigen binding molecule protein/polypeptide/agent", "anti-PD-1 single domain antibody", "anti-PD-1 single immunoglobulin variable domain", "anti-PD-1 heavy chain only antibody" or "anti-PD-1 antibody" all refer to a molecule capable of specifically binding to the human PD-1 antigen. The binding reaction may be shown by standard methods, for example with reference to a negative control test using an antibody of unrelated specificity. The term "PD-1 binding molecule/agent" includes a PD-1 binding protein.

The PD-1-binding V$_H$ single domain antibody used in the bi- or multispecific fusion protein has one or more of the following properties: binding to human PD-1 with high affinity, modulation of the interaction of PD-1 with PD-L1 and/or PD-L2, blockade of the functional interaction of PD-1 with PD-L1 and/or PD-L2 and/or stimulation or enhancement of T-cell activation.

In another aspect, the invention thus provides binding molecules comprising a single domain antibody that binds human LAG-3 as described herein and comprising a single domain antibody that binds human PD-1, blocks the interaction of PD-1 with PD-L1 and/or the interaction of PD-1 with PD-L2 as described herein and/or stimulates or enhances T-cell activation.

The PD-1-binding $V_H$ single domain antibody used in the bi- or multispecific fusion protein has one or more or all of the following properties:
(a) binds to human PD-1;
(b) increases IL-2 secretion in an MLR assay;
(c) binds to human PD-1 and cynomolgus monkey PD-1;
(d) does not bind to mouse PD-1;
(e) inhibits the binding of PD-L1 and/or PD-L2 to PD-1 and/or
(f) inhibits tumor cell growth in vivo.

The PD-1 binding $V_H$ single domain antibodies may specifically bind to human PD-1 with high affinity, the KD can be least about $10^{-8}$ M to $10^{-12}$ such as $10^{-8}$ M, $10^{-9}$ M, $10^{-19}$ M, $10^{-11}$ M or $10^{-12}$ M as measured by surface plasmon resonance (biomolecular interaction analysis, BIAcore®) analysis. The PD-1 binding $V_H$ single domain antibodies may have an 1050 value for inhibition of PD-1 in $10^{-8}$ M to $10^{-9}$ M range as determined in a functional assay. Potency of the bispecific constructs on PD-1 positive cells is >30-fold lower than monoclonal antibodies as shown in the examples.

In some embodiments, the $V_H$ single domain antibodies block the binding of PD-1 to PD-L1, PD-L2 and/or stimulate or enhance T-cell activation and are selected from table 5. It has been shown that these $V_H$ have one or more or all of the properties a) to f) listed above.

The $V_H$ single domain antibody that binds to PD-1 may be selected from one disclosed in WO2018127710, incorporated herein by reference.

TABLE 5

Exemplary $V_H$ single domain antibodies that bind to PD-1 and can be used in the multispecific molecules of the invention

| Clone name | Full length |
|---|---|
| 2.1 | SEQ ID NO. 13<br>QVQLVESGGGLVKPGGSLRLSCAASGFTFSDYTMTWMRQAPGKGLEWVSYISTGGTIKYYTDSVKGRFTISR<br>DNAKNSLYLQMNSLRADDTAVYYCAREAPLRLGESPHDAFDIWGQGTMVTVSS |
| 2.2 | SEQ ID NO. 14<br>EVQLLESGGGLVKPGGSLRLSCAASGFTFSDYTMTWMRQAPGKGLEWVSYISTGGSIKYYTDSVKGRFTISR<br>DNAKNSLYLQMNSLRADDTAVYYCAREAPLRLGESPHDAFDIWGQGTMVTVSS |
| 2.3 | SEQ ID NO. 15<br>QVQLVESGGGLVKPGGSLRLSCAASGFTFSDYTMTWMRQAPGKGLEWVSYISTGGSIKYYTDSVKGRFTISR<br>DNAKNSLYLQMNSLRADDTAVYYCAREAPLRLGESPHDAFDIWGQGTMVTVSS |
| 2.4 | SEQ ID NO. 16<br>QVQLVESGGGLVKPGGSLRLSCAASGFTFSDYYMIWMRQAPGKGLEWVSYISGGGTTKYYTDSVKGRFTISR<br>DNAKNSLYLQMNSLRADDTAVYYCAREAPLRLGETPHDAFDIWGQGTMVTVSS |
| 2.5 | SEQ ID NO. 17<br>EVQLVESGGGLVKPGGSLRLSCAASGFTFSDYTMTWMRQAPGKGLEWVSYISTGGNTKYYTDSVKGRFTISR<br>DNAKNSLYLQMNSLRADDTAVYYCAREAPLRLGESPHDAFDIWGQGTMVTVSS |
| 2.6 | SEQ ID NO. 18<br>EVQLLESGGGLVKPGGSLRLSCAASGFTFSDYTMTWMRQAPGKGLEWVSYISTGGTIKYYTDSVKGRFTISR<br>DNAKNSLYLQMSSLRADDTAVYYCAREAPLRLGESPHDAFDIWGQGTMVTVSS |
| 2.7 | SEQ ID NO. 19<br>EVQLVESGGGLVKPGGSLRLSCAASGFTFSDYTMTWMRQAPGKGLEWVSYISTGGTIKYYTDSVKGRFTISR<br>DNAKNSLYLQMNSLRADDTAVYYCAREAPLRLGESPHDAFDIWGQGTMVTVSS |
| 2.8 | SEQ ID NO. 20<br>EVQLVESGGGLVKPGGSLRLSCAASGFTFSDYTMTWMRQAPGKGLEWVSYISTGGSIKYYTDSVKGRFTISR<br>DNAKNSLYLQMNSLRAGDTAVYYCAREAPLRLGESPHDAFDIWGQGTMVTVSS |
| 2.9 | SEQ ID NO. 21<br>QVQLVESGGGLVKPGGSLRLSCAASGFTFGDYTMTWMRQAPGKGLEWVSYISTGGTIKYYTDSVKGRFTISR<br>DNAKNSLYLQMDSLRADDTAVYYCAREAPLRLGESPHDAFDIWGQGTMVTVSS |
| 2.10 | SEQ ID NO. 22<br>QVQLVESGGGLVKPGGSLRLSCAASGFTFSDYTMSWMRQAPGKGLEWISYISLGGNTKYYTDSVKGRFTISR<br>DNAKNSLYLQMNSLRADDTAVYYCAREAPLRLGESPHDAFDIWGQGTMVTVSS |
| 2.11 | SEQ ID NO. 23<br>EVQLLESGGGLVKPGGSLRLSCAASGFTFSDYDMTWIRQAPGKGQEWVSYISRGGSTKYYADSVKGRFTISR<br>DNAKNSLYLQMNSLRAEDTAVYYCAREAPLRLGETPHDAFDIWGQGTMVTVSS |
| 2.12 | SEQ ID NO. 24<br>EVQLLESGGGVVKPGGSLRLSCAASGFTFSDYYMGWIRQAPGKGLEWISYISSSGSTIYYADSVKGRFTISR<br>DNAKNSLYLQMNSLRAEDTAVYYCAREAPLRLGESPHDAFDIWGQGTMVTVSS |
| 2.13 | SEQ ID NO. 25<br>EVQLLESGGGLVKPGGSLRLSCAASGFTFSDYTMTWMRQAPGKGLEWVSYISTGGTIKYYTDSVKGRFTISR<br>DNAKNSLYLQMNSLRADDTAVYYCAREAPLRLGESPHDAFDIWGQGTMVTVSS |

TABLE 5-continued

Exemplary V_H single domain antibodies that bind to PD-1 and
can be used in the multispecific molecules of the invention Clone name　Full length 2.14　SEQ ID NO. 26
EVQLVESGGGLVQPGRSLRLSCAASGFTFSDYTMTWMRQAPGKGLEWVSYISTGGTIKYYTDSVKGRFTISR
DNAKNSLYLQMNSLRADDTAVYYCAREAPLRLGESPHDAFDIWGQGTMVTVSS 2.15　SEQ ID NO. 27
QVQLVESGGGLVKPGGSLRLSCAASGFTFSDNSMSWIRQAPGKGLEWVSYISSSGSTIYYADSVKGRFTISR
DNAKNSLYLQMNTLRAEDTAVYYCAKEAPLRLGESPHDAFDIWGQGTMVTVSS 2.16　SEQ ID NO. 28
EVQLVESGGGLVKPGGSLRLSCAASGFTFSDYTMSWMRQAPGKGLEWVSYISTGGSIKYYTDSVKGRFTISR
DNAKNSLYLQMNSLRADDTAVYYCAREAPLRLGESPHDAFDIWGQGTMVTVSS 2.17　SEQ ID NO. 29
EVQLVESGGGLVKPGGSLRLSCAASGFTFSDYTMTWMRQAPGKGLEWVSYISTGGSIKYYTDSVKGRFTISR
DNAKNSLYLQMNSLRVDDTAVYYCAREAPLRLGESPHDAFDIWGQGTMVTVSS 2.18　SEQ ID NO. 30
QVQLLESGGGLVKPGGSLRLSCAASGFTFSDYTMTWMRQAPGKGLEWVSYISTGGTIKYYTDSVKGRFTISR
DNAKNSLYLQMNSLRADDTAVYYCAREAPLRLGESPHDAFDIWGQGTMVTVSS 2.19　SEQ ID NO. 31
QVQLVESGGGLVKPGGSLRLSCAASGFTFSDYTMTWMRQAPGKGLEWVSYISTGGSIKYYTDSVKGRFTISR
DNAKNSLYLQMNSLRAEDTAVYYCAREAPLRLGETPHDAFDIWGQGTMVTVSS 2.20　SEQ ID NO. 32
EVQLLESGGGLVKPGGSLRLSCAASGFTFSDYTMTWMRQAPGKGLEWVSYISSGGSIKFYADSVKGRFTISR
DNAKNSLYLQMNSLRAEDTAVYYCAREAPLRLGESPHDAFDIWGQGTMVTVSS 2.21　SEQ ID NO. 33
EVQLVESGGGLVKPGGSLRLSCAASGFTFSDYTMTWMRQAPGKGLEWVSYISTGGSIKYYTDSVKGRFTISR
DNAKNSLYLQMNSLRADDTAVYYCAREAPLRLGESPHDAFDTWGQGTMVTVSS 2.22　SEQ ID NO. 34
EVQLVESGGGLVKPGGSLRLSCAASGFTFSDYTMTWMRQAPGKGLEWVSYISTGGSIKYYTDSVKGRFTISR
DNAKNSLYLQMNSLRADDTAVYYCAREAPLRLGESPHDAFDIWGQGTMVTVSS 2.23　SEQ ID NO. 35
QITLKESGGGLVKPGGSLRLSCAASGFTFSDYTMSWMRQAPGKGLEWVSYISTGGTIKYYTDSVKGRFTISR
DNAKNSLYLQMNSLRADDTAVYYCAREAPLRLGESPHDAFDIWGQGTMVTVSS 2.24　SEQ ID NO. 36
QVTLKESGGGLVKPGGSLRLSCAASGFTFSDYDMYWIRQAPGKGLEWVSYISRGGSVTYYADSVKGRFTISR
DNAKNALYLQMNSLRAEDMAVYFCATEAPLRLGETPHAAFDIWGQGTMVTVSS 2.25　SEQ ID NO. 37
QVTLKESGGGLVKPGGSLRLSCAASGFTFSDYYMSWFRQAPGKEREWISFISSSGSTTYYADSVKGRFTISR
DNAKNSLYLQMNSLRAEDTAVYYCAREAPLRLGESPHDAFDFWGQGTMVTVSS 2.26　SEQ ID NO. 38
QVTLKESGGGLVKPGGSLRLSCAASGFTFSDNSMSWIRQAPGKGLEWVSYISSSGSTIYYADSVKGRFTISR
DNAKNSLYLQMNTLRAEDTAVYYCAKEAPLRLGESPHDAFDIWGQGTMVTVSS 2.27　SEQ ID NO. 39
QVTLKESGGGLVKPGGSLRLSCAASGFTFSDYTMTWMRQAPGKGLEWVSYISTGGSIKYYTDSVKGRFTISR
DNAKNSLYLQMNSLRADDTAVYYCAREAPLRLGESPHDAFDIWGQGTMVTVSS 2.28　SEQ ID NO. 40
QITLKESGGGLVKPGGSLRLSCAASGFTFSDYDMYWIRQAPGKGLEWVSYISRGGSVTYYADSVKGRFTISR
DNAKNALYLQMNSLRAEDMAVYFCATEAPLRLGETPHAAFDIWGQGTMVTVSS 2.29　SEQ ID NO. 41
QVTLKESGGGLVKPGGSLRLSCAASGFTFSDYTMSWMRQAPGKGLEWVSYISTGGTIKYYTDSVKGRFTISR
DNAKNSLYLQMNSLRADDTAVYYCAREAPLRLGESPHDAFDIWGQGTMVTVSS 2.30　SEQ ID NO. 42
QVTLKESGGGLVKPGGSLRLSCAASGFTFSDYTMTWMRQAPGKGLEWVSYISTGGSIKYYTDSVKGRFTISR
DNARNSLYLQMNSLRAEDTAVYYCAREAPLRLGESPHDAFDIWGQGTMVTVSS 2.31　SEQ ID NO. 43
QVTLKESGGGLVKPGGSLRLSCAASGFTFSDYTMTWMRQAPGKGLEWVSYISTGGSTKYYTDSVKGRFTISR
DNAKNSLYLQMNSLRADDTAVYYCAREAPLRLGESPHDAFDIWGQGTMVTVSS TABLE 5-continued Exemplary V$_H$ single domain antibodies that bind to PD-1 and
can be used in the multispecific molecules of the invention

| Clone name | Full length |
|---|---|
| 2.32 | SEQ ID NO. 44<br>QVTLKESGGGLVKPGGSLRLSCAASGFTFSDDYMMWIRQAPGKGLEWVSYISSGGSIIYYADSVKGRFTISR<br>DNAKNSLYLQMNSLRAEDTAVYYCAREAPLRLGESPHDAFDIRGQGTMVTVSS |
| 2.33 | SEQ ID NO. 45<br>QITLKESGGGLVKPGGSLRLSCAASGFTFSDYDMYWVRQAPGKGLEWVSYISRGGSVTYYADSVKGRFTISR<br>DNAKNALYLQMNSLRAEDMAVYFCATEAPLRLGETPHAAFDIWGQGTMVTVSS |
| 2.34 | SEQ ID NO. 46<br>EVQLVESGGGLVKPGGSLRLSCAASGFTFSDYTMTWMRQAPGKGLEWVSYISTGGSVKYYTDSVKGRFTISR<br>DNAKNSLYLQMNSLRADDTAVYYCAREAPLRLGESPHDAFDIWGQGTMVTVSS |
| 2.35 | SEQ ID NO. 47<br>EVQLLESGGGLVKPGGSLRLSCAASGFTFSDYTMTWMRQAPGKGLEWVSYISTGGSIKYYTDSVKGRFTISR<br>DNAKNSLYLQMNSLRVD DTAVYYCAREAPLRLGESPHDAFDIWGQGTMVTVSS |
| 2.36 | SEQ ID NO. 48<br>EVQLVESGGGLVKPGGSLRLSCAASGFTFSDYTMTWMRQAPGKGLEWVSYISTGGTIKYYTDSVKGRFTISR<br>DNAKNSLFLQMNSLRADDTAVYYCAREAPLRLGESPHDAFDIWGQGTMVTVSS |
| 2.37 | SEQ ID NO. 49<br>QVQLVESGGGLVKPGGSLRLSCAASGFTFSDYTMTWMRQAPGKGLEWVSYISTGGSIKYYTDSVKGRFTISR<br>DNAKNSLFLQMNSLRADDTAVYYCAREAPLRLGESPHDAFDIWGQGTMVTVSS |
| 2.38 | SEQ ID NO. 50<br>EVQLVESGGGLVQPGGSLRLSCAASGFTFSDYTMTWMRQAPGKGLEWVSYISTGGTIKYYTDSVKGRFTISR<br>DNAKNSLYLQMNSLRADDTAVYYCAREAPLRLGESPHDAFDIWGQGTMVTVSS |
| 2.39 | SEQ ID NO. 51<br>QVQLQESGGGLVKPGGSLRLSCAASGFTFSDYTMTWMRQAPGKGLEWVSYISTGGSIKYYTDSVKGRFTISR<br>DNAKNSLYLQMNSLRADDTAVYYCAREAPLRLGESPHDAFDIWGQGTMVTVSS |
| 2.40 | SEQ ID NO. 52<br>EVQLVESGGGLVKPGGSLRLSCAASGFTFSDSSMSWIRQAPGRGLEWISYISSGGGIIYYTDSVKGRFTISR<br>DNAKNSLYLQMNSLRVEDTAVYYCAKEAPLRLGESPHDAFDIWGHGTMVTVSS |
| 2.41 | SEQ ID NO. 53<br>QVQLVESGGGLVKPGGSLRLSCAASGFTFSDNSMTWMRQAPGKGLEWVSYISSGGGVIFYADSVKGRFTISR<br>DNAKNSLYLQMNSLRADDTAVYYCAREAPLRLGESPHDAFDIWGQGTMVTVSS |
| 2.42 | SEQ ID NO. 54<br>QVQLVESGGGLVKPGGSLRLSCAASGFTFSDNSMTWMRQAPGKGLEWVSYISSGGGVKFYADSVKGRFTISR<br>DNAKNSLYLQMNSLRADDTAVYYCAREAPLRLGESPHDAFDIWGQGTMVTVSS |
| 2.43 | SEQ ID NO. 55<br>QVQLVESGGGLVKPGGSLRLSCAASGFTFSDSSMTWMRQAPGKGLEWVSYISSGGGVIFYADSVKGRFTISR<br>DNAKNSLYLQMNSLRADDTAVYYCAREAPLRLGESPHDAFDIWGQGTMVTVSS |
| 2.44 | SEQ ID NO. 56<br>QVQLVESGGGLVKPGGSLRLSCAASGFTFSDNSMTWMRQAPGKGLEWVSYISSGGAVKFYADSVKGRFTISR<br>DNAKNSLYLQMNSLRADDTAVYYCAREAPLRLGESPHDAFDIWGQGTMVTVSS |
| 2.45 | SEQ ID NO. 57<br>QVQLVESGGGLVKPGGSLRLSCAASGFTFSDYSMSWMRQAPGKGLEWVSYISSGGGVIFYADSVKGRFTISR<br>DNAKNSLYLQMNSLRADDTAVYYCAREAPLRLGESPHDAFDIWGQGTMVTVSS |
| 2.46 | SEQ ID NO. 58<br>QVQLVESGGGLVKPGGSLRLSCAASGFTFSDSSMSWMRQAPGKGLEWVSYISSGGGVIFYADSVKGRFTISR<br>DNAKNSLYLQMNSLRADDTAVYYCAREAPLRLGESPHDAFDIWGQGTMVTVSS |
| 2.47 | SEQ ID NO. 59<br>QVQLVESGGGLVKPGGSLRLSCAASGFTFSDNSMSWMRQAPGKGLEWVSYISSGGGVIFYADSVKGRFTISR<br>DNAKNSLYLQMNSLRADDTAVYYCAREAPLRLGESPHDAFDIWGQGTMVTVSS |
| 2.48 | SEQ ID NO. 60<br>QVQLVESGGGLVKPGGSLRLSCAASGFTFSDSSMTWMRQAPGKGLEWVSYISSGGGVKFYADSVKGRFTISR<br>DNAKNSLYLQMNSLRADDTAVYYCAREAPLRLGESPHDAFDIWGQGTMVTVSS |
| 2.49 | SEQ ID NO. 61<br>QVQLVESGGGLVKPGGSLRLSCAASGFTFSDSSMSWMRQAPGKGLEWVSYISTGGGVKFYADSVKGRFTISR<br>DNAKNSLYLQMNSLRADDTAVYYCAREAPLRLGESPHDAFDIWGQGTMVTVSS |

TABLE 5-continued

Exemplary V_H single domain antibodies that bind to PD-1 and
can be used in the multispecific molecules of the invention

| Clone name | Full length |
|---|---|
| 2.50 | SEQ ID NO. 62<br>QVQLVESGGGLVKPGGSLRLSCAASGFTFSDNSMTWMRQAPGKGLEWVSYISSGGTIKFYADSVKGRFTISR<br>DNAKNSLYLQMNSLRADDTAVYYCAREAPLRLGESPHDAFDIWGQGTMVTVSS |
| 2.51 | SEQ ID NO. 63<br>QVQLVESGGGLVKPGGSLRLSCAASGFTFSDSSMTWMRQAPGKGLEWVSYISSGGAVKFYTDSVKGRFTISR<br>DNAKNSLYLQMNSLRADDTAVYYCAREAPLRLGESPHDAFDIWGQGTMVTVSS |
| 2.52 | SEQ ID NO. 64<br>QVQLVESGGGLVKPGGSLRLSCAASGFTFSDNSMTWMRQAPGKGLEWVSYISSGGGVKYYADSVKGRFTISR<br>DNAKNSLYLQMNSLRADDTAVYYCAREAPLRLGESPHDAFDIWGQGTMVTVSS |
| 2.53 | SEQ ID NO. 65<br>QVQLVESGGGLVKPGGSLRLSCAASGFTFSDNSMTWMRQAPGKGLEWVSYISSGGSVKFYADSVKGRFTISR<br>DNAKNSLYLQMNSLRADDTAVYYCAREAPLRLGESPHDAFDIWGQGTMVTVSS |
| 2.54 | SEQ ID NO. 66<br>QVQLVESGGGLVKPGGSLRLSCAASGFTFSDDSMTWMRQAPGKGLEWVSYISSGGGVIFYADSVKGRFTISR<br>DNAKNSLYLQMNSLRADDTAVYYCAREAPLRLGESPHDAFDIWGQGTMVTVSS |
| 2.55 | SEQ ID NO. 67<br>QVQLVESGGGLVKPGGSLRLSCAASGFTFSDNSMTWMRQAPGKGLEWVSYISSGGGVKFYADSVKGRFTISR<br>DNAKNSLYLQMNSLRADDTAVYYCAREAPLRLGESPHDAFDISGQGTMVTVSS |
| 2.56 | SEQ ID NO. 68<br>QVQLVESGGGLVKPGGSLRLSCAASGFTFSDNSMTWMRQAPGKGLEWVSYISSGGAVKFYADSVKGRFTISR<br>DNAKNSLYLQMNSLRADDTAVYYCAREAPLRLGESPHDAFDILGQGTMVTVSS |
| 2.57 | SEQ ID NO. 69<br>QVQLVESGGGLVKPGGSLRLSCAASGFTFSDNSMTWMRQAPGKGLEWVSYISSGGGVIFYADSVKGRFTISR<br>DNAKNSLYLQMNSLRADDTAVYYCAREAPLRLGESPHDAFDISGQGTMVTVSS |
| 2.58 | SEQ ID NO. 70<br>QVQLVESGGGLVKPGGSLRLSCAASGFTFSDYTMTWMRQAPGKGLEWVSYISTGGTIKYYTDSVKGRFTISR<br>DNAKNSLYLQMNSLRADDTAVYYCAREAPLRLGESPHDAFDIWGQGTMVTVSS |
| 2.59 | SEQ ID NO. 71<br>QVQLVESGGGLVKPGGSLRLSCAASGFTFSDNTMTWMRQAPGKGLEWVSYISTGGGVKFYADSVKGRFTISR<br>DNAKNSLYLQMNSLRADDTAVYYCAREAPLRLGESPHDAFDIWGQGTMVTVSS |
| 2.60 | SEQ ID NO. 72<br>QVQLVESGGGLVKPGGSLRLSCAASGFTFSDNSMSWMRQAPGKGLEWVSYISSGGSVKFYADSVKGRFTISR<br>DNAKNSLYLQMNSLRADDTAVYYCAREAPLRLGESPHDAFDIWGQGTMVTVSS |
| 2.61 | SEQ ID NO. 73<br>QVQLVESGGGLVKPGGSLRLSCAASGFTFSDNSMTWMRQAPGKGLEWVSYISTGGGVKYYADSVKGRFTISR<br>DNAKNSLYLQMNSLRADDTAVYYCAREAPLRLGESPHDAFDIWGQGTMVTVSS |
| 2.62 | SEQ ID NO. 74<br>QVQLVESGGGLVKPGGSLRLSCAASGFTFSDSSMTWMRQAPGKGLEWVSYISSGGAVKFYTDSVKGRFTISR<br>DNAKNSLYLQMNSLRADDTAVYYCAREAPLRLGESPHDAFDISGQGTMVTVSS |
| 2.63 | SEQ ID NO. 75<br>EVQLVESGGGLVKPGGSLRLSCAASGFTFSDSSMTWMRQAPGKGLEWVSYISSGGGVKFYTDSVKGRFTISR<br>DNAKNSLYLQMNSLRADDTAVYYCAREAPLRLGESPHDAFDISGQGTMVTVSS |
| 2.64 | SEQ ID NO. 76<br>EVQLVESGGGLVKPGGSLRLSCAASGFTFSDSSMTWMRQAPGKGLEWVSYISSGGGVKFYADSVKGRFTISR<br>DNAKNSLYLQMNSLRADDTAVYYCAREAPLRLGESPHDAFDISGQGTMVTVSS |
| 2.65 | SEQ ID NO. 77<br>QVQLVESGGGLVKPGGSLRLSCAASGFTFSDSSMTWMRQAPGKGLEWVSYISSGGGVKFYADSVKGRFTISR<br>DNAKNSLYLQMNSLRADDTAVYYCAREAPLRLGESPHDAFDISGQGTMVTVSS |
| 2.66 | SEQ ID NO. 78<br>QVQLVESGGGLVKPGGSLRLSCAASGFTFSDSSMTWMRQAPGKGLEWVSYISSGGGVKFYTDSVKGRFTISR<br>DNAKNSLYLQMDSLRADDTAVYYCAREAPLRLGESPHDAFDTSGQGTMVTVSS |
| 2.67 | SEQ ID NO. 79<br>QVQLVESGGGLVKPGGSLRLSCAASGFTFSGSSMTWMRQAPGKGLEWVSYISSGGGVIFYADSVKGRFTISR<br>DNAKNSLYLQMNSLRADDTAVYYCAREAPLRLGESPHDAFDISGQGTMVTVSS |
| 2.68 | SEQ ID NO. 80<br>QVQLVESGGGLVKPGGSLRLSCAASGFTFGDNSMTWMRQAPGKGLEWVSYISSGGGVIFYADSVKGRFTISR<br>DNAKNSLYLQMNSLRADDTAVYYCAREAPLRLGESPHDAFDISGRGTTVTVSS |

TABLE 5-continued

Exemplary V_H single domain antibodies that bind to PD-1 and
can be used in the multispecific molecules of the invention Clone name | Full length 2.69  SEQ ID NO. 81
QVQLVESGGGLVKPGGSLRLSCAASGFTFSDNSMSWMRQAPGKGLEWVSYISSGGGVIFYADSVKGRFTISR
DNAKNSLYLQMNSLRADDTAVYYCAREAPLRLGESPHDAFDISGQGTMVTVSS 2.70  SEQ ID NO. 82
QVQLVESGGGLVKPGGSLRLSCAASGFTFGDSSMTWMRQAPGKGLEWVSYISSGGAVKFYTDSVKGRFTISR
DNAKNSLYLQMNSLRADDTAVYYCAREAPLRLGESPHDAFDISGQGTMVTVSS 2.71  SEQ ID NO. 83
QVQLVESGGGLVKPGGSLRLSCAASGFTFGGSSMTWMRQAPGKGLEWVSYISSGGGVKFYTDSVKGRFTISR
DNAKNSLYLQMNSLRADDTAVYYCAREAPLRLGESPHDAFDISGQGTMVTVSS 2.72  SEQ ID NO. 84
QVQLVESGGGLVKPGGSLRLSCAASGFTFSDSSMSWMRQAPGKGLEWVSYISSGGGVIFYADSVKGRFTISR
DNAKNSLYLQMNSLRADDTAVYYCAREAPLRLGESPHDAFDISGQGTMVTVSS 2.73  SEQ ID NO. 85
QVQLVESGGGLVKPGGSLRLSCAATGFTFSDSSMTWMRQAPGKGLEWVSYISAGGGVRFYTDSVKGRFTISR
DNAKNSLYLQMNSLRADDTAVYYCAREAPLRLGESPHDAFDISGQGTMVTVSS 2.74  SEQ ID NO. 86
EVQLVESGGGLVKPGGSLRLSCAASGFTFSDSSMTWIRQAPGKGLEWVSYISSGGGVKFYTDSVKGRFTISR
DNAKNSLYLQMNSLRADDTAVYYCAREAPLRLGESPHDAFDISGQGTMVTVSS 2.75  SEQ ID NO. 87
EVQLVESGGGLVKPGGSLRLSCAASGFTFSDSSMTWIRQAPGKGLEWVSYISSGGGVKFYTDSVKGRFTISR
DNAKNSLYLQMNSLRAEDTAVYYCAREAPLRLGESPHDAFDISGQGTMVTVSS 2.76  SEQ ID NO. 88
EVQLVESGGGLVKPGGSLRLSCAASGFTFSDSSMTWIRQAPGKGLEWVSYISSGGGVKFYADSVKGRFTISR
DNAKNSLYLQMNSLRADDTAVYYCAREAPLRLGESPHDAFDISGQGTMVTVSS 2.77  SEQ ID NO. 89
EVQLVESGGGLVKPGGSLRLSCAASGFTFSDSSMTWIRQAPGKGLEWVSYISSGGGVKFYTDSVKGRFTISR
DNAKNSLYLQMNSLRAEDTAVYYCAREAPLRLGESPHDAFDISGQGTMVTVSS 2.78  SEQ ID NO. 90
EVQLVESGGGLVKPGGSLRLSCAASGFTFSDSSMTWIRQAPGKGLEWVSYISSGGGVKFYADSVKGRFTISR
DNAKNSLYLQMNSLRAEDTAVYYCAREAPLRLGESPHDAFDISGQGTMVTVSS 2.79  SEQ ID NO. 91
EVQLVESGGGLVKPGGSLRLSCAASGFTFSDSSMTWKRQAPGKGLEWVSYISSGGGVKFYADSVKGRFTISR
DNAKNSLYLQMNSLRAEDTAVYYCAREAPLRLGESPHDAFDISGQGTMVTVSS 2.80  SEQ ID NO. 92
EVQLVESGGGLVKPGGSLRLSCAASGFTFSDSSMTWMRQAPGKGLEWVSYISSGGGVKFYADSVKGRFTISR
DNAKNSLYLQMNSLRAEDTAVYYCAREAPLRLGESPHDAFDISGQGTMVTVSS 2.81  SEQ ID NO. 93
EVQLVESGGGLVKPGGSLRLSCAASGFTFSDSSMTWVRQAPGKGLEWVSYISSGGGVKFYADSVKGRFTISR
DNAKNSLYLQMNSLRAEDTAVYYCAREAPLRLGESPHDAFDISGQGTMVTVSS 2.82  SEQ ID NO. 94
EVQLVESGGGLVKPGGSLRLSCAASGFTFSDTSMTWMRQAPGKGLEWVSYISSGGGVKFYTDSVKGRFTISR
DNAKNSLYLQMNSLRAEDTAVYYCAREAPLRLGESPHDAFDISGQGTMVTVSS 2.83  SEQ ID NO. 95
EVQLVESGGGLVKPGGSLRLSCAASGFTFSDESMTWFRQAPGKGLEWVSYISSGGGVKFYTDSVKGRFTISR
DNAKNSLYLQMNSLRAEDTAVYYCAREAPLRLGESPHDAFDISGQGTMVTVSS 2.84  SEQ ID NO. 96
EVQLVESGGGLVKPGGSLRLSCAASGFTFSDESMTWMRQAPGKGLEWVSYISSGGGVKFYTDSVKGRFTISR
DNAKNSLYLQMNSLRAEDTAVYYCAREAPLRLGESPHDAFDISGQGTMVTVSS 2.85  SEQ ID NO. 97
EVQLVESGGGLVKPGGSLRLSCAASGFTFSDYSMTWMRQAPGKGLEWVSYISSGGGVKFYTDSVKGRFTISR
DNAKNSLYLQMNSLRAEDTAVYYCAREAPLRLGESPHDAFDISGQGTMVTVSS 2.86  SEQ ID NO. 98
EVQLVESGGGLVKPGGSLRLSCAASGFTFSDASMTWMRQAPGKGLEWVSYISSGGGVKFYTDSVKGRFTISR
DNAKNSLYLQMNSLRAEDTAVYYCAREAPLRLGESPHDAFDISGQGTMVTVSS TABLE 5-continued Exemplary V_H single domain antibodies that bind to PD-1 and
can be used in the multispecific molecules of the invention Clone name  Full length 2.87    SEQ ID NO. 99
        EVQLVESGGGLVKPGGSLRLSCAASGFTFSDKSMTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.88    SEQ ID NO. 100
        EVQLVESGGGLVKPGGSLRLSCAASGFTFSDRSMTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.89    SEQ ID NO. 101
        EVQLVESGGGLVKPGGSLRLSCAASGFTFSDYSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.90    SEQ ID NO. 102
        EVQLVESGGGLVKPGGSLRLSCAASGFTFSDVSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.91    SEQ ID NO. 103
        EVQLVESGGGLVKPGGSLRLSCAASGFTFSDQSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.92    SEQ ID NO. 104
        EVQLVESGGGLVKPGGSLRLSCAASGFTFSDESMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.93    SEQ ID NO. 105
        EVQLVESGGGLVKPGGSLRLSCAASGFTFSDASMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.94    SEQ ID NO. 106
        EVQLVESGGGLVKPGGSLRLSCAASGFTFSDWSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.95    SEQ ID NO. 107
        EVQLVESGGGLVKPGGSLRLSCAASGFTFSDGSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.96    SEQ ID NO. 108
        EVQLVESGGGLVKPGGSLRLSCAASGFTFSDTSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.97    SEQ ID NO. 109
        EVQLVESGGGLVKPGGSLRLSCAASGFTFSDISMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.98    SEQ ID NO. 110
        EVQLVESGGGLVKPGGSLRLSCAASGFTFSDKSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.99    SEQ ID NO. 111
        EVQLVESGGGLVKPGGSLRLSCAASGFTFSDRSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.100   SEQ ID NO. 112
        EVQLVESGGGLVKPGGSLRLSCAASGFTFSDLSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.101   SEQ ID NO. 113
        EVQLVESGGGLVKPGGSLRLSCAASGFTFSDFSMTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.102   SEQ ID NO. 114
        EVQLVESGGGLVKPGGSLRLSCAASGFTFSDESVTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.103   SEQ ID NO. 115
        EVQLVESGGGLVKPGGSLRLSCAASGFTFSDESQTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.104   SEQ ID NO. 116
        EVQLVESGGGLVKPGGSLRLSCAASGFTFSDESFTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.105   SEQ ID NO. 117
        EVQLVESGGGLVKPGGSLRLSCAASGFTFSDESLTWMRQAPGKGLEWVSYISSGGGVKFYTDSVKGRFTISR
        DNAKNSLYLQMNSLRAEDTAVYYCAREAPLRLGESPHDAFDISGQGTMVTVSS TABLE 5-continued Exemplary V$_H$ single domain antibodies that bind to PD-1 and
can be used in the multispecific molecules of the invention Clone name   Full length 2.106   SEQ ID NO. 118
        EVQLVESGGGLVKPGGSLRLSCAASGFTFSDESKTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.107   SEQ ID NO. 119
        EVQLVESGGGLVKPGGSLRLSCAASGFTFSDESYTWMRQAPGKGLEWVSYISSGGGVKFYTDSVKGRFTISR
        DNAKNSLYLQMNSLRAEDTAVYYCAREAPLRLGESPHDAFDISGQGTMVTVSS 2.108   SEQ ID NO. 120
        EVQLVESGGGLVKPGGSLRLSCAASGFTFSDESATWMRQAPGKGLEWVSYISSGGGVKFYADSVKGRFTISR
        DNAKNSLYLQMNSLRAEDTAVYYCAREAPLRLGESPHDAFDISGQGTMVTVSS 2.109   SEQ ID NO. 121
        EVQLVESGGGLVKPGGSLRLSCAASGFTFSDESFTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.110   SEQ ID NO. 122
        EVQLVESGGGLVKPGGSLRLSCAASGFTFSDESNTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.111   SEQ ID NO. 123
        EVQLVESGGGLVKPGGSLRLSCAASGFTFSDESWTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.112   SEQ ID NO. 124
        EVQLVESGGGLVKPGGSLRLSCAASGFTFSDESITWMRQAPGKGLEWVSYISSGGGVKFYADSVKGRFTISR
        DNAKNSLYLQMNSLRAEDTAVYYCAREAPLRLGESPHDAFDISGQGTMVTVSS 2.113   SEQ ID NO. 125
        EVQLVESGGGLVKPGGSLRLSCAASGFTFSDESSTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.114   SEQ ID NO. 126
        EVQLVESGGGLVKPGGSLRLSCAASGFTFSDESHTWMRQAPGKGLEWVSYISSGGGVKFYADSVKGRFTISR
        DNAKNSLYLQMNSLRAEDTAVYYCAREAPLRLGESPHDAFDISGQGTMVTVSS 2.115   SEQ ID NO. 127
        EVQLVESGGGLVKPGGSLRLSCAASGFTFSDESGTWMRQAPGKGLEWVSYISSGGGVKFYADSVKGRFTISR
        DNAKNSLYLQMNSLRAEDTAVYYCAREAPLRLGESPHDAFDISGQGTMVTVSS These are encoded by nucleic acids having SEQ ID NO: 128 to 242.

In one embodiment, the V$_H$ that binds to PD-1 is selected from V$_H$ 2.63, 2.77 or 2.92 (SEQ ID NO: 104) as shown above or a sequence having at least 75% homology or identity thereto, for example 80%, 85%, 90% or 95%. In one embodiment, the V$_H$ is V$_H$ 2.63. In one embodiment, the V$_H$ is V$_H$ 2.77. In one embodiment, the V$_H$ is V$_H$ 2.92.

In one aspect, we provide a bi- or multispecific molecule having a first V$_H$ single domain antibody that binds to LAG-3 and a second V$_H$ single domain antibody that binds to PD-1, i.e. a molecule wherein a first single domain antibody is linked to a second single domain antibody of the formula V$_H$(A)-L-V$_H$(B) having one or more of the following properties:

a) binds to LAG-3 and PD-1 on the same cell;
b) brings PD-1 and LAG-3 expressed on the same cell into physical proximity with potency greater than a larger bispecific antibody as demonstrated in table 10;
c) binds to stimulated T cells with greater median fluorescence intensity than LAG-3 or PD-1 V$_H$ alone;
d) stimulates IL-2 in human PBMCs stimulated with superantigen at a level higher than the combination of individual units and higher than the combination of monoclonal antibodies to PD-1 and LAG-3;
e) inhibits tumour growth in mouse model greater than a clinical PD-1 monoclonal antibody
f) induces proliferation of antigen-specific CD8+ T cells greater than PD-1 V$_H$ alone and LAG-3 blockade alone;
g) induces greater proliferation of patient CD4 and CD8 T cells than a PD1 monoclonal antibody;
h) significantly reduces inhibitory signalling in cells unresponsive to combination;
i) binds to LAG3 with substantially higher affinity when PD1 is present;
j) binds to PD1 with substantially higher affinity when LAG3 is present;
k) has lower potency PD1 blockade on PD1+ single positive cells than PD1 antibodies but enhanced targeting of LAG3+PD1+ cells and/or
l) able to rescue T cells in an ex vivo system (see example 8).

In another aspect, we provide a bi- or multispecific binding agent comprising one or more V$_H$ single domain antibody that binds to LAG-3 wherein said V$_H$ single domain antibody is as described herein linked to a V$_H$ single domain antibody that binds to PD-1. In one embodiment, the V$_H$ single domain antibody that binds to PD-1 is selected from one of the V$_H$ single domain antibodies listed in Table 5. In one embodiment, the bi- or multispecific binding agent has one or more of the properties listed above in a) to f).

In some embodiments, the PD-1 binding V$_H$ single domain antibody is a variant of any of the above single V$_H$ domain antibodies binding to human PD-1. The term variant is defined elsewhere herein. For example, the variant is a variant of $V_H$ 2.1 and has 1 to 20, for example 1 to 10 or 1 to 5 amino acid substitutions. In another embodiment, the variant is a variant of $V_H$ and has at least 75% sequence homology or identity thereto, for example 80%, 85%, 90% or 95%.

In one embodiment, the bispecific molecule comprises one single domain antibody that binds to LAG-3 as described herein. In another embodiment, the bispecific molecule comprises two single domain antibodies that bind to LAG-3 as described herein.

In another aspect, we also provide a bispecific binding agent that binds to PD-1 and LAG-3 comprising two single domain antibodies that bind to LAG-3 and one single domain antibody that binds to PD-1. In one embodiment, the two single domain antibodies that bind to LAG-3 are as described above. In one embodiment, the single domain antibody that binds to PD-1 is as described above. The inventors have surprisingly demonstrated that such binding agent comprising two single domain antibodies that bind to LAG-3 has enhanced potency compared to a binding agent comprising one single domain antibody that binds to LAG-3. This can be seen in FIG. 3c which shows enhanced stimulation of IL-2 release. Having two single domain antibodies that bind to LAG-3 that are linked to a single domain antibody that binds to PD-1 in the bi- or multispecific molecule thus provides at least additive effects compared to a binding agent having one single domain antibody that binds to LAG-3. Thus, in one embodiment, the molecule has the following formula: $V_H(A)$-L1-$V_H(A)$-L2-$V_H(B)$ optionally comprises a further C terminal moiety and/or sequence. Thus, there are two single domain antibodies of the same sequence that bind to LAG3 and one single domain antibody that binds to PD-1. Exemplary molecules are the following: $V_H1.1$-L-$V_H1.1$-L-$V_H2.63$; $V_H1.1$-L-$V_H1.1$-L-$V_H2.63$; $V_H2.77$-L-$V_H1.1$-L-$V_H1.1$; and $V_H1.2$-L-$V_H1.2$-L-$V_H2.92$. In one embodiment, the molecule is $V_H1.2$-L-$V_H1.2$-L-$V_H2.92$. L is a linker as further defined herein.

In one embodiment, the molecule is selected from: $V_H1.1$-6GS-$V_H1.1$-6GS-$V_H2.63$; $V_H1.1$-6GS-$V_H1.1$-9GS-$V_H2.63$; $V_H2.77$-9GS-$V_H1.1$-6GS-$V_H1.1$; and $V_H1.2$-6GS-$V_H1.2$-6GS-$V_H2.92$. In one embodiment, the molecule is $V_H1.2$-6GS-$V_H1.2$-6GS-$V_H2.92$ (SEQ ID NO: 259).

In another embodiment, the bispecific binding agent, that is the fusion protein, that simultaneously binds to LAG-3 and PD-1 as described above comprises further binding molecules. Thus, the binding agent can be trispecific or tetraspecific. Additional specificities are also envisaged. Any combination of the aforesaid molecules can be made in a multispecific binding agent, for example, a trispecific binding agent that includes a single domain antibody that binds to LAG-3 and a second and third binding specificity. For example, as explained in more detail below, the third binding specificity may be to human serum albumin (HSA). Thus, the binding agent may comprise the following building blocks: one or two $V_H$ single domain antibodies that bind to LAG-3 as described herein, for example selected from table 1, a $V_H$ single domain antibody that binds to PD-1 and a $V_H$ single domain antibody that binds to HSA. The entities are linked via linkers as described herein. The order of the entities can be flexible, for example the $V_H$ single domain antibody that binds to PD-1 can be located C- or N-terminally.

Thus, in another aspect, we provide a multispecific binding agent as described above which comprises a further moiety that binds to a third target. Said further moiety can be a $V_H$ single domain antibody. This has, for example one of the following formula: $V_H(C)$-L1-$V_H(A)$-L2-$V_H(B)$, $V_H(A)$-L1-$V_H(B)$-L2-$V_H(C)$, $V_H(A')$-L1-$V_H(A')$-L2-$V_H(B)$-L3-$V_H(C)$ or $V_H(C)$-L1-$V_H(A')$-L2-$V_H(A')$-L3-$V_H(B)$. For example, $V_H(A)$ and $V_H(A')$ are both $V_H$ single domain antibodies that bind to LAG-3, $V_H(B)$ is a $V_H$ single domain antibody that binds PD-1 and $V_H(C)$ is a $V_H$ single domain antibody that binds to HSA.

Whilst the preferred aspects relate to molecules that comprise or consist of single domain antibodies, that is molecules that do not have other antibody parts, the invention also extends to molecules that have two binding moiety that bind to LAG3 and one binding moiety that binds to another target, e.g. PD-1. Importantly, the inventors have shown that a bispecific molecule that binds with high affinity to LAG3 favours cells that express both LAG3 and PD-1 and reduces binding to PD-1 single positive cells.

In yet another aspect, we provide a method of simultaneously inhibiting immune PD-1 and LAG-3 by administration of a binding agent as described herein.

Conjugation with Molecules that Prolong Half Life or with Other Moieties

In one embodiment, the further moiety (e.g. the second or third, fourth etc moiety) may serve to prolong the half-life of the binding molecule. The further moiety may comprise a protein, for example an antibody, or part thereof that binds a serum albumin, e.g., human serum albumin (HSA) or mouse serum albumin (MSA). The further moiety may comprise a $V_H$ domain that binds serum albumin, e.g., human serum albumin (HSA) or mouse serum albumin (MSA).

The further moiety may comprise a serum albumin, e.g. a human serum albumin (HSA) or a variant thereof such as HSA C34S. The half life extending moiety may be located at the C terminal end, N terminal end or elsewhere within the binding molecule e.g. "a chain" of linked $V_H$ single domain antibodies.

In one embodiment, the anti-LAG-3 single domain antibodies or multivalent binding agents described herein are labelled with a detectable or functional label. A label can be any molecule that produces or can be induced to produce a signal, including but not limited to fluorophores, fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In still other embodiments, the anti-LAG-3 single domain antibodies or multivalent binding agents described herein are coupled to at least one therapeutic moiety, such as a drug, an enzyme or a toxin. In one embodiment, the therapeutic moiety is a toxin, for example a cytotoxic radionuclide, chemical toxin or protein toxin.

In another aspect, the anti-LAG-3 single domain antibodies or multivalent binding agents described herein are modified to increase half-life, for example by a chemical modification, especially by PEGylation, or by incorporation in a liposome or using a serum albumin protein.

Half-life may be increased by at least 1.5 times, preferably at least 2 times, such as at least 5 times, for example at least 10 times or more than 20 times, greater than the half-life of the corresponding $V_H$ single domain antibodies described herein. For example, increased half-life may be more than 1 hours, preferably more than 2 hours, more preferably more than 6 hours, such as more than 12 hours, or even more than 24, 48 or 72 hours, compared to the corresponding $V_H$ single domain antibodies described herein.

Linkers

In the multivalent binding agents, the subunits can be linked via a chemical or peptide linker. The linkage can be covalent or non-covalent. A preferred covalent linkage is via a peptide bond. As described elsewhere, the multivalent binding agents are preferably in the form of protein fusions. In some embodiments, the multivalent binding agents as described herein, two or more binding molecules are for example connected by a linker, such as a polypeptide linker (L). Suitable linkers include for example a linker with GS residues such as (Gly 4 Ser)n, where n=from 1 to 20, e.g., 1 to 12, e.g. 1, 2, 3, 4, 5, 6, 7, 8, 9, 10, 11 or 12. In one embodiment, n=5, 6, 8 or 12.

Exemplary linkers are 2GS, 4GS, 6GS, 9GS, that is SEQ ID NO: 243, 244, 245, 246, 247, 248, 249 or 250 respectively.

Other linkers will be known to the skilled person.

Exemplary Methods for Making the Single Domain Antibody

A single domain antibody described herein can be obtained or obtainable from a transgenic rodent that expresses heavy chain only antibodies upon stimulation with a recombinant LAG-3 antigen as described in the examples. The transgenic rodent, for example a mouse, preferably has a reduced capacity to express endogenous antibody genes. Thus, in one embodiment, the rodent has a reduced capacity to express endogenous light and/or heavy chain antibody genes. The rodent may therefore comprise modifications to disrupt expression of endogenous kappa and lambda light and/or heavy chain antibody genes so that no functional light and/or heavy chains are produced, for example as further explained below. Exemplary methods for generating a sdAb of the invention are described below.

A method for producing a human heavy chain only antibody capable of binding human LAG-3 said method comprises a) immunising a transgenic rodent with an LAG-3 antigen wherein said rodent expresses a nucleic acid construct comprising unrearranged human heavy chain V genes and is not capable of making functional endogenous light or heavy chains, b) isolating human heavy chain only antibodies.

Further steps can include isolating a $V_H$ domain from said heavy chain only antibody, for example by generating a library of sequences comprising $V_H$ domain sequences from said mouse and isolating sequences comprising $V_H$ domain sequences from said libraries.

A method for producing a single $V_H$ domain antibody capable of binding human LAG-3 said method comprises a) immunising a transgenic rodent with an LAG-3 antigen wherein said rodent expresses a nucleic acid construct comprising unrearranged human heavy chain V genes and is not capable of making functional endogenous light or heavy chains, b) generating a library of sequences comprising $V_H$ domain sequences from said mouse and c) isolating sequences comprising $V_H$ domain sequences from said libraries.

Further steps may include identifying a single $V_H$ domain antibody or heavy chain only antibody that binds to human LAG-3, for example by using functional assays as shown in the examples.

Methods for preparing or generating the polypeptides, nucleic acids, host cells, products and compositions described herein using in vitro expression libraries can comprise the steps of:

a) providing a set, collection or library of nucleic acid sequences encoding amino acid sequences; and b) screening said set, collection or library for amino acid sequences that can bind to/have affinity for LAG-3 and c) isolating the amino acid sequence(s) that can bind to/have affinity for LAG-3.

In the above method, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

Libraries, for example phage libraries, are generated by isolating a cell or tissue expressing an antigen-specific, heavy chain-only antibody, cloning the sequence encoding the $V_H$ domain(s) from mRNA derived from the isolated cell or tissue and displaying the encoded protein using a library. The $V_H$ domain(s) can be expressed in bacterial, yeast or other expression systems.

Another aspect also relates to an isolated $V_H$ single domain antibody or an isolated heavy chain only antibody comprising a $V_H$ domain binding to LAG-3 comprising an amino acid product of or derived from a human $V_H$ germline sequence. The heavy chain only antibody may be fully human or comprise mouse sequences.

The term rodent may relate to a mouse or a rat.

In one embodiment, the rodent is a mouse. The mouse may comprise a non-functional endogenous lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be deleted or rendered non-functional through insertion or other modification as described above. In one embodiment, the locus is functionally silenced so that the mouse does not make a functional lambda light chain.

Furthermore, the mouse may comprise a non-functional endogenous kappa light chain locus. Thus, the mouse does not make a functional endogenous kappa light chain. In one embodiment, the kappa light chain locus is deleted in part or completely or rendered non-functional through insertion, inversion, a recombination event, gene editing or gene silencing. In one embodiment, the locus is functionally silenced so that the mouse does not make a functional kappa light chain.

The mouse having functionally-silenced endogenous lambda and kappa L-chain loci may, for example, be made as disclosed in WO 2003/000737, which is hereby incorporated by reference in its entirety.

Furthermore, the mouse may comprise a non-functional endogenous heavy chain locus. Thus, the mouse does not make a functional endogenous heavy chain. In one embodiment, the heavy chain locus is deleted in part or completely or rendered non-functional through insertion, inversion, a recombination event, gene editing or gene silencing. In one embodiment, the locus is functionally silenced so that the mouse does not make a functional heavy chain.

For example, as described in WO 2004/076618 (hereby incorporated by reference in its entirety), all 8 endogenous heavy chain constant region immunoglobulin genes (μ, δ, γ3, γ1, γ2a, γ2b, ε and α) are absent in the mouse, or partially absent to the extent that they are non-functional, or genes δ, γ3, γ1, γ2a, γ2b and ε are absent and the flanking genes μ, and α are partially absent to the extent that they are rendered non-functional, or genes μ, δ, γ3, γ1, γ2a, γ2b and ε are absent and α is partially absent to the extent that it is rendered non-functional, or δ, γ3, γ1, γ2a, γ2b, ε and α are absent and μ, is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

In one embodiment, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse may comprise a vector, for example a Yeast Artificial Chromosome (YAC) for expressing a heterologous, preferably a human, heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002 Macmillan Publishers Ltd, Nature Publishing Group).

For example, the YAC may comprise a plethora of unrearranged human $V_H$, D and J genes in combination with mouse immunoglobulin constant region genes lacking $C_H1$ domains, mouse enhancer and regulatory regions. The human $V_H$, D and J genes are human $V_H$, D and J loci and they are unrearranged genes that are fully human.

Alternative methods known in the art may be used for deletion or inactivation of endogenous mouse or rat immunoglobulin genes and introduction of human $V_H$, D and J genes in combination with mouse immunoglobulin constant region genes lacking $C_H1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos. Regardless of how the genetic material is introduced, the manipulated embryos are transferred to pseudo-pregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, either conventional or with the inclusion of an IVF step to give efficient scaling of the process. However, it is also possible to include the TKO background during the transgenesis procedure. For example, for microinjection, the oocytes may be derived from TKO donors. Similarly, ES cells from TKO embryos can be derived for use in transgenesis.

Triple knock-out mice into which transgenes have been introduced to express immunoglobulin loci are referred to herein as TKO/Tg. In one embodiment, the mouse is as described in WO 2016/062990 hereby incorporated in its entirety.

Exemplary pharmaceutical compositions In another aspect, there is provided a pharmaceutical composition comprising a binding molecule of the invention e.g. a single domain antibody that binds to LAG-3 as disclosed herein or a binding molecule described herein that comprises a single domain antibody that binds to LAG-3, including bispecific molecules as described herein that binds to both LAG-3 and PD-1, and optionally a pharmaceutically acceptable carrier. A single domain antibody, binding molecule or pharmaceutical composition described herein can be administered by any convenient route, including but not limited to oral, topical, parenteral, sublingual, rectal, vaginal, ocular, intranasal, pulmonary, intradermal, intravitreal, intratumoural, intramuscular, intraperitoneal, intravenous, subcutaneous, intracerebral, transdermal, transmucosal, by inhalation, or topical, particularly to the ears, nose, eyes, or skin or by inhalation. In another embodiment, delivery is of the nucleic acid encoding the drug, e.g. a nucleic acid encoding the molecule of the invention is delivered.

Parenteral administration includes, for example, intravenous, intramuscular, intraarterial, intraperitoneal, intranasal, rectal, intravesical, intradermal, topical or subcutaneous administration. Preferably, the compositions are administered parenterally.

The pharmaceutically acceptable carrier or vehicle can be particulate, so that the compositions are, for example, in tablet or powder form. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the single domain antibody of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The pharmaceutical composition can be in the form of a liquid, e.g., a solution, syrup, solution, emulsion or suspension. The liquid can be useful for oral administration or for delivery by injection, infusion (e.g., IV infusion) or subcutaneously.

When intended for oral administration, the composition can be in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Compositions can take the form of one or more dosage units.

In specific embodiments, it can be desirable to administer the composition locally to the area in need of treatment, or by intravenous injection or infusion.

The amount of the single domain antibody or binding molecule described herein that is effective/active in the treatment of a particular disease or condition will depend on the nature of the disease or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

Typically, the amount is at least about 0.01% of a single domain antibody of the present invention by weight of the composition. When intended for oral administration, this amount can be varied to range from about 0.1% to about 80% by weight of the composition. Preferred oral compositions can comprise from about 4% to about 50% of the sdAb of the present invention by weight of the composition.

Compositions can be prepared so that a parenteral dosage unit contains from about 0.01% to about 2% by weight of the single domain antibody of the present invention.

For administration by injection, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

In another aspect, we provide a CAR construct which comprises an isolated anti —LAG3 $V_H$ single domain antibody as described herein or a multispecific binding agent as described herein, specifically binding agents with single domain antibodies to both PD-1 and LAG3 as described herein.

CARs are synthetic receptors typically consisting of a targeting/binding moiety that is associated with one or more signaling domains in a single fusion molecule. The binding moiety of a CAR typically consists of an antigen-binding domain of a single-chain antibody (scFv) comprising the light and heavy chain variable fragments of a monoclonal antibody joined by a flexible linker. The scFv retains the same specificity and a similar affinity as the full antibody from which it was derived and is capable of binding to the specific target of interest. When a CAR construct is expressed on the surface of a T cell and binds its target protein, T cell activation is triggered. T cell activation is a powerful weapon and non-specific activation of T cells is therefore a major safety concern. scFv are typically used as targeting agents, but they have a number of characteristics that can have a negative impact on the therapeutic efficacy of CAR-Ts. scFv are characterised by poor expression and stability, prone to unfolding and aggregation. As a result, they often make it challenging to achieve CAR expression or are non-specific for targeting of T cells and non-specific for the initiation of signalling. CAR-Ts that have scFv can also form clusters on the membrane due to crosslinking of heavy and light chains of different CAR-Ts. This results in unwanted constitutive signalling.

Furthermore, scFv used in CAR-Ts are also usually derived from mouse mAbs and thus have potential immunogenicity issues as the anti-scFv response not only initiates T cell response by potentially crosslinking but also eradicates CAR-Ts from circulation.

Without wishing to be bound by theory, these problems are likely to be compounded when scFvs are used to design CAR-Ts having bispecific, bivalent or biparatopic antigen binding moieties. Thus, in one aspect, the invention relates to an isolated CAR comprising an antigen binding domain, a transmembrane domain and an intracellular signalling domain wherein said antigen binding domain an isolated anti—LAG3 $V_H$ single domain antibody as described herein or a multispecific binding agent as described herein, specifically binding agents with single domain antibodies to both PD-1 and LAG3 as described herein. The invention also relates to an isolated nucleic acid encoding a CAR according to the invention. The invention also relates to a vector comprising a nucleic acid of the invention. In another aspect, the invention relates to a host cell comprising a nucleic acid or vector of the invention. The invention also relates to an isolated cell or cell population comprising one or more CAR of the invention. Such cell has been genetically modified to express a CAR of the invention. In one embodiment, the cell is a T cell (CAR-T). The invention further relates to a method for treating cancer comprising administering a T cell or pharmaceutical composition of the invention.

Exemplary Therapeutic Applications

The invention also relates to therapeutic applications of the LAG-3 binding molecules of the invention. In one aspect, we provide methods of treating a LAG-3-mediated disease in a mammal, e.g., a human patient, comprising administering an effective amount of a binding molecule of the invention e.g. a binding molecule comprising at least one single domain antibody that binds to LAG-3 as described herein to a mammal in need thereof.

As used herein, "treat", "treating" or "treatment" means inhibiting or relieving a disease. For example, treatment can include a postponement of development of the symptoms associated with a disease, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the term "effective amount" means an amount of an anti-LAG-3 antibody, that when administered alone or in combination with an additional therapeutic agent to a cell, tissue, or subject, is effective to achieve the desired therapeutic or prophylactic effect under the conditions of administration.

The invention also relates to a single domain antibody, binding molecule or pharmaceutical composition described herein for use in the treatment or prevention of a disease.

In another aspect, the invention relates to the use of a single domain antibody, binding molecule or pharmaceutical composition described herein in the treatment or prevention of a disease.

In another aspect, the disclosure relates to the use of a single domain antibody or binding molecule described herein in the manufacture of a medicament for the treatment or prevention of a disease as listed herein.

The disease can be selected from a cancer, an immune disease, neurological disease, inflammatory disease, allergy, transplant rejection, viral infection, immune deficiency, and other immune system-related disease.

In one embodiment, the disease is cancer. The cancer can be selected from a solid or non-solid tumor. For example, the cancer may be selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, prostate cancer, mesothelioma, adrenocortical carcinoma, lymphomas, such as such as Hodgkin's disease, non-Hodgkin's, gastric cancer, leukemias such as ALL, CLL, AML, urothelial carcinoma leukemia and multiple myelomas.

In one embodiment, the tumor is a solid tumor. Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS, neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

In one embodiment, the tumor is a non-solid tumor. Examples of non-solid tumors include leukemia, multiple myeloma and lymphoma.

In one embodiment, the cancer is locally advanced unresectable, metastatic, or recurrent cancer.

Cancers include those whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer).

In one embodiment, the cancer has progressed after another treatment, for example chemotherapy. In one embodiment, the patients are cancer patients treated with anti-PD-1 or anti-PD-L1 therapy. In one embodiment, the patient is selected from a PD1-refractory patient Anticipated improved targeting to double-positive cells could mean improved safety The immune disease can be selected from graft vs. host disease, arthritis, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis.

The inventors have demonstrated that sdAbs that bind to LAG-3 can block the interaction of LAG-3 with alpha synuclein. Alpha-synuclein (also α-synuclein) is a presynaptic neuronal protein that is linked genetically and neuropathologically to Parkinson's disease. α-Synuclein may contribute to PD pathogenesis in a number of ways, but it is generally thought that its aberrant soluble oligomeric conformations, termed protofibrils, are the toxic species that mediate disruption of cellular homeostasis and neuronal death, through effects on various intracellular targets, including synaptic function. Targeting the toxic functions conferred by this protein when it is dysregulated may lead to novel therapeutic strategies not only in PD, but also in other neurodegenerative conditions, termed synucleinopathies (Stefanis, Cold Spring Harb Perspect Med. 2012 February; 2(2)).

Thus, in one embodiment of the aspects recited above, the disease is a neurological disease, for example a synucleinopathy. The neurological disease can be selected from Alzheimer's disease, epilepsy, Parkinson's disease, dementia, multiple sclerosis, peripheral neuropathy or post-herpetic neuralgia.

In one embodiment, the disease is selected from an infectious disease, such as HIV, HCV or parasitic infection.

The single domain antibody, binding molecule or pharmaceutical composition described herein may be administered as the sole active ingredient or in combination with one or more other therapeutic agent. A therapeutic agent is a compound or molecule which is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes.

In one embodiment, single domain antibody, binding molecule or pharmaceutical composition described herein is used in combination with an existing therapy or therapeutic agent, for example an anti-cancer therapy. Thus, in another aspect, the invention also relates to a combination therapy comprising administration of a single domain antibody or pharmaceutical composition of the invention and an anti-cancer therapy. The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the single domain antibody is used in combination with surgery.

In one embodiment, the single domain antibody, binding agent or pharmaceutical composition as described herein is administered together with an immunomodulator, a checkpoint modulator, an agent involved in T-cell activation, a tumor microenvironment modifier (TME) or a tumour-specific target. For example, the immunomodulator can be an inhibitor of an immune checkpoint molecule selected from an inhibitor of one or more of PD-1, PD-L1, PD-L2, CTLA-4, TIM-3, CEACAM, VISTA, BTLA, TIGIT, LAIR1, CD160, 2B4 or TGFR beta. In another embodiment, the immunomodulator can be an activator of a costimulatory molecule selected from an agonist of one or more of OX40, OX40L, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3 or CD83 ligand, CD3, CD8, CD28, CD4 or ICAM-1.

In a specific embodiment of the present invention, the composition is administered concurrently with a chemotherapeutic agent or with radiation therapy. In another specific embodiment, the chemotherapeutic agent or radiation therapy is administered prior or subsequent to administration of the composition of the present invention, preferably at least an hour, five hours, 12 hours, a day, a week, a month, more preferably several months (e. g. up to three months), prior or subsequent to administration of composition of the present invention.

In some embodiments, the single domain antibodies or binding agents described herein may be administered with two or more therapeutic agents. In some embodiments, the binding agents of the invention may be administered with two or more therapeutic agents.

The single domain antibody, pharmaceutical composition or binding molecule described herein may be administered at the same time or at a different time as the other therapy or therapeutic compound or therapy, e.g., simultaneously, separately or sequentially.

In yet another aspect, we provide a method of modulating an immune response in a subject comprising administering to the subject the single domain antibody, pharmaceutical composition or binding molecule described herein such that the immune response in the subject is modulated. In one embodiment, the single domain antibody, pharmaceutical composition or binding molecule described herein enhances, stimulates or increases the immune response in the subject.

In a further aspect, we provide a method of inhibiting growth of tumor cells in a subject, comprising administering to a subject a therapeutically effective amount of a single domain antibody, pharmaceutical composition or binding molecule described herein.

In a further aspect, we provide a method for selectively targeting cells that display PD-1 and LAG3 on their surface providing a binding agent of the invention, for example by administering such binding agent to a patient. In a further aspect, we provide a method for dual blockade of PD-1 and LAG3 on their surface providing a binding agent of the invention, for example by administering such binding agent to a patient. In one embodiment, the method is an in vitro or ex vivo method.

In another aspect, the invention relates to an immunoconjugate comprising a single domain antibody, pharmaceutical composition or binding molecule described herein conjugated to at least one therapeutic and/or diagnostic agent.

We have also identified that E3 ubiquitin ligases Cbl-b and/or c-Cbl can be used as predictive biomarkers for therapy with a bispecific anti-LAG+anti-PD1 binding molecule. A prognostic biomarker provides information about the patients overall cancer outcome, regardless of therapy, whilst a predictive biomarker gives information about the effect of a therapeutic intervention. Thus, the invention also relates to the use of Cbl-b and/or c-Cbl as a predictive biomarker in cancer therapy with a bispecific anti-LAG+anti-PD1 binding molecule. The invention also relates to a method for identifying a subject that responds to therapy with a bispecific anti-LAG+anti-PD1 binding molecule, for example as described herein, such as $V_H1.2\text{-}L\text{-}V_H1.2\text{-}L\text{-}Vh2.92$, by measuring the protein or RNA expression of Cbl-b and/or c-Cbl in said subject or a sample thereof exposed to the bispecific therapy. Suppression or reduction of Cbl-b and/or c-Cbl expression indicates that the subject is responsive to the therapy. This is supported by the data in example 9 showing the link between these markers and proliferation of cells.

We also provide a method for providing a prediction of the outcome of a therapy for a subject with cancer or a method for selecting therapy for a suffering from cancer, the method comprising:
a) contacting a biological sample from the subject with a bispecific anti-LAG+anti-PD1 binding molecule, for example as described herein, such as $V_H1.2\text{-}L\text{-}V_H1.2\text{-}L\text{-}V_H2.92$;
b) measuring protein or RNA expression of Cbl-b and/or c-Cbl in the sample;
c) determining a riskscore of the subject based on the protein or RNA levels of expression of Cbl-b and/or c-Cbl in the sample; and
d) providing a prognosis for the response to therapy with the bispecific binding molecule based on the risk score of the subject.

In one aspect, we provide a method of treatment of a subject with cancer comprising the steps of predicting a level of response to therapy for a subject with cancer the method comprising
a) contacting a biological sample from the subject with a bispecific anti-LAG+anti-PD1 binding molecule, for example as described herein, such as $V_H1.2\text{-}L\text{-}V_H1.2\text{-}L\text{-}V_H2.92$;
b) measuring protein or RNA expression of Cbl-b and/or c-Cbl in the sample;
c) determining a riskscore of the subject based on the protein or RNA levels of expression of Cbl-b and/or c-Cbl in the sample;
d) comparing the riskscore to a threshold to predict whether the subject is likely to respond to therapy with the bispecific binding molecule;
e) selecting a treatment and
f) administering the treatment.

In one embodiment, the treatment is with a bispecific molecule as described herein.

In one embodiment, the sample is incubated with the bispecific binding agent. In one embodiment, the sample is a blood sample. In one embodiment, T cells are isolated form the blood sample and incubated with the agent. Expression of Cbl-b and/or c-Cbl can be measured using standard methods, for example using agents that bind to the protein or RNA, including primers. Also is provided a kit for use in a method as above which comprises reagents that bind to Cbl-b and/or c-Cbl and can be used to measure protein or nucleic acid expression.

Kits and Diagnostic Tests

In another aspect, the invention provides a kit for the treatment or prevention of a disease or an immune response and/or for detecting LAG-3 for diagnosis, prognosis or monitoring disease comprising a single domain antibody of the invention. Such a kit may contain other components, packaging, instructions, or material to aid in the detection of LAG-3 protein. The kit may include a labeled single domain antibody or binding agent as described herein and one or more compounds for detecting the label.

The invention in another aspect provides a single domain antibody or binding agent as described herein of the invention packaged in lyophilized form, or packaged in an aqueous medium.

The invention also relates to a single domain antibody or a binding molecule as described herein with reference to the figures and examples.

In another aspect, a single domain antibody or a binding molecule as described herein are used for non-therapeutic purposes, such as diagnostic tests and assays. A method for detecting the presence of human LAG-3 in a test sample, e.g. serum or plasma, comprises contacting said sample with a single domain antibody as described herein and at least one detectable label and detecting binding of said single domain antibody to human LAG-3.

In one embodiment, the invention relates to a method of diagnosing a LAG-3-mediated adaptive immune resistance in a patient who has cancer. The method comprises contacting a sample with a single domain antibody disclosed herein that has been labelled with a detectable moiety; and detecting expression of LAG-3 on immune cells, for example CD4+ T cells, CD8+ T cells, T regulatory cells, B cells, NK cells and plasmacytoid dendritic cells. The sample may be tumor tissue.

Modifications of antibodies for diagnostic purposes are well known in the art. For example, antibodies may be modified with a ligand group such as biotin, or a detectable marker group such as a fluorescent group, a radioisotope, or an enzyme. Compounds of the invention can be labelled using conventional techniques. Suitable detectable labels include but are not limited to fluorophores, chromophores, radioactive atoms, electron-dense reagents, enzymes, and ligands having specific binding partners.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene accession numbers and references to patent publications. "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1. Construction of Tg/TKO Mice

Mice carrying a human heavy-chain antibody transgenic locus in germline configuration within a background that is silenced for endogenous heavy and light chain antibody expression (triple knock-out, or TKO) were created as previously described (WO2004/076618, WO2003/000737, Ren et al., Genomics, 84, 686, 2004; Zou et al., J. Immunol., 170, 1354, 2003 and WO2016/062990). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K.

Yeast Artificial Chromosomes, Encyclopedia of Life Sciences, 2002, Macmillan Publishers Ltd., Nature Publishing Group/www.els.net).

The YAC used comprised multiple human heavy chain V genes, multiple human heavy chain D and J genes, a murine $C_H1$ gene and a murine 3' enhancer gene. It lacks the $C_H1$ exon.

The transgenic founder mice were back crossed with animals that lacked endogenous immunoglobulin expression to create the Tg/TKO lines used in the immunisation studies described below.

Example 2. Antigen for Immunisation and Characterisation

LAG-3

Human and monkey LAG-3 extracellular domains were made as IgG fusion proteins for immunisation of transgenic mice or for binding studies. Human LAG-3 sequence accession NM_002286. Rhesus LAG-3 accession XM_001108923. The amino acid sequence for Rhesus monkey matches that of Cynomolgus monkey for LAG3 domains 1-3 (NC_022282). Mouse LAG3 was from R&D Biotechne (cat 3328-L3). Human LAG-3 domains 1~4 and 1-2 were cloned using standard molecular biology techniques. Domains were identified as per Huard et al 1997 PNAS 94:5744-9. Expression was performed in HEK 293 cells and the LAG3 proteins were purified using size exclusion chromatography. Chinese Hamster Ovary (CHO) cells expressing human LAG-3 were generated using the human LAG-3 sequence within an inducible expression vector. The plasmid was transfected using lipofection and stable cell pool selected with antibiotics. Cells expressing LAG-3 were sorted based on positive binding of mouse anti-LAG3 antibody (clone 17B4, Abcam).

PD-1

The immunisations used recombinant human PD-1 Fc chimera purchased from R&D, catalogue number 1086-PD. CHO cell lines expressing human PD-1 on the surface were used for characterisation.

Example 3. Immunisation Protocol

Tg/TKO mice aged 8-12 weeks of age each received an initial prime dose of 40 μg of recombinant purified human LAG-3-Fc protein emulsified in Complete Freund's Adjuvant and delivered subcutaneously, followed by three boosts of 10 μg of the recombinant protein, emulsified in Incomplete Freund's Adjuvant, also administered subcutaneously, given at various intervals following the initial priming. A final dose of 20 μg recombinant purified human LAG-3-Fc protein antigen was administered intraperitoneally, in phosphate buffered saline, in the absence of adjuvant.

For immunisations to generate PD-1 blockers, Tg/TKO mice aged 8-12 weeks of age each received an initial prime dose of either 50 μg or 10 μg of recombinant purified human PD-1-Fc protein

Example 4. Generation of Anti-LAG3 Libraries from Immunised Mice

Generation of libraries from immunised mice described above followed standard protocols of library generation as summarised below:

a) Tissue Collection and Homogenisation, RNA Extraction and RT-PCR

Spleen, inguinal and brachial lymph nodes were collected into RNAlater® from several immunised mice. RNA was extracted from total spleen using Qiagen RNeasy® kit (cat 74104) following the manufacturer's protocol or via the Kingfisher automated system (Thermo) using Pure RNA Tissue kit (cat 98040496). $V_H$ sequences were mined from the RNA samples using Superscript III RT-PCR high-fidelity kit (Invitrogen cat 12574-035) according to the manufacturer's protocol.

b) Cloning into Phagemid Vector

The phagemid vector, pUCG3, was employed in these studies. A conventional PCR-based method was used to construct the $V_H$ phagemid libraries from the amplified $V_H$ sequences. Purified $V_H$ RT-PCR products were used to prime a PCR reaction from the linearised pUCG3 resulting in a heterogeneous population of $V_H$ cloned into pUCG3.

PCR products were analysed on a 1% (w/v) agarose gel.

c) Generation of Phagemid Library $V_H$/phagemid PCR products were purified using Fermentas PCR purification kit (cat. no. K0702) according to the manufacturer's instructions. Eluted DNA was used to transform TG1 E. coli (Lucigen, cat. no. 60502-2) by electroporation using the Bio-Rad GenePulser Xcell. Electroporated cells were pooled and plated on large format 2xTY agar Bioassay dishes supplemented with 2% (w/v) glucose and 100 µg/ml ampicillin. All agar plates were incubated overnight at 30° C.

Libraries were harvested by adding broth to the large format bioassay dishes and resuspension of the colonies. Bacterial colonies were pooled and used in a phage selection process.

Example 5. Selection Strategies for Isolation of $V_H$

Preparation of library phage stocks and phage display selections were performed according to published methods (Antibody Engineering, edited by Benny Lo, chapter 8, p161-176, 2004). In most cases, phage display combined with a panning approach was used to isolate binding $V_H$ domains. However, a variety of different selection methods are well described in the art, including soluble selection and selections performed under stress (e.g., heat).

Example 6. Formatting

Each individual $V_H$ clone as identified as binding to LAG-3 recombinant protein or CHO cells expressing LAG-3 was sequenced from the phagemid and grouped based on $V_H$ germline and CDR3 amino acid similarity.

Screening of Periplasmic Extracts for Binding to CHO human PD-1 Cells and Inhibition of PD-L1 Binding PD-1 was carried out. Following selections of the libraries, specific $V_H$ that bound to CHO cells expressing human PD-1 and inhibited the interaction between recombinant human PD-1 protein and recombinant human PD-L1 protein were identified by single point screening of bacterial periplasmic extracts. Families of $V_H$ were identified that bound to the CHO human PD-1 cells with FL2 fluorescence >1000 and that inhibited PD-1 binding to PD-L1.

Constructs bivalent for LAG-3 binding were generated by PCR assembly, using glycine-serine linkers between $V_H$. Assembled constructs were cloned into DNA vectors for expression in microbial cells. Examples of such sequences with different linkers are shown below. The construct used in the experiments each additionally included a C terminal sequence with three alanines and a His tag of six histidines.

$V_H1.1-6GS-V_H1.1-6GS-V_H2.63-His6$
SEQ ID NO. 251
EVQLVESGGGVVRPGGSLRLSCSASGFTFDDYGMSWVRQAPGKGLEWVSG
IHWNGGNSGYADSVKGRFTISRDNAKNSLYLQMNSLRAEDTALYYCARIP
REDCSSASCYTDAIDFWGPGTMVTVSSGGGGSGGGGSGGGGSGGGGSGGG
GSGGGGSEVQLVESGGGVVRPGGSLRLSCSASGFTFDDYGMSWVRQAPGK
GLEWVSGIHWNGGNSGYADSVKGRFTISRDNAKNSLYLQMNSLRAEDTAL
YYCARIPREDCSSASCYTDAIDFWGPGTMVTVSSGGGGSGGGGSGGGGSG
GGGSGGGGSGGGGSEVQLVESGGGLVKPGGSLRLSCAASGFTFSDSSMTW
MRQAPGKGLEWVSYISSGGGVKFYTDSVKGRFTISRDNAKNSLYLQMNSL
RADDTAVYYCAREAPLRLGESPHDAFDISGQGTMVTVSSAAAHHHHHH $V_H1.1-6GS-V_H1.1-9GS-V_H2.63-His6$
SEQ ID NO. 252
EVQLVESGGGVVRPGGSLRLSCSASGFTFDDYGMSWVRQAPGKGLEWVSG
IHWNGGNSGYADSVKGRFTISRDNAKNSLYLQMNSLRAEDTALYYCARIP
REDCSSASCYTDAIDFWGPGTMVTVSSGGGGSGGGGSGGGGSGGGGSGGG
GSGGGGSEVQLVESGGGVVRPGGSLRLSCSASGFTFDDYGMSWVRQAPGK
GLEWVSGIHWNGGNSGYADSVKGRFTISRDNAKNSLYLQMNSLRAEDTAL
YYCARIPREDCSSASCYTDAIDFWGPGTMVTVSSGGGGSGGGGSGGGGSG
GGGSGGGGSGGGGSEVQLVESGGGLVKPGGSLRLSCAASGFTFSDSSMTW
MRQAPGKGLEWVSYISSGGGVKFYTDSVKGRFTISRDNAKNSLYLQMNSL
RADDTAVYYCAREAPLRLGESPHDAFDISGQGTMVTVSSAAAHHHHHH $V_H1.1-6GS-V_H1.1-His6$
SEQ ID NO. 253
EVQLVESGGGVVRPGGSLRLSCSASGFTFDDYGMSWVRQAPGKGLEWVSG
IHWNGGNSGYADSVKGRFTISRDNAKNSLYLQMNSLRAEDTALYYCARIP
REDCSSASCYTDAIDFWGPGTMVTVSSGGGGSGGGGSGGGGSGGGGSGGG
GSGGGGSEVQLVESGGGVVRPGGSLRLSCSASGFTFDDYGMSWVRQAPGK
GLEWVSGIHWNGGNSGYADSVKGRFTISRDNAKNSLYLQMNSLRAEDTAL
YYCARIPREDCSSASCYTDAIDFWGPGTMVTVSSAAAHHHHHH $V_H1.1-4GS-V_H1.1-His6$
SEQ ID NO. 254
EVQLVESGGGVVRPGGSLRLSCSASGFTFDDYGMSWVRQAPGKGLEWVSG
IHWNGGNSGYADSVKGRFTISRDNAKNSLYLQMNSLRAEDTALYYCARIP
REDCSSASCYTDAIDFWGPGTMVTVSSGGGGSGGGGSGGGGSGGGGSEVQ
LVESGGGVVRPGGSLRLSCSASGFTFDDYGMSWVRQAPGKGLEWVSGIHW
NGGNSGYADSVKGRFTISRDNAKNSLYLQMNSLRAEDTALYYCARIPRED
CSSASCYTDAIDFWGPGTMVTVSSAAAHHHHHH $V_H1.1-8GS-V_H1.1-His6$
SEQ ID NO. 255
EVQLVESGGGVVRPGGSLRLSCSASGFTFDDYGMSWVRQAPGKGLEWVSG
IHWNGGNSGYADSVKGRFTISRDNAKNSLYLQMNSLRAEDTALYYCARIP
REDCSSASCYTDAIDFWGPGTMVTVSSGGGGSGGGGSGGGGSGGGGSGGG
GSGGGGSGGGGSEVQLVESGGGVVRPGGSLRLSCSASGFTFDDYG
MSWVRQAPGKGLEWVSGIHWNGGNSGYADSVKGRFTISRDNAKNSLYLQM
NSLRAEDTALYYCARIPREDCSSASCYTDAIDFWGPGTMVTVSSAAAHHH
HHH $V_H1.1-12GS-V_H1.1-His6$
SEQ ID NO. 256
EVQLVESGGGVVRPGGSLRLSCSASGFTFDDYGMSWVRQAPGKGLEWVSG
IHWNGGNSGYADSVKGRFTISRDNAKNSLYLQMNSLRAEDTALYYCARIP
REDCSSASCYTDAIDFWGPGTMVTVSSGGGGSGGGGSGGGGSGGGGSGGG
GSGGGGSGGGGSGGGGSGGGGSGGGGSGGGGSEVQLVESGGGVVR
PGGSLRLSCSASGFTFDDYGMSWVRQAPGKGLEWVSGIHWNGGNSGYADS
VKGRFTISRDNAKNSLYLQMNSLRAEDTALYYCARIPREDCSSASCYTDA
IDFWGPGTMVTVSSAAAHHHHHH

-continued

V$_H$2.77-9GS-V$_H$1.1-6GS-V$_H$1.1-His6
SEQ ID NO. 257
EVQLVESGGGLVKPGGSLRLSCAASGFTFSDSSMTWMRQAPGKGLEWVSY

ISSGGGVKFYTDSVKGRFTISRDNAKNSLYLQMNSLRAEDTAVYYCAREA

PLRLGESPHDAFDISGQGTMVTVSSGGGGSGGGGSGGGGSGGGGSGGGGS

GGGGSGGGGSGGGGSGGGGSEVQLVESGGGVVRPGGSLRLSCSASGFTFD

DYGMSWVRQAPGKGLEWVSGIHWNGGNSGYADSVKGRFTISRDNAKNSLY

LQMNSLRAEDTALYYCARIPREDCSSASCYTDAIDFWGPGTMVTVSSGGG

GSGGGGSGGGGSGGGGSGGGGSGGGGSEVQLVESGGGVVRPGGSLRLSCS

ASGFTFDDYGMSWVRQAPGKGLEWVSGIHWNGGNSGYADSVKGRFTISRD

NAKNSLYLQMNSLRAEDTALYYCARIPREDCSSASCYTDAIDFWGPGTMV

TVSSAAAHHHHHH

V$_H$1.2-6GS-V$_H$1.2-6GS-V$_H$2.92-His6
SEQ ID NO. 258
EVQLVESGGGVVRPGGSLRLSCAASGFTFDDYGMSWVRQAPGKGLEWVSG

IHWNGGSTGYADSVKGRFTISRDNAKNSLYLQMNSLRAEDTALYYCARIP

REDCSSASCYTDAIDFWGQGTMVTVSSGGGGSGGGGSGGGGSGGGGSGGG

GSGGGGSEVQLVESGGGVVRPGGSLRLSCAASGFTFDDYGMSWVRQAPGK

GLEWVSGIHWNGGSTGYADSVKGRFTISRDNAKNSLYLQMNSLRAEDTAL

YYCARIPREDCSSASCYTDAIDFWGQGTMVTVSSGGGGSGGGGSGGGGSG

GGGSGGGGSGGGGSEVQLVESGGGLVKPGGSLRLSCAASGFTFSDESMTW

MRQAPGKGLEWVSYISSGGGVKFYADSVKGRFTISRDNAKNSLYLQMNSL

RAEDTAVYYCAREAPLRLGESPHDAFDISGQGTMVTVSSAAAHHHHHH

V$_H$1.2-6GS-V$_H$1.2-6GS-V$_H$2.92
SEQ ID NO. 259
EVQLVESGGGVVRPGGSLRLSCAASGFTFDDYGMSWVRQAPGKGLEWVSG

IHWNGGSTGYADSVKGRFTISRDNAKNSLYLQMNSLRAEDTALYYCARIP

REDCSSASCYTDAIDFWGQGTMVTVSSGGGGSGGGGSGGGGSGGGGSGGG

GSGGGGSEVQLVESGGGVVRPGGSLRLSCAASGFTFDDYGMSWVRQAPGK

GLEWVSGIHWNGGSTGYADSVKGRFTISRDNAKNSLYLQMNSLRAEDTAL

YYCARIPREDCSSASCYTDAIDFWGQGTMVTVSSGGGGSGGGGSGGGGSG

GGGSGGGGSGGGGSEVQLVESGGGLVKPGGSLRLSCAASGFTFSDESMTW

MRQAPGKGLEWVSYISSGGGVKFYADSVKGRFTISRDNAKNSLYLQMNSL

RAEDTAVYYCAREAPLRLGESPHDAFDISGQGTMVTVSS

Mutations were made to V$_H$ 1.1 in order to revert parts of the sequence to germline, improve binding kinetics or to remove biophysical liabilities such as isomerisation or deamidation. Individual mutations or randomisation was achieved using standard overlap extension PCR methodology. V$_H$ 1.2 (SEQ ID NO: 8) is an example of such a sequence.

Bispecific constructs were generated by PCR assembly. Table 5 show amino sequences of PD1 clones that may be combined with sequences from Table 1 in any orientation, using linkers. Corresponding nucleic acid sequences are also provided herein. Assembled constructs were cloned into DNA vectors for expression in microbial cells.

Example 7. Preparation of Purified V$_H$

Humabody® V$_H$ were expressed by microbial cell systems. Protein was resolved from cell supernatant using affinity purification. Yields of purified protein were estimated spectrophotometrically and purity was assessed using UPLC-SEC. Stability was assessed by overnight incubation at 40° C. and analysis by size exclusion chromatography. Briefly, purified V$_H$ were stored at 3-10 mg/ml in PBS buffer at either 4° C. or 40° C., and then analysed using a Waters H-Class Bio UPLC containing a PDA detector (detection at 280 nm) with separation on a Waters ACQUITY BEH 125 Å SEC column. Samples were injected in 10 µl volumes and were run in a mobile phase containing 200 mM NaCl, 100 mM sodium phosphate, pH 7.4+5% propan-1-ol at a flow rate of 0.4 ml/min. Data were collected for 6 minutes and the percentage of monomer remaining after storage as compared to that present at the start (T=0) was calculated.

V$_H$ 1.1 at 10 mg/ml was incubated at 40° C. for 14 days and size exclusion chromatography demonstrated 97.67% purity of the V$_H$ peak relative to unheated peak area.

V$_H$ 1.1-6GS-V$_H$ 1.1 at 3 mg/ml was incubated at 40° C. overnight and peak area was 100.1% of T=0. 1.1-6GS-1.1-9GS-2.63 at 1.5 mg/ml was incubated at 40° C. overnight and peak area was 100.34% of T=0. Therefore these formats demonstrate excellent stability.

Example 8. Binding Characteristics of Constructs

Purified V$_H$ were tested for their ability to bind to the following: human LAG-3 (R&D Systems cat no. 2319-L3), Rhesus monkey LAG-3 (see example 2), mouse LAG-3 (Sino Biological cat no. 53069-M02H), human LAG-3 domains 1-2 (see example 2), CHO cells expressing human LAG-3, human PD-1 (R&D systems cat no. 1086-PD) and activated T cells.

For screening for binding to CHO cells expressing human LAG-3, reagents were prepared in FMAT assay buffer (pH 7.4) containing PBS, 0.1% Bovine Serum Albumin, 0,01% Sodium Azide. V$_H$ were transferred into 384 well assay plates (Costar cat. no. 3655) and incubated for 2 hours with 1.5 nM Anti-His (Millipore cat. no. 05-949)/3 nM Goat Anti-Mouse Alexa Fluor-488 (Jackson Immunolabs cat. no. 115-545-071) and 2000 CHO human LAG-3 cells prestained with DRAQ5 (Thermo Scientific cat. no. 62251). Plates were read in the FL2 (502 nm-537 nm) and FL5 (677-800 nm) channels on the TTP Mirrorball plate reader following excitation at 488 nm and 640 nm. Data was gated on FL5 perimeter and peak intensity and the FL2 median mean fluorescence intensity of the gated data used for determination of V$_H$ binding. V$_H$ 1.1 demonstrated binding to LAG-3 expressed on CHO cells with a mean EC50 of 1.8E-09M, n=2.

To screen specificity by ELISA, antigens were coated at 1-5 ug/ml and blocked with Marvel milk powder. V$_H$ were added at 10 µg/ml and incubated for 1 hour. After washing, HRP-conjugated anti-HIS antibody (Miltenyi cat no. 130-092-785) was added. TMB substrate and acidic solution were used to develop colorimetric signal. V$_H$ 1.1 and V$_H$ 1.1-6GS-V$_H$ 1.1 bind to human LAG-3, cynomolgus LAG-3 and human LAG3 domains 1-2 with a signal >10fold over background. They did not demonstrate binding to mouse LAG-3, human IgG1, mouse IgG2a or closely related antigen, CD4 (R&D Biotechne 514-CD). 1.2-6GS-1.2-6GS-2.92 shows no binding to CD4, CD28, CTLA4 proteins when testing with real-time bio-layer interferometer based biosensor Octet (ForteBio).

Binding kinetics were measured in real-time bio-layer interferometer based biosensor Octet (ForteBio). Recombinant human LAG-3-Fc was immobilized by standard amine coupling to amine reactive biosensors in 10 mM sodium acetate at pH 5.0. All the binding studies were performed in HBS-ET Octet kinetics buffer. Biosensors were washed in Octet kinetics buffer in between different steps. A seven point, two-fold dilution series of each Humabody® $V_H$ was made with a top concentration of 1.6 µM. The contact time for each of the association steps was 150 seconds and the dissociation step was 300-400 seconds. Kinetic association (k a) and dissociation (K) rate constants were determined by processing and fitting the data to a 1:1 binding model using ForteBio Analysis software. The calculated affinity constants for a selection of sequences are shown in Table 6 below.

| $V_H$ ID | KD (M) | kon (1/Ms) | kdis (1/s) |
|---|---|---|---|
| 1.1 | 3.13E−08 | 2.62E+04 | 8.90E−04 |
| variant 1 | 3.55E−08 | 2.70E+04 | 9.12E−04 |
| variant 5 | 7.90E−09 | 6.55E+04 | 5.17E−04 |
| variant 8 | 1.30E−08 | 9.67E+04 | 1.26E−03 |
| variant 6 | 3.13E−08 | 1.10E+05 | 3.43E−03 |
| variant 7 | 3.55E−08 | 2.39E+04 | 8.47E−04 |
| variant 4 | 8.41E−09 | 5.69E+04 | 4.79E−04 |
| variant 3 | 3.45E−08 | 2.61E+04 | 8.99E−04 |
| 1.2 | 7.21E−08 | 2.48E+04 | 1.79E−03 |
| Variant 9 | 5.32E−08 | 7.21E+04 | 3.83E−03 |

Binding kinetics for multi-valent and bispecific $V_H$ were also measured in real-time bio-layer interferometer based biosensor Octet (ForteBio). Recombinant human LAG-3-Fc or domains1-2-Fc were immobilized by protein G biosensors. All the binding studies were performed in HBS-ET Octet kinetics buffer. Biosensors were washed in Octet kinetics buffer in between different steps. A seven point, two-fold dilution series of each Humabody® $V_H$ was made with a top concentration of 25 nM (full length LAG-3, or 400 nM truncated). The contact time for each of the association steps was 150 seconds and the dissociation step was 400 seconds. To measure kinetics for cynomoigus LAG-3, protein was immobilised using ARG2 sensors in 10 mM sodium acetate pH5, $V_H$ concentration started at 1.6 µM and association time was 180 seconds. To compare the constructs, kinetic association ($k_a$) and dissociation ($k_d$) rate constants were determined by processing and fitting the data to a 1:1 binding model using ForteBio Analysis software. Values are shown in table 7.

TABLE 7

| | Humabody | $K_{on}$ (1/Ms) | $K_{dis}$ (1/s) | $K_D$ (M) |
|---|---|---|---|---|
| Human LAG3 | 1.1-6GS-1.1 | 1.13E+06 | 4.70E−04 | 4.17E−10 |
| | 1.1 | 2.78E+04 | 9.05E−04 | 3.26E−08 |
| | 1.1-6GS-1.1-9GS-2.63 | 7.62E+05 | 3.03E−04 | 3.97E−10 |
| | 1.1-6GS-1.1-6GS-2.63 | 7.64E+05 | 3.05E−04 | 3.99E−10 |
| | 1.2-6GS-1.2 | 1.50 + 06 | 1.12E−03 | 7.44E−10 |
| LAG3 domains 1-2 | 1.1-6GS-1.1 | 6.44E+05 | 5.22E−04 | 8.11E−10 |
| | 1.1 | 1.62E+04 | 1.10E−03 | 6.75E−08 |
| Cynomolgus LAG3 | 1.2-6GS-1.2 | 2.76E+05 | 1.48E−04 | 5.36E−10 |
| | 1.1 | 8.65E+03 | 2.22E−04 | 2.56E−08 |

Binding to PD-1 was measured by HTRF (homogeneous time resolved fluorescence). Serially diluted HIS-tagged constructs were prepared in assay buffer containing PBS, 0.1% BSA and 0.4M Potassium Fluoride. Samples or assay buffer (non-specific binding) were incubated with 1-2 nM human LAG-3-Fc/PD-1-Fc, 1 nM Anti human-Fc Cryptate PAb (Cisbio cat. no. 61HFCKLB) and 15 nM anti His-D2 (CisBio cat no 61HISDLA) in plates for a minimum of 3 hours at room temperature. Time-resolved fluorescent emission at 620 nm and 665 nm was measured following excitation at 337 nm on the BMG PHERAstar plate reader. The HTRF ratio were calculated ((665 nm emission/620 nm emission)*10000) and the data corrected for (non-specific binding) to give the specific binding signal. EC50 were calculated from the titration curve (table 8 below).

TABLE 8

| | 1.1-6GS-1.1-9GS-2.63 | 1.1-6GS-1.1-6GS-2.63 |
|---|---|---|
| LAG-3-Fc HTRF EC50 (M) | 7.8E−10 | 5.1E−1 0 |
| PD-1-Fc HTRF EC50 (M) | 6.0E−10 | 5.9E−10 |

The binding of 1.2-6GS-1.2-6GS-2.92 to proteins was measured using bio-layer interferometer based biosensor Octet (ForteBio). LAG3 antigens were coupled to ARG2 sensors via amine coupling and sample tested in dilution series. PD1 antigens were captured using Protein G sensors. The affinity measurements are shown in table 9.

TABLE 9

| Target | $K_D$ (M) | $k_{on}$ (1/(Ms)) | $k_{dis}$ (1/s) |
|---|---|---|---|
| Human LAG3 | 1.42E−09 | 1.45E+05 | 2.06E−04 |
| Cynomolgus LAG3 | 1.32E−09 | 1.40E+05 | 1.84E−04 |
| Human PD1 | 2.94E−09 | 2.26E+05 | 6.65E−04 |
| Cynomolgus PD1 | 4.36E−09 | 1.57E+05 | 6.85E−04 |

The ability of the construct to bind both targets simultaneously was demonstrated using bio-layer interferometer based biosensor Octet (ForteBio). Recombinant LAG3-Fc (10 µg/ml) was immobilised by standard amine coupling to amine reactive biosensors in 10 mM sodium acetate at pH6. The binding steps were performed in 0.1% BSA 0.02% Tween20 in PBS. 100 nM of Humabody® were used in the first binding step, followed by binding of human PD1-Fc at 5 µg/ml. The contact time for association and dissociation was 200 seconds. FIG. 1 shows 1.1-6GS-1.1-6GS-2.63 binding to LAG-3 and PD-1.

The binding to targets on the cell surface was demonstrating using a cell line developed by DiscoverX corporation. Human LAG-3 and human PD-1 were expressed on the surface of cells and their intracellular domains fused to enzyme fragments. Dimerization of the receptors forces complementation of the enzyme fragments and addition of substrate generates chemiluminescent signal. EC50 were calculated from fold increase in relative light units above background and are shown in table 10. The bispecific molecules show higher signal and improved EC50 over that of a bispecific antibody of a larger size, demonstrating potent dual-engagement.

TABLE 10

| Binding molecule | $EC_{50}$ (M) (n = 2) | Top fold increase in RLU (n = 2) |
|---|---|---|
| $V_H$ 1.2-6GS- $V_H$ 1.2-6GS- $V_H$ 2.92 | 5.5E−11, 7.6E−11 | 3.7, 5.7 |
| $V_H$ 1.2-6GS- $V_H$ 1.2 | No signal | n/a |
| $V_H$ 1.2-6GS- $V_H$ 1.2 + $V_H$ 2.92 | No signal | n/a |

TABLE 10-continued

| Binding molecule | EC$_{50}$ (M) (n = 2) | Top fold increase in RLU (n = 2) |
|---|---|---|
| bispecific antibody with 4 binding sites (2 for LAG-3 and 2 for PD-1) and an Fc region | 1.2E–10, 1.5E–10 | 3.2, 4.4 |

Binding of Humabody® constructs to LAG3 and PD1 antigen was determined using Dynamic Biosensors switchSENSE technology with dual-colour detection. The antigens were covalently attached to the biosensor surface using amine-coupling method, each antigen was linked to a different nanolever, with red or green fluorescent tag. Binding of a bispecific construct was measured to individual antigens alone or where both antigens were present on the surface simultaneously. Kinetics of the interactions with each antigen are shown in table 11.

Binding of 1.2-6GS-1.2-6GS-2.92 to LAG3 improves affinity KD 68-fold when PD-1 is present. Binding to PD1 has a 107 fold improvement in KD when LAG3 is present. These demonstrate that the bispecific has enhanced avidity to target when both are present.

TABLE 11

| Ligand antigen | Detection channel | Affinity/ avidity KD | kon (M-1s-1) | koff (s-1) |
|---|---|---|---|---|
| LAG3 | LAG3 | 1.4 nM | 4.83 ± 0.78 E + 5 | 6.74 ± 0.84 E – 4 |
| LAG3 and PD1 | LAG3 | 20.7 pM | 3.62 ± 0.36 E + 6 | 7.51 ± 0.43 E – 5 |
| LAG3 and PD1 | PD1 | 41 pM | 2.12 ± 0.07 E + 6 | 8.67 ± 0.09 E – 5 |
| PD1 | PD1 | 4.4 nM | 1.10 ± 0.46 E + 5 | 4.88 ± 0.37 E – 4 |

Binding onto human activated T cells was measured by cytometry. PBMC or magnetically isolated T cells were isolated from leukocytes cones and cells were incubated in 96 well plates coated with anti-CD3 (OKT3) at 5 μg/ml. Anti-CD28 (CD28.2) was added at 1 μg/ml in RPMI media and foetal bovine serum. After 72-96 hours, cells were harvested and stained using standard flow cytometry methods. Humabody® construct was titrated in 3-fold series and detected using anti-HIS biotin (Biotechne BAM050) with Streptavidin Alexa-Fluor 488 (ThermoFisher). Fluorescently labelled anti-CD4 and anti-CD8 were included in PBMC cultures and a live/dead dye. Stained cells were analysed using the IQue cytometer (Intellicyte). EC50 were calculated from the titration curve of median fluorescence of Humabody, gating on CD4+ or CD8+ cells if using mixed cells. For cynomolgus cells, pan T cells were isolated using magnetic separation and stimulated with CD3/CD28 beads as per manufacturer's instructions (Miltenyi). After 72 hours of culture, cells were stained for flow cytometry as per human cells. EC50 were calculated from titration curve of percentage CD4 or CD8 that were positive. Table 12 shows EC50 for T cell binding. Bispecifics show potent binding to human T cells and cross-reactivity with monkey. Monovalent LAG-3 V$_H$ 1.1 binds weakly to cells whereas formatting as a bivalent enhances this, see FIG. 2.

Bispecific binding agents show higher median fluorescence that PD1 or LAG3 components alone, (FIG. 2). This can indicate binding to LAG3+, PD1+ and LAG3+PD1+ cells. Bispecific binding agents targets double-positive cells with higher avidity than single positive cells.

TABLE 12

| V$_H$ | huCD4+ T cells Mean EC50 n = 6 | huCD8+ T cells Mean EC50 n = 6 | cynoCD4+ T cells EC50 n = 1 | cynoCD8+ T cells EC50 n = 1 |
|---|---|---|---|---|
| V$_H$ 1.2-6GS- V$_H$ 1.2-6GS- V$_H$ 2.92 | 2.5E–10 | 1.4E–10 | | |
| V$_H$ 1.2-6GS- V$_H$ 1.2 | | | 5.7E–09 | 6.9E–09 |
| V$_H$ 2.92 | | | 1.4E–08 | 1.6E–08 |

Example 9. Inhibition of Ligands a) PD-1:PD-L1 Inhibition

The ability of the Humabody® to inhibit functional responses in a transfected Jurkat cells as a result of PD-1: PD-L1 blockade was assessed using an NFAT-Luciferase Reporter Gene assay. A Jurkat reporter cell line expressing human PD-1 and a luciferase reporter gene under the control of a promoter with an NFAT response element and a CHO cell line expressing a T-Cell Receptor activator and human PDL1 under the control of a tetracycline inducible promotor were generated by standard methods.

CHO human PD-L1/TCR activator cells were plated at 10000 cells/well in a 96 well white plate. Plates were incubated at 37° C. overnight in a 5% CO2 incubator. Samples were serially diluted in assay medium (RPMI+2% FBS). Jurkat PD-1 reporter cells were diluted into assay medium at 5e5 cells/mi. The media was removed from the CHO cells and 50p1 diluted sample or assay media (background control) added to the plates followed by 50p1 of the diluted Jurkat reporter cells. The plates were incubated for 6 hours at 37° C. overnight in a CO2 incubator, then removed from the incubator and equilibrated to room temperature for 20 mins. NanoGlo substrate (100 μl of substrate diluted 1:50 in NanGlo buffer (Promega cat no. N1120) was added and the plates incubated for 20 mins at room temperature prior to measurement of luminescence signal (RLU). Data was expressed as fold/background signal.

Humabody® V$_H$ showed dose-dependent enhancement of luciferase signal in the assay demonstrating blockade of the PD-1:PD-L1 interaction. EC50 were calculated from fold/ background non-linear regression curve fits and data for selected clones and constructs is shown in table 13.

Potency of the bispecific constructs on PD-1 positive cells is >30-fold lower than monoclonal antibodies. This could be of benefit in vivo where non-specific T cells can be activated by anti-PD1. A lower potency on single PD1+ cells but high potency on PD1+LAG3+ cells allows the function to be targeted towards specific 'exhausted' T cells.
Table 13

TABLE 13

| $V_H$ | EC50 (M) |
|---|---|
| 2.63 | 1.2E−08 |
| 2.77 | 9.7E−09 |
| 2.92 | 1.4E−08 |
| 1.1-6GS-1.1-6GS-2.63 | 4.2E−08 |
| 1.1-6GS-1.1-9GS-2.63 | 3.0E−08 |
| 2.77-6GS-1.1-6GS-1.1 | 3.7E−08 |
| 1.2-6GS-1.2-6GS-2.92 | 4.6E−08 |
| anti-PD-1 monoclonal antibody (Pembrolizumab analogue) | 1.3E−09 |

The ability of purified monovalent $V_H$ to inhibit PD-L1 binding to CHO human PD-1 cells was tested using an FMAT Inhibition assay.

All reagents and serially diluted $V_H$ were prepared in FMAT assay buffer. $V_H$, buffer (total binding controls) or excess competitor (non-specific binding control) were incubated with 100 μM human Fc tagged human PDL-1, 3 nM anti human Fc-Alexa Fluor-488 and 2000 per well CHO human PD-1 DRAQ5 stained cells in a 384 well black clear-bottomed assay plates. Plates were incubated for 2 hours at room temperature then fluorescence measured in the FL2 (502 nm-537 nm) and FL5 (677-800 nm) channels on the Mirrorball plate reader (TTP) following excitation at 488 nm and 640 nm. Data was expressed as a % of the total binding control (i.e. % control) after subtraction of the background signal determined from the non-specific binding control wells. IC50 are shown in Table 14, monovalent anti-PD1 $V_H$ have highly similar sequence and activity.

TABLE 14

| Humabody ® | CHO PD1:PDL1 IC50 (M) |
|---|---|
| 2.63 | 4.5E−09 |
| 2.92 | 2.8E−09 |
| 2.80 | 1.82E−09 | b) LAG-3: MHCII Inhibition

The ability of the $V_H$ to inhibit functional responses in T cells as a result of LAG-3:MHCII inhibition was assessed using an NFAT-Luciferase Reporter Gene assay (Promega LAG-3 assay). A Jurkat reporter cell line expressing human LAG-3 and a luciferase reporter gene under the control of a promoter with an NFAT response element was incubated with a Raji B cell line expressing MHC class II. A T cell activator, *Staphylococcus* Enterotoxin D is added to stimulate the T cells and increased luciferase signal can be seen when LAG-3:MHCII is blocked by antibodies such as 17B4.

Samples were serially diluted and reagents added as per manufacturer's instructions. Luminescence signal (RLU) is read after 6 hours. Data was expressed as fold/background signal.

Humabody® enhance NFAT signalling in the assay demonstrating blockade of LAG-3:MHCII interaction. EC50 were calculated from fold/background non-linear regression curve fits and data for selected clones and constructs is shown in table 15.

TABLE 15

| $V_H$ | EC50 (M) |
|---|---|
| 1.1 | >3.3E−07 |
| 1.1-6GS-1.1 | 4.1E−09 |

TABLE 15-continued

| $V_H$ | EC50 (M) |
|---|---|
| 2.1-6GS-2.1 | 2.3E−09 |
| 1.1-6GS-1.1-6GS-2.63 | 3.3E−09 |
| 1.1-6GS-1.1-9GS-2.63 | 3.2E−09 |
| Commercially available (e.g. Abcam) Mouse anti-LAG3 antibody clone 17B4 | 3.2E−08 |
| Human anti-LAG3 antibody (Relatlimab analogue) | 4.0E−09 |
| 1.1-4GS-1.1 | 1.4E−09 |
| 1.1-8GS-1.1 | 5.4E−09 |
| 1.1-12GS-1.1 | 3.3E−09 |
| 1.2-6GS-1.2-6GS-2.92 | 5.9E−09 |
| 2.77-6GS-1.1-6GS-1.1 | 6.6E−09 | c) Alternative Ligand Inhibition

Galectin-3 (Peprotech cat no. 450-38-100) LSECtin (R&D systems cat no. 2947-CL) or alpha-synuclein (R&D systems cat no.SP480-500) were coated on a maxisorp ELISA plate at 1-2 ug/ml. The plate was blocked with 3% Marvel skimmed milk powder in PBS. LAG-3-Fc was pre-incubated with $V_H$ for 1 hour before adding to the coated plate. LAG-3 binding was detected using anti-human IgG conjugated to HRP. Wash steps were done 3 times with PBS 0.05% Tween. Colour was developed using TMB and 0.5M sulphuric acid solution. LAG-3-specific Humabody® $V_H$ block LAG-3:Galectin, LAG-3:LSECtin and LAG3:asynuclein interactions. EC50 were calculated from absorbance fitted to non-linear regression curves and example data are shown in table 16. Irrelevant $V_H$ that bind to PD-1 do not inhibit these interactions.

TABLE 16

| $V_H$ | IC50 (M) | | |
|---|---|---|---|
| | LSECtin | Galectin-3 | Alpha-synuclein |
| 1.1 | 2.1E−07 | | 4.5E−08 |
| 1.1-6GS-1.1 | 5.5E−08 | 3.4E−08 | |
| 1.1-6GS-1.1-9GS-2.63 | 5.4E−08 | 3.8E−08 | |

Example 10. Enhancement of Immune Cell Function a) Superantigen Assay

Figure 3A:
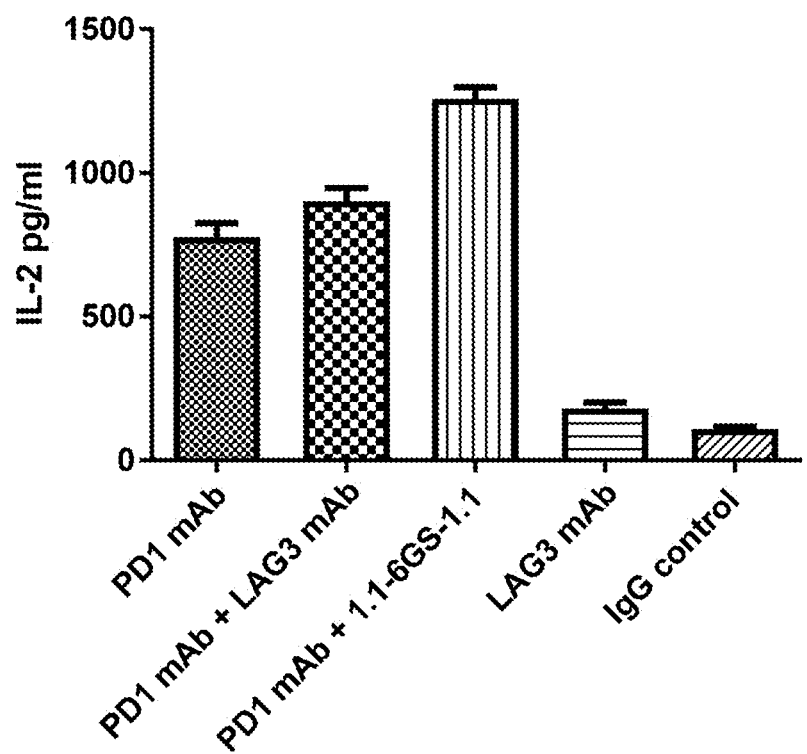
Figure 3B:
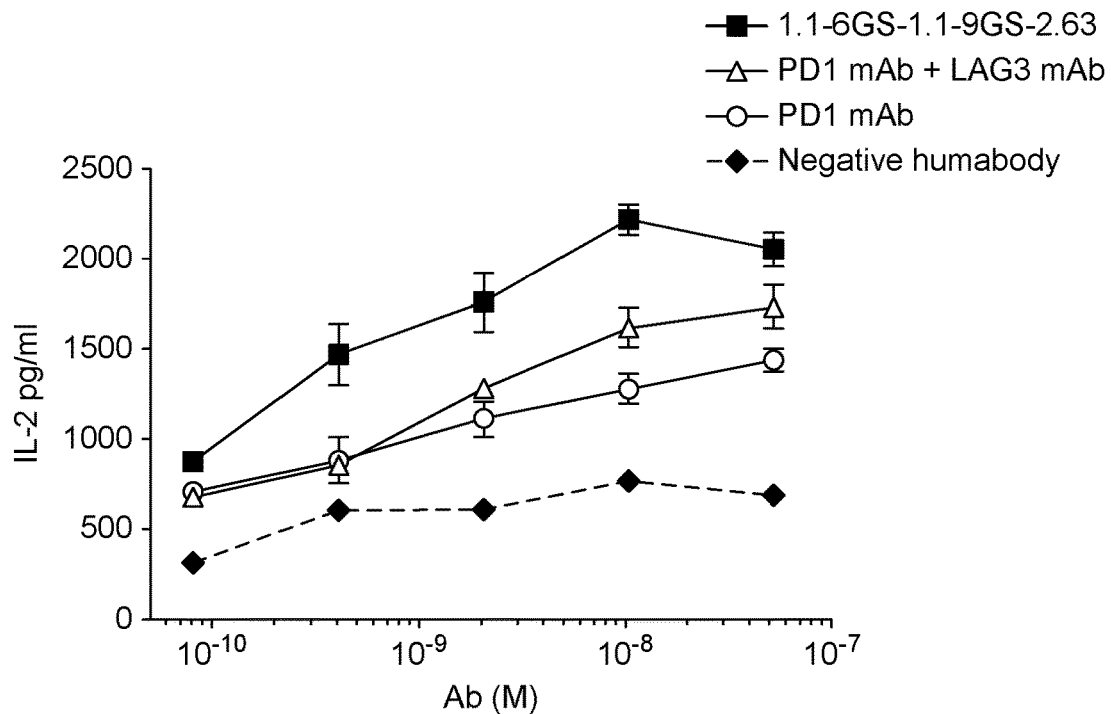
Figure 3C:
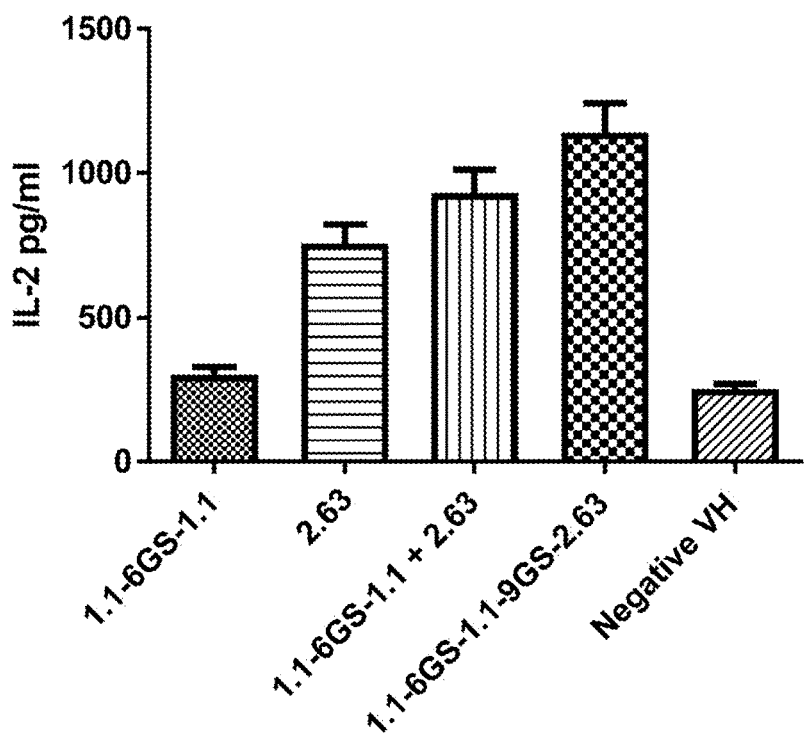
Figure 3D:
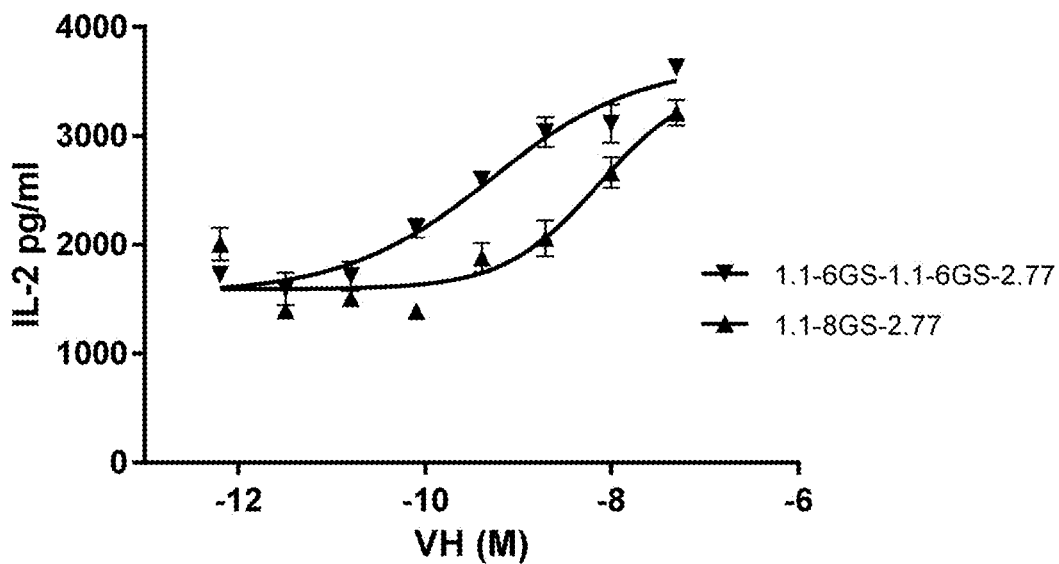
Figure 3E:
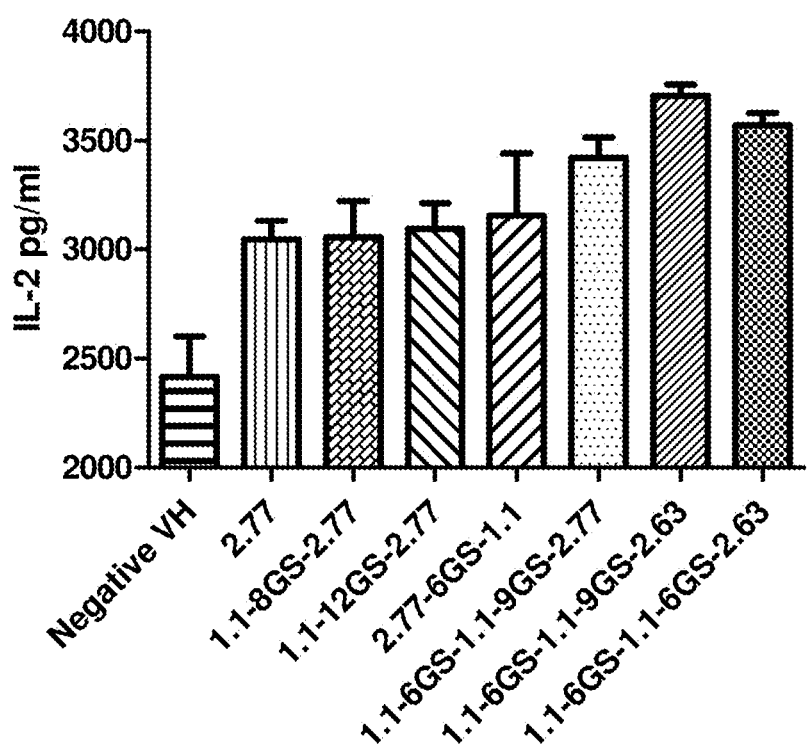
Figure 3F:
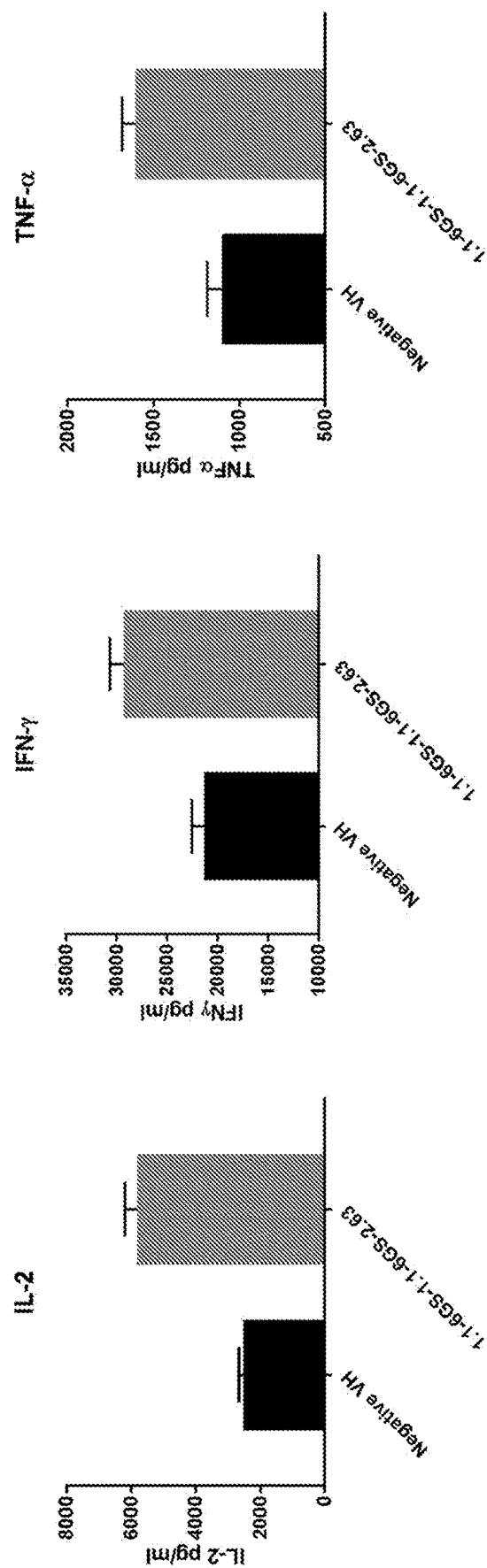

PBMC from healthy human donors were isolated from leukocyte cones using density gradient centrifugation. PBMC were stimulated using 10-100 ng/ml Staphylococcal Enterotoxin B (SEB) for 2-3 days. Cells were re-stimulated with varied concentrations of SEB in the presence of antibody or Humabody®. IL-2 secreted into the supernatant was measured using HTRF (Cisbio Human IL-2 kit Cat no. 64IL1PEB). Bivalent $V_H$ 1.1-6GS-1.1 enhances T cell stimulation when in combination with PD-1 blockade (FIG. 3a). Bivalent Humabody alone has only minimal enhancement above a Humabody® negative control or IgG negative control. Humabody® 1.1-6GS-1.1-9GS-2.63 enhances T cell stimulation above benchmark PD-1 and LAG-3 antibodies (FIG. 3b). 1.2-6GS-1.2-6GS-2.92 shows similar enhancement above benchmarks (Relatlimab analogue and Nivolumab analogue). Humabody® 1.1-6GS-1.1-9GS-2.63 enhances T cell stimulation above the combination of its components (FIG. 3c). Bispecific formats containing 2 LAG3 $V_H$ stimulate higher IL-2 production than those with 1 LAG-3 $V_H$(FIGS. 3d and 3e). This data shows that the asymmetric format has functional benefits over other LAG3:PD1 binding formats. FIG. 3f shows induction of proinflammatory cytokines, IL-2, TNF-alpha and Interferon-gamma after 6 days of culture.

b) Antigen-Specific Assay

PBMC from 8 human donors were used in a CMV peptide stimulation system. PBMC were pulsed with a pool of CMV peptides for 1 hour and then Humabody® were added before incubation. Cells were cultured in the presence of 25 ng/ml IL-7 and 10 U/ml IL-2. On day 5, cells were washed and stained for flow cytometry. CMV tetramers of varied HLA types were used to stain the cells and the percentage of CD8+ tetramer+ cells were calculated. The fold increase in percentage was calculated relative to an irrelevant $V_H$. FIG. 4 shows that there is an increase in proliferation with treatment of the bispecific 1.1-6GS-1.1-9GS-2.63. In some responses, bispecific has an effect where a biparatopic PD-1 binder (having two VHs binding to PD-1) and LAG3 bivalent do not.

Example 7. In Vivo Efficacy 24 hu-PBMC NCG mice were engrafted with $3 \times 10^7$ hPBMC by tail vein injection 7 days before subcutaneous implant of $5 \times 10^6$ RKO colon carcinoma cells in 50% Matrigel. Digital caliper measurements were initiated to determine tumor volume 2× weekly when tumors became palpable. Mice were randomized based on tumor volumes when the tumor volumes reached approximately 30-60 mm 3. Mice were dosed according to Table 17 beginning on Study Day 1. A number of agents were tested as set out in table 17.

Body weights, clinical observations, and digital caliper measurements were recorded 2× weekly post dose initiation. Bispecific can mediate inhibition of tumour growth (FIG. 5). MSA designates a $V_H$ that binds to mouse serum albumin. HEL4 is a negative control $V_H$ that does not bind to the targets.

TABLE 17

| Gr. | N | Agent tested | Regimen 1 | | |
|---|---|---|---|---|---|
| | | | mg/kg | Route | Schedule |
| 1 | 6 | HEL4-6GS-MSA | 5 | ip | qod for 20 days |
| 2 | 6 | 1.1-6GS-1.1-6GS-2.77-4GS-MSA | 2 | ip | qod for 20 days |
| 3 | 6 | 1.1-6GS-1.1-6GS-2.77-4GS-MSA | 10 | ip | qod for 20 days |
| 4 | 6 | monoclonal clinical stage anti PD-1 antibody (Pembrolizumab analogue) | 5 | ip | biwk × 3 |

Example 8 Proliferation of Patient T Cells 1.2-6GS-1.2-6GS-2.92 is able to rescue T cells in a patient ex vivo cell system that models cancer cell and T cell interactions. PBMC from NSCLC patients were incubated with a lung adenocarcinoma cell line that provided weak TCR stimulus by anti-CD3. In CD4+ and CD8+ cells, the percentage of Ki67+ proliferating cells increased in the presence of 1.2-6GS-1.2-6GS-2.92. This was significantly higher than treatment with PD-1 antibodies, which only modestly increased proliferation (FIG. 6). These patients may be non-responsive to PD1 antibody treatment therefore the stimulation of T cell proliferation provided by the bispecific confers benefit. Bispecific enhances proliferation greater than combination treatment in cells from 4 further patients (Table 18).

TABLE 18

| Cells | Patient | Negative VH | 2.80 | 2.80 + 1.2-6GS-1.2 | 1.2-6GS-1.2-6GS-2.92 |
|---|---|---|---|---|---|
| % | 1 | 29.4 | 26.1 | 30.8 | 56 |
| Ki67+ | 2 | 15.3 | 11.2 | 9.24 | 42 |
| CD4+ | 3 | 2.6 | 1.7 | 3.71 | 21 |
| CD28+ | 4 | 3 | 2.8* | 3.32 | 50 |
| % | 1 | 67 | 64 | 79.2 | 98 |
| Ki67+ | 2 | 90 | 90.5 | 92 | 96 |
| CD4+ | 3 | 49.1 | 32.5 | 58.5 | 98 |
| CD28− | 4 | 93 | 85* | 75 | 92 |
| % | 1 | 49.6 | 55.8 | 56 | 80 |
| Ki67+ | 2 | 3.2 | 1 | 5 | 50 |
| CD8+ | 3 | 1.84 | 2.8 | 4.1 | 34.9 |
| CD28+ | 4 | 4.4 | 4.7* | 4.4 | 59.7 |
| % | 1 | 45.1 | 46.3 | 62 | 72 |
| Ki67+ | 2 | 11 | 10.5 | 7.41 | 33.5 |
| CD8+ | 3 | 5.07 | 6.1 | 6 | 29.1 |
| CD28− | 4 | 2.8 | 2.2* | 3 | 38.3 |

*Nivolumab analog was used instead of 2.80

Example 9 Suppression of Inhibitory Signalling

NSCLC patient CD4 or CD8 T cells were incubated with a human lung cancer adenocarcinoma cell line (A549) that provides weak TCR stimulus. Cultures were treated with LAG3 bivalent, PD1 monovalent or antibody or equal concentrations of LAG3 bivalent and PD1 monovalent $V_H$ in combination and these were compared to the bispecific 1.2-6GS-1.2-6GS-2.92. Cells were analysed for the expression of the negative T cell regulators CBL-b and c-CBL by flow cytometry. The percentage of cells or mean fluorescence intensity for cells expressing E3 ubiquitin ligases Cbl-b (Uniprot accession number Q13191 or NCBI reference NP_001308717.1) and c-Cbl (C-CBL, also known as CBL), Uniprot P22681) were calculated, table 19. E3 Ubiquitin ligases have been implicated in the PD-1/PD-L1 signalling pathway (Karwacz et al, EMBO MOI Med 3, 581-592, 2011).

TABLE 19

| Marker | Patient | Negative Humabody | 2.80 | 1.2-6GS-1.2 | 2.80 + 1.2-6GS-1.2 | 1.2-6GS-1.2-6GS-2.92 |
|---|---|---|---|---|---|---|
| % CBL-b | 1 | 44 | 32 | 48 | 30 | 6 |
| CD4+ | 2 | 50 | 41 | 48 | 38 | 10 |
| cells | 3 | 48 | 30 | 50 | 32 | 8 |
| | 4 | 55 | 45* | 53 | 46 | 10 |
| % CBL-b | 1 | 26 | 23 | 28 | 25 | 5 |
| CD8+ | 2 | 30 | 27 | 33 | 30 | 8 |
| cells | 3 | 35 | 33 | 33 | 35 | 10 |
| | 4 | 28 | 24* | 27 | 32 | 5 |
| MFI c-CBL | 1 | 4147 | 5412 | 5342 | 5234 | 2262 |
| CD4+ | 2 | 3854 | 3987 | 4323 | 4532 | 1254 |
| cells | 3 | 4234 | 4354 | 4325 | 4454 | 2322 |
| | 4 | 3987 | 4654* | 4321 | 4325 | 1987 |
| MFI c-CBL | 1 | 3877 | 5088 | 4987 | 4123 | 2078 |
| CD8+ | 2 | 4321 | 4654 | 4553 | 4325 | 1998 |
| cells | 3 | 2986 | 3423 | 3675 | 3123 | 1322 |
| | 4 | 4567 | 5432* | 4678 | 4987 | 2087 |

*Nivolumab analog was used instead of 2.80

PD1 blockade reduces Cbl-b in CD4+ T cells but LAG3 bivalent has no effect. The combination of PD1 and LAG3 blockade has no additive effect over PD1 blockade alone. The bispecific significantly inhibits Cbl-b and c-cbl expression in both CD4+ and CD8+ T cells from NSCLC patients. Therefore, in agreement with the data shown in FIG. 6 on proliferation, the engagement of targets by the bispecific is different to combination treatment and enables suppression of a biomarker of T cell inhibitory signalling. The only treatment to reduce c-Cbl and Cbl-b protein expression was the bispecific, suggesting that the dual target engagement by the bispecific enables alternative signalling pathways compared to a combination of treatments.

The invention claimed is:

1. An isolated human heavy chain variable domain ($V_H$) single domain antibody that binds to human LAG-3 comprising a CDR1 sequence as shown in SEQ ID NO: 1 or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 or a CDR2 sequence as shown in SEQ ID NO: 2 comprising a N to S substitution in CDR2 at position 57 of the sequence as shown in SEQ ID NO: 4, a S to T substitution in CDR2 at position 58 of the sequence as shown in SEQ ID NO: 4, a N to I substitution in CDR2 at position 54 of the sequence as shown in SEQ ID NO: 4, a G to S substitution in CDR2 at position 55 of the sequence as shown in SEQ ID NO: 4, a G to D substitution in CDR2 at position 56 of the sequence as shown in SEQ ID NO: 4, a N to I substitution in CDR2 at position 57 of the sequence as shown in SEQ ID NO: 4, or a G to A substitution in CDR2 at position 59 of the sequence as shown in SEQ ID NO: 4, and a CDR3 sequence as shown in SEQ ID NO: 3 or a CDR3 sequence as shown in SEQ ID NO: 3 comprising a S to V substitution in CDR3 at position 106 of the sequence as shown in SEQ ID NO: 4, a S to A substitution in CDR3 at position 108 of the sequence as shown in SEQ ID NO: 4, or a A to T substitution in CDR3 at position 107 of the sequence as shown in SEQ ID NO: 4, or a CDR1 sequence as shown in SEQ ID NO: 5, a CDR2 sequence as shown in SEQ ID NO: 6, and a CDR3 sequence as shown in SEQ ID NO: 7.

2. The single domain antibody according to claim 1 comprising a sequence selected from SEQ ID NOs: 4 or 8 or a sequence as shown in SEQ ID NO: 4 comprising a S23A, P119Q, D30N, or Y95H substitution.

3. The isolated single domain antibody according to claim 1, wherein said single domain antibody is conjugated to a label, therapeutic molecule or other chemical moiety, including a toxin, enzyme or radioisotope, or a half-life extending moiety which is selected from the group consisting of an albumin binding moiety, a transferrin binding moiety, a polyethylene glycol molecule, a recombinant polyethylene glycol molecule, human serum albumin, a fragment of human serum albumin, an albumin binding peptide, and a single domain antibody that binds to human serum albumin.

4. The isolated single domain antibody according to claim 1 obtained or obtainable from a transgenic rodent that expresses a transgene comprising human V, D and J regions optionally wherein said rodent does not produce any functional endogenous light and heavy chains.

5. A multispecific binding agent comprising a $V_H$ single domain antibody according to claim 1 and an additional functional moiety that binds to PD-1.

6. The multispecific binding agent according to claim 5, wherein the additional functional moiety that binds to PD-1 is an antibody or a fragment thereof, optionally a $V_H$ single domain antibody.

7. The multispecific binding agent according to claim 5, wherein the additional functional moiety that binds PD-1 is selected from a $V_H$ single domain antibody with the amino acid sequence set forth in one of SEQ ID NOs: 13-127.

8. The multispecific binding agent according to claim 5, wherein the additional functional moiety that binds PD-1 has the amino acid sequence selected from the group consisting of SEQ ID NO: 75, SEQ ID NO: 251, SEQ ID NO: 252, SEQ ID NO: 89, SEQ ID NO: 257, SEQ ID NO: 104, SEQ ID NO: 258, and SEQ ID NO: 259.

9. The multispecific binding agent according to claim 5 comprising two $V_H$ single domain antibodies that bind LAG-3.

10. The multispecific binding agent according to claim 5 comprising two $V_H$ single domain antibodies that bind LAG3, wherein the two $V_H$ single domain antibodies that bind LAG-3 have the sequence of SEQ ID NO: 8.

11. A pharmaceutical composition comprising a single domain antibody according to claim 1 and a pharmaceutical carrier.

12. A method for treating a cancer comprising administering to a patient in need thereof a therapeutically effective amount of the single domain antibody according to claim 1.

13. The method according to claim 12, wherein said cancer is selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, including cancer of the thyroid gland, cancer of the parathyroid gland or cancer of the adrenal gland, kidney cancer, including renal cancer, sarcoma of soft tissue, cancer of the urethra, cancer of the bladder, urothelial carcinoma, lung cancer, including non-small cell lung cancer, thymoma, a leukemia, prostate cancer, mesothelioma, adrenocortical carcinoma, a lymphoma, including Hodgkin's disease or non-Hodgkin's lymphoma, or a multiple myeloma.

14. An isolated binding agent comprising a first ($V_H$) single domain antibody that binds to human LAG-3 and a second ($V_H$) single domain antibody that binds to human LAG-3, wherein the first and/or second ($V_H$) single domain antibody that binds to human LAG-3 comprises a CDR1 sequence as shown in SEQ ID NO: 1 or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 or a CDR2 sequence as shown in SEQ ID NO: 2 comprising a N to S substitution in CDR2 at position 57 of the sequence as shown in SEQ ID NO: 4, a S to T substitution in CDR2 at position 58 of the sequence as shown in SEQ ID NO: 4, a N to I substitution in CDR2 at position 54 of the sequence as shown in SEQ ID NO: 4, a G to S substitution in CDR2 at position 55 of the sequence as shown in SEQ ID NO: 4, a G to D substitution in CDR2 at position 56 of the sequence as shown in SEQ ID NO: 4, a N to I substitution in CDR2 at position 57 of the sequence as shown in SEQ ID NO: 4, or a G to A substitution in CDR2 at position 59 of the sequence as shown in SEQ ID NO: 4, and a CDR3 sequence as shown from SEQ ID NO: 3 or a CDR3 sequence as shown in SEQ ID NO: 3 comprising a S to V substitution in CDR3 at position 106 of the sequence as shown in SEQ ID NO: 4, a S to A substitution in CDR3 at position 108 of the sequence as shown in SEQ ID NO: 4, or a A to T substitution in CDR3 at position 107 of the sequence as shown in SEQ ID NO: 4, or a CDR1 sequence as shown in SEQ ID NO: 5, a CDR2 sequence as shown in SEQ ID NO: 6, and a CDR3 sequence as shown in SEQ ID NO: 7.

15. The isolated binding agent according to claim 14 linked to an additional functional moiety having a different binding specificity than said single domain antibody, optionally wherein said additional functional moiety is an antibody or a fragment thereof.

16. The isolated binding agent according to claim 14, wherein the first ($V_H$) single domain antibody that binds to human LAG-3 or the second ($V_H$) single domain antibody that binds to human LAG-3 comprises the sequence of SEQ ID NO: 4, SEQ ID NO: 8 or a sequence as shown in SEQ ID NO: 4 comprising a S23A, P119Q, D30N, or Y95H substitution.

17. The binding agent according to claim 14 linked to an additional functional moiety having a different binding specificity than said single domain antibody and conjugated to a therapeutic molecule or chemical moiety, including a toxin, enzyme or radioisotope, or a half-life extending moiety which is selected from the group consisting of an albumin binding moiety, a transferrin binding moiety, a polyethylene glycol molecule, a recombinant polyethylene glycol molecule, human serum albumin, a fragment of human serum albumin, an albumin binding peptide, and a single domain antibody that binds to human serum albumin.

18. The isolated binding agent according to claim 15, wherein the additional functional moiety binds to PD-1 and is an antibody or a fragment thereof, optionally a $V_H$ single domain antibody.

19. The isolated binding agent according to claim 18, wherein the additional functional moiety binding PD-1 is selected from a $V_H$ single domain antibody with the amino acid sequence set forth in one of SEQ ID NO: 13-127.

20. The multispecific binding agent according to claim 18, wherein the additional functional moiety that binds PD-1 has the amino acid sequence selected from the group consisting of SEQ ID NO: 75, SEQ ID NO: 251, SEQ ID NO: 252, SEQ ID NO: 89, SEQ ID NO: 257, SEQ ID NO: 104, SEQ ID NO: 258, and SEQ ID NO: 259.

21. An isolated human heavy chain variable domain ($V_H$) single domain antibody that binds to human LAG-3 comprising a CDR1 sequence as shown in SEQ ID NO: 1, a CDR2 sequence as shown in SEQ ID NO: 2 comprising a N to S substitution in CDR2 at position 57 of the sequence as shown in SEQ ID NO: 4 and a S to T substitution in CDR2 at position 58 of the sequence as shown in SEQ ID NO: 4, and a CDR3 sequence as shown in SEQ ID NO: 3, or a CDR1 sequence as shown in SEQ ID NO: 1, a CDR2 sequence as shown in SEQ ID NO: 2 comprising a N to I substitution in CDR2 at position 54 of the sequence as shown in SEQ ID NO: 4, and a CDR3 sequence as shown in SEQ ID NO: 3, or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 comprising a S to T substitution in CDR2 at position 58 of the sequence as shown in SEQ ID NO: 4, and a CDR3 sequence as shown in SEQ ID NO: 3, or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 comprising a G to S substitution in CDR2 at position 55 of the sequence as shown in SEQ ID NO: 4, a G to D substitution in CDR2 at position 56 of the sequence as shown in SEQ ID NO: 4, a N to I substitution in CDR2 at position 57 of the sequence as shown in SEQ ID NO: 4, a S to T substitution in CDR2 at position 58 of the sequence as shown in SEQ ID NO: 4, and a G to A substitution in CDR2 at position 59 of the sequence as shown in SEQ ID NO: 4, and a CDR3 sequence as shown in SEQ ID NO: 3, or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 comprising a S to T substitution in CDR2 at position 58 of the sequence as shown in SEQ ID NO: 4, and a CDR3 sequence as shown in SEQ ID NO: 3 comprising a S to V substitution in CDR3 at position 106 of the sequence as shown in SEQ ID NO: 4 and a S to A substitution in CDR3 at position 108 of the sequence as shown in SEQ ID NO: 4, or a CDR1 sequence as shown in SEQ ID NO: 1, a CDR2 sequence as shown in SEQ ID NO: 2, and a CDR3 sequence as shown in SEQ ID NO: 3 comprising a A to T substitution in CDR3 at position 107 of the sequence as shown in SEQ ID NO: 4, or a CDR1 sequence as shown in SEQ ID NO: 1, a CDR2 sequence as shown in SEQ ID NO: 2 comprising a G to D substitution in CDR2 at position 56 of the sequence as shown in SEQ ID NO: 4, a N to S substitution in CDR2 at position 57 of the sequence as shown in SEQ ID NO: 4, and a S to T substitution in CDR2 at position 58 of the sequence as shown in SEQ ID NO: 4, and a CDR3 sequence as shown in SEQ ID NO: 3.

22. An isolated human heavy chain variable domain ($V_H$) single domain antibody that binds to human LAG-3 The single domain antibody according to claim 1 comprising a sequence a shown in SEQ ID NO: 4 comprising a S23A substitution or a sequence a shown in SEQ ID NO: 4 comprising S23A, N57S, and S58T substitutions or a sequence a shown in SEQ ID NO: 4 comprising S23A and N54I substitutions or a sequence a shown in SEQ ID NO: 4 comprising S23A, D30N, Y32F, and S58T substitutions or a sequence a shown in SEQ ID NO: 4 comprising S23A, Y32F, G55S, G56D, N57I, S58T, and G59A substitutions or a sequence a shown in SEQ ID NO: 4 comprising S23A, Y32F, S58T, S106V, and S108A substitutions or a sequence a shown in SEQ ID NO: 4 comprising S23A, D30N, and A107T substitutions or a sequence a shown in SEQ ID NO: 4 comprising S23A, Y95H, G56D, N57S, and S58T substitutions or a sequence a shown in SEQ ID NO: 8.

23. An isolated binding agent comprising a first ($V_H$) single domain antibody that binds to human LAG-3 and a second ($V_H$) single domain antibody that binds to human LAG-3, wherein the first and/or second ($V_H$) single domain antibody that binds to human LAG-3 comprises a CDR1 sequence as shown in SEQ ID NO: 1, a CDR2 sequence as shown in SEQ ID NO: 2 comprising a N to S substitution in CDR2 at position 57 of the sequence as shown in SEQ ID NO: 4 and a S to T substitution in CDR2 at position 58 of the sequence as shown in SEQ ID NO: 4, and a CDR3 sequence as shown in SEQ ID NO: 3, or a CDR1 sequence as shown in SEQ ID NO: 1, a CDR2 sequence as shown in SEQ ID NO: 2 comprising a N to I substitution in CDR2 at position 54 of the sequence as shown in SEQ ID NO: 4, and a CDR3 sequence as shown in SEQ ID NO: 3, or a CDR1 sequence as shown in SEQ ID NO: 1 comprising a Y to F substitution in CDR1 at position 32 of the sequence as shown in SEO ID NO: 4, a CDR2 sequence as shown in SEQ ID NO: 2 comprising a S to T substitution in CDR2 at position 58 of the sequence as shown in SEQ ID NO: 4, and a CDR3 sequence as shown in SEQ ID NO: 3, or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 comprising a G to S substitution in CDR2 at position 55 of the sequence as shown in SEQ ID NO: 4, a G to D substitution in CDR2 at position 56 of the sequence as shown in SEQ ID NO: 4, a N to I substitution in CDR2 at position 57 of the sequence as shown in SEQ ID NO: 4, a S to T substitution in CDR2 at position 58 of the sequence as shown in SEQ ID NO: 4, and a G to A substitution in CDR2 at position 59 of the sequence as shown in SEQ ID NO: 4, and a CDR3 sequence as shown in SEQ ID NO: 3, or a CDR1 sequence as shown in SEQ ID NO: 1 comprising a Y to F substitution in CDR1 at position 32 of the sequence as shown in SEQ ID NO: 4, a CDR2 sequence as shown in SEQ ID NO: 2 comprising a S to T substitution in CDR2 at position 58 of the sequence as shown in SEQ ID NO: 4, and a CDR3 sequence as shown in SEQ ID NO: 3 comprising a S to V substitution in CDR3 at position 106 of the sequence as shown in SEQ ID NO: 4 and a S to A substitution in CDR3 at position 108 of the sequence as shown in SEQ ID NO: 4, or a CDR1 sequence as shown in SEQ ID NO: 1, a CDR2 sequence as shown in SEQ ID NO: 2, and a CDR3 sequence as shown in SEQ ID NO: 3 comprising a A to T substitution in CDR3 at position 107 of the sequence as shown in SEQ ID NO: 4, or a CDR1 sequence as shown in SEQ ID NO: 1, a CDR2 sequence as shown in SEQ ID NO: 2 comprising a G to D substitution in CDR2 at position 56 of the sequence as shown in SEQ ID NO: 4, a N to S substitution in CDR2 at position 57 of the sequence as shown in SEQ ID NO: 4, and S to T substitution in CDR2 at position 58 of the sequence as shown in SEQ ID NO: 4, and a CDR3 sequence as shown in SEQ ID NO: 3.

24. An isolated binding agent comprising a first ($V_H$) single domain antibody that binds to human LAG-3 and a second ($V_H$) single domain antibody that binds to human LAG-3, wherein the first and/or second ($V_H$) single domain antibody that binds to human LAG-3 comprises a sequence a shown in SEQ ID NO: 4 comprising a S23A substitution or a sequence a shown in SEQ ID NO: 4 comprising S23A, N57S, and S58T substitutions or a sequence a shown in SEQ ID NO: 4 comprising S23A and N54I substitutions or a sequence a shown in SEQ ID NO: 4 comprising S23A, D30N, Y32F, and S58T substitutions or a sequence a shown in SEQ ID NO: 4 comprising S23A, Y32F, G55S, G56D, N57I, S58T, and G59A substitutions or a sequence a shown in SEQ ID NO: 4 comprising S23A, Y32F, S58T, S106V, and S108A substitutions or a sequence a shown in SEQ ID NO: 4 comprising S23A, D30N, and A107T substitutions or a sequence a shown in SEQ ID NO: 4 comprising S23A, Y95H, G56D, N57S, and S58T substitutions or a sequence a shown in SEQ ID NO: 8.

* * * * *

```
                              SEQUENCE LISTING

<160> NUMBER OF SEQ ID NOS: 259

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SeqID NO. 4

<400> SEQUENCE: 1

Asp Tyr Gly Met Ser
1               5

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SeqID NO.4

<400> SEQUENCE: 2

Gly Ile His Trp Asn Gly Gly Asn Ser Gly Tyr Ala Asp Ser Val Lys
1               5                   10                  15

Gly

<210> SEQ ID NO 3
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: CDR3 of SeqID NO. 4

<400> SEQUENCE: 3

Ile Pro Arg Glu Asp Cys Ser Ser Ala Ser Cys Tyr Thr Asp Ala Ile
1               5                   10                  15

Asp Phe

<210> SEQ ID NO 4
<211> LENGTH: 127
<212> TYPE: PRT
<213> ORGANISM: Homo sapiens
<220> FEATURE:
<221> NAME/KEY: MISC_FEATURE
<222> LOCATION: (1)..(127)
<223> OTHER INFORMATION: VH binding to LAG-3

<400> SEQUENCE: 4

Glu Val Gln Leu Val Glu Ser Gly Gly Gly Val Val Arg Pro Gly Gly
1               5                   10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Gly Asn Ser Gly Tyr Ala Asp Ser Val
    50                  55                  60
```

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Pro Gly Thr Met Val Thr Val Ser Ser
        115                 120                 125

<210> SEQ ID NO 5
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SeqID NO. 8

<400> SEQUENCE: 5

Asp Tyr Gly Met Ser
1               5

<210> SEQ ID NO 6
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of Seq ID NO.8

<400> SEQUENCE: 6

Gly Ile His Trp Asn Gly Gly Ser Thr Gly Tyr Ala Asp Ser Val Lys
1               5                   10                  15

Gly

<210> SEQ ID NO 7
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: CDR3 of SeqID NO.8

<400> SEQUENCE: 7

Ile Pro Arg Glu Asp Cys Ser Ser Ala Ser Cys Tyr Thr Asp Ala Ile
1               5                   10                  15

Asp Phe

<210> SEQ ID NO 8
<211> LENGTH: 127
<212> TYPE: PRT
<213> ORGANISM: Homo sapiens
<220> FEATURE:
<221> NAME/KEY: MISC_FEATURE
<222> LOCATION: (1)..(127)
<223> OTHER INFORMATION: VH that binds to LAG-3

<400> SEQUENCE: 8

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30
```

Gly Met Ser Trp Val Arg Gln Ala Pro Gly Lys Gly Leu Glu Trp Val
            35                  40                  45

Ser Gly Ile His Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Gln Gly Thr Met Val Thr Val Ser Ser
            115                 120                 125

<210> SEQ ID NO 9
<211> LENGTH: 525
<212> TYPE: PRT
<213> ORGANISM: Homo sapiens

<400> SEQUENCE: 9

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
            130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
            210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val

```
                    275                 280                 285
    Gly Thr Arg Ser Phe Leu Thr Ala Lys Trp Thr Pro Gly Gly Gly
        290                 295                 300

Pro Asp Leu Leu Val Thr Gly Asp Asn Gly Asp Phe Thr Leu Arg Leu
    305                 310                 315                 320

Glu Asp Val Ser Gln Ala Gln Ala Gly Thr Tyr Thr Cys His Ile His
                    325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
                355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
    385                 390                 395                 400

Gln Glu Ala Gln Leu Leu Ser Gln Pro Trp Gln Cys Gln Leu Tyr Gln
                    405                 410                 415

Gly Glu Arg Leu Leu Gly Ala Ala Val Tyr Phe Thr Glu Leu Ser Ser
                420                 425                 430

Pro Gly Ala Gln Arg Ser Gly Arg Ala Pro Gly Ala Leu Pro Ala Gly
                435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
    465                 470                 475                 480

Arg Arg Phe Ser Ala Leu Glu Gln Gly Ile His Pro Pro Gln Ala Gln
                    485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Pro Glu Gln Leu
                515                 520                 525

<210> SEQ ID NO 10
<211> LENGTH: 381
<212> TYPE: DNA
<213> ORGANISM: Homo sapiens
<220> FEATURE:
<221> NAME/KEY: misc_feature
<222> LOCATION: (1)..(381)
<223> OTHER INFORMATION: Nucleic acid sequence encoding the VH of SeqID
      NO. 4

<400> SEQUENCE: 10
gaggtgcagc tggtggagtc tgggggaggt gtggtacggc ctgggggtc cctgagactc      60 tcctgttcag cctctggatt cacctttgat gattatggca tgagctgggt ccgccaagct    120
ccagggaagg gctggagtg gtctctggt attcattgga atggtggtaa ctcaggttat     180
gcagactctg tgaagggccg attcaccatc tccagagaca cgccaaaaa ctccctgtat    240 ctgcaaatga acagtctgag agccgaggac acggccttgt attactgtgc gagaatcccc   300
cgagaagatt gtagtagtgc cagctgctat acggatgcta ttgatttctg gggcccaggg   360
acaatggtca ctgtctcctc a                                              381

<210> SEQ ID NO 11
<211> LENGTH: 381
<212> TYPE: DNA
<213> ORGANISM: Homo sapiens
```

```
<220> FEATURE:
<221> NAME/KEY: misc_feature
<222> LOCATION: (1)..(381)
<223> OTHER INFORMATION: Nucleic acid sequence encoding the VH domain of
      SEQ ID NO. 8

<400> SEQUENCE: 11
gaggtgcagc tggtggagtc tgggggaggt gtggtacggc ctggggggtc cctgagactc    60
tcctgtgcag cctctggatt cacctttgat gattatggca tgagctgggt ccgccaagct   120
ccagggaagg ggctggagtg ggtctctggt attcattgga atggtggtag cacaggttat   180
gcagactctg tgaagggccg attcaccatc tccagagaca cgccaaaaa ctccctgtat    240 ctgcaaatga acagtctgag agccgaggac acggccttgt attactgtgc gagaatcccc   300
cgagaagatt gtagtagtgc cagctgctat acggatgcta ttgatttctg gggccaaggg   360
acaatggtca ctgtctcctc a                                             381

<210> SEQ ID NO 12
<211> LENGTH: 288
<212> TYPE: PRT
<213> ORGANISM: Homo sapiens

<400> SEQUENCE: 12

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
```

```
                    260                 265                 270
Ser Ala Gln Pro Leu Arg Pro Glu Asp Gly His Cys Ser Trp Pro Leu
                275                 280                 285

<210> SEQ ID NO 13
<211> LENGTH: 125
<212> TYPE: PRT
<213> ORGANISM: Homo sapiens

<400> SEQUENCE: 13

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
                35                  40                  45

Ser Tyr Ile Ser Thr Gly Gly Thr Ile Lys Tyr Tyr Thr Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
                115                 120                 125

<210> SEQ ID NO 14
<211> LENGTH: 125
<212> TYPE: PRT
<213> ORGANISM: Homo sapiens

<400> SEQUENCE: 14

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
                35                  40                  45

Ser Tyr Ile Ser Thr Gly Gly Ser Ile Lys Tyr Tyr Thr Asp Ser Val
                50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
                115                 120                 125

<210> SEQ ID NO 15
<211> LENGTH: 125
<212> TYPE: PRT
<213> ORGANISM: Homo sapiens

<400> SEQUENCE: 15

Gln Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                   80

Leu Gln Met Asn Ser Leu Arg Ala Asp Asp Thr Ala Val Tyr Tyr Cys
            85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 16
<211> LENGTH: 125
<212> TYPE: PRT
<213> ORGANISM: Homo sapiens

<400> SEQUENCE: 16

Gln Val Gln Leu Val Glu Ser Gly Gly Gly Leu Val Lys Pro Gly Gly
 1                5                  10                  15

Ser Leu Arg Leu Ser Cys Ala Ala Ser Gly Phe Thr Phe Ser Asp Tyr
            20                  25                  30

Tyr Met Ile Trp Met Arg Gln Ala Pro Gly Lys Gly Leu Glu Trp Val
            35                  40                  45

Ser Tyr Ile Ser Gly Gly Gly Thr Thr Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                   80

Leu Gln Met Asn Ser Leu Arg Ala Asp Asp Thr Ala Val Tyr Tyr Cys
            85                  90                  95

Ala Arg Glu Ala Pro Leu Arg Leu Gly Glu Thr Pro His Asp Ala Phe
            100                 105                 110

Asp Ile Trp Gly Gln Gly Thr Met Val Thr Val Ser Ser
            115                 120                 125

<210> SEQ ID NO 17
<211> LENGTH: 125
<212> TYPE: PRT
<213> ORGANISM: Homo sapiens

<400> SEQUENCE: 17

Glu Val Gln Leu Val Glu Ser Gly Gly Gly Leu Val Lys Pro Gly Gly
 1                5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Asn Thr Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                   80

Leu Gln Met Asn Ser Leu Arg Ala Asp Asp Thr Ala Val Tyr Tyr Cys
            85                  90                  95
```

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 18
<211> LENGTH: 125
<212> TYPE: PRT
<213> ORGANISM: Homo sapiens

<400> SEQUENCE: 18

Glu Val Gln Leu Leu Glu Ser Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
            35                  40                  45

Ser Tyr Ile Ser Thr Gly Gly Thr Ile Lys Tyr Tyr Thr Asp Ser Val
        50                  55                  60

Lys Gly Arg Phe Thr Ile Ser Arg Asp Asn Ala Lys Asn Ser Leu Tyr
 65                 70                  75                  80

Leu Gln Met Ser Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 19
<211> LENGTH: 125
<212> TYPE: PRT
<213> ORGANISM: Homo sapiens

<400> SEQUENCE: 19

Glu Val Gln Leu Val Glu Ser Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
            35                  40                  45

Ser Tyr Ile Ser Thr Gly Gly Thr Ile Lys Tyr Tyr Thr Asp Ser Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 20
<211> LENGTH: 125
<212> TYPE: PRT
<213> ORGANISM: Homo sapiens

<400> SEQUENCE: 20

-continued

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
            85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 21
<211> LENGTH: 125
<212> TYPE: PRT
<213> ORGANISM: Homo sapiens

<400> SEQUENCE: 21

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Asp Asp Thr Ala Val Tyr Tyr Cys
            85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 22
<211> LENGTH: 125
<212> TYPE: PRT
<213> ORGANISM: Homo sapiens

<400> SEQUENCE: 22

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Ser Trp Met Arg Gln Ala Pro Gly Lys Gly Leu Glu Trp Ile
            35                  40                  45

Ser Tyr Ile Ser Leu Gly Gly Asn Thr Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120             125
```

<210> SEQ ID NO 23
<211> LENGTH: 125
<212> TYPE: PRT
<213> ORGANISM: Homo sapiens

<400> SEQUENCE: 23

```
Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Asp Met Thr Trp Ile Arg Gln Ala Pro Gly Lys Gly Gln Glu Trp Val
            35                  40                  45

Ser Tyr Ile Ser Arg Gly Gly Ser Thr Lys Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Thr Pro His Asp Ala Phe
            100                 105                 110

Asp Ile Trp Gly Gln Gly Thr Met Val Thr Val Ser Ser
            115                 120             125
```

<210> SEQ ID NO 24
<211> LENGTH: 125
<212> TYPE: PRT
<213> ORGANISM: Homo sapiens

<400> SEQUENCE: 24

```
Glu Val Gln Leu Leu Glu Ser Gly Gly Val Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Gly Trp Ile Arg Gln Ala Pro Gly Lys Gly Leu Glu Trp Ile
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120             125
```

<210> SEQ ID NO 25
<211> LENGTH: 125
<212> TYPE: PRT
<213> ORGANISM: Homo sapiens

<400> SEQUENCE: 25

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 26
<211> LENGTH: 125
<212> TYPE: PRT
<213> ORGANISM: Homo sapiens

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 27
<211> LENGTH: 125
<212> TYPE: PRT
<213> ORGANISM: Homo sapiens

<400> SEQUENCE: 27

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asn Thr Leu Arg Ala Glu Asp Thr Ala Val Tyr Tyr Cys
                    85                  90                  95

Ala Lys Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 28
<211> LENGTH: 125
<212> TYPE: PRT
<213> ORGANISM: Homo sapiens

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Thr Met Ser Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Thr Ala Val Tyr Tyr Cys
                    85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 29
<211> LENGTH: 125
<212> TYPE: PRT
<213> ORGANISM: Homo sapiens

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Asp Asp Thr Ala Val Tyr Tyr Cys
                    85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 30
<211> LENGTH: 125
<212> TYPE: PRT
```

<213> ORGANISM: Homo sapiens

<400> SEQUENCE: 30

Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 31
<211> LENGTH: 125
<212> TYPE: PRT
<213> ORGANISM: Homo sapiens

<400> SEQUENCE: 31

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Thr Pro His Asp Ala Phe
            100                 105                 110

Asp Ile Trp Gly Gln Gly Thr Met Val Thr Val Ser Ser
            115                 120                 125

<210> SEQ ID NO 32
<211> LENGTH: 125
<212> TYPE: PRT
<213> ORGANISM: Homo sapiens

<400> SEQUENCE: 32

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Ser Gly Gly Ser Ile Lys Phe Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 33
<211> LENGTH: 125
<212> TYPE: PRT
<213> ORGANISM: Homo sapiens

<400> SEQUENCE: 33

Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Thr Trp Gly Gln Gly Thr Met Val Thr Val Ser Ser
        115                 120                 125

<210> SEQ ID NO 34
<211> LENGTH: 125
<212> TYPE: PRT
<213> ORGANISM: Homo sapiens

<400> SEQUENCE: 34

Glu Val Gln Leu Val Glu Ser Gly Gly Gly Leu Val Lys Pro Gly Gly
 1               5                   10                  15

Ser Leu Arg Leu Ser Cys Ala Ala Ser Gly Phe Thr Phe Ser Asp Tyr
                20                  25                  30

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 35
```

```
<211> LENGTH: 125
<212> TYPE: PRT
<213> ORGANISM: Homo sapiens

<400> SEQUENCE: 35

Gln Ile Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Ser Trp Met Arg Gln Ala Pro Gly Lys Gly Leu Glu Trp Val
        35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 36
<211> LENGTH: 125
<212> TYPE: PRT
<213> ORGANISM: Homo sapiens

<400> SEQUENCE: 36

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Asp Met Tyr Trp Ile Arg Gln Ala Pro Gly Lys Gly Leu Glu Trp Val
        35                  40                  45

Ser Tyr Ile Ser Arg Gly Gly Ser Val Thr Tyr Tyr Ala Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Ser Leu Arg Ala Glu Asp Met Ala Val Tyr Phe Cys
                85                  90                  95

Ala Thr Glu Ala Pro Leu Arg Leu Gly Glu Thr Pro His Ala Ala Phe
            100                 105                 110

Asp Ile Trp Gly Gln Gly Thr Met Val Thr Val Ser Ser
        115                 120                 125

<210> SEQ ID NO 37
<211> LENGTH: 125
<212> TYPE: PRT
<213> ORGANISM: Homo sapiens

<400> SEQUENCE: 37

Gln Val Thr Leu Lys Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Glu Arg Glu Trp Ile
        35                  40                  45
```

Ser Phe Ile Ser Ser Ser Gly Ser Thr Thr Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Phe Trp Gly Gln Gly Thr Met Val Thr Val Ser Ser
                115                 120                 125

<210> SEQ ID NO 38
<211> LENGTH: 125
<212> TYPE: PRT
<213> ORGANISM: Homo sapiens

<400> SEQUENCE: 38

Gln Val Thr Leu Lys Glu Ser Gly Gly Leu Val Lys Pro Gly Gly
 1               5                  10                  15

Ser Leu Arg Leu Ser Cys Ala Ala Ser Gly Phe Thr Phe Ser Asp Asn
                 20                  25                  30

Ser Met Ser Trp Ile Arg Gln Ala Pro Gly Lys Gly Leu Glu Trp Val
                 35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Thr Leu Arg Ala Glu Asp Thr Ala Val Tyr Tyr Cys
                 85                  90                  95

Ala Lys Glu Ala Pro Leu Arg Leu Gly Glu Ser Pro His Asp Ala Phe
                100                 105                 110

Asp Ile Trp Gly Gln Gly Thr Met Val Thr Val Ser Ser
                115                 120                 125

<210> SEQ ID NO 39
<211> LENGTH: 125
<212> TYPE: PRT
<213> ORGANISM: Homo sapiens

<400> SEQUENCE: 39

Gln Val Thr Leu Lys Glu Ser Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Thr Met Thr Trp Met Arg Gln Ala Pro Gly Lys Gly Leu Glu Trp Val
                 35                  40                  45

Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
                115                 120                 125

<210> SEQ ID NO 40
<211> LENGTH: 125
<212> TYPE: PRT
<213> ORGANISM: Homo sapiens

<400> SEQUENCE: 40

Gln Ile Thr Leu Lys Glu Ser Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Asp Met Tyr Trp Ile Arg Gln Ala Pro Gly Lys Gly Leu Glu Trp Val
        35                  40                  45

Ser Tyr Ile Ser Arg Gly Gly Ser Val Thr Tyr Tyr Ala Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Ser Leu Arg Ala Glu Asp Met Ala Val Tyr Phe Cys
                85                  90                  95

Ala Thr Glu Ala Pro Leu Arg Leu Gly Glu Thr Pro His Ala Ala Phe
            100                 105                 110

Asp Ile Trp Gly Gln Gly Thr Met Val Thr Val Ser Ser
        115                 120                 125

<210> SEQ ID NO 41
<211> LENGTH: 125
<212> TYPE: PRT
<213> ORGANISM: Homo sapiens

<400> SEQUENCE: 41

Gln Val Thr Leu Lys Glu Ser Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Ser Trp Met Arg Gln Ala Pro Gly Lys Gly Leu Glu Trp Val
        35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 42
<211> LENGTH: 125
<212> TYPE: PRT
<213> ORGANISM: Homo sapiens

<400> SEQUENCE: 42

Gln Val Thr Leu Lys Glu Ser Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val

```
                    35                  40                  45
Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Arg Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 43
<211> LENGTH: 125
<212> TYPE: PRT
<213> ORGANISM: Homo sapiens

<400> SEQUENCE: 43

Gln Val Thr Leu Lys Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
                 20                  25                  30

Thr Met Thr Trp Met Arg Gln Ala Pro Gly Lys Gly Leu Glu Trp Val
             35                  40                  45

Ser Tyr Ile Ser Thr Gly Gly Ser Thr Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 44
<211> LENGTH: 125
<212> TYPE: PRT
<213> ORGANISM: Homo sapiens

<400> SEQUENCE: 44

Gln Val Thr Leu Lys Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Asp
                 20                  25                  30

Tyr Met Met Trp Ile Arg Gln Ala Pro Gly Lys Gly Leu Glu Trp Val
             35                  40                  45

Ser Tyr Ile Ser Ser Gly Gly Ser Ile Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Arg Gly Gln Gly Thr Met Val Thr Val Ser Ser
```

```
                     115                 120                 125

<210> SEQ ID NO 45
<211> LENGTH: 125
<212> TYPE: PRT
<213> ORGANISM: Homo sapiens

<400> SEQUENCE: 45

Gln Ile Thr Leu Lys Glu Ser Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Asp Met Tyr Trp Val Arg Gln Ala Pro Gly Lys Gly Leu Glu Trp Val
        35                  40                  45

Ser Tyr Ile Ser Arg Gly Gly Ser Val Thr Tyr Tyr Ala Asp Ser Val
    50                  55                  60

Lys Gly Arg Phe Thr Ile Ser Arg Asp Asn Ala Lys Asn Ala Leu Tyr
65                  70                  75                  80

Leu Gln Met Asn Ser Leu Arg Ala Glu Asp Met Ala Val Tyr Phe Cys
                85                  90                  95

Ala Thr Glu Ala Pro Leu Arg Leu Gly Glu Thr Pro His Ala Ala Phe
            100                 105                 110

Asp Ile Trp Gly Gln Gly Thr Met Val Thr Val Ser Ser
        115                 120                 125

<210> SEQ ID NO 46
<211> LENGTH: 125
<212> TYPE: PRT
<213> ORGANISM: Homo sapiens

<400> SEQUENCE: 46

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Ser Val Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 47
<211> LENGTH: 125
<212> TYPE: PRT
<213> ORGANISM: Homo sapiens

<400> SEQUENCE: 47

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 48
<211> LENGTH: 125
<212> TYPE: PRT
<213> ORGANISM: Homo sapiens

<400> SEQUENCE: 48

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Thr Ile Lys Tyr Tyr Thr Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 49
<211> LENGTH: 125
<212> TYPE: PRT
<213> ORGANISM: Homo sapiens

<400> SEQUENCE: 49

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Ser Ile Lys Tyr Tyr Thr Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

```
Asp Ile Trp Gly Gln Gly Thr Met Val Thr Val Ser Ser
            115                 120                 125

<210> SEQ ID NO 50
<211> LENGTH: 125
<212> TYPE: PRT
<213> ORGANISM: Homo sapiens

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Thr Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 51
<211> LENGTH: 125
<212> TYPE: PRT
<213> ORGANISM: Homo sapiens

<400> SEQUENCE: 51

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
        35                  40                  45

Ser Tyr Ile Ser Thr Gly Gly Ser Ile Lys Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 52
<211> LENGTH: 125
<212> TYPE: PRT
<213> ORGANISM: Homo sapiens

<400> SEQUENCE: 52

Glu Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Ser Asp Ser
            20                  25                  30

Ser Met Ser Trp Ile Arg Gln Ala Pro Gly Arg Gly Leu Glu Trp Ile
        35                  40                  45

Ser Tyr Ile Ser Ser Gly Gly Gly Ile Ile Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95

Ala Lys Glu Ala Pro Leu Arg Leu Gly Glu Ser Pro His Asp Ala Phe
            100                 105                 110

Asp Ile Trp Gly His Gly Thr Met Val Thr Val Ser Ser
            115                 120                 125

<210> SEQ ID NO 53
<211> LENGTH: 125
<212> TYPE: PRT
<213> ORGANISM: Homo sapiens

<400> SEQUENCE: 53

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 54
<211> LENGTH: 125
<212> TYPE: PRT
<213> ORGANISM: Homo sapiens

<400> SEQUENCE: 54

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

```
Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 55
<211> LENGTH: 125
<212> TYPE: PRT
<213> ORGANISM: Homo sapiens

<400> SEQUENCE: 55

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 56
<211> LENGTH: 125
<212> TYPE: PRT
<213> ORGANISM: Homo sapiens

<400> SEQUENCE: 56

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Ala Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 57
<211> LENGTH: 125
<212> TYPE: PRT
<213> ORGANISM: Homo sapiens

<400> SEQUENCE: 57

Gln Val Gln Leu Val Glu Ser Gly Gly Gly Leu Val Lys Pro Gly Gly
```

```
  1               5                  10                 15
Ser Leu Arg Leu Ser Cys Ala Ala Ser Gly Phe Thr Phe Ser Asp Tyr
            20                  25                 30

Ser Met Ser Trp Met Arg Gln Ala Pro Gly Lys Gly Leu Glu Trp Val
            35                  40                 45

Ser Tyr Ile Ser Ser Gly Gly Gly Val Ile Phe Tyr Ala Asp Ser Val
            50                  55                 60

Lys Gly Arg Phe Thr Ile Ser Arg Asp Asn Ala Lys Asn Ser Leu Tyr
65                  70                  75                 80

Leu Gln Met Asn Ser Leu Arg Ala Asp Asp Thr Ala Val Tyr Tyr Cys
            85                  90                 95

Ala Arg Glu Ala Pro Leu Arg Leu Gly Glu Ser Pro His Asp Ala Phe
            100                 105                110

Asp Ile Trp Gly Gln Gly Thr Met Val Thr Val Ser Ser
            115                 120                125

<210> SEQ ID NO 58
<211> LENGTH: 125
<212> TYPE: PRT
<213> ORGANISM: Homo sapiens

<400> SEQUENCE: 58

Gln Val Gln Leu Val Glu Ser Gly Gly Gly Leu Val Lys Pro Gly Gly
1               5                  10                 15

Ser Leu Arg Leu Ser Cys Ala Ala Ser Gly Phe Thr Phe Ser Asp Ser
            20                  25                 30

Ser Met Ser Trp Met Arg Gln Ala Pro Gly Lys Gly Leu Glu Trp Val
            35                  40                 45

Ser Tyr Ile Ser Ser Gly Gly Gly Val Ile Phe Tyr Ala Asp Ser Val
            50                  55                 60

Lys Gly Arg Phe Thr Ile Ser Arg Asp Asn Ala Lys Asn Ser Leu Tyr
65                  70                  75                 80

Leu Gln Met Asn Ser Leu Arg Ala Asp Asp Thr Ala Val Tyr Tyr Cys
            85                  90                 95

Ala Arg Glu Ala Pro Leu Arg Leu Gly Glu Ser Pro His Asp Ala Phe
            100                 105                110

Asp Ile Trp Gly Gln Gly Thr Met Val Thr Val Ser Ser
            115                 120                125

<210> SEQ ID NO 59
<211> LENGTH: 125
<212> TYPE: PRT
<213> ORGANISM: Homo sapiens

<400> SEQUENCE: 59

Gln Val Gln Leu Val Glu Ser Gly Gly Gly Leu Val Lys Pro Gly Gly
1               5                  10                 15

Ser Leu Arg Leu Ser Cys Ala Ala Ser Gly Phe Thr Phe Ser Asp Asn
            20                  25                 30

Ser Met Ser Trp Met Arg Gln Ala Pro Gly Lys Gly Leu Glu Trp Val
            35                  40                 45

Ser Tyr Ile Ser Ser Gly Gly Gly Val Ile Phe Tyr Ala Asp Ser Val
            50                  55                 60

Lys Gly Arg Phe Thr Ile Ser Arg Asp Asn Ala Lys Asn Ser Leu Tyr
65                  70                  75                 80

Leu Gln Met Asn Ser Leu Arg Ala Asp Asp Thr Ala Val Tyr Tyr Cys
```

85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 60
<211> LENGTH: 125
<212> TYPE: PRT
<213> ORGANISM: Homo sapiens

<400> SEQUENCE: 60

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 61
<211> LENGTH: 125
<212> TYPE: PRT
<213> ORGANISM: Homo sapiens

<400> SEQUENCE: 61

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Ser Trp Met Arg Gln Ala Pro Gly Lys Gly Leu Glu Trp Val
        35                  40                  45

Ser Tyr Ile Ser Thr Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Trp Gly Gln Gly Thr Met Val Thr Val Ser Ser
            115                 120                 125

<210> SEQ ID NO 62
<211> LENGTH: 125
<212> TYPE: PRT
<213> ORGANISM: Homo sapiens

<400> SEQUENCE: 62

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Thr Ile Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
            85                  90                  95

Ala Arg Glu Ala Pro Leu Arg Leu Gly Glu Ser Pro His Asp Ala Phe
        100                 105                 110

Asp Ile Trp Gly Gln Gly Thr Met Val Thr Val Ser Ser
        115                 120                 125

<210> SEQ ID NO 63
<211> LENGTH: 125
<212> TYPE: PRT
<213> ORGANISM: Homo sapiens

<400> SEQUENCE: 63

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Ala Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
            85                  90                  95

Ala Arg Glu Ala Pro Leu Arg Leu Gly Glu Ser Pro His Asp Ala Phe
        100                 105                 110

Asp Ile Trp Gly Gln Gly Thr Met Val Thr Val Ser Ser
        115                 120                 125

<210> SEQ ID NO 64
<211> LENGTH: 125
<212> TYPE: PRT
<213> ORGANISM: Homo sapiens

<400> SEQUENCE: 64

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 65
<211> LENGTH: 125
<212> TYPE: PRT
<213> ORGANISM: Homo sapiens

<400> SEQUENCE: 65

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
            35                  40                  45

Ser Tyr Ile Ser Ser Gly Gly Ser Val Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 66
<211> LENGTH: 125
<212> TYPE: PRT
<213> ORGANISM: Homo sapiens

<400> SEQUENCE: 66

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Ser Met Thr Trp Met Arg Gln Ala Pro Gly Lys Gly Leu Glu Trp Val
            35                  40                  45

Ser Tyr Ile Ser Ser Gly Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
        115                 120                 125

<210> SEQ ID NO 67
<211> LENGTH: 125
<212> TYPE: PRT
<213> ORGANISM: Homo sapiens

<400> SEQUENCE: 67

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
            85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 68
<211> LENGTH: 125
<212> TYPE: PRT
<213> ORGANISM: Homo sapiens

<400> SEQUENCE: 68

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Ala Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
            85                  90                  95

Ala Arg Glu Ala Pro Leu Arg Leu Gly Glu Ser Pro His Asp Ala Phe
            100                 105                 110

Asp Ile Leu Gly Gln Gly Thr Met Val Thr Val Ser Ser
            115                 120                 125

<210> SEQ ID NO 69
<211> LENGTH: 125
<212> TYPE: PRT
<213> ORGANISM: Homo sapiens

<400> SEQUENCE: 69

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 70
<211> LENGTH: 125
<212> TYPE: PRT
<213> ORGANISM: Homo sapiens

<400> SEQUENCE: 70

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Thr Met Thr Trp Met Arg Gln Ala Pro Gly Lys Gly Leu Glu Trp Val
            35                  40                  45

Ser Tyr Ile Ser Thr Gly Gly Thr Ile Lys Tyr Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 71
<211> LENGTH: 125
<212> TYPE: PRT
<213> ORGANISM: Homo sapiens

<400> SEQUENCE: 71

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Thr Met Thr Trp Met Arg Gln Ala Pro Gly Lys Gly Leu Glu Trp Val
            35                  40                  45

Ser Tyr Ile Ser Thr Gly Gly Val Lys Phe Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 72
<211> LENGTH: 125

```
<212> TYPE: PRT
<213> ORGANISM: Homo sapiens

<400> SEQUENCE: 72

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Ser Trp Met Arg Gln Ala Pro Gly Lys Gly Leu Glu Trp Val
        35                  40                  45

Ser Tyr Ile Ser Ser Gly Gly Ser Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 73
<211> LENGTH: 125
<212> TYPE: PRT
<213> ORGANISM: Homo sapiens

<400> SEQUENCE: 73

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Ser Met Thr Trp Met Arg Gln Ala Pro Gly Lys Gly Leu Glu Trp Val
        35                  40                  45

Ser Tyr Ile Ser Thr Gly Gly Val Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Trp Gly Gln Gly Thr Met Val Thr Val Ser Ser
            115                 120                 125

<210> SEQ ID NO 74
<211> LENGTH: 125
<212> TYPE: PRT
<213> ORGANISM: Homo sapiens

<400> SEQUENCE: 74

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Ala Val Lys Phe Tyr Thr Asp Ser Val
```

```
                50                 55                 60
Lys Gly Arg Phe Thr Ile Ser Arg Asp Asn Ala Lys Asn Ser Leu Tyr
 65                 70                 75                 80

Leu Gln Met Asn Ser Leu Arg Ala Asp Asp Thr Ala Val Tyr Tyr Cys
                    85                 90                 95

Ala Arg Glu Ala Pro Leu Arg Leu Gly Glu Ser Pro His Asp Ala Phe
                100                105                110

Asp Ile Ser Gly Gln Gly Thr Met Val Thr Val Ser Ser
                115                120                125

<210> SEQ ID NO 75
<211> LENGTH: 125
<212> TYPE: PRT
<213> ORGANISM: Homo sapiens

<400> SEQUENCE: 75

Glu Val Gln Leu Val Glu Ser Gly Gly Gly Leu Val Lys Pro Gly Gly
 1               5                  10                 15

Ser Leu Arg Leu Ser Cys Ala Ala Ser Gly Phe Thr Phe Ser Asp Ser
                 20                 25                 30

Ser Met Thr Trp Met Arg Gln Ala Pro Gly Lys Gly Leu Glu Trp Val
             35                 40                 45

Ser Tyr Ile Ser Ser Gly Gly Val Lys Phe Tyr Thr Asp Ser Val
         50                 55                 60

Lys Gly Arg Phe Thr Ile Ser Arg Asp Asn Ala Lys Asn Ser Leu Tyr
 65                 70                 75                 80

Leu Gln Met Asn Ser Leu Arg Ala Asp Asp Thr Ala Val Tyr Tyr Cys
                    85                 90                 95

Ala Arg Glu Ala Pro Leu Arg Leu Gly Glu Ser Pro His Asp Ala Phe
                100                105                110

Asp Ile Ser Gly Gln Gly Thr Met Val Thr Val Ser Ser
                115                120                125

<210> SEQ ID NO 76
<211> LENGTH: 125
<212> TYPE: PRT
<213> ORGANISM: Homo sapiens

<400> SEQUENCE: 76

Glu Val Gln Leu Val Glu Ser Gly Gly Gly Leu Val Lys Pro Gly Gly
 1               5                  10                 15

Ser Leu Arg Leu Ser Cys Ala Ala Ser Gly Phe Thr Phe Ser Asp Ser
                 20                 25                 30

Ser Met Thr Trp Met Arg Gln Ala Pro Gly Lys Gly Leu Glu Trp Val
             35                 40                 45

Ser Tyr Ile Ser Ser Gly Gly Val Lys Phe Tyr Ala Asp Ser Val
         50                 55                 60

Lys Gly Arg Phe Thr Ile Ser Arg Asp Asn Ala Lys Asn Ser Leu Tyr
 65                 70                 75                 80

Leu Gln Met Asn Ser Leu Arg Ala Asp Asp Thr Ala Val Tyr Tyr Cys
                    85                 90                 95

Ala Arg Glu Ala Pro Leu Arg Leu Gly Glu Ser Pro His Asp Ala Phe
                100                105                110

Asp Ile Ser Gly Gln Gly Thr Met Val Thr Val Ser Ser
                115                120                125
```

```
<210> SEQ ID NO 77
<211> LENGTH: 125
<212> TYPE: PRT
<213> ORGANISM: Homo sapiens

<400> SEQUENCE: 77

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 78
<211> LENGTH: 125
<212> TYPE: PRT
<213> ORGANISM: Homo sapiens

<400> SEQUENCE: 78

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Thr Ser Gly Gln Gly Thr Met Val Thr Val Ser Ser
        115                 120                 125

<210> SEQ ID NO 79
<211> LENGTH: 125
<212> TYPE: PRT
<213> ORGANISM: Homo sapiens

<400> SEQUENCE: 79

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Gly Ser
            20                  25                  30

Ser Met Thr Trp Met Arg Gln Ala Pro Gly Lys Gly Leu Glu Trp Val
        35                  40                  45
```

Ser Tyr Ile Ser Ser Gly Gly Val Ile Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 80
<211> LENGTH: 125
<212> TYPE: PRT
<213> ORGANISM: Homo sapiens

<400> SEQUENCE: 80

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Gly Asp Asn
                 20                  25                  30

Ser Met Thr Trp Met Arg Gln Ala Pro Gly Lys Gly Leu Glu Trp Val
            35                  40                  45

Ser Tyr Ile Ser Ser Gly Gly Val Ile Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Arg Gly Thr Thr Val Thr Val Ser Ser
                115                 120                 125

<210> SEQ ID NO 81
<211> LENGTH: 125
<212> TYPE: PRT
<213> ORGANISM: Homo sapiens

<400> SEQUENCE: 81

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Asn
                 20                  25                  30

Ser Met Ser Trp Met Arg Gln Ala Pro Gly Lys Gly Leu Glu Trp Val
            35                  40                  45

Ser Tyr Ile Ser Ser Gly Gly Val Ile Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 82
<211> LENGTH: 125
<212> TYPE: PRT
<213> ORGANISM: Homo sapiens

<400> SEQUENCE: 82

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Gly Asp Ser
            20                  25                  30
Ser Met Thr Trp Met Arg Gln Ala Pro Gly Lys Gly Leu Glu Trp Val
        35                  40                  45
Ser Tyr Ile Ser Ser Gly Gly Ala Val Lys Phe Tyr Thr Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
            115                 120                 125
```

<210> SEQ ID NO 83
<211> LENGTH: 125
<212> TYPE: PRT
<213> ORGANISM: Homo sapiens

<400> SEQUENCE: 83

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Gly Gly Ser
            20                  25                  30
Ser Met Thr Trp Met Arg Gln Ala Pro Gly Lys Gly Leu Glu Trp Val
        35                  40                  45
Ser Tyr Ile Ser Ser Gly Gly Val Lys Phe Tyr Thr Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
            115                 120                 125
```

<210> SEQ ID NO 84
<211> LENGTH: 125
<212> TYPE: PRT
<213> ORGANISM: Homo sapiens

<400> SEQUENCE: 84

```
Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Ser
            20                  25                  30
```

```
Ser Met Ser Trp Met Arg Gln Ala Pro Gly Lys Gly Leu Glu Trp Val
            35                  40                  45
Ser Tyr Ile Ser Ser Gly Gly Val Ile Phe Tyr Ala Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
            115                 120                 125
```

<210> SEQ ID NO 85
<211> LENGTH: 125
<212> TYPE: PRT
<213> ORGANISM: Homo sapiens

<400> SEQUENCE: 85

```
Gln Val Gln Leu Val Glu Ser Gly Gly Gly Leu Val Lys Pro Gly Gly
 1                5                  10                  15
Ser Leu Arg Leu Ser Cys Ala Ala Thr Gly Phe Thr Phe Ser Asp Ser
            20                  25                  30
Ser Met Thr Trp Met Arg Gln Ala Pro Gly Lys Gly Leu Glu Trp Val
            35                  40                  45
Ser Tyr Ile Ser Ala Gly Gly Val Arg Phe Tyr Thr Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
Asp Ile Ser Gly Gln Gly Thr Met Val Thr Val Ser Ser
            115                 120                 125
```

<210> SEQ ID NO 86
<211> LENGTH: 125
<212> TYPE: PRT
<213> ORGANISM: Homo sapiens

<400> SEQUENCE: 86

```
Glu Val Gln Leu Val Glu Ser Gly Gly Gly Leu Val Lys Pro Gly Gly
 1                5                  10                  15
Ser Leu Arg Leu Ser Cys Ala Ala Ser Gly Phe Thr Phe Ser Asp Ser
            20                  25                  30
Ser Met Thr Trp Ile Arg Gln Ala Pro Gly Lys Gly Leu Glu Trp Val
            35                  40                  45
Ser Tyr Ile Ser Ser Gly Gly Val Lys Phe Tyr Thr Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Asp Asp Thr Ala Val Tyr Tyr Cys
                85                  90                  95
Ala Arg Glu Ala Pro Leu Arg Leu Gly Glu Ser Pro His Asp Ala Phe
            100                 105                 110
```

```
Asp Ile Ser Gly Gln Gly Thr Met Val Thr Val Ser Ser
            115                 120                 125

<210> SEQ ID NO 87
<211> LENGTH: 125
<212> TYPE: PRT
<213> ORGANISM: Homo sapiens

<400> SEQUENCE: 87

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 88
<211> LENGTH: 125
<212> TYPE: PRT
<213> ORGANISM: Homo sapiens

<400> SEQUENCE: 88

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 89
<211> LENGTH: 125
<212> TYPE: PRT
<213> ORGANISM: Homo sapiens

<400> SEQUENCE: 89

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
```

```
            20                  25                  30
Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 90
<211> LENGTH: 125
<212> TYPE: PRT
<213> ORGANISM: Homo sapiens

<400> SEQUENCE: 90

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Ile Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 91
<211> LENGTH: 125
<212> TYPE: PRT
<213> ORGANISM: Homo sapiens

<400> SEQUENCE: 91

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Lys Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
```

Asp Ile Ser Gly Gln Gly Thr Met Val Thr Val Ser Ser
            115                 120                 125

<210> SEQ ID NO 92
<211> LENGTH: 125
<212> TYPE: PRT
<213> ORGANISM: Homo sapiens

<400> SEQUENCE: 92

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 93
<211> LENGTH: 125
<212> TYPE: PRT
<213> ORGANISM: Homo sapiens

<400> SEQUENCE: 93

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Ser Met Thr Trp Val Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 94
<211> LENGTH: 125
<212> TYPE: PRT
<213> ORGANISM: Homo sapiens

<400> SEQUENCE: 94

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Thr Phe Ser Asp Thr
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 95
<211> LENGTH: 125
<212> TYPE: PRT
<213> ORGANISM: Homo sapiens

<400> SEQUENCE: 95

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Phe Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 96
<211> LENGTH: 125
<212> TYPE: PRT
<213> ORGANISM: Homo sapiens

<400> SEQUENCE: 96

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 97
<211> LENGTH: 125
<212> TYPE: PRT
<213> ORGANISM: Homo sapiens

<400> SEQUENCE: 97

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 98
<211> LENGTH: 125
<212> TYPE: PRT
<213> ORGANISM: Homo sapiens

<400> SEQUENCE: 98

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 99
<211> LENGTH: 125
<212> TYPE: PRT
<213> ORGANISM: Homo sapiens

<400> SEQUENCE: 99

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Lys
                20                  25                  30

Ser Met Thr Trp Met Arg Gln Ala Pro Gly Lys Gly Leu Glu Trp Val
            35                  40                  45

Ser Tyr Ile Ser Ser Gly Gly Val Lys Phe Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 100
<211> LENGTH: 125
<212> TYPE: PRT
<213> ORGANISM: Homo sapiens

<400> SEQUENCE: 100

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Arg
                20                  25                  30

Ser Met Thr Trp Met Arg Gln Ala Pro Gly Lys Gly Leu Glu Trp Val
            35                  40                  45

Ser Tyr Ile Ser Ser Gly Gly Val Lys Phe Tyr Thr Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125
```

<210> SEQ ID NO 101
<211> LENGTH: 125
<212> TYPE: PRT
<213> ORGANISM: Homo sapiens

<400> SEQUENCE: 101

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Ser Met Thr Trp Met Arg Gln Ala Pro Gly Lys Gly Leu Glu Trp Val
            35                  40                  45

Ser Tyr Ile Ser Ser Gly Gly Val Lys Phe Tyr Ala Asp Ser Val
        50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
            85                  90                  95

Ala Arg Glu Ala Pro Leu Arg Leu Gly Glu Ser Pro His Asp Ala Phe
        100                 105                 110

Asp Ile Ser Gly Gln Gly Thr Met Val Thr Val Ser Ser
        115                 120                 125

<210> SEQ ID NO 102
<211> LENGTH: 125
<212> TYPE: PRT
<213> ORGANISM: Homo sapiens

<400> SEQUENCE: 102

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Val
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Ala Pro Leu Arg Leu Gly Glu Ser Pro His Asp Ala Phe
        100                 105                 110

Asp Ile Ser Gly Gln Gly Thr Met Val Thr Val Ser Ser
        115                 120                 125

<210> SEQ ID NO 103
<211> LENGTH: 125
<212> TYPE: PRT
<213> ORGANISM: Homo sapiens

<400> SEQUENCE: 103

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Gln
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Ala Pro Leu Arg Leu Gly Glu Ser Pro His Asp Ala Phe
        100                 105                 110

Asp Ile Ser Gly Gln Gly Thr Met Val Thr Val Ser Ser
        115                 120                 125

<210> SEQ ID NO 104
<211> LENGTH: 125
<212> TYPE: PRT
<213> ORGANISM: Homo sapiens -continued

<400> SEQUENCE: 104

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 105
<211> LENGTH: 125
<212> TYPE: PRT
<213> ORGANISM: Homo sapiens

<400> SEQUENCE: 105

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 106
<211> LENGTH: 125
<212> TYPE: PRT
<213> ORGANISM: Homo sapiens

<400> SEQUENCE: 106

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Trp
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Val Tyr Tyr Cys
                    85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 107
<211> LENGTH: 125
<212> TYPE: PRT
<213> ORGANISM: Homo sapiens

<400> SEQUENCE: 107

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Gly
                20                  25                  30

Ser Met Thr Trp Met Arg Gln Ala Pro Gly Lys Gly Leu Glu Trp Val
            35                  40                  45

Ser Tyr Ile Ser Ser Gly Gly Val Lys Phe Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 108
<211> LENGTH: 125
<212> TYPE: PRT
<213> ORGANISM: Homo sapiens

<400> SEQUENCE: 108

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Thr
                20                  25                  30

Ser Met Thr Trp Met Arg Gln Ala Pro Gly Lys Gly Leu Glu Trp Val
            35                  40                  45

Ser Tyr Ile Ser Ser Gly Gly Val Lys Phe Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 109
<211> LENGTH: 125
<212> TYPE: PRT
```

<213> ORGANISM: Homo sapiens

<400> SEQUENCE: 109

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ile
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 110
<211> LENGTH: 125
<212> TYPE: PRT
<213> ORGANISM: Homo sapiens

<400> SEQUENCE: 110

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Lys
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 111
<211> LENGTH: 125
<212> TYPE: PRT
<213> ORGANISM: Homo sapiens

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Arg
            20                  25                  30

Ser Met Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 112
<211> LENGTH: 125
<212> TYPE: PRT
<213> ORGANISM: Homo sapiens

<400> SEQUENCE: 112

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Leu
             20                  25                  30

Ser Met Thr Trp Met Arg Gln Ala Pro Gly Lys Gly Leu Glu Trp Val
         35                  40                  45

Ser Tyr Ile Ser Ser Gly Gly Val Lys Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 113
<211> LENGTH: 125
<212> TYPE: PRT
<213> ORGANISM: Homo sapiens

<400> SEQUENCE: 113

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Phe
             20                  25                  30

Ser Met Thr Trp Met Arg Gln Ala Pro Gly Lys Gly Leu Glu Trp Val
         35                  40                  45

Ser Tyr Ile Ser Ser Gly Gly Val Lys Phe Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 114
```

-continued

```
<211> LENGTH: 125
<212> TYPE: PRT
<213> ORGANISM: Homo sapiens

<400> SEQUENCE: 114

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Val Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 115
<211> LENGTH: 125
<212> TYPE: PRT
<213> ORGANISM: Homo sapiens

<400> SEQUENCE: 115

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Gln Thr Trp Met Arg Gln Ala Pro Gly Lys Gly Leu Glu Trp Val
        35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 116
<211> LENGTH: 125
<212> TYPE: PRT
<213> ORGANISM: Homo sapiens

<400> SEQUENCE: 116

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Phe Thr Trp Met Arg Gln Ala Pro Gly Lys Gly Leu Glu Trp Val
        35                  40                  45
```

```
Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 117
<211> LENGTH: 125
<212> TYPE: PRT
<213> ORGANISM: Homo sapiens

<400> SEQUENCE: 117

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
                20                  25                  30

Ser Leu Thr Trp Met Arg Gln Ala Pro Gly Lys Gly Leu Glu Trp Val
            35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 118
<211> LENGTH: 125
<212> TYPE: PRT
<213> ORGANISM: Homo sapiens

<400> SEQUENCE: 118

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
                20                  25                  30

Ser Lys Thr Trp Met Arg Gln Ala Pro Gly Lys Gly Leu Glu Trp Val
            35                  40                  45

Ser Tyr Ile Ser Ser Gly Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125
```

<210> SEQ ID NO 119
<211> LENGTH: 125
<212> TYPE: PRT
<213> ORGANISM: Homo sapiens

<400> SEQUENCE: 119

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Tyr Thr Trp Met Arg Gln Ala Pro Gly Lys Gly Leu Glu Trp Val
        35                  40                  45

Ser Tyr Ile Ser Ser Gly Gly Val Lys Phe Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 120
<211> LENGTH: 125
<212> TYPE: PRT
<213> ORGANISM: Homo sapiens

<400> SEQUENCE: 120

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Ala Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 121
<211> LENGTH: 125
<212> TYPE: PRT
<213> ORGANISM: Homo sapiens

<400> SEQUENCE: 121

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Phe Thr Trp Met Arg Gln Ala Pro Gly Lys Gly Leu Glu Trp Val

```
                35                  40                  45

Ser Tyr Ile Ser Ser Gly Gly Gly Val Lys Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 122
<211> LENGTH: 125
<212> TYPE: PRT
<213> ORGANISM: Homo sapiens

<400> SEQUENCE: 122

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Glu
                 20                  25                  30

Ser Asn Thr Trp Met Arg Gln Ala Pro Gly Lys Gly Leu Glu Trp Val
                 35                  40                  45

Ser Tyr Ile Ser Ser Gly Gly Gly Val Lys Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
                115                 120                 125

<210> SEQ ID NO 123
<211> LENGTH: 125
<212> TYPE: PRT
<213> ORGANISM: Homo sapiens

<400> SEQUENCE: 123

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Glu
                 20                  25                  30

Ser Trp Thr Trp Met Arg Gln Ala Pro Gly Lys Gly Leu Glu Trp Val
                 35                  40                  45

Ser Tyr Ile Ser Ser Gly Gly Gly Val Lys Phe Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
                100                 105                 110

Asp Ile Ser Gly Gln Gly Thr Met Val Thr Val Ser Ser
```

115                 120                 125

<210> SEQ ID NO 124
<211> LENGTH: 125
<212> TYPE: PRT
<213> ORGANISM: Homo sapiens

<400> SEQUENCE: 124

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Ile Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 125
<211> LENGTH: 125
<212> TYPE: PRT
<213> ORGANISM: Homo sapiens

<400> SEQUENCE: 125

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Ser Thr Trp Met Arg Gln Ala Pro Gly Lys Gly Leu Glu Trp Val
        35                  40                  45

Ser Tyr Ile Ser Ser Gly Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
            115                 120                 125

<210> SEQ ID NO 126
<211> LENGTH: 125
<212> TYPE: PRT
<213> ORGANISM: Homo sapiens

<400> SEQUENCE: 126

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

-continued

Ser His Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 127
<211> LENGTH: 125
<212> TYPE: PRT
<213> ORGANISM: Homo sapiens

<400> SEQUENCE: 127

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Glu
            20                  25                  30

Ser Gly Thr Trp Met Arg Gln Ala Pro Gly Lys Gly Leu Glu Trp Val
        35                  40                  45

Ser Tyr Ile Ser Ser Gly Gly Val Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Pro Leu Arg Leu Gly Glu Ser Pro His Asp Ala Phe
            100                 105                 110

Asp Ile Ser Gly Gln Gly Thr Met Val Thr Val Ser Ser
        115                 120                 125

<210> SEQ ID NO 128
<211> LENGTH: 375
<212> TYPE: DNA
<213> ORGANISM: Homo sapiens

<400> SEQUENCE: 128
caggtgcagc tggtggagtc tgggggaggc ttggtcaagc ctggagggtc cctgagactc      60
tcctgtgcag cctctggatt caccttcagt gactacacca tgacctggat gcggcaggct    120
ccagggaagg gctggagtg gtttcctac ataagtactg gtggtactat caaatattac      180
acagactctg tgaagggccg attcaccatc tccagggaca cgccaagaa ctcactgtat     240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                     375

<210> SEQ ID NO 129
<211> LENGTH: 375
<212> TYPE: DNA
<213> ORGANISM: Homo sapiens

<400> SEQUENCE: 129

```
gaggtgcagc tgttggagtc tgggggaggc ttggtcaagc ctggagggtc cctgagactc    60
tcctgtgcag cctctggatt caccttcagt gactacacca tgacctggat gcgccaggct   120
ccagggaagg ggctggagtg ggtttcatat ataagtactg gtggtagtat caaatattac   180
acagactctg tgaagggccg attcaccatc tccagggaca acgccaagaa ctcactgtat   240
ctgcaaatga acagcctgag agccgacgac acggccgtgt attactgtgc gagagaggcc   300
cctttacgtt tgggggagtc cccccatgat gcttttgata tctggggcca agggacaatg   360
gtcactgtct cctca                                                    375
```

<210> SEQ ID NO 130
<211> LENGTH: 375
<212> TYPE: DNA
<213> ORGANISM: Homo sapiens

<400> SEQUENCE: 130

```
caggtgcagc tggtggagtc tgggggaggc ttggtcaagc ctggagggtc cctgagactc    60
tcctgtgcag cctctggatt caccttcagt gactacacca tgacctggat gcgccaggct   120
ccagggaagg ggctggagtg ggtttcttac ataagtactg gtggtagtat caaatattat   180
acagactctg tgaagggccg attcaccatc tccagggaca acgccaagaa ctcactgtat   240
ctgcaaatga acagcctgag agccgacgac acggccgtgt attactgtgc gagagaggcc   300
cctttacgtt tgggggagtc cccccatgat gcttttgata tctggggcca agggacaatg   360
gtcactgtct cctca                                                    375
```

<210> SEQ ID NO 131
<211> LENGTH: 375
<212> TYPE: DNA
<213> ORGANISM: Homo sapiens

<400> SEQUENCE: 131

```
caagtgcagc tggtggagtc tgggggaggc ttggtcaagc ctggagggtc cctgagactc    60
tcctgtgcag cctctggatt caccttcagt gactactaca tgatctggat gcgccaggct   120
ccagggaagg ggctggagtg ggtttcctac attagtggtg gtggtactac caaatattac   180
acagactctg tgaagggccg attcaccatc tccagggaca acgccaagaa ctcactgtat   240
ctgcaaatga acagcctgag agccgacgac acggccgtgt actactgtgc gagagaggcc   300
cctttacgtt tgggggagac cccccatgat gcttttgata tctggggcca agggacaatg   360
gtcactgtct cctca                                                    375
```

<210> SEQ ID NO 132
<211> LENGTH: 375
<212> TYPE: DNA
<213> ORGANISM: Homo sapiens

<400> SEQUENCE: 132

```
gaagtgcagc tggtggagtc tgggggaggc ttggtcaagc ctggagggtc cctgagactc    60
tcctgtgcag cctctggatt caccttcagt gactacacca tgacctggat gcgccaggct   120
ccagggaagg ggctggagtg ggtttcatac ataagtactg gtggtaatac caaatattac   180
acagactctg tgaagggccg cttcaccatc tccagggaca acgccaagaa ctcactgtat   240
ctgcaaatga acagcctgag agccgacgac acggccgtat attactgtgc gagagaggcc   300
cctttacgtt tgggggagtc cccccatgat gcttttgata tctggggcca agggacaatg   360
```

```
gtcactgtct cttca                                                        375

<210> SEQ ID NO 133
<211> LENGTH: 375
<212> TYPE: DNA
<213> ORGANISM: Homo sapiens

<400> SEQUENCE: 133
gaggtgcagc tgttggagtc tgggggaggc ttggtcaagc ctggagggtc cctgagactc        60
tcctgtgcag cctctggatt caccttcagt gactacacca tgacctggat gcggcaggct       120
ccagggaagg ggctggagtg ggtttcctac ataagtactg gtggtactat caaatattac       180
acagactctg tgaagggccg attcaccatc tccagggaca cgccaagaa ctcactgtat        240 ctgcaaatga gcagcctgag agccgacgac acggccgtgt attactgtgc gcgagaggcc       300
cctttacgtt tgggggagtc cccccatgat gcttttgata tctggggcca agggacaatg       360
gtcactgtct cctca                                                        375

<210> SEQ ID NO 134
<211> LENGTH: 375
<212> TYPE: DNA
<213> ORGANISM: Homo sapiens

<400> SEQUENCE: 134
gaagtgcagc tgtggagtc tgggggaggc ttggtcaagc ctggagggtc cctgagactc         60
tcctgtgcag cctctggatt caccttcagt gactacacca tgacctggat gcgccaggct       120
ccagggaagg ggctggagtg ggtttcctac ataagtactg gtggtactat caaatattac       180
acagactctg tgaagggccg attcaccatc tccagggaca cgccaagaa ctcactgtat        240 ctgcaaatga acagcctgag agccgacgac acggccgtgt attactgtgc gcgagaggcc       300
cctttacgtt tgggggagtc cccccatgat gcttttgata tctggggcca agggacaatg       360
gtcactgtct cttca                                                        375

<210> SEQ ID NO 135
<211> LENGTH: 375
<212> TYPE: DNA
<213> ORGANISM: Homo sapiens

<400> SEQUENCE: 135
gaggtgcagc tgtggagtc tgggggaggc ttggtcaagc ctggagggtc cctgagactc         60
tcctgtgcag cctctggatt caccttcagt gactacacca tgacctggat gcgccaggct       120
ccagggaagg ggctggagtg ggtttcatac ataagtactg gtgtagtat taaatattac        180 acagactctg tgaagggccg attcaccatc tccagggaca cgccaagaa ctcactgtat        240 ctgcaaatga acagcctgag agccggcgac acggccgtgt attactgtgc gagagaggcc       300
cctttacgtt tgggggagtc cccccatgat gcttttgata tctggggcca agggacaatg       360
gtcaccgtct cttca                                                        375

<210> SEQ ID NO 136
<211> LENGTH: 375
<212> TYPE: DNA
<213> ORGANISM: Homo sapiens

<400> SEQUENCE: 136
caggtgcagc tgtggagtc tgggggaggc ttggtcaagc ctggagggtc cctgagactc         60
```

-continued

| | |
|---|---|
| tcctgtgcag cctctggatt caccttcggt gactacacca tgacctggat gcggcaggct | 120 |
| ccagggaagg ggctggagtg ggtttcctac ataagtactg gtggtactat caaatattac | 180 |
| acagactctg tgaagggccg attcaccatc tccagggaca acgccaagaa ctcactgtat | 240 |
| ctgcaaatgg acagcctgag agccgacgac acggccgtgt attactgtgc gcgagaggcc | 300 |
| cctttacgtt tgggggagtc cccccatgat gcttttgata tctggggcca agggacaatg | 360 |
| gtcactgtct cttca | 375 |

<210> SEQ ID NO 137
<211> LENGTH: 375
<212> TYPE: DNA
<213> ORGANISM: Homo sapiens

<400> SEQUENCE: 137

| | |
|---|---|
| caggtgcagc tggtggagtc tgggggaggc ttggtcaagc ctggagggtc cctgagactc | 60 |
| tcctgtgcag cctctggatt caccttcagt gactacacca tgagctggat gcgccaggct | 120 |
| ccagggaagg ggctggagtg gatttcatac ataagtcttg gtggtaatac caaatattac | 180 |
| acagactctg tgaagggccg attcaccatc tccagggaca acgccaagaa ctcactgtat | 240 |
| ctgcaaatga acagcctgcg agccgacgac acggccgtgt attactgtgc gagagaggcc | 300 |
| cctttacgtt tgggggagtc cccccatgat gcttttgata tctggggcca agggacaatg | 360 |
| gtcaccgtct cctca | 375 |

<210> SEQ ID NO 138
<211> LENGTH: 375
<212> TYPE: DNA
<213> ORGANISM: Homo sapiens

<400> SEQUENCE: 138

| | |
|---|---|
| gaggtgcagc tgttggagtc tgggggaggc ttggtcaagc ctggagggtc cctgagactc | 60 |
| tcctgtgcag cctctggatt caccttcagt gactatgaca tgacctggat ccgccaggct | 120 |
| ccagggaagg ggcaggagtg ggtttcatat attagtcgtg gtggtagtac caaatactac | 180 |
| gcagactctg tgaagggccg attcaccatc tccagggaca acgccaagaa ctcactgtat | 240 |
| ctgcaaatga acagcctgag agccgaggac acggccgtat actactgtgc gagagaggcc | 300 |
| cctttacgtt tgggggagac cccccacgat gcttttgata tctggggcca agggacaatg | 360 |
| gtcaccgtct cttca | 375 |

<210> SEQ ID NO 139
<211> LENGTH: 375
<212> TYPE: DNA
<213> ORGANISM: Homo sapiens

<400> SEQUENCE: 139

| | |
|---|---|
| gaggtgcagc tgttggagtc tgggggaggc gtggtcaagc ctggagggtc cctgagactc | 60 |
| tcctgtgcag cctctggatt caccttcagt gactactata tgggctggat ccgccaggct | 120 |
| ccagggaagg ggctggagtg gatttcatac attagtagta gtggtagtac catatactac | 180 |
| gcagactctg tgaagggccg attcaccatc tccagggaca acgccaagaa ctcactgtat | 240 |
| ctgcaaatga acagcctgag agccgaggac acggccgtgt attactgtgc gagagaggcc | 300 |
| cctttgcgtt tgggggagtc cccccatgat gcttttgata tctggggcca agggacaatg | 360 |
| gtcactgtct cttca | 375 |

```
<210> SEQ ID NO 140
<211> LENGTH: 375
<212> TYPE: DNA
<213> ORGANISM: Homo sapiens

<400> SEQUENCE: 140
gaggtgcagc tgttggagtc tgggggaggc ttggtcaagc ctggagggtc cctgagactc      60
tcctgtgcag cctctggatt caccttcagt gactacacca tgacctggat gcggcaggct     120
ccagggaagg ggctggagtg ggtttcctac ataagtactg gtggtactat caaatattac     180
acagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctggggcca agggacaatg     360
gtcactgtct cttca                                                      375

<210> SEQ ID NO 141
<211> LENGTH: 375
<212> TYPE: DNA
<213> ORGANISM: Homo sapiens

<400> SEQUENCE: 141
gaggtgcagc tggtggagtc tgggggaggc ttggtacagc ctggcaggtc cctgagactc      60
tcctgtgcag cctctggatt caccttcagt gactacacca tgacctggat gcggcaggct     120
ccagggaagg ggctggagtg ggtttcctac ataagtactg gtggtactat caaatattac     180
acagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                      375

<210> SEQ ID NO 142
<211> LENGTH: 375
<212> TYPE: DNA
<213> ORGANISM: Homo sapiens

<400> SEQUENCE: 142
caggtgcagc tggtggagtc tgggggaggc ttggtcaagc ctggagggtc cctgagactc      60
tcctgtgcag cctctggatt caccttcagt gacaattcca tgagctggat ccgccaggct     120
ccagggaagg ggctggagtg ggtttcatac attagtagta gtggtagtac catatactac     180
gcagactctg tgaagggccg attcaccatc tccagggaca cgccaagaa ctcactgtat      240 ctgcaaatga acaccctgag agccgaggac acggccgtgt attactgtgc gaaagaggcc     300
cctttacgtt tgggggagtc cccccatgat gcttttgata tctggggcca agggacaatg     360
gtcaccgtct cttca                                                      375

<210> SEQ ID NO 143
<211> LENGTH: 375
<212> TYPE: DNA
<213> ORGANISM: Homo sapiens

<400> SEQUENCE: 143
gaagtgcagc tggtggagtc tgggggaggc ttggtcaagc ctggagggtc cctgagactc      60
tcctgtgcag cctctggatt caccttcagt gactacacca tgagctggat cgccaggct      120 ccagggaagg ggctggagtg ggtttcatac ataagtactg gtggtagtat caaatattac     180
```

| | |
|---|---|
| acagactctg tgaagggccg attcaccatc tccagggaca acgccaagaa ctcactgtat | 240 |
| ctgcaaatga acagcctgag agccgacgac acggccgtgt attactgtgc gagagaggcc | 300 |
| cctttacgtt tgggggagtc cccccatgat gcttttgata tctggggcca agggacaatg | 360 |
| gtcaccgtct cctca | 375 |

<210> SEQ ID NO 144
<211> LENGTH: 375
<212> TYPE: DNA
<213> ORGANISM: Homo sapiens

<400> SEQUENCE: 144

| | |
|---|---|
| gaggtgcagc tggtggagtc tgggggaggc ttggtcaagc ctggagggtc cctgagactc | 60 |
| tcctgtgcag cctctggatt caccttcagt gactacacca tgacctggat gcgccaggct | 120 |
| ccagggaagg ggctggagtg ggtttcatac ataagtactg gtggcagtat caaatattac | 180 |
| acagactctg tgaagggccg attcaccatc tccagggaca acgccaagaa ctcactgtat | 240 |
| ctgcaaatga acagcctgag agtcgacgac acggccgtgt attactgtgc gagagaggcc | 300 |
| cctttacgtt tgggggagtc cccccatgat gcttttgata tctggggcca agggacaatg | 360 |
| gtcaccgtct cctca | 375 |

<210> SEQ ID NO 145
<211> LENGTH: 375
<212> TYPE: DNA
<213> ORGANISM: Homo sapiens

<400> SEQUENCE: 145

| | |
|---|---|
| caggtgcagc tgttggagtc tgggggaggc ttggtcaagc ctggagggtc cctgagactc | 60 |
| tcctgtgcag cctctggatt caccttcagt gactacacca tgacctggat gcggcaggct | 120 |
| ccagggaagg ggctggagtg ggtttcctac ataagtactg gtggtactat caaatattac | 180 |
| acagactctg tgaagggccg attcaccatc tccagggaca acgccaagaa ctcactgtat | 240 |
| ctgcaaatga acagcctgag agccgacgac acggccgtgt attactgtgc gcgagaggcc | 300 |
| cctttacgtt tgggggagtc cccccatgat gcttttgata tctggggcca agggacaatg | 360 |
| gtcactgtct cttca | 375 |

<210> SEQ ID NO 146
<211> LENGTH: 375
<212> TYPE: DNA
<213> ORGANISM: Homo sapiens

<400> SEQUENCE: 146

| | |
|---|---|
| caggtgcagc tggtggagtc tgggggaggc ttggtcaagc ctggagggtc cctgagactc | 60 |
| tcctgtgcag cctctggatt caccttcagt gactacacca tgacctggat gcgccaggct | 120 |
| ccagggaagg ggctggagtg ggtttcatac ataagtactg gtggtagtat caaatattac | 180 |
| acagactctg tgaagggccg attcaccatc tccagggaca acgccaagaa ctcactgtat | 240 |
| ctgcaaatga acagcctgag agccgaggac acggccgtat actactgtgc gagagaggcc | 300 |
| cctttacgtt tgggggagac cccccacgat gcttttgata tctggggcca agggacaatg | 360 |
| gtcaccgtct cttca | 375 |

<210> SEQ ID NO 147
<211> LENGTH: 375
<212> TYPE: DNA
<213> ORGANISM: Homo sapiens

<400> SEQUENCE: 147

| gaggtgcagc | tgttggagtc | tgggggaggc | ttggtcaagc | ctggagggtc | cctgagactc | 60 |
|---|---|---|---|---|---|---|
| tcctgtgcag | cctctggatt | caccttcagt | gactacacca | tgacctggat | gcgccaggct | 120 |
| ccagggaagg | ggctggagtg | ggtttcatac | attagtagtg | gtggtagtat | caaattctac | 180 |
| gcagactctg | tgaagggccg | attcaccatc | tccagggaca | acgccaaaaa | ctcactgtat | 240 |
| ctgcaaatga | acagcctgag | agccgaggac | acggccgtgt | attactgtgc | gagagaggcc | 300 |
| cctttacgtt | tggggagtc | cccccatgat | gcttttgata | tctggggcca | agggacaatg | 360 |
| gtcaccgtct | cctca | | | | | 375 |

<210> SEQ ID NO 148
<211> LENGTH: 375
<212> TYPE: DNA
<213> ORGANISM: Homo sapiens

<400> SEQUENCE: 148

| gaggtgcagc | tggtggagtc | tgggggaggc | ttggtcaagc | ctggagggtc | cctgagactc | 60 |
|---|---|---|---|---|---|---|
| tcctgtgcag | cctctggatt | caccttcagt | gactacacca | tgacctggat | gcgccaggct | 120 |
| ccagggaagg | ggctggagtg | ggtttcatat | ataagtactg | gtggtagtat | caaatattac | 180 |
| acagactctg | tgaagggccg | attcaccatc | tccagggaca | acgccaagaa | ctcactgtat | 240 |
| ctgcaaatga | acagcctgag | agccgacgac | acggccgtgt | attactgtgc | gagagaggcc | 300 |
| cctttacgtt | tggggagtc | cccccatgat | gcttttgata | cctggggcca | agggacaatg | 360 |
| gtcaccgtct | cttca | | | | | 375 |

<210> SEQ ID NO 149
<211> LENGTH: 375
<212> TYPE: DNA
<213> ORGANISM: Homo sapiens

<400> SEQUENCE: 149

| gaagtgcagc | tggtggagtc | tgggggaggc | ttggtcaagc | ctggagggtc | cctgagactc | 60 |
|---|---|---|---|---|---|---|
| tcctgtgcag | cctctggatt | caccttcagt | gactacacca | tgacctggat | gcgccaggct | 120 |
| ccagggaagg | ggctggagtg | ggtttcatac | ataagtactg | gtggtagtat | caaatattac | 180 |
| acagactctg | tgaagggccg | attcaccatc | tccagggaca | acgccaagaa | ctcattgtat | 240 |
| ctgcaaatga | acagcctgag | agccgacgac | acggccgtgt | attactgtgc | gagagaggcc | 300 |
| cctttacgtt | tggggagtc | cccccatgat | gcttttgata | tctggggcca | agggacaatg | 360 |
| gtcactgtct | cttca | | | | | 375 |

<210> SEQ ID NO 150
<211> LENGTH: 375
<212> TYPE: DNA
<213> ORGANISM: Homo sapiens

<400> SEQUENCE: 150

| cagatcacct | tgaaggagtc | tgggggaggc | ttggtcaagc | ctggagggtc | cctgagactc | 60 |
|---|---|---|---|---|---|---|
| tcctgtgcag | cctctggatt | caccttcagt | gactacacca | tgagctggat | gcggcaggct | 120 |
| ccagggaagg | ggctggagtg | ggtttcctac | ataagtactg | gtggtactat | caaatattac | 180 |
| acagactctg | tgaagggccg | attcaccatc | tccagggaca | acgccaagaa | ctcactgtat | 240 |
| ctgcaaatga | acagcctgag | agccgacgac | acggccgtgt | attactgtgc | gcgagaggcc | 300 |

```
cctttacgtt tggggagtc ccccatgat gcttttgata tctggggcca agggacaatg      360
gtcaccgtct cctca                                                      375

<210> SEQ ID NO 151
<211> LENGTH: 375
<212> TYPE: DNA
<213> ORGANISM: Homo sapiens

<400> SEQUENCE: 151
caggtcacct tgaaggagtc tggggggagc ttggtcaagc ctggagggtc cctgagactc      60
tcctgtgcag cctctggatt caccttcagt gactatgaca tgtactggat ccgccaggct     120
ccagggaagg ggctggagtg ggtttcatat attagtcgtg gtggtagtgt aacatactac     180
gcagactctg tgaagggccg attcaccatt tccagggaca cgccaagaa cgcactgtat      240 ctgcaaatga acagcctgag agccgaggac atggccgtat atttttgtgc gacagaggcc     300
cctttacgtt tgggggagac ccccatgct gcttttgata tctggggcca agggacaatg      360
gtcaccgtct cctca                                                      375

<210> SEQ ID NO 152
<211> LENGTH: 375
<212> TYPE: DNA
<213> ORGANISM: Homo sapiens

<400> SEQUENCE: 152
caggtcacct tgaaggagtc tggggggagc ttggtcaagc ctggagggtc cctgagactc      60
tcctgtgcag cctctggatt caccttcagt gactactaca tgagctggtt ccgccaggct     120
ccagggaagg aacgggagtg gatttcattt attagtagta gtggtagtac cacatactac     180
gcagactctg tgaagggccg attcaccatc tccagggaca cgccaagaa ctcactgtat      240 ctgcaaatga acagcctgag agccgaggat acggccgtct attactgtgc gagagaggcc     300
cctttacgtt tggggagtc ccccatgat gcttttgatt tctggggcca agggacaatg       360
gtcaccgtct cttca                                                      375

<210> SEQ ID NO 153
<211> LENGTH: 375
<212> TYPE: DNA
<213> ORGANISM: Homo sapiens

<400> SEQUENCE: 153
caggtcacct tgaaggagtc tggggggagc ttggtcaagc ctggagggtc cctgagactc      60
tcctgtgcag cctctggatt caccttcagt gacaattcca tgagctggat ccgccaggct     120
ccagggaagg ggctggagtg ggtttcatac attagtagta gtggtagtac catatactac     180
gcagactctg tgaagggccg attcaccatc tccagggaca cgccaagaa ctcactgtat      240 ctgcaaatga acaccctgag agccgaggac acggccgtgt attactgtgc gaaagaggcc     300
cctttacgtt tggggagtc ccccatgat gcttttgata tctggggcca agggacaatg       360
gtcaccgtct cctca                                                      375

<210> SEQ ID NO 154
<211> LENGTH: 375
<212> TYPE: DNA
<213> ORGANISM: Homo sapiens

<400> SEQUENCE: 154
caggtcacct tgaaggagtc tggggggagc ttggtcaagc ctggagggtc cctgagactc      60
```

```
tcctgtgcag cctctggatt caccttcagt gactacacca tgacctggat gcgccaggct      120
ccagggaagg ggctggagtg ggtttcatac ataagtactg tggtagtat caaatattac       180 acagactctg tgaagggccg attcaccatc tccagggaca acgccaagaa ctcactgtat      240
ctgcaaatga acagcctgag agccgacgac acggccgtgt attactgtgc gagagaggcc     300
cctttacgtt tgggggagtc cccccatgat gcttttgata tctggggcca agggacaatg     360
gtcaccgtct cttca                                                       375
```

<210> SEQ ID NO 155
<211> LENGTH: 375
<212> TYPE: DNA
<213> ORGANISM: Homo sapiens

<400> SEQUENCE: 155

```
cagatcacct tgaaggagtc tgggggaggc ttggtcaagc ctggagggtc cctgagactc       60
tcctgtgcag cctctggatt caccttcagt gactatgaca tgtactggat ccgccaggct     120
ccagggaagg ggctggagtg ggtttcatat attagtcgtg gtggtagtgt aacatactac      180
gcagactctg tgaagggccg attcaccatt tccagggaca acgccaagaa cgcactgtat      240
ctgcaaatga acagcctgag agccgaggac atggccgtat attttgtgc gacagaggcc      300 cctttacgtt tgggggagac ccccccatgct gcttttgata tctggggcca agggacaatg     360
gtcaccgtct cttca                                                       375
```

<210> SEQ ID NO 156
<211> LENGTH: 375
<212> TYPE: DNA
<213> ORGANISM: Homo sapiens

<400> SEQUENCE: 156

```
caggtcacct tgaaggagtc tgggggaggc ttggtcaagc ctggagggtc cctgagactc       60
tcctgtgcag cctctggatt caccttcagt gactacacca tgagctggat gcggcaggct     120
ccagggaagg ggctggagtg ggtttcctac ataagtactg tggtactat caaatattac       180 acagactctg tgaagggccg attcaccatc tccagggaca acgccaagaa ctcactgtat      240
ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cttca                                                       375
```

<210> SEQ ID NO 157
<211> LENGTH: 375
<212> TYPE: DNA
<213> ORGANISM: Homo sapiens

<400> SEQUENCE: 157

```
caggtcacct tgaaggagtc tgggggaggc ttggtcaagc ctggagggtc cctgagactc       60
tcctgtgcag cctctggatt caccttcagt gactacacca tgacctggat gcgccaggct     120
ccagggaagg ggctggagtg ggtttcatac ataagtactg tggtagtat caaatattac       180 acagactctg tgaagggccg attcaccatc tccagggaca acgccaggaa ctcactatat      240
ctgcagatga acagcctgag agccgaggac acggccgtgt attactgtgc gagagaggcc     300
cctttacgtt tgggggagtc cccccatgat gcttttgata tctggggcca agggacaatg     360
gtcaccgtct cttca                                                       375
```

<210> SEQ ID NO 158
<211> LENGTH: 375
<212> TYPE: DNA
<213> ORGANISM: Homo sapiens

<400> SEQUENCE: 158

| | | | | | | |
|---|---|---|---|---|---|---|
| caggtcacct | tgaaggagtc | tgggggaggc | ttggtcaagc | ctggagggtc | cctgagactc | 60 |
| tcctgtgcag | cctctggatt | caccttcagt | gactacacca | tgacctggat | gcgccaggct | 120 |
| ccagggaagg | ggctggagtg | ggtttcatac | ataagtactg | gtggtagtac | caaatattac | 180 |
| acagactctg | tgaagggccg | attcaccatc | tccaggaca | acgccaagaa | ctcactgtat | 240 |
| ctgcaaatga | acagcctgag | agccgacgac | acggccgtgt | attactgtgc | gagagaggcc | 300 |
| cctttacgtt | tgggggagtc | cccccatgat | gcttttgata | tctggggcca | agggacaatg | 360 |
| gtcactgtct | cctca | | | | | 375 |

<210> SEQ ID NO 159
<211> LENGTH: 375
<212> TYPE: DNA
<213> ORGANISM: Homo sapiens

<400> SEQUENCE: 159

| | | | | | | |
|---|---|---|---|---|---|---|
| caggtcacct | tgaaggagtc | tgggggaggc | ttggtcaagc | cgggagggtc | cctgagactc | 60 |
| tcctgtgcag | cctctggatt | caccttcagt | gacgactaca | tgatgtggat | ccgccaggct | 120 |
| ccagggaagg | ggctggagtg | ggtttcatac | attagtagtg | gtggtagtat | tatatactac | 180 |
| gcagactctg | tgaagggccg | attcaccatt | tccaggaca | acgccaagaa | ctcactgtat | 240 |
| ctgcaaatga | acagcctgag | agccgaggac | acggccgtgt | attactgtgc | gagagaggcc | 300 |
| cctttacgtt | tgggggagtc | cccccatgat | gcttttgata | tcaggggcca | agggacaatg | 360 |
| gtcactgtct | cctca | | | | | 375 |

<210> SEQ ID NO 160
<211> LENGTH: 375
<212> TYPE: DNA
<213> ORGANISM: Homo sapiens

<400> SEQUENCE: 160

| | | | | | | |
|---|---|---|---|---|---|---|
| caggtcacct | tgaaggagtc | tgggggaggc | ttggtcaagc | ctggagggtc | cctgagactc | 60 |
| tcctgtgcag | cctctggatt | caccttcagt | gactatgaca | tgtactgggt | ccgccaggct | 120 |
| ccagggaagg | ggctggagtg | ggtttcatat | attagtcgtg | gtggtagtgt | aacatactac | 180 |
| gcagactctg | tgaagggccg | attcaccatt | tccaggaca | acgccaagaa | cgcactgtat | 240 |
| ctgcaaatga | acagcctgag | agccgaggac | atggccgtat | attttgcgc | gacagaggcc | 300 |
| cctttacgtt | tgggggagac | cccccatgct | gcttttgata | tctggggcca | agggacaatg | 360 |
| gtcaccgtct | cctca | | | | | 375 |

<210> SEQ ID NO 161
<211> LENGTH: 375
<212> TYPE: DNA
<213> ORGANISM: Homo sapiens

<400> SEQUENCE: 161

| | | | | | | |
|---|---|---|---|---|---|---|
| gaggtgcagc | tggtggagtc | tgggggaggc | ttggtcaagc | ctggagggtc | cctgagactc | 60 |
| tcctgtgcag | cctctggatt | caccttcagt | gactacacca | tgacctggat | gcgccaggct | 120 |
| ccagggaagg | ggctggagtg | ggtttcatac | ataagtactg | gtggtagtgt | taaatattac | 180 |

| | |
|---|---|
| acagactctg tgaagggccg attcaccatc tccagggaca acgccaagaa ctcactgtat | 240 |
| ctgcaaatga acagcctgag agccgacgac acggccgtgt attactgtgc gagagaggcc | 300 |
| cctttacgtt tgggggagtc cccccatgat gcttttgata tctggggcca agggacaatg | 360 |
| gtcactgtct cctca | 375 |

<210> SEQ ID NO 162
<211> LENGTH: 375
<212> TYPE: DNA
<213> ORGANISM: Homo sapiens

<400> SEQUENCE: 162

| | |
|---|---|
| gaggtgcagc tgttggagtc tgggggaggc ttggtcaagc ctggagggtc cctgagactc | 60 |
| tcctgtgcag cctctggatt caccttcagt gactacacca tgacctggat gcgccaggct | 120 |
| ccagggaagg ggctggagtg ggtttcttac ataagtactg gtggtagtat caaatattac | 180 |
| acagactctg tgaagggccg attcaccatc tccagggaca acgccaagaa ctcactgtat | 240 |
| ctgcaaatga acagcctgag agtcgacgac acggccgtgt attactgtgc gagagaggcc | 300 |
| cctttacgtt tgggggagtc cccccatgat gcttttgata tctggggcca agggacaatg | 360 |
| gtcaccgtct cctca | 375 |

<210> SEQ ID NO 163
<211> LENGTH: 375
<212> TYPE: DNA
<213> ORGANISM: Homo sapiens

<400> SEQUENCE: 163

| | |
|---|---|
| gaagtgcagc tggtggagtc tgggggaggc ttggtcaagc ctggagggtc cctgagactc | 60 |
| tcctgtgcag cctctggatt caccttcagt gactacacca tgacctggat gcggcaggct | 120 |
| ccagggaagg ggctggagtg ggtttcctac ataagtactg gtggtactat caaatattat | 180 |
| acagactctg tgaagggccg attcaccatc tccagggaca acgccaagaa ttcactgttt | 240 |
| ctgcaaatga acagcctgag agccgacgac acggccgttt attactgtgc gagagaggcc | 300 |
| cctttacgtt tgggggagtc cccccatgat gcttttgata tctggggcca agggacaatg | 360 |
| gtcactgtct cttca | 375 |

<210> SEQ ID NO 164
<211> LENGTH: 375
<212> TYPE: DNA
<213> ORGANISM: Homo sapiens

<400> SEQUENCE: 164

| | |
|---|---|
| caggtgcagc tggtggagtc tgggggaggc ttggtcaagc ctggagggtc cctgagactc | 60 |
| tcctgtgcag cctctggatt caccttcagt gactacacca tgacctggat gcgccaggct | 120 |
| ccagggaagg ggctggagtg ggtttcttac ataagtactg gtggtagtat caaatattat | 180 |
| acagactctg tgaagggccg attcaccatc tccagggaca acgccaagaa ttcactgttt | 240 |
| ctgcaaatga acagcctgag agccgacgac acggccgtgt attactgtgc gagagaggcc | 300 |
| cctttacgtt tgggggagtc cccccatgat gcttttgata tctggggcca agggacaatg | 360 |
| gtcaccgtct cctca | 375 |

<210> SEQ ID NO 165
<211> LENGTH: 375
<212> TYPE: DNA

<213> ORGANISM: Homo sapiens

<400> SEQUENCE: 165

| gaggtgcagc tggtggagtc tgggggaggc ttggtccagc ctgggggtc cctgagactc | 60 |
| tcctgtgcag cctctggatt caccttcagt gactacacca tgacctggat gcggcaggct | 120 |
| ccagggaagg ggctggagtg ggtttcctac ataagtactg gtggtactat caaatattac | 180 |
| acagactctg tgaagggccg attcaccatc tccagggaca cgccaagaa ctcactgtat | 240 |
| ctgcaaatga acagcctgag agccgacgac acggccgtgt attactgtgc gcgagaggcc | 300 |
| cctttacgtt tgggggagtc cccccatgat gcttttgata tctggggcca agggacaatg | 360 |
| gtcaccgtct cctca | 375 |

<210> SEQ ID NO 166
<211> LENGTH: 375
<212> TYPE: DNA
<213> ORGANISM: Homo sapiens
<220> FEATURE:
<221> NAME/KEY: misc_feature
<222> LOCATION: (273)..(273)
<223> OTHER INFORMATION: n is a, c, g, or t

<400> SEQUENCE: 166

| caggtgcagc tgcaggagtc gggggaggc ttggtcaagc ctggagggtc cctgagactc | 60 |
| tcctgtgcag cctctggatt caccttcagt gactacacca tgacctggat gccgccaggct | 120 |
| ccagggaagg ggctggagtg ggtttcatac ataagtactg gtggtagtat caaatattac | 180 |
| acagactctg tgaagggccg attcaccatc tccagggaca cgccaagaa ctcactgtat | 240 |
| ctgcaaatga acagcctgag agccgacgac acngccgtgt attactgtgc gagagaggcc | 300 |
| cctttacgtt tgggggagtc cccccatgat gcttttgata tctggggcca agggacaatg | 360 |
| gtcactgtct cttca | 375 |

<210> SEQ ID NO 167
<211> LENGTH: 375
<212> TYPE: DNA
<213> ORGANISM: Homo sapiens

<400> SEQUENCE: 167

| gaggtgcagc tggtggagtc tgggggaggc ttggtcaagc ctggagggtc cctgagactc | 60 |
| tcctgtgcag cctctggatt caccttcagt gactcctcca tgagctggat ccgccaggct | 120 |
| ccagggaggg ggctggaatg gatttcatac attagtagtg gtggtggtat catatactac | 180 |
| acagactctg tgaagggccg attcaccatc tccagggaca cgccaagaa ctcactgtat | 240 |
| ctacagatga acagcctgag agtcgaggac acggccgtgt attactgtgc gaaagaggcc | 300 |
| cctttacgtt tgggggagtc cccccatgat gcttttgata tctggggcca cgggacaatg | 360 |
| gtcaccgtct cttca | 375 |

<210> SEQ ID NO 168
<211> LENGTH: 375
<212> TYPE: DNA
<213> ORGANISM: Homo sapiens

<400> SEQUENCE: 168

| caggtgcagc tggttgagtc tgggggaggc ttggtcaagc ctggagggtc cctgagactc | 60 |
| tcctgtgcag cctctggatt caccttcagt gacaactcca tgacctggat gcggcaggct | 120 |
| ccagggaagg ggctggagtg ggtttcctac ataagttctg gtggtggtgt catattttac | 180 |

```
gcagactctg tgaagggccg attcaccatc tccagggaca acgccaagaa ctcactgtat    240
ctgcaaatga acagcctgag agccgacgac acggccgtgt attactgtgc gcagagaggcc   300 cctttacgtt tgggggagtc cccccatgat gcttttgata tctggggcca agggacaatg    360
gtcaccgtct cctca                                                     375

<210> SEQ ID NO 169
<211> LENGTH: 375
<212> TYPE: DNA
<213> ORGANISM: Homo sapiens

<400> SEQUENCE: 169
caggtgcagc tggtggagtc tgggggaggc ttggtcaagc ctggagggtc cctgagactc    60
tcctgtgcag cctctggatt caccttcagt gacaactcca tgacctggat gcggcaggct    120
ccagggaagg ggctggagtg ggtttcctac ataagttctg gtggtggtgt catattttac    180
gcagactctg tgaagggccg attcaccatc tccagggaca acgccaagaa ctcactgtat    240
ctgcaaatga acagcctgag agccgacgac acggccgtgt attactgtgc gcagagaggcc   300 cctttacgtt tgggggagtc cccccatgat gcttttgata tctggggcca agggacaatg    360
gtcaccgtct cctca                                                     375

<210> SEQ ID NO 170
<211> LENGTH: 375
<212> TYPE: DNA
<213> ORGANISM: Homo sapiens

<400> SEQUENCE: 170
caggtgcagc tggtggagtc tgggggaggc ttggtcaagc ctggagggtc cctgagactc    60
tcctgtgcag cctctggatt caccttcagt gacaactcca tgacctggat gcggcaggct    120
ccagggaagg ggctggagtg ggtttcctac ataagttctg gtggtggtgt catattttac    180
gcagactctg tgaagggccg attcaccatc tccagggaca acgccaagaa ctcactgtat    240
ctgcaaatga acagcctgag agccgacgac acggccgtgt attactgtgc gcagagaggcc   300 cctttacgtt tgggggagtc cccccatgat gcttttgata tctggggcca agggacaatg    360
gtcaccgtct cctca                                                     375

<210> SEQ ID NO 171
<211> LENGTH: 375
<212> TYPE: DNA
<213> ORGANISM: Homo sapiens

<400> SEQUENCE: 171
caggtgcagc tggtggagtc tgggggaggc ttggtcaagc ctggagggtc cctgagactc    60
tcctgtgcag cctctggatt caccttcagt gacaactcca tgacctggat gcggcaggct    120
ccagggaagg ggctggagtg ggtttcctac ataagttctg gtggtgctgt caaattttac    180
gcagactctg tgaagggccg attcaccatc tccagggaca acgccaagaa ctcactgtat    240
ctgcaaatga acagcctgag agccgacgac acggccgtgt attactgtgc gcagagaggcc   300 cctttacgtt tgggggagtc cccccatgat gcttttgata tctggggcca agggacaatg    360
gtcaccgtct cctca                                                     375

<210> SEQ ID NO 172
<211> LENGTH: 375
<212> TYPE: DNA
```

<213> ORGANISM: Homo sapiens

<400> SEQUENCE: 172

| caggtgcagc tggtggagtc tgggggaggc ttggtcaagc ctggagggtc cctgagactc | 60 |
| tcctgtgcag cctctggatt caccttcagt gactactcca tgtcctggat gcggcaggct | 120 |
| ccagggaagg ggctggagtg ggtttcctac ataagttctg gtggtggtgt catattttac | 180 |
| gcagactctg tgaagggccg attcaccatc tccagggaca acgccaagaa ctcactgtat | 240 |
| ctgcaaatga acagcctgag agccgacgac acggccgtgt attactgtgc gcgagaggcc | 300 |
| cctttacgtt tgggggagtc cccccatgat gcttttgata tctggggcca agggacaatg | 360 |
| gtcaccgtct cctca | 375 |

<210> SEQ ID NO 173
<211> LENGTH: 375
<212> TYPE: DNA
<213> ORGANISM: Homo sapiens

<400> SEQUENCE: 173

| caggtgcagc tggtggagtc tgggggaggc ttggtcaagc ctggagggtc cctgagactc | 60 |
| tcctgtgcag cctctggatt caccttcagt gacagctcca tgtcctggat gcggcaggct | 120 |
| ccagggaagg ggctggagtg ggtttcctac ataagttctg gtggtggtgt catattttac | 180 |
| gcagactctg tgaagggccg attcaccatc tccagggaca acgccaagaa ctcactgtat | 240 |
| ctgcaaatga acagcctgag agccgacgac acggccgtgt attactgtgc gcgagaggcc | 300 |
| cctttacgtt tgggggagtc cccccatgat gcttttgata tctggggcca agggacaatg | 360 |
| gtcaccgtct cctca | 375 |

<210> SEQ ID NO 174
<211> LENGTH: 375
<212> TYPE: DNA
<213> ORGANISM: Homo sapiens

<400> SEQUENCE: 174

| caggtgcagc tggtggagtc tgggggaggc ttggtcaagc ctggagggtc cctgagactc | 60 |
| tcctgtgcag cctctggatt caccttcagt gacaactcca tgtcctggat gcggcaggct | 120 |
| ccagggaagg ggctggagtg ggtttcctac ataagttctg gtggtggtgt catattttac | 180 |
| gcagactctg tgaagggccg attcaccatc tccagggaca acgccaagaa ctcactgtat | 240 |
| ctgcaaatga acagcctgag agccgacgac acggccgtgt attactgtgc gcgagaggcc | 300 |
| cctttacgtt tgggggagtc cccccatgat gcttttgata tctggggcca agggacaatg | 360 |
| gtcaccgtct cctca | 375 |

<210> SEQ ID NO 175
<211> LENGTH: 375
<212> TYPE: DNA
<213> ORGANISM: Homo sapiens

<400> SEQUENCE: 175

| caggtgcagc tggtggagtc tgggggaggc ttggtcaagc ctggagggtc cctgagactc | 60 |
| tcctgtgcag cctctggatt caccttcagt gacagctcca tgacctggat gcggcaggct | 120 |
| ccagggaagg ggctggagtg ggtttcctac ataagttctg gtggtggtgt caaattttac | 180 |
| gcagactctg tgaagggccg attcaccatc tccagggaca acgccaagaa ctcactgtat | 240 |
| ctgcaaatga acagcctgag agccgacgac acggccgtgt attactgtgc gcgagaggcc | 300 |

```
cctttacgtt tggggagtc cccccatgat gcttttgata tctggggcca agggacaatg    360
gtcaccgtct cctca                                                    375
```

<210> SEQ ID NO 176
<211> LENGTH: 375
<212> TYPE: DNA
<213> ORGANISM: Homo sapiens

<400> SEQUENCE: 176

```
caggtgcaac tggttgaaag cggcggcggg ttagtaaaac ccggaggctc cctgcgactg    60
agttgcgcgg ccagtgggtt cacatttagc gattccagca tgtcatggat gcgtcaagct    120
cccggtaaag gcttagagtg ggtttcgtac attagcacag gtggtggtgt caaattctat    180
gctgattctg tcaaaggccg ttttaccatc tcccgggata tgcaaagaa ctcgttgtat     240 ttgcagatga acagcttacg cgccgacgat actgcagtct attattgcgc acgcgaagct    300
cctctgcgct taggtgagag cccacatgac gcctttgata tatgggggca aggaacaatg    360
gtgaccgtgt ccagc                                                    375
```

<210> SEQ ID NO 177
<211> LENGTH: 375
<212> TYPE: DNA
<213> ORGANISM: Homo sapiens

<400> SEQUENCE: 177

```
caggtgcagc tggtggagtc tgggggaggc ttggtcaagc ctggagggtc cctgagactc    60
tcctgtgcag cctctggatt caccttcagt gacaactcca tgacctggat gcggcaggct    120
ccagggaagg ggctggagtg ggtttcctac ataagttctg gtggtactat caaatttac     180 gcagactctg tgaagggccg attcaccatc tccagggaca cgccaagaa ctcactgtat     240 ctgcaaatga acagcctgag agccgacgac acggccgtgt attactgtgc gcagagggcc    300
cctttacgtt tggggagtc cccccatgat gcttttgata tctggggcca agggacaatg     360
gtcaccgtct cctca                                                    375
```

<210> SEQ ID NO 178
<211> LENGTH: 375
<212> TYPE: DNA
<213> ORGANISM: Homo sapiens

<400> SEQUENCE: 178

```
caggtgcagc tggtggagtc tgggggaggc ttggtcaagc ctggagggtc cctgagactc    60
tcctgtgcag cctctggatt caccttcagt gacagctcca tgacctggat gcggcaggct    120
ccagggaagg ggctggagtg ggtttcctac ataagttctg gtggtgctgt caaatttac     180 acagactctg tgaagggccg attcaccatc tccagggaca cgccaagaa ctcactgtat     240 ctgcaaatga acagcctgag agccgacgac acggccgtgt attactgtgc gcagagggcc    300
cctttacgtt tggggagtc cccccatgat gcttttgata tctggggcca agggacaatg     360
gtcaccgtct cctca                                                    375
```

<210> SEQ ID NO 179
<211> LENGTH: 375
<212> TYPE: DNA
<213> ORGANISM: Homo sapiens

<400> SEQUENCE: 179

```
caggtgcagc tggtggagtc tgggggaggc ttggtcaagc ctggagggtc cctgagactc      60
tcctgtgcag cctctggatt caccttcagt gacaactcca tgacctggat gcggcaggct     120
ccagggaagg ggctggagtg ggtttcctac ataagttctg gtggtggtgt caaatattac     180
gcagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                       375
```

<210> SEQ ID NO 180
<211> LENGTH: 375
<212> TYPE: DNA
<213> ORGANISM: Homo sapiens

<400> SEQUENCE: 180

```
caggtgcagc tggtggagtc tgggggaggc ttggtcaagc ctggagggtc cctgagactc      60
tcctgtgcag cctctggatt caccttcagt gacaactcca tgacctggat gcggcaggct     120
ccagggaagg ggctggagtg ggtttcctac ataagttctg gtggtagtgt caaattttac     180
gcagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                       375
```

<210> SEQ ID NO 181
<211> LENGTH: 375
<212> TYPE: DNA
<213> ORGANISM: Homo sapiens

<400> SEQUENCE: 181

```
caggtgcagc tggtggagtc tgggggaggc ttggtcaagc ctggagggtc cctgagactc      60
tcctgtgcag cctctggatt caccttcagt gacgactcca tgacctggat gcggcaggct     120
ccagggaagg ggctggagtg ggtttcctac ataagttctg gtggtggtgt catattttac     180
gcagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                       375
```

<210> SEQ ID NO 182
<211> LENGTH: 375
<212> TYPE: DNA
<213> ORGANISM: Homo sapiens

<400> SEQUENCE: 182

```
caggtgcagc tggtggagtc tgggggaggc ttggtcaagc ctggagggtc cctgagactc      60
tcctgtgcag cctctggatt caccttcagt gacaactcca tgacctggat gcggcaggct     120
ccagggaagg ggctggagtg ggtttcctac ataagttctg gtggtggtgt caaattttac     180
gcagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc ccctcatgat gcttttgata tctcgggcca agggacaatg     360
gtcaccgtct cctca                                                       375
```

```
<210> SEQ ID NO 183
<211> LENGTH: 375
<212> TYPE: DNA
<213> ORGANISM: Homo sapiens

<400> SEQUENCE: 183
caggtgcagc tggtggagtc tgggggaggc ttggtcaagc ctggagggtc cctgagactc        60
tcctgtgcag cctctggatt caccttcagt gacaactcca tgacctggat gcggcaggct       120
ccagggaagg gctggagtg gttccctac ataagttctg gtggtgctgt caaattttac        180
gcagactctg tgaagggccg attcaccatc tccaggaca acgccaagaa ctcactgtat       240
ctgcaaatga acagcctgag agccgacgac acggccgtgt attactgtgc gcgagaggcc      300
cctttacgtt tggggagtc ccccatgat gcttttgata tcttgggcca agggacaatg       360
gtcaccgtct cctca                                                       375

<210> SEQ ID NO 184
<211> LENGTH: 375
<212> TYPE: DNA
<213> ORGANISM: Homo sapiens

<400> SEQUENCE: 184
caggtgcagc tggtggagtc tgggggaggc ttggtcaagc ctggagggtc cctgagactc        60
tcctgtgcag cctctggatt caccttcagt gacaactcca tgacctggat gcggcaggct       120
ccagggaagg gctggagtg gttccctac ataagttctg gtggtggtgt catatttac        180 gcagactctg tgaagggccg attcaccatc tccaggaca acgccaagaa ctcactgtat       240
ctgcaaatga acagcctgag agccgacgac acggccgtgt attactgtgc gcgagaggcc      300
cctttacgtt tggggagtc ccccatgat gcttttgata tctcgggcca agggacaatg       360
gtcaccgtct cctca                                                       375

<210> SEQ ID NO 185
<211> LENGTH: 375
<212> TYPE: DNA
<213> ORGANISM: Homo sapiens

<400> SEQUENCE: 185
caggtgcagc tggtggagtc tgggggaggc ttggtcaagc ctggagggtc cctgagactc        60
tcctgtgcag cctctggatt caccttcagt gacaacacca tgacctggat gcggcaggct       120
ccagggaagg gctggagtg gttccctac ataagtactg gtggtggtgt caaattttac        180
gcagactctg tgaagggccg attcaccatc tccaggaca acgccaagaa ctcactgtat       240
ctgcaaatga acagcctgag agccgacgac acggccgtgt attactgtgc gcgagaggcc      300
cctttacgtt tggggagtc ccccatgat gcttttgata tctgggcca agggacaatg       360 gtcaccgtct cctca                                                       375

<210> SEQ ID NO 186
<211> LENGTH: 375
<212> TYPE: DNA
<213> ORGANISM: Homo sapiens

<400> SEQUENCE: 186
caggtgcagc tggtggagtc tgggggaggc ttggtcaagc ctggagggtc cctgagactc        60
tcctgtgcag cctctggatt caccttcagt gacaactcca tgtcctggat gcggcaggct       120
```

```
ccagggaagg ggctggagtg ggtttcctac ataagttctg gtggtagtgt caaatttac      180 gcagactctg tgaagggccg attcaccatc tccagggaca acgccaagaa ctcactgtat     240
ctgcaaatga acagcctgag agccgacgac acggccgtgt attactgtgc gcgagaggcc     300
cctttacgtt tgggggagtc cccccatgat gcttttgata tctggggcca agggacaatg     360
gtcaccgtct cctca                                                      375

<210> SEQ ID NO 187
<211> LENGTH: 375
<212> TYPE: DNA
<213> ORGANISM: Homo sapiens

<400> SEQUENCE: 187
caggtgcagc tggtggagtc tgggggaggc ttggtcaagc ctggagggtc cctgagactc     60
tcctgtgcag cctctggatt caccttcagt gacaactcca tgacctggat gcggcaggct    120
ccagggaagg ggctggagtg ggtttcctac ataagtactg gtggtggtgt caaatattac    180
gcagactctg tgaagggccg attcaccatc tccagggaca acgccaagaa ctcactgtat    240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                    375

<210> SEQ ID NO 188
<211> LENGTH: 375
<212> TYPE: DNA
<213> ORGANISM: Homo sapiens

<400> SEQUENCE: 188
caggtgcagc tggtggagtc tgggggaggc ttggtcaagc ctggagggtc cctgagactc     60
tcctgtgcag cctctggatt caccttcagt gactacacca tgtcctggat gcggcaggct    120
ccagggaagg ggctggagtg ggtttcctac ataagtactg gtggtggtgt caaatttac     180 gcagactctg tgaagggccg attcaccatc tccagggaca atgccaagaa ctcactgtat    240
ctgcaaatga acagcctgag agccgacgac acggccgtgt attactgtgc gcgagaggcc    300
cctttacgtt tgggggagtc cccccatgat gcttttgata tctggggcca agggacaatg    360
gtcaccgtct cctca                                                    375

<210> SEQ ID NO 189
<211> LENGTH: 375
<212> TYPE: DNA
<213> ORGANISM: Homo sapiens

<400> SEQUENCE: 189
caggtgcagc tggtggagtc tgggggaggc ttggtcaagc ctggagggtc cctgagactc     60
tcctgtgcag cctctggatt caccttcagt gacagctcca tgacctggat gcggcaggct    120
ccagggaagg ggctggagtg ggtttcctac ataagttctg gtggtgctgt caaatttac     180 acagactctg tgaagggccg attcaccatc tccagggaca acgccaagaa ctcactgtat    240
ctgcaaatga acagcctgag agccgacgac acggccgtgt attactgtgc gcgagaggcc    300
cctttacgtt tgggggagtc cccccatgat gcttttgata tctcgggcca agggacaatg    360
gtcaccgtct cctca                                                    375

<210> SEQ ID NO 190
<211> LENGTH: 375
```

```
<212> TYPE: DNA
<213> ORGANISM: Homo sapiens

<400> SEQUENCE: 190
gaggtgcagc tggtggagtc tgggggaggc ttggtcaagc ctggagggtc cctgagactc      60
tcctgtgcag cctctggatt caccttcagt gacagctcca tgacctggat gcggcaggct     120
ccagggaagg ggctggagtg ggtttcctac ataagttctg gtggtggtgt caaattttac     180
acagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 191
<211> LENGTH: 375
<212> TYPE: DNA
<213> ORGANISM: Homo sapiens

<400> SEQUENCE: 191
gaggtgcagc tggtggagtc tgggggaggc ttggtcaagc ctggagggtc cctgagactc      60
tcctgtgcag cctctggatt caccttcagt gacagctcca tgacctggat gcggcaggct     120
ccagggaagg ggctggagtg ggtttcctac ataagttctg gtggtggtgt caaattttac     180
gcagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 192
<211> LENGTH: 375
<212> TYPE: DNA
<213> ORGANISM: Homo sapiens

<400> SEQUENCE: 192
caggtgcagc tggtggagtc tgggggaggc ttggtcaagc ctggagggtc cctgagactc      60
tcctgtgcag cctctggatt caccttcagt gacagctcca tgacctggat gcggcaggct     120
ccagggaagg ggctggagtg ggtttcctac ataagttctg gtggtggtgt caaattttac     180
gcagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 193
<211> LENGTH: 375
<212> TYPE: DNA
<213> ORGANISM: Homo sapiens

<400> SEQUENCE: 193
caggtgcagc tggtggagtc tgggggaggc ttggtcaagc ctggagggtc cctgagactc      60
tcctgtgcag cctctggatt caccttcagt gacagctcca tgacctggat gcggcaggct     120
ccagggaagg ggctggagtg ggtttcctac ataagttctg gtggtggtgt caaattttac     180
acagactctg tgaagggccg attcaccatc tccagggaca cgccaagaa ctcactgtat      240
```

```
ctgcaaatgg acagcctgag agccgacgac acggccgtgt attactgtgc gcgagaggcc      300
cctttacgtt tggggagtc cccccatgat gctttttgata cctcgggcca agggacaatg      360
gtcaccgtct cctca                                                       375

<210> SEQ ID NO 194
<211> LENGTH: 375
<212> TYPE: DNA
<213> ORGANISM: Homo sapiens

<400> SEQUENCE: 194
caggtgcagc tggtggagtc tgggggaggc ttggtcaagc ctggagggtc cctgagactc       60
tcctgtgcag cctctggatt caccttcagt ggcagctcca tgacctggat gcggcaggct      120
ccagggaagg ggctggagtg ggtttcctac ataagttctg gtggcggtgt catattttac      180
gcagactctg tgaagggccg attcaccatc tccagggaca acgccaagaa ctcactgtat      240
ctgcaaatga acagcctgag ggccgacgac acggccgtgt actactgtgc gcgagaggcc      300
cctttacgtt tggggagtc cccccatgac gctttcgata tctcgggcca agggacaatg      360
gtcaccgtct cctca                                                       375

<210> SEQ ID NO 195
<211> LENGTH: 375
<212> TYPE: DNA
<213> ORGANISM: Homo sapiens

<400> SEQUENCE: 195
caggtgcagc tggtggagtc tgggggaggc ttggtcaagc ctggagggtc cctgagactc       60
tcctgtgcag cctctggatt caccttcggt gacaactcca tgacctggat gcggcaggct      120
ccagggaagg ggctggagtg ggtttcctac ataagttctg gtggtggtgt catattttac      180
gcagactctg tgaagggccg attcaccatc tccagggaca acgccaagaa ctcactgtat      240
ctgcaaatga acagcctgag agccgacgac acggccgtgt attactgtgc gcgagaggcc      300
cctttacgtt tggggagtc cccccatgat gctttttgata tctcgggccg agggacaacg      360
gtcaccgtct cctca                                                       375

<210> SEQ ID NO 196
<211> LENGTH: 375
<212> TYPE: DNA
<213> ORGANISM: Homo sapiens

<400> SEQUENCE: 196
caggtgcagc tggtggagtc tgggggaggc ttggtcaagc ctggagggtc cctgagactc       60
tcctgtgcag cctctggatt caccttcagt gacaactcca tgtcctggat gcggcaggct      120
ccagggaagg ggctggagtg ggtttcctac ataagttctg gtggtggtgt catattttac      180
gcagactctg tgaagggccg attcaccatc tccagggaca acgccaagaa ctcactgtat      240
ctgcaaatga acagcctgag ggccgacgac acggccgtgt attactgtgc gcgagaggcc      300
cctttacgtt tggggagtc cccccatgat gctttttgata tctcgggcca agggacaatg      360
gtcaccgtct cttca                                                       375

<210> SEQ ID NO 197
<211> LENGTH: 375
<212> TYPE: DNA
<213> ORGANISM: Homo sapiens

<400> SEQUENCE: 197
```

```
caggtgcagc tggtggagtc tgggggaggt ttggtcaagc ctggagggtc cctgagactc      60
tcctgtgcag cctctggatt caccttcggt gacagctcca tgacctggat gcggcaggct     120
ccagggaagg ggctggagtg ggtttcctac ataagttctg tggtgctgt caagttttac      180 acagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctcgggcca agggacaatg     360
gtcaccgtct cctca                                                       375
```

<210> SEQ ID NO 198
<211> LENGTH: 375
<212> TYPE: DNA
<213> ORGANISM: Homo sapiens

<400> SEQUENCE: 198

```
caggtgcagc tggtggagtc tgggggaggc ttggtcaagc ctggagggtc cctgaggctc      60
tcctgtgcag cctcaggatt caccttcggt ggcagctcca tgacctggat gcggcaggct     120
ccagggaagg ggctggagtg ggtttcctac ataagttctg tggtggtgt caaattttac      180 acagactctg tgaagggccg attcaccatc tccagggaca cgccaagaa ctcactgtat      240 ctgcaaatga acagcctgag agccgacgac acggccgtgt attactgtgc gcgagaggcc     300
cctttacgtt tgggggagtc cccccatgat gcttttgata tctcgggcca ggggacaatg     360
gtcaccgtct cctca                                                       375
```

<210> SEQ ID NO 199
<211> LENGTH: 375
<212> TYPE: DNA
<213> ORGANISM: Homo sapiens

<400> SEQUENCE: 199

```
caggtgcagc tggtggagtc tgggggaggc ttggtcaagc ctggagggtc cctgagactc      60
tcctgtgcag cctctggatt caccttcagt gacagctcca tgtcctggat gcggcaggct     120
ccagggaagg ggctggagtg ggtttcctac ataagttctg tggtggtgt catattttac      180 gcagactctg tgaagggccg attcaccatc tccagggaca cgccaagaa ctcgctgtat      240 ctgcaaatga acagcctgag agccgacgac acggccgtgt attactgtgc gcgagaggcc     300
cctttacgtt tgggggagtc cccccatgat gcttttgata tctcgggcca agggacaatg     360
gtcaccgtct cttca                                                       375
```

<210> SEQ ID NO 200
<211> LENGTH: 375
<212> TYPE: DNA
<213> ORGANISM: Homo sapiens

<400> SEQUENCE: 200

```
caggtgcagc tggtggagtc tgggggaggc ttggtcaagc ctggagggtc cctgagactc      60
tcctgtgcag ccactggatt caccttcagt gacagctcca tgacctggat gcggcaggct     120
ccagggaagg ggctggagtg ggtttcctac ataagtgctg tggtggtgt cagattttac      180 acagactctg tgaagggccg attcaccatc tccagggaca cgccaagaa ctcactgtat      240 ctgcaaatga acagcctgag ggccgacgac acggccgtgt attactgtgc gcgagaggcc     300
cctttacgtt tgggggagtc cccccatgat gcttttgata tctcgggcca agggacaatg     360
```

```
gtcaccgtct catca                                                         375

<210> SEQ ID NO 201
<211> LENGTH: 375
<212> TYPE: DNA
<213> ORGANISM: Homo sapiens

<400> SEQUENCE: 201
gaggtgcagc tggtggagtc tgggggaggc ttggtcaagc ctggagggtc cctgagactc         60
tcctgtgcag cctctggatt caccttcagt gacagctcca tgacctggat tcggcaggct        120
ccagggaagg ggctggagtg ggtttcctac ataagttctg gtggtggtgt caaattttac        180
acagactctg tgaagggccg attcaccatc tccaggaca acgccaagaa ctcactgtat         240
ctgcaaatga acagcctgag agccgacgac acggccgtgt attactgtgc gcgagaggcc        300
cctttacgtt tgggggagtc cccccatgat gcttttgata tctcgggcca agggacaatg        360
gtcaccgtct cctca                                                         375

<210> SEQ ID NO 202
<211> LENGTH: 375
<212> TYPE: DNA
<213> ORGANISM: Homo sapiens

<400> SEQUENCE: 202
gaggtgcagc tggtggagtc tgggggaggc ttggtcaagc ctggagggtc cctgagactc         60
tcctgtgcag cctctggatt caccttcagt gacagctcca tgacctggat tcggcaggct        120
ccagggaagg ggctggagtg ggtttcctac ataagttctg gtggtggtgt caaattttac        180
acagactctg tgaagggccg attcaccatc tccaggaca acgccaagaa ctcactgtat         240
ctgcaaatga acagcctgag agccgaagac acggccgtgt attactgtgc gcgagaggcc        300
cctttacgtt tgggggagtc cccccatgat gcttttgata tctcgggcca agggacaatg        360
gtcaccgtct cctca                                                         375

<210> SEQ ID NO 203
<211> LENGTH: 375
<212> TYPE: DNA
<213> ORGANISM: Homo sapiens

<400> SEQUENCE: 203
gaggtgcagc tggtggagtc tgggggaggc ttggtcaagc ctggagggtc cctgagactc         60
tcctgtgcag cctctggatt caccttcagt gacagctcca tgacctggat tcggcaggct        120
ccagggaagg ggctggagtg ggtttcctac ataagttctg gtggtggtgt caaattttac        180
gcagactctg tgaagggccg attcaccatc tccaggaca acgccaagaa ctcactgtat         240
ctgcaaatga acagcctgag agccgacgac acggccgtgt attactgtgc gcgagaggcc        300
cctttacgtt tgggggagtc cccccatgat gcttttgata tctcgggcca agggacaatg        360
gtcaccgtct cctca                                                         375

<210> SEQ ID NO 204
<211> LENGTH: 375
<212> TYPE: DNA
<213> ORGANISM: Homo sapiens

<400> SEQUENCE: 204
gaggtgcagc tggtggagtc tgggggaggc ttggtcaagc ctggagggtc cctgagactc         60
tcctgtgcag cctctggatt caccttcagt gacagctcca tgacctggat gcggcaggct        120
```

```
ccagggaagg ggctggagtg ggtttcctac ataagttctg gtggtggtgt caaattttac      180
acagactctg tgaagggccg attcaccatc tccagggaca acgccaagaa ctcactgtat      240
ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 205
<211> LENGTH: 375
<212> TYPE: DNA
<213> ORGANISM: Homo sapiens

<400> SEQUENCE: 205
gaggtgcagc tggtggagtc tgggggaggc ttggtcaagc ctggagggtc cctgagactc       60
tcctgtgcag cctctggatt caccttcagt gacagctcca tgacctggat tcggcaggct      120
ccagggaagg ggctggagtg ggtttcctac ataagttctg gtggtggtgt caaattttac      180
gcagactctg tgaagggccg attcaccatc tccagggaca acgccaagaa ctcactgtat      240
ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 206
<211> LENGTH: 375
<212> TYPE: DNA
<213> ORGANISM: Homo sapiens

<400> SEQUENCE: 206
gaggtgcagc tggtggagtc tgggggaggc ttggtcaagc ctggagggtc cctgagactc       60
tcctgtgcag cctctggatt caccttcagt gacagctcca tgacctggaa gcggcaggct      120
ccagggaagg ggctggagtg ggtttcctac ataagttctg gtggtggtgt caaattttac      180
gcagactctg tgaagggccg attcaccatc tccagggaca acgccaagaa ctcactgtat      240
ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 207
<211> LENGTH: 375
<212> TYPE: DNA
<213> ORGANISM: Homo sapiens

<400> SEQUENCE: 207
gaggtgcagc tggtggagtc tgggggaggc ttggtcaagc ctggagggtc cctgagactc       60
tcctgtgcag cctctggatt caccttcagt gacagctcca tgacctggat gcggcaggct      120
ccagggaagg ggctggagtg ggtttcctac ataagttctg gtggtggtgt caaattttac      180
gcagactctg tgaagggccg attcaccatc tccagggaca acgccaagaa ctcactgtat      240
ctgcaaatga acagcctgag agccgaagac acggccgtgt attactgtgc gcgagaggcc      300
cctttacgtt tgggggagtc cccccatgat gcttttgata tctcgggcca agggacaatg      360
gtcaccgtct cctca                                                      375

<210> SEQ ID NO 208
```

<211> LENGTH: 375
<212> TYPE: DNA
<213> ORGANISM: Homo sapiens

<400> SEQUENCE: 208

```
gaggtgcagc tggtggagtc tggggggaggc ttggtcaagc ctggagggtc cctgagactc      60
tcctgtgcag cctctggatt caccttcagt gacagctcca tgacctgggt gcggcaggct     120
ccagggaagg ggctggagtg ggtttcctac ataagttctg gtggtggtgt caaattttac     180
gcagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                      375
```

<210> SEQ ID NO 209
<211> LENGTH: 375
<212> TYPE: DNA
<213> ORGANISM: Homo sapiens

<400> SEQUENCE: 209

```
gaggtgcagc tggtggagtc tggggggaggc ttggtcaagc ctggagggtc cctgagactc      60
tcctgtgcag cctctggatt caccttcagt gacacctcca tgacctggat gcggcaggct     120
ccagggaagg ggctggagtg ggtttcctac ataagttctg gtggtggtgt caaattttac     180
acagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                      375
```

<210> SEQ ID NO 210
<211> LENGTH: 375
<212> TYPE: DNA
<213> ORGANISM: Homo sapiens

<400> SEQUENCE: 210

```
gaggtgcagc tggtggagtc tggggggaggc ttggtcaagc ctggagggtc cctgagactc      60
tcctgtgcag cctctggatt caccttcagt gacgaatcca tgacctggtt tcggcaggct     120
ccagggaagg ggctggagtg ggtttcctac ataagttctg gtggtggtgt caaattttac     180
acagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                      375
```

<210> SEQ ID NO 211
<211> LENGTH: 375
<212> TYPE: DNA
<213> ORGANISM: Homo sapiens

<400> SEQUENCE: 211

```
gaggtgcagc tggtggagtc tggggggaggc ttggtcaagc ctggagggtc cctgagactc      60
tcctgtgcag cctctggatt caccttcagt gacgaatcca tgacctggat gcggcaggct     120
ccagggaagg ggctggagtg ggtttcctac ataagttctg gtggtggtgt caaattttac     180
acagactctg tgaagggccg attcaccatc tccagggaca acgccaagaa ctcactgtat     240
```

```
ctgcaaatga acagcctgag agccgaagac acggccgtgt attactgtgc gcgagaggcc      300
cctttacgtt tggggagtc ccccatgat gcttttgata tctcgggcca agggacaatg       360
gtcaccgtct cctca                                                       375
```

```
<210> SEQ ID NO 212
<211> LENGTH: 375
<212> TYPE: DNA
<213> ORGANISM: Homo sapiens

<400> SEQUENCE: 212
```

```
gaggtgcagc tggtggagtc tggggagggc ttggtcaagc ctggagggtc cctgagactc      60
tcctgtgcag cctctggatt caccttcagt gactattcca tgacctggat gcggcaggct     120
ccagggaagg ggctggagtg ggtttcctac ataagttctg gtggtggtgt caaattttac     180
acagactctg tgaagggccg attcaccatc tccagggaca cgccaagaa ctcactgtat      240 ctgcaaatga acagcctgag agccgaagac acggccgtgt attactgtgc gcgagaggcc    300
cctttacgtt tggggagtc ccccatgat gcttttgata tctcgggcca agggacaatg      360
gtcaccgtct cctca                                                      375
```

```
<210> SEQ ID NO 213
<211> LENGTH: 375
<212> TYPE: DNA
<213> ORGANISM: Homo sapiens

<400> SEQUENCE: 213
```

```
gaggtgcagc tggtggagtc tggggagggc ttggtcaagc ctggagggtc cctgagactc     60
tcctgtgcag cctctggatt caccttcagt gacgcctcca tgacctggat gcggcaggct    120
ccagggaagg ggctggagtg ggtttcctac ataagttctg gtggtggtgt caaattttac    180
acagactctg tgaagggccg attcaccatc tccagggaca cgccaagaa ctcactgtat     240 ctgcaaatga acagcctgag agccgaagac acggccgtgt attactgtgc gcgagaggcc   300
cctttacgtt tggggagtc ccccatgat gcttttgata tctcgggcca agggacaatg     360
gtcaccgtct cctca                                                     375
```

```
<210> SEQ ID NO 214
<211> LENGTH: 375
<212> TYPE: DNA
<213> ORGANISM: Homo sapiens

<400> SEQUENCE: 214
```

```
gaggtgcagc tggtggagtc tggggagggc ttggtcaagc ctggagggtc cctgagactc     60
tcctgtgcag cctctggatt caccttcagt gacaaatcca tgacctggat gcggcaggct    120
ccagggaagg ggctggagtg ggtttcctac ataagttctg gtggtggtgt caaattttac    180
acagactctg tgaagggccg attcaccatc tccagggaca cgccaagaa ctcactgtat     240 ctgcaaatga acagcctgag agccgaagac acggccgtgt attactgtgc gcgagaggcc   300
cctttacgtt tggggagtc ccccatgat gcttttgata tctcgggcca agggacaatg     360
gtcaccgtct cctca                                                     375
```

```
<210> SEQ ID NO 215
<211> LENGTH: 375
<212> TYPE: DNA
<213> ORGANISM: Homo sapiens
```

<400> SEQUENCE: 215
gaggtgcagc tggtggagtc tggggaggc ttggtcaagc ctggagggtc cctgagactc   60
tcctgtgcag cctctggatt caccttcagt gaccgttcca tgacctggat gcggcaggct  120
ccagggaagg ggctggagtg ggtttcctac ataagttctg gtggtggtgt caaattttac  180
acagactctg tgaagggccg attcaccatc tccagggaca cgccaagaa ctcactgtat  240 ctgcaaatga acagcctgag agccgaagac acggccgtgt attactgtgc gcgagaggcc  300
cctttacgtt tgggggagtc ccccatgat gcttttgata tctcgggcca agggacaatg  360
gtcaccgtct cctca                                                  375

<210> SEQ ID NO 216
<211> LENGTH: 375
<212> TYPE: DNA
<213> ORGANISM: Homo sapiens

<400> SEQUENCE: 216
gaggtgcagc tggtggagtc tggggaggc ttggtcaagc ctggagggtc cctgagactc   60
tcctgtgcag cctctggatt caccttcagt gactattcca tgacctggat gcggcaggct  120
ccagggaagg ggctggagtg ggtttcctac ataagttctg gtggtggtgt caaattttac  180
gcagactctg tgaagggccg attcaccatc tccagggaca cgccaagaa ctcactgtat  240 ctgcaaatga acagcctgag agccgaagac acggccgtgt attactgtgc gcgagaggcc  300
cctttacgtt tgggggagtc ccccatgat gcttttgata tctcgggcca agggacaatg  360
gtcaccgtct cctca                                                  375

<210> SEQ ID NO 217
<211> LENGTH: 375
<212> TYPE: DNA
<213> ORGANISM: Homo sapiens

<400> SEQUENCE: 217
gaggtgcagc tggtggagtc tggggaggc ttggtcaagc ctggagggtc cctgagactc   60
tcctgtgcag cctctggatt caccttcagt gacgtgtcca tgacctggat gcggcaggct  120
ccagggaagg ggctggagtg ggtttcctac ataagttctg gtggtggtgt caaattttac  180
gcagactctg tgaagggccg attcaccatc tccagggaca cgccaagaa ctcactgtat  240 ctgcaaatga acagcctgag agccgaagac acggccgtgt attactgtgc gcgagaggcc  300
cctttacgtt tgggggagtc ccccatgat gcttttgata tctcgggcca agggacaatg  360
gtcaccgtct cctca                                                  375

<210> SEQ ID NO 218
<211> LENGTH: 375
<212> TYPE: DNA
<213> ORGANISM: Homo sapiens

<400> SEQUENCE: 218
gaggtgcagc tggtggagtc tggggaggc ttggtcaagc ctggagggtc cctgagactc   60
tcctgtgcag cctctggatt caccttcagt gaccagtcca tgacctggat gcggcaggct  120
ccagggaagg ggctggagtg ggtttcctac ataagttctg gtggtggtgt caaattttac  180
gcagactctg tgaagggccg attcaccatc tccagggaca cgccaagaa ctcactgtat  240 ctgcaaatga acagcctgag agccgaagac acggccgtgt attactgtgc gcgagaggcc  300
cctttacgtt tgggggagtc ccccatgat gcttttgata tctcgggcca agggacaatg  360

```
gtcaccgtct cctca                                                          375

<210> SEQ ID NO 219
<211> LENGTH: 375
<212> TYPE: DNA
<213> ORGANISM: Homo sapiens

<400> SEQUENCE: 219
gaggtgcagc tggtggagtc tgggggaggc ttggtcaagc ctggagggtc cctgagactc           60
tcctgtgcag cctctggatt caccttcagt gacgaatcca tgacctggat gcggcaggct          120
ccagggaagg ggctggagtg ggtttcctac ataagttctg gtggtggtgt caaattttac          180
gcagactctg tgaagggccg attcaccatc tccagggaca acgccaagaa ctcactgtat          240
ctgcaaatga acagcctgag agccgaagac acggccgtgt attactgtgc gcgagaggcc          300
cctttacgtt tgggggagtc cccccatgat gcttttgata tctcgggcca agggacaatg          360
gtcaccgtct cctca                                                          375

<210> SEQ ID NO 220
<211> LENGTH: 375
<212> TYPE: DNA
<213> ORGANISM: Homo sapiens

<400> SEQUENCE: 220
gaggtgcagc tggtggagtc tgggggaggc ttggtcaagc ctggagggtc cctgagactc           60
tcctgtgcag cctctggatt caccttcagt gacgcctcca tgacctggat gcggcaggct          120
ccagggaagg ggctggagtg ggtttcctac ataagttctg gtggtggtgt caaattttac          180
gcagactctg tgaagggccg attcaccatc tccagggaca acgccaagaa ctcactgtat          240
ctgcaaatga acagcctgag agccgaagac acggccgtgt attactgtgc gcgagaggcc          300
cctttacgtt tgggggagtc cccccatgat gcttttgata tctcgggcca agggacaatg          360
gtcaccgtct cctca                                                          375

<210> SEQ ID NO 221
<211> LENGTH: 375
<212> TYPE: DNA
<213> ORGANISM: Homo sapiens

<400> SEQUENCE: 221
gaggtgcagc tggtggagtc tgggggaggc ttggtcaagc ctggagggtc cctgagactc           60
tcctgtgcag cctctggatt caccttcagt gactggtcca tgacctggat gcggcaggct          120
ccagggaagg ggctggagtg ggtttcctac ataagttctg gtggtggtgt caaattttac          180
gcagactctg tgaagggccg attcaccatc tccagggaca acgccaagaa ctcactgtat          240
ctgcaaatga acagcctgag agccgaagac acggccgtgt attactgtgc gcgagaggcc          300
cctttacgtt tgggggagtc cccccatgat gcttttgata tctcgggcca agggacaatg          360
gtcaccgtct cctca                                                          375

<210> SEQ ID NO 222
<211> LENGTH: 375
<212> TYPE: DNA
<213> ORGANISM: Homo sapiens

<400> SEQUENCE: 222
gaggtgcagc tggtggagtc tgggggaggc ttggtcaagc ctggagggtc cctgagactc           60
```

```
tcctgtgcag cctctggatt caccttcagt gacggctcca tgacctggat gcggcaggct    120
ccagggaagg ggctggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375

<210> SEQ ID NO 223
<211> LENGTH: 375
<212> TYPE: DNA
<213> ORGANISM: Homo sapiens

<400> SEQUENCE: 223
gaggtgcagc tggtggagtc tgggggaggc ttggtcaagc ctggagggtc cctgagactc     60
tcctgtgcag cctctggatt caccttcagt gacacctcca tgacctggat gcggcaggct    120
ccagggaagg ggctggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375

<210> SEQ ID NO 224
<211> LENGTH: 375
<212> TYPE: DNA
<213> ORGANISM: Homo sapiens

<400> SEQUENCE: 224
gaggtgcagc tggtggagtc tgggggaggc ttggtcaagc ctggagggtc cctgagactc     60
tcctgtgcag cctctggatt caccttcagt gacatttcca tgacctggat gcggcaggct    120
ccagggaagg ggctggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375

<210> SEQ ID NO 225
<211> LENGTH: 375
<212> TYPE: DNA
<213> ORGANISM: Homo sapiens

<400> SEQUENCE: 225
gaggtgcagc tggtggagtc tgggggaggc ttggtcaagc ctggagggtc cctgagactc     60
tcctgtgcag cctctggatt caccttcagt gacaaatcca tgacctggat gcggcaggct    120
ccagggaagg ggctggagtg ggtttcctac ataagttctg gtggtggtgt caaattttac    180
gcagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375
```

```
<210> SEQ ID NO 226
<211> LENGTH: 375
<212> TYPE: DNA
<213> ORGANISM: Homo sapiens

<400> SEQUENCE: 226
gaggtgcagc tggtggagtc tggggaggc ttggtcaagc ctggagggtc cctgagactc      60
tcctgtgcag cctctggatt caccttcagt gaccgttcca tgacctggat gcggcaggct     120
ccagggaagg ggctggagtg ggtttcctac ataagttctg gtggtggtgt caaattttac     180
gcagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 227
<211> LENGTH: 375
<212> TYPE: DNA
<213> ORGANISM: Homo sapiens

<400> SEQUENCE: 227
gaggtgcagc tggtggagtc tggggaggc ttggtcaagc ctggagggtc cctgagactc      60
tcctgtgcag cctctggatt caccttcagt gacctgtcca tgacctggat gcggcaggct     120
ccagggaagg ggctggagtg ggtttcctac ataagttctg gtggtggtgt caaattttac     180
gcagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 228
<211> LENGTH: 375
<212> TYPE: DNA
<213> ORGANISM: Homo sapiens

<400> SEQUENCE: 228
gaggtgcagc tggtggagtc tggggaggc ttggtcaagc ctggagggtc cctgagactc      60
tcctgtgcag cctctggatt caccttcagt gactttccca tgacctggat gcggcaggct     120
ccagggaagg ggctggagtg ggtttcctac ataagttctg gtggtggtgt caaattttac     180
gcagactctg tgaagggccg attcaccatc tccagggaca acgccaagaa ctcactgtat     240
ctgcaaatga acagcctgag agccgaagac acggccgtgt attactgtgc gcgagaggcc     300
cctttacgtt tgggggagtc cccccatgat gcttttgata tctcgggcca agggacaatg     360
gtcaccgtct cctca                                                     375

<210> SEQ ID NO 229
<211> LENGTH: 375
<212> TYPE: DNA
<213> ORGANISM: Homo sapiens

<400> SEQUENCE: 229
gaggtgcagc tggtggagtc tggggaggc ttggtcaagc ctggagggtc cctgagactc      60
tcctgtgcag cctctggatt caccttcagt gacgaatccg tgacctggat gcggcaggct     120
ccagggaagg ggctggagtg ggtttcctac ataagttctg gtggtggtgt caaattttac     180
```

```
acagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                    375

<210> SEQ ID NO 230
<211> LENGTH: 375
<212> TYPE: DNA
<213> ORGANISM: Homo sapiens

<400> SEQUENCE: 230
gaggtgcagc tggtggagtc tgggggaggc ttggtcaagc ctggagggtc cctgagactc     60
tcctgtgcag cctctggatt caccttcagt gacgaatccc agacctggat gcggcaggct    120
ccagggaagg ggctggagtg ggtttcctac ataagttctg gtggtggtgt caaattttac    180
acagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                    375

<210> SEQ ID NO 231
<211> LENGTH: 375
<212> TYPE: DNA
<213> ORGANISM: Homo sapiens

<400> SEQUENCE: 231
gaggtgcagc tggtggagtc tgggggaggc ttggtcaagc ctggagggtc cctgagactc     60
tcctgtgcag cctctggatt caccttcagt gacgaatcct ttacctggat gcggcaggct    120
ccagggaagg ggctggagtg ggtttcctac ataagttctg gtggtggtgt caaattttac    180
acagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                    375

<210> SEQ ID NO 232
<211> LENGTH: 375
<212> TYPE: DNA
<213> ORGANISM: Homo sapiens

<400> SEQUENCE: 232
gaggtgcagc tggtggagtc tgggggaggc ttggtcaagc ctggagggtc cctgagactc     60
tcctgtgcag cctctggatt caccttcagt gacgaatccc tgacctggat gcggcaggct    120
ccagggaagg ggctggagtg ggtttcctac ataagttctg gtggtggtgt caaattttac    180
acagactctg tgaagggccg attcaccatc tccagggaca acgccaagaa ctcactgtat    240
ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                    375

<210> SEQ ID NO 233
<211> LENGTH: 375
<212> TYPE: DNA
<213> ORGANISM: Homo sapiens
```

<400> SEQUENCE: 233

| | | |
|---|---|---|
| gaggtgcagc tggtggagtc tgggggaggc ttggtcaagc ctggagggtc cctgagactc | 60 | |
| tcctgtgcag cctctggatt caccttcagt gacgaatcca aaacctggat gcggcaggct | 120 | |
| ccagggaagg ggctggagtg ggtttcctac ataagttctg gtggtggtgt caaattttac | 180 | |
| acagactctg tgaagggccg attcaccatc tccagggaca acgccaagaa ctcactgtat | 240 | |
| ctgcaaatga acagcctgag agccgaagac acggccgtgt attactgtgc gcgagaggcc | 300 | |
| cctttacgtt tgggggagtc cccccatgat gcttttgata tctcgggcca agggacaatg | 360 | |
| gtcaccgtct cctca | 375 | |

<210> SEQ ID NO 234
<211> LENGTH: 375
<212> TYPE: DNA
<213> ORGANISM: Homo sapiens

<400> SEQUENCE: 234

| | | |
|---|---|---|
| gaggtgcagc tggtggagtc tgggggaggc ttggtcaagc ctggagggtc cctgagactc | 60 | |
| tcctgtgcag cctctggatt caccttcagt gacgaatcct atacctggat gcggcaggct | 120 | |
| ccagggaagg ggctggagtg ggtttcctac ataagttctg gtggtggtgt caaattttac | 180 | |
| acagactctg tgaagggccg attcaccatc tccagggaca acgccaagaa ctcactgtat | 240 | |
| ctgcaaatga acagcctgag agccgaagac acggccgtgt attactgtgc gcgagaggcc | 300 | |
| cctttacgtt tgggggagtc cccccatgat gcttttgata tctcgggcca agggacaatg | 360 | |
| gtcaccgtct cctca | 375 | |

<210> SEQ ID NO 235
<211> LENGTH: 375
<212> TYPE: DNA
<213> ORGANISM: Homo sapiens

<400> SEQUENCE: 235

| | | |
|---|---|---|
| gaggtgcagc tggtggagtc tgggggaggc ttggtcaagc ctggagggtc cctgagactc | 60 | |
| tcctgtgcag cctctggatt caccttcagt gacgaatccg cgacctggat gcggcaggct | 120 | |
| ccagggaagg ggctggagtg ggtttcctac ataagttctg gtggtggtgt caaattttac | 180 | |
| gcagactctg tgaagggccg attcaccatc tccagggaca acgccaagaa ctcactgtat | 240 | |
| ctgcaaatga acagcctgag agccgaagac acggccgtgt attactgtgc gcgagaggcc | 300 | |
| cctttacgtt tgggggagtc cccccatgat gcttttgata tctcgggcca agggacaatg | 360 | |
| gtcaccgtct cctca | 375 | |

<210> SEQ ID NO 236
<211> LENGTH: 375
<212> TYPE: DNA
<213> ORGANISM: Homo sapiens

<400> SEQUENCE: 236

| | | |
|---|---|---|
| gaggtgcagc tggtggagtc tgggggaggc ttggtcaagc ctggagggtc cctgagactc | 60 | |
| tcctgtgcag cctctggatt caccttcagt gacgaatcct tcacctggat gcggcaggct | 120 | |
| ccagggaagg ggctggagtg ggtttcctac ataagttctg gtggtggtgt caaattttac | 180 | |
| gcagactctg tgaagggccg attcaccatc tccagggaca acgccaagaa ctcactgtat | 240 | |
| ctgcaaatga acagcctgag agccgaagac acggccgtgt attactgtgc gcgagaggcc | 300 | |

| cctttacgtt tgggggagtc cccccatgat gcttttgata tctcgggcca agggacaatg | 360 |
| gtcaccgtct cctca | 375 |

<210> SEQ ID NO 237
<211> LENGTH: 375
<212> TYPE: DNA
<213> ORGANISM: Homo sapiens

<400> SEQUENCE: 237

| gaggtgcagc tggtggagtc tggggaggc ttggtcaagc ctggagggtc cctgagactc | 60 |
| tcctgtgcag cctctggatt caccttcagt gacgaatcca acacctggat gcggcaggct | 120 |
| ccagggaagg ggctggagtg ggtttcctac ataagttctg gtggtggtgt caaattttac | 180 |
| gcagactctg tgaagggccg attcaccatc tccaggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 238
<211> LENGTH: 375
<212> TYPE: DNA
<213> ORGANISM: Homo sapiens

<400> SEQUENCE: 238

| gaggtgcagc tggtggagtc tggggaggc ttggtcaagc ctggagggtc cctgagactc | 60 |
| tcctgtgcag cctctggatt caccttcagt gacgaatcct ggacctggat gcggcaggct | 120 |
| ccagggaagg ggctggagtg ggtttcctac ataagttctg gtggtggtgt caaattttac | 180 |
| gcagactctg tgaagggccg attcaccatc tccaggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 239
<211> LENGTH: 375
<212> TYPE: DNA
<213> ORGANISM: Homo sapiens

<400> SEQUENCE: 239

| gaggtgcagc tggtggagtc tggggaggc ttggtcaagc ctggagggtc cctgagactc | 60 |
| tcctgtgcag cctctggatt caccttcagt gacgaatcca tcacctggat gcggcaggct | 120 |
| ccagggaagg ggctggagtg ggtttcctac ataagttctg gtggtggtgt caaattttac | 180 |
| gcagactctg tgaagggccg attcaccatc tccaggaca acgccaagaa ctcactgtat | 240 |
| ctgcaaatga acagcctgag agccgaagac acggccgtgt attactgtgc gcgagaggcc | 300 |
| cctttacgtt tgggggagtc cccccatgat gcttttgata tctcgggcca agggacaatg | 360 |
| gtcaccgtct cctca | 375 |

<210> SEQ ID NO 240
<211> LENGTH: 375
<212> TYPE: DNA
<213> ORGANISM: Homo sapiens

<400> SEQUENCE: 240

| gaggtgcagc tggtggagtc tggggaggc ttggtcaagc ctggagggtc cctgagactc | 60 |

```
tcctgtgcag cctctggatt caccttcagt gacgaatcca gcacctggat gcggcaggct    120
ccagggaagg ggctggagtg ggtttcctac ataagttctg gtggtggtgt caaattttac    180
gcagactctg tgaagggccg attcaccatc tccagggaca cgccaagaa ctcactgtat     240 ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375
```

<210> SEQ ID NO 241
<211> LENGTH: 375
<212> TYPE: DNA
<213> ORGANISM: Homo sapiens

<400> SEQUENCE: 241

```
gaggtgcagc tggtggagtc tgggggaggc ttggtcaagc ctggagggtc cctgagactc     60
tcctgtgcag cctctggatt caccttcagt gacgaatccc acacctggat gcggcaggct    120
ccagggaagg ggctggagtg ggtttcctac ataagttctg gtggtggtgt caaattttac    180
gcagactctg tgaagggccg attcaccatc tccagggaca cgccaagaa ctcactgtat     240 ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375
```

<210> SEQ ID NO 242
<211> LENGTH: 375
<212> TYPE: DNA
<213> ORGANISM: Homo sapiens

<400> SEQUENCE: 242

```
gaggtgcagc tggtggagtc tgggggaggc ttggtcaagc ctggagggtc cctgagactc     60
tcctgtgcag cctctggatt caccttcagt gacgaatccg ggacctggat gcggcaggct    120
ccagggaagg ggctggagtg ggtttcctac ataagttctg gtggtggtgt caaattttac    180
gcagactctg tgaagggccg attcaccatc tccagggaca cgccaagaa ctcactgtat     240 ctgcaaatga acagcctgag agccgaagac acggccgtgt attactgtgc gcgagaggcc    300
cctttacgtt tgggggagtc cccccatgat gcttttgata tctcgggcca agggacaatg    360
gtcaccgtct cctca                                                     375
```

<210> SEQ ID NO 243
<211> LENGTH: 10
<212> TYPE: PRT
<213> ORGANISM: Artificial Sequence
<220> FEATURE:
<223> OTHER INFORMATION: Linker Peptides
<220> FEATURE:
<221> NAME/KEY: MISC_FEATURE
<222> LOCATION: (1)..(10)
<223> OTHER INFORMATION: 2GS Linker Peptide

<400> SEQUENCE: 243

Gly Gly Gly Gly Ser Gly Gly Gly Gly Ser
1               5                   10

<210> SEQ ID NO 244
<211> LENGTH: 30
<212> TYPE: DNA
<213> ORGANISM: Artificial Sequence
<220> FEATURE:
<223> OTHER INFORMATION: Linker Peptide
<220> FEATURE:
<221> NAME/KEY: misc_feature
<222> LOCATION: (1)..(30)
<223> OTHER INFORMATION: Nucleic acid encoding Seq ID NO.243

<400> SEQUENCE: 244
ggaggtggag gttcaggtgg aggtggtagt        30

<210> SEQ ID NO 245
<211> LENGTH: 20
<212> TYPE: PRT
<213> ORGANISM: Artificial Sequence
<220> FEATURE:
<223> OTHER INFORMATION: Linker Peptide
<220> FEATURE:
<221> NAME/KEY: MISC_FEATURE
<222> LOCATION: (1)..(20)
<223> OTHER INFORMATION: 4GS Linker Peptide

<400> SEQUENCE: 245

Gly Gly Gly Gly Ser Gly Gly Gly Gly Ser Gly Gly Gly Gly Ser Gly
1               5                   10                  15

Gly Gly Gly Ser
            20

<210> SEQ ID NO 246
<211> LENGTH: 60
<212> TYPE: DNA
<213> ORGANISM: Artificial Sequence
<220> FEATURE:
<223> OTHER INFORMATION: Linker Peptide Sequence
<220> FEATURE:
<221> NAME/KEY: misc_feature
<222> LOCATION: (1)..(60)
<223> OTHER INFORMATION: Nucleic acid encoding SeqID NO. 245

<400> SEQUENCE: 246
ggaggtggag gttcaggagg tggtggttct ggtggtggcg gttcaggtgg aggtggtagt        60

<210> SEQ ID NO 247
<211> LENGTH: 30
<212> TYPE: PRT
<213> ORGANISM: Artificial Sequence
<220> FEATURE:
<223> OTHER INFORMATION: Linker Peptide
<220> FEATURE:
<221> NAME/KEY: MISC_FEATURE
<222> LOCATION: (1)..(30)
<223> OTHER INFORMATION: 6GS Linker Peptide

<400> SEQUENCE: 247

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser
            20                  25                  30

<210> SEQ ID NO 248
<211> LENGTH: 90
<212> TYPE: DNA
<213> ORGANISM: Artificial Sequence
<220> FEATURE:
<223> OTHER INFORMATION: Linker Peptide Sequence
<220> FEATURE:
<221> NAME/KEY: misc_feature
<222> LOCATION: (1)..(90)
<223> OTHER INFORMATION: Nucleic acid encoding SeqID No.247

-continued

<400> SEQUENCE: 248

```
ggtggtggcg gttcaggcgg aggtggctct ggaggtggag gttcaggagg tggtggttct    60
ggcggcggtg gatcgggtgg aggtggtagt                                      90
```

<210> SEQ ID NO 249
<211> LENGTH: 45
<212> TYPE: PRT
<213> ORGANISM: Artificial Sequence
<220> FEATURE:
<223> OTHER INFORMATION: Peptide Linker
<220> FEATURE:
<221> NAME/KEY: MISC_FEATURE
<222> LOCATION: (1)..(45)
<223> OTHER INFORMATION: 9GS Peptide Linker

<400> SEQUENCE: 249

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 250
<211> LENGTH: 135
<212> TYPE: DNA
<213> ORGANISM: Artificial Sequence
<220> FEATURE:
<223> OTHER INFORMATION: Peptide Linker Sequence
<220> FEATURE:
<221> NAME/KEY: misc_feature
<222> LOCATION: (1)..(135)
<223> OTHER INFORMATION: Nucleic acid encoding SeqID NO. 249

<400> SEQUENCE: 250

```
ggaggtggag gttcaggagg tggtggttct ggtggtggcg gttcaggtgg aggtggtagt    60
ggaggaggtg gttctggcgg aggaggatcg ggtggaggtg gctcaggtgg tggaggtagt   120
ggaggcggtg gcagc                                                    135
```

<210> SEQ ID NO 251
<211> LENGTH: 448
<212> TYPE: PRT
<213> ORGANISM: Artificial Sequence
<220> FEATURE:
<223> OTHER INFORMATION: Trivalent bispecific construct
<220> FEATURE:
<221> NAME/KEY: MISC_FEATURE
<222> LOCATION: (1)..(448)
<223> OTHER INFORMATION: VH1.1-6GS-VH1.1-6GS-VH2.63-His6

<400> SEQUENCE: 251

Glu Val Gln Leu Val Glu Ser Gly Gly Gly Val Val Arg Pro Gly Gly
1               5                   10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Gly Asn Ser Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys

```
                     85                  90                  95
Ala Arg Ile Pro Arg Glu Asp Cys Ser Ser Ala Ser Cys Tyr Thr Asp
                100                 105                 110

Ala Ile Asp Phe Trp Gly Pro Gly Thr Met Val Thr Val Ser Ser Gly
            115                 120                 125

Gly Gly Gly Ser Gly Gly Gly Ser Gly Gly Gly Ser Gly Gly
        130                 135                 140

Gly Gly Ser Gly Gly Gly Ser Gly Gly Gly Ser Glu Val Gln
145                 150                 155                 160

Leu Val Glu Ser Gly Gly Gly Val Val Arg Pro Gly Gly Ser Leu Arg
                165                 170                 175

Leu Ser Cys Ser Ala Ser Gly Phe Thr Phe Asp Asp Tyr Gly Met Ser
                180                 185                 190

Trp Val Arg Gln Ala Pro Gly Lys Gly Leu Glu Trp Val Ser Gly Ile
                195                 200                 205

His Trp Asn Gly Gly Asn Ser Gly Tyr Ala Asp Ser Val Lys Gly Arg
            210                 215                 220

Phe Thr Ile Ser Arg Asp Asn Ala Lys Asn Ser Leu Tyr Leu Gln Met
225                 230                 235                 240

Asn Ser Leu Arg Ala Glu Asp Thr Ala Leu Tyr Tyr Cys Ala Arg Ile
                245                 250                 255

Pro Arg Glu Asp Cys Ser Ser Ala Ser Cys Tyr Thr Asp Ala Ile Asp
                260                 265                 270

Phe Trp Gly Pro Gly Thr Met Val Thr Val Ser Ser Gly Gly Gly Gly
            275                 280                 285

Ser Gly Gly Gly Gly Ser Gly Gly Gly Gly Ser Gly Gly Gly Gly Ser
        290                 295                 300

Gly Gly Gly Gly Ser Gly Gly Gly Gly Ser Glu Val Gln Leu Val Glu
305                 310                 315                 320

Ser Gly Gly Gly Leu Val Lys Pro Gly Gly Ser Leu Arg Leu Ser Cys
                325                 330                 335

Ala Ala Ser Gly Phe Thr Phe Ser Asp Ser Ser Met Thr Trp Met Arg
                340                 345                 350

Gln Ala Pro Gly Lys Gly Leu Glu Trp Val Ser Tyr Ile Ser Ser Gly
                355                 360                 365

Gly Gly Val Lys Phe Tyr Thr Asp Ser Val Lys Gly Arg Phe Thr Ile
            370                 375                 380

Ser Arg Asp Asn Ala Lys Asn Ser Leu Tyr Leu Gln Met Asn Ser Leu
385                 390                 395                 400

Arg Ala Asp Asp Thr Ala Val Tyr Tyr Cys Ala Arg Glu Ala Pro Leu
                405                 410                 415

Arg Leu Gly Glu Ser Pro His Asp Ala Phe Asp Ile Ser Gly Gln Gly
            420                 425                 430

Thr Met Val Thr Val Ser Ser Ala Ala Ala His His His His His His
            435                 440                 445

<210> SEQ ID NO 252
<211> LENGTH: 463
<212> TYPE: PRT
<213> ORGANISM: Artificial Sequence
<220> FEATURE:
<223> OTHER INFORMATION: Trivalent bispecific construct
<220> FEATURE:
<221> NAME/KEY: MISC_FEATURE
<222> LOCATION: (1)..(463)
<223> OTHER INFORMATION: VH1.1-6GS-VH1.1-9GS-VH2.63-His6
```

<400> SEQUENCE: 252

Glu Val Gln Leu Val Glu Ser Gly Gly Val Val Arg Pro Gly Gly
1               5                   10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Asn Ser Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Pro Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Ser Gly Gly Gly Ser Glu Val Gln
145                 150                 155                 160

Leu Val Glu Ser Gly Gly Val Val Arg Pro Gly Gly Ser Leu Arg
                165                 170                 175

Leu Ser Cys Ser Ala Ser Gly Phe Thr Phe Asp Asp Tyr Gly Met Ser
            180                 185                 190

Trp Val Arg Gln Ala Pro Gly Lys Gly Leu Glu Trp Val Ser Gly Ile
        195                 200                 205

His Trp Asn Gly Gly Asn Ser Gly Tyr Ala Asp Ser Val Lys Gly Arg
    210                 215                 220

Phe Thr Ile Ser Arg Asp Asn Ala Lys Asn Ser Leu Tyr Leu Gln Met
225                 230                 235                 240

Asn Ser Leu Arg Ala Glu Asp Thr Ala Leu Tyr Tyr Cys Ala Arg Ile
                245                 250                 255

Pro Arg Glu Asp Cys Ser Ser Ala Ser Cys Tyr Thr Asp Ala Ile Asp
            260                 265                 270

Phe Trp Gly Pro Gly Thr Met Val Thr Val Ser Ser Gly Gly Gly Gly
        275                 280                 285

Ser Gly Gly Gly Gly Ser Gly Gly Gly Gly Ser Gly Gly Gly Gly Ser
    290                 295                 300

Gly Gly Gly Gly Ser Gly Gly Gly Ser Gly Gly Gly Gly Ser Gly
305                 310                 315                 320

Gly Gly Gly Ser Gly Gly Gly Ser Glu Val Gln Leu Val Glu Ser
                325                 330                 335

Gly Gly Gly Leu Val Lys Pro Gly Gly Ser Leu Arg Leu Ser Cys Ala
            340                 345                 350

Ala Ser Gly Phe Thr Phe Ser Asp Ser Ser Met Thr Trp Met Arg Gln
        355                 360                 365

Ala Pro Gly Lys Gly Leu Glu Trp Val Ser Tyr Ile Ser Ser Gly Gly
    370                 375                 380

Gly Val Lys Phe Tyr Thr Asp Ser Val Lys Gly Arg Phe Thr Ile Ser
385                 390                 395                 400

Arg Asp Asn Ala Lys Asn Ser Leu Tyr Leu Gln Met Asn Ser Leu Arg

```
                    405                 410                 415
Ala Asp Asp Thr Ala Val Tyr Tyr Cys Ala Arg Glu Ala Pro Leu Arg
            420                 425                 430

Leu Gly Glu Ser Pro His Asp Ala Phe Asp Ile Ser Gly Gln Gly Thr
            435                 440                 445

Met Val Thr Val Ser Ser Ala Ala His His His His His His
            450                 455                 460
```

<210> SEQ ID NO 253
<211> LENGTH: 293
<212> TYPE: PRT
<213> ORGANISM: Artificial Sequence
<220> FEATURE:
<223> OTHER INFORMATION: Bivalent VH construct
<220> FEATURE:
<221> NAME/KEY: MISC_FEATURE
<222> LOCATION: (1)..(293)
<223> OTHER INFORMATION: VH1.1-6GS-VH1.1-His6

<400> SEQUENCE: 253

```
Glu Val Gln Leu Val Glu Ser Gly Gly Gly Val Val Arg Pro Gly Gly
1               5                   10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
            35                  40                  45

Ser Gly Ile His Trp Asn Gly Gly Asn Ser Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Ile Pro Arg Glu Asp Cys Ser Ser Ala Ser Cys Tyr Thr Asp
            100                 105                 110

Ala Ile Asp Phe Trp Gly Pro Gly Thr Met Val Thr Val Ser Ser Gly
            115                 120                 125

Gly Gly Gly Ser Gly Gly Gly Ser Gly Gly Gly Ser Gly
            130                 135                 140

Gly Gly Ser Gly Gly Gly Ser Gly Gly Gly Ser Glu Val Gln
145                 150                 155                 160

Leu Val Glu Ser Gly Gly Val Val Arg Pro Gly Gly Ser Leu Arg
            165                 170                 175

Leu Ser Cys Ser Ala Ser Gly Phe Thr Phe Asp Asp Tyr Gly Met Ser
            180                 185                 190

Trp Val Arg Gln Ala Pro Gly Lys Gly Leu Glu Trp Val Ser Gly Ile
            195                 200                 205

His Trp Asn Gly Gly Asn Ser Gly Tyr Ala Asp Ser Val Lys Gly Arg
            210                 215                 220

Phe Thr Ile Ser Arg Asp Asn Ala Lys Asn Ser Leu Tyr Leu Gln Met
225                 230                 235                 240

Asn Ser Leu Arg Ala Glu Asp Thr Ala Leu Tyr Tyr Cys Ala Arg Ile
            245                 250                 255

Pro Arg Glu Asp Cys Ser Ser Ala Ser Cys Tyr Thr Asp Ala Ile Asp
            260                 265                 270

Phe Trp Gly Pro Gly Thr Met Val Thr Val Ser Ser Ala Ala His
            275                 280                 285
```

His His His His His
    290

<210> SEQ ID NO 254
<211> LENGTH: 283
<212> TYPE: PRT
<213> ORGANISM: Artificial Sequence
<220> FEATURE:
<223> OTHER INFORMATION: Bivalent VH construct
<220> FEATURE:
<221> NAME/KEY: MISC_FEATURE
<222> LOCATION: (1)..(283)
<223> OTHER INFORMATION: VH1.1-4GS-VH1.1-His6

<400> SEQUENCE: 254

```
Glu Val Gln Leu Val Glu Ser Gly Gly Gly Val Val Arg Pro Gly
1               5                  10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Gly Asn Ser Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Pro Gly Thr Met Val Thr Val Ser Ser Gly
        115                 120                 125

Gly Gly Gly Ser Gly Gly Gly Ser Gly Gly Gly Ser Gly Gly
    130                 135                 140

Gly Gly Ser Glu Val Gln Leu Val Glu Ser Gly Gly Gly Val Val Arg
145                 150                 155                 160

Pro Gly Gly Ser Leu Arg Leu Ser Cys Ser Ala Ser Gly Phe Thr Phe
                165                 170                 175

Asp Asp Tyr Gly Met Ser Trp Val Arg Gln Ala Pro Gly Lys Gly Leu
            180                 185                 190

Glu Trp Val Ser Gly Ile His Trp Asn Gly Gly Asn Ser Gly Tyr Ala
        195                 200                 205

Asp Ser Val Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Leu
225                 230                 235                 240

Tyr Tyr Cys Ala Arg Ile Pro Arg Glu Asp Cys Ser Ser Ala Ser Cys
                245                 250                 255

Tyr Thr Asp Ala Ile Asp Phe Trp Gly Pro Gly Thr Met Val Thr Val
            260                 265                 270

Ser Ser Ala Ala Ala His His His His His His
    275                 280
```

<210> SEQ ID NO 255
<211> LENGTH: 303
<212> TYPE: PRT
<213> ORGANISM: Artificial Sequence
<220> FEATURE:
<223> OTHER INFORMATION: Bivalent VH construct
<220> FEATURE:

```
<221> NAME/KEY: MISC_FEATURE
<222> LOCATION: (1)..(303)
<223> OTHER INFORMATION: VH1.1-8GS-VH1.1-His6

<400> SEQUENCE: 255
```

Glu Val Gln Leu Val Glu Ser Gly Gly Val Val Arg Pro Gly Gly
1               5                   10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Gly Asn Ser Gly Tyr Ala Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Pro Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Gly Gly Gly
145                 150                 155                 160

Gly Ser Gly Gly Gly Ser Glu Val Gln Leu Val Glu Ser Gly Gly
            165                 170                 175

Gly Val Val Arg Pro Gly Gly Ser Leu Arg Leu Ser Cys Ser Ala Ser
        180                 185                 190

Gly Phe Thr Phe Asp Asp Tyr Gly Met Ser Trp Val Arg Gln Ala Pro
    195                 200                 205

Gly Lys Gly Leu Glu Trp Val Ser Gly Ile His Trp Asn Gly Gly Asn
210                 215                 220

Ser Gly Tyr Ala Asp Ser Val Lys Gly Arg Phe Thr Ile Ser Arg Asp
225                 230                 235                 240

Asn Ala Lys Asn Ser Leu Tyr Leu Gln Met Asn Ser Leu Arg Ala Glu
                245                 250                 255

Asp Thr Ala Leu Tyr Tyr Cys Ala Arg Ile Pro Arg Glu Asp Cys Ser
            260                 265                 270

Ser Ala Ser Cys Tyr Thr Asp Ala Ile Asp Phe Trp Gly Pro Gly Thr
        275                 280                 285

Met Val Thr Val Ser Ser Ala Ala Ala His His His His His His
    290                 295                 300

```
<210> SEQ ID NO 256
<211> LENGTH: 323
<212> TYPE: PRT
<213> ORGANISM: Artificial Sequence
<220> FEATURE:
<223> OTHER INFORMATION: Bivalent VH construct
<220> FEATURE:
<221> NAME/KEY: MISC_FEATURE
<222> LOCATION: (1)..(323)
<223> OTHER INFORMATION: VH1.1-12GS-VH1.1-His6

<400> SEQUENCE: 256
```

Glu Val Gln Leu Val Glu Ser Gly Gly Gly Val Val Arg Pro Gly Gly
1               5                   10                  15

Ser Leu Arg Leu Ser Cys Ser Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Gly Asn Ser Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Pro Gly Thr Met Val Thr Val Ser Ser Gly
        115                 120                 125

Gly Gly Gly Ser Gly Gly Gly Ser Gly Gly Gly Gly Ser Gly Gly Gly
    130                 135                 140

Gly Gly Ser Gly Gly Gly Ser Gly Gly Gly Gly Ser Gly Gly Gly Gly
145                 150                 155                 160

Gly Ser Gly Gly Gly Ser Gly Gly Gly Ser Gly Gly Gly Gly Gly Gly
                165                 170                 175

Ser Gly Gly Gly Ser Gly Gly Gly Ser Glu Val Gln Leu Val
            180                 185                 190

Glu Ser Gly Gly Gly Val Val Arg Pro Gly Gly Ser Leu Arg Leu Ser
        195                 200                 205

Cys Ser Ala Ser Gly Phe Thr Phe Asp Asp Tyr Gly Met Ser Trp Val
    210                 215                 220

Arg Gln Ala Pro Gly Lys Gly Leu Glu Trp Val Ser Gly Ile His Trp
225                 230                 235                 240

Asn Gly Gly Asn Ser Gly Tyr Ala Asp Ser Val Lys Gly Arg Phe Thr
                245                 250                 255

Ile Ser Arg Asp Asn Ala Lys Asn Ser Leu Tyr Leu Gln Met Asn Ser
            260                 265                 270

Leu Arg Ala Glu Asp Thr Ala Leu Tyr Tyr Cys Ala Arg Ile Pro Arg
        275                 280                 285

Glu Asp Cys Ser Ser Ala Ser Cys Tyr Thr Asp Ala Ile Asp Phe Trp
    290                 295                 300

Gly Pro Gly Thr Met Val Thr Val Ser Ser Ala Ala Ala His His His
305                 310                 315                 320

His His His

<210> SEQ ID NO 257
<211> LENGTH: 463
<212> TYPE: PRT
<213> ORGANISM: Artificial Sequence
<220> FEATURE:
<223> OTHER INFORMATION: Trivalent bispecific construct
<220> FEATURE:
<221> NAME/KEY: MISC_FEATURE
<222> LOCATION: (1)..(463)
<223> OTHER INFORMATION: VH2.77-9GS- VH 1.1-6GS- VH 1.1-His6

<400> SEQUENCE: 257

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

```
Ser Met Thr Trp Met Arg Gln Ala Pro Gly Lys Gly Leu Glu Trp Val
         35                  40                  45

Ser Tyr Ile Ser Ser Gly Gly Val Lys Phe Tyr Thr Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Pro Leu Arg Leu Gly Glu Ser Pro His Asp Ala Phe
             100                 105                 110

Asp Ile Ser Gly Gln Gly Thr Met Val Thr Val Ser Ser Gly Gly Gly
             115                 120                 125

Gly Ser Gly Gly Gly Gly Ser Gly Gly Gly Ser Gly Gly Gly Gly
130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Ser Glu Val Gln Leu Val Glu
                 165                 170                 175

Ser Gly Gly Gly Val Val Arg Pro Gly Gly Ser Leu Arg Leu Ser Cys
             180                 185                 190

Ser Ala Ser Gly Phe Thr Phe Asp Asp Tyr Gly Met Ser Trp Val Arg
             195                 200                 205

Gln Ala Pro Gly Lys Gly Leu Glu Trp Val Ser Gly Ile His Trp Asn
             210                 215                 220

Gly Gly Asn Ser Gly Tyr Ala Asp Ser Val Lys Gly Arg Phe Thr Ile
225                 230                 235                 240

Ser Arg Asp Asn Ala Lys Asn Ser Leu Tyr Leu Gln Met Asn Ser Leu
                 245                 250                 255

Arg Ala Glu Asp Thr Ala Leu Tyr Tyr Cys Ala Arg Ile Pro Arg Glu
             260                 265                 270

Asp Cys Ser Ser Ala Ser Cys Tyr Thr Asp Ala Ile Asp Phe Trp Gly
             275                 280                 285

Pro Gly Thr Met Val Thr Val Ser Ser Gly Gly Gly Gly Ser Gly Gly
             290                 295                 300

Gly Gly Ser Gly Gly Gly Gly Ser Gly Gly Gly Gly Ser Gly Gly Gly
305                 310                 315                 320

Gly Ser Gly Gly Gly Ser Glu Val Gln Leu Val Glu Ser Gly Gly
                 325                 330                 335

Gly Val Val Arg Pro Gly Gly Ser Leu Arg Leu Ser Cys Ser Ala Ser
             340                 345                 350

Gly Phe Thr Phe Asp Asp Tyr Gly Met Ser Trp Val Arg Gln Ala Pro
             355                 360                 365

Gly Lys Gly Leu Glu Trp Val Ser Gly Ile His Trp Asn Gly Gly Asn
             370                 375                 380

Ser Gly Tyr Ala Asp Ser Val Lys Gly Arg Phe Thr Ile Ser Arg Asp
385                 390                 395                 400

Asn Ala Lys Asn Ser Leu Tyr Leu Gln Met Asn Ser Leu Arg Ala Glu
                 405                 410                 415

Asp Thr Ala Leu Tyr Tyr Cys Ala Arg Ile Pro Arg Glu Asp Cys Ser
             420                 425                 430

Ser Ala Ser Cys Tyr Thr Asp Ala Ile Asp Phe Trp Gly Pro Gly Thr
             435                 440                 445
```

```
Met Val Thr Val Ser Ser Ala Ala His His His His His
    450                 455                 460
```

<210> SEQ ID NO 258
<211> LENGTH: 448
<212> TYPE: PRT
<213> ORGANISM: Artificial Sequence
<220> FEATURE:
<223> OTHER INFORMATION: Trivalent bispecific construct
<220> FEATURE:
<221> NAME/KEY: MISC_FEATURE
<222> LOCATION: (1)..(448)
<223> OTHER INFORMATION: VH 1.2-6GS- VH 1.2-6GS- VH 2.92-His6

<400> SEQUENCE: 258

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile His Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
            100                 105                 110

Ala Ile Asp Phe Trp Gly Gln Gly Thr Met Val Thr Val Ser Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Gly Gly Gly Ser Glu Val Gln
145                 150                 155                 160

Leu Val Glu Ser Gly Gly Gly Val Val Arg Pro Gly Gly Ser Leu Arg
                165                 170                 175

Leu Ser Cys Ala Ala Ser Gly Phe Thr Phe Asp Asp Tyr Gly Met Ser
            180                 185                 190

Trp Val Arg Gln Ala Pro Gly Lys Gly Leu Glu Trp Val Ser Gly Ile
        195                 200                 205

His Trp Asn Gly Gly Ser Thr Gly Tyr Ala Asp Ser Val Lys Gly Arg
    210                 215                 220

Phe Thr Ile Ser Arg Asp Asn Ala Lys Asn Ser Leu Tyr Leu Gln Met
225                 230                 235                 240

Asn Ser Leu Arg Ala Glu Asp Thr Ala Leu Tyr Tyr Cys Ala Arg Ile
                245                 250                 255

Pro Arg Glu Asp Cys Ser Ser Ala Ser Cys Tyr Thr Asp Ala Ile Asp
            260                 265                 270

Phe Trp Gly Gln Gly Thr Met Val Thr Val Ser Ser Gly Gly Gly Gly
        275                 280                 285

Ser Gly Gly Gly Ser Gly Gly Gly Ser Gly Gly Gly Ser
    290                 295                 300

Gly Gly Gly Ser Gly Gly Gly Ser Glu Val Gln Leu Val Glu
305                 310                 315                 320

Ser Gly Gly Gly Leu Val Lys Pro Gly Gly Ser Leu Arg Leu Ser Cys
                325                 330                 335
```

-continued

Ala Ala Ser Gly Phe Thr Phe Ser Asp Glu Ser Met Thr Trp Met Arg
                340                 345                 350

Gln Ala Pro Gly Lys Gly Leu Glu Trp Val Ser Tyr Ile Ser Ser Gly
            355                 360                 365

Gly Gly Val Lys Phe Tyr Ala Asp Ser Val Lys Gly Arg Phe Thr Ile
370                 375                 380

Ser Arg Asp Asn Ala Lys Asn Ser Leu Tyr Leu Gln Met Asn Ser Leu
385                 390                 395                 400

Arg Ala Glu Asp Thr Ala Val Tyr Tyr Cys Ala Arg Glu Ala Pro Leu
                405                 410                 415

Arg Leu Gly Glu Ser Pro His Asp Ala Phe Asp Ile Ser Gly Gln Gly
            420                 425                 430

Thr Met Val Thr Val Ser Ser Ala Ala Ala His His His His His His
                435                 440                 445

<210> SEQ ID NO 259
<211> LENGTH: 439
<212> TYPE: PRT
<213> ORGANISM: Artificial Sequence
<220> FEATURE:
<223> OTHER INFORMATION: Trivalent and bispecific construct
<220> FEATURE:
<221> NAME/KEY: MISC_FEATURE
<222> LOCATION: (1)..(439)
<223> OTHER INFORMATION: VH 1.2-6GS- VH 1.2-6GS- VH 2.92

<400> SEQUENCE: 259

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
            35                  40                  45

Ser Gly Ile His Trp Asn Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Ile Pro Arg Glu Asp Cys Ser Ser Ala Ser Cys Tyr Thr Asp
                100                 105                 110

Ala Ile Asp Phe Trp Gly Gln Gly Thr Met Val Thr Val Ser Ser Gly
            115                 120                 125

Gly Gly Gly Ser Gly Gly Gly Gly Ser Gly Gly Gly Gly Ser Gly Gly
130                 135                 140

Gly Gly Ser Gly Gly Gly Ser Gly Gly Gly Gly Ser Glu Val Gln
145                 150                 155                 160

Leu Val Glu Ser Gly Gly Val Val Arg Pro Gly Gly Ser Leu Arg
                165                 170                 175

Leu Ser Cys Ala Ala Ser Gly Phe Thr Phe Asp Asp Tyr Gly Met Ser
            180                 185                 190

Trp Val Arg Gln Ala Pro Gly Lys Gly Leu Glu Trp Val Ser Gly Ile
        195                 200                 205

His Trp Asn Gly Ser Thr Gly Tyr Ala Asp Ser Val Lys Gly Arg
        210                 215                 220

Phe Thr Ile Ser Arg Asp Asn Ala Lys Asn Ser Leu Tyr Leu Gln Met

-continued

```
            225                 230                 235                 240
Asn Ser Leu Arg Ala Glu Asp Thr Ala Leu Tyr Tyr Cys Ala Arg Ile
                245                 250                 255

Pro Arg Glu Asp Cys Ser Ser Ala Ser Cys Tyr Thr Asp Ala Ile Asp
            260                 265                 270

Phe Trp Gly Gln Gly Thr Met Val Thr Val Ser Ser Gly Gly Gly
        275                 280                 285

Ser Gly Gly Gly Gly Ser Gly Gly Gly Gly Ser Gly Gly Gly Gly Ser
        290                 295                 300

Gly Gly Gly Gly Ser Gly Gly Gly Ser Glu Val Gln Leu Val Glu
305                 310                 315                 320

Ser Gly Gly Gly Leu Val Lys Pro Gly Gly Ser Leu Arg Leu Ser Cys
                325                 330                 335

Ala Ala Ser Gly Phe Thr Phe Ser Asp Glu Ser Met Thr Trp Met Arg
            340                 345                 350

Gln Ala Pro Gly Lys Gly Leu Glu Trp Val Ser Tyr Ile Ser Ser Gly
            355                 360                 365

Gly Gly Val Lys Phe Tyr Ala Asp Ser Val Lys Gly Arg Phe Thr Ile
        370                 375                 380

Ser Arg Asp Asn Ala Lys Asn Ser Leu Tyr Leu Gln Met Asn Ser Leu
385                 390                 395                 400

Arg Ala Glu Asp Thr Ala Val Tyr Tyr Cys Ala Arg Glu Ala Pro Leu
            405                 410                 415

Arg Leu Gly Glu Ser Pro His Asp Ala Phe Asp Ile Ser Gly Gln Gly
            420                 425                 430

Thr Met Val Thr Val Ser Ser
        435
```